United States Patent
Bringley et al.

(10) Patent No.: US 9,562,058 B2
(45) Date of Patent: Feb. 7, 2017

(54) CRYSTALLINE FORMS OF AN ANTIVIRAL COMPOUND

(71) Applicant: GILEAD SCIENCES, INC., Foster City, CA (US)

(72) Inventors: Dustin Bringley, San Carlos, CA (US); Johann Chan, Foster City, CA (US); Peter Fung, Newport, NY (US); Katie Keaton, Burlingame, CA (US); Olga Lapina, Newark, CA (US); Henry Morrison, Dublin, CA (US); Dominika Pcion, San Francisco, CA (US)

(73) Assignee: GILEAD SCIENCES, INC., Foster City, CA (US)

( * ) Notice: Subject to any disclaimer, the term of this patent is extended or adjusted under 35 U.S.C. 154(b) by 0 days.

(21) Appl. No.: 14/575,966

(22) Filed: Dec. 18, 2014

(65) Prior Publication Data

US 2015/0175625 A1 Jun. 25, 2015

Related U.S. Application Data

(60) Provisional application No. 61/920,427, filed on Dec. 23, 2013.

(51) Int. Cl.
| | |
|---|---|
| *A61K 31/4985* | (2006.01) |
| *C07D 498/16* | (2006.01) |
| *A61K 45/06* | (2006.01) |
| *C07K 5/083* | (2006.01) |

(52) U.S. Cl.
CPC ......... *C07D 498/16* (2013.01); *A61K 31/4985* (2013.01); *A61K 45/06* (2013.01); *C07K 5/0808* (2013.01)

(58) Field of Classification Search
CPC .................................................. C07D 498/16
See application file for complete search history.

(56) References Cited

PUBLICATIONS

Intl. Search Report—Written Opinion dated Feb. 27, 2015 for PCT/US2014/071310.

*Primary Examiner* — Brian McDowell

(57) ABSTRACT

Crystalline forms of the anti-HCV compound (1aR,5S,8S, 9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide (Compound I) were prepared and characterized in the solid state:

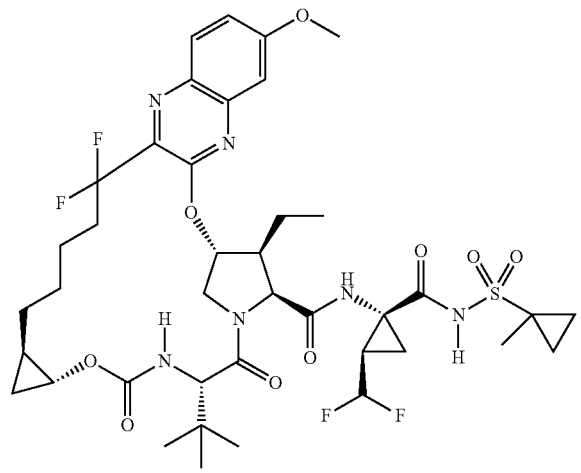

Also provided are processes of manufacture and methods of using the crystalline forms.

13 Claims, 125 Drawing Sheets

CRYSTALLINE FORMS OF AN ANTIVIRAL COMPOUND

This application claims priority under 35 U.S.C. §119(e) to U.S. Provisional Application Ser. No. 61/920,427 filed on Dec. 23, 2013, the entirety of which is incorporated herein by reference.

BACKGROUND

The present disclosure relates generally to crystalline forms of the antiviral compound named (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide, processes for making the forms, and their therapeutic methods of use.

The hepatitis C virus (HCV), a member of the hepacivirus genera within the Flaviviridae family, is the leading cause of chronic liver disease worldwide (Boyer, N. et al. J Hepatol. 2000, 32, 98-112). Consequently, a significant focus of current antiviral research is directed toward the development of improved methods for the treatment of chronic HCV infections in humans (Ciesek, S., von Hahn T., and Manns, M P., Clin. Liver Dis., 2011, 15, 597-609; Soriano, V. et al, J. Antimicrob. Chemother., 2011, 66, 1573-1686; Brody, H., Nature Outlook, 2011, 474, S1-S7; Gordon, C. P., et al., J. Med. Chem. 2005, 48, 1-20; Maradpour, D., et al., Nat. Rev. Micro. 2007, 5, 453-463).

There remains a need to develop effective treatments for HCV infections. Suitable compounds for the treatment of HCV infections are disclosed in U.S. Publication No. 2014-0017198, titled "Inhibitors of Hepatitis C Virus" filed on Jul. 2, 2013 including the compound of formula I:

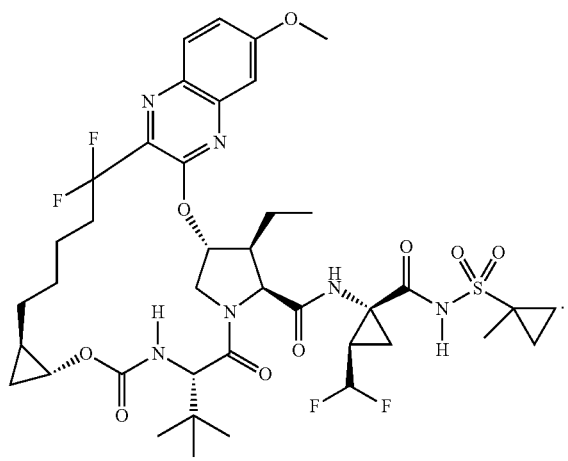

I

However, Compound I was not heretofore known in any crystalline form.

SUMMARY

The present disclosure fulfills these needs and others by providing crystalline forms of Compound I and salts, co-crystals, hydrates and solvates thereof. The present disclosure also provides pharmaceutical compositions comprising crystalline forms of Compound I. The disclosure also provides processes for making the crystalline forms and methods for using them in the treatment of HCV.

Thus, one embodiment is directed to crystalline (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide ethanol solvate (Compound I Form I). Compound I Form I is characterized by an X-ray powder diffractogram comprising the following peaks (±0.2°): at 8.6, 11.1, and 15.5 °2θ, as determined on a diffractometer using Cu—Kα radiation.

Another embodiment is directed to crystalline (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide ethyl acetate solvate (Compound I Form II). Compound I Form II is characterized by an X-ray powder diffractogram comprising the following peaks (±0.2°): at 8.7, 13.0, and 17.4 °2θ, as determined on a diffractometer using Cu—Kα radiation.

Another embodiment is directed to crystalline (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide isopropanol solvate (Compound I Form III). Compound I Form III is characterized by an X-ray powder diffractogram comprising the following peaks (±0.2°): at 11.1, 12.8, and 19.7 °2θ, as determined on a diffractometer using Cu—Kα radiation.

Another embodiment is directed to crystalline (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide dihydrate (Compound I Form IV). Compound I Form IV is characterized by an X-ray powder diffractogram comprising the following peaks (±0.2°): at 8.7, 8.9, and 16.0 °2θ as determined on a diffractometer using Cu—Kα radiation.

Another embodiment is directed to crystalline (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide methanol solvate (Compound I Form V). Compound I Form V is characterized by an X-ray powder diffractogram comprising the following peaks (±0.2°): at 6.2, 12.4, and 19.6 °2θ, as determined on a diffractometer using Cu—Kα radiation.

Another embodiment is directed to crystalline (1aR,5S,8S,9S,10R,22aR)-5-tert-butyl-N-[(1R,2R)-2-(difluoromethyl)-1-{[(1-methylcyclopropyl)sulfonyl]

carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide (anhydrous, Compound I Form VI). Compound I Form VI is characterized by an X-ray powder diffractogram comprising the following peaks (±0.2°): at 14.6, 15.4, and 20.0 °2θ, as determined on a diffractometer using Cu—Kα radiation.

Another embodiment is directed to crystalline (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide (anhydrous, Compound I Form VII). Compound I Form VII is characterized by an X-ray powder diffractogram comprising the following peaks (±0.2°): at 6.5, 8.5, and 18.7 °2θ, as determined on a diffractometer using Cu—Kα radiation.

Another embodiment is directed to crystalline (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide (anhydrous, Compound I Form VIII). Compound I Form VIII is characterized by an X-ray powder diffractogram comprising the following peaks (±0.2°): at 7.8, 8.2, and 20.2 °2θ, as determined on a diffractometer using Cu—Kα radiation.

Another embodiment is directed to crystalline (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide (anhydrous, Compound I Form IX). Compound I Form IX is characterized by an X-ray powder diffractogram comprising the following peaks (±0.2°): at 6.1, 9.5, and 19.4 °2θ, as determined on a diffractometer using Cu—Kα radiation.

Another embodiment is directed to crystalline (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide hemihydrate (Compound I Form X). Compound I Form X is characterized by an X-ray powder diffractogram comprising the following peaks (±0.2°): at 8.0, 19.0, and 20.4 °2θ, as determined on a diffractometer using Cu—Kα radiation.

Another embodiment is directed to crystalline (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide dihydrate (Compound I Form XI). Compound I Form XI is characterized by an X-ray powder diffractogram comprising the following peaks (±0.2°): at 11.0, 13.9, and 20.9 °2θ, as determined on a diffractometer using Cu—Kα radiation.

Another embodiment is directed to crystalline (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide tetrahydrate (Compound I Form XII). Compound I Form XII is characterized by an X-ray powder diffractogram comprising the following peaks (±0.2°): at 12.4, 14.6, and 19.3 °2θ, as determined on a diffractometer using Cu—Kα radiation.

Another embodiment is directed to crystalline (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide isopropyl acetate solvate (Compound I Form XIII). Compound I Form XIII is characterized by an X-ray powder diffractogram comprising the following peaks (±0.2°): at 8.5, 11.0, and 15.4 °2θ, as determined on a diffractometer using Cu—Kα radiation.

Another embodiment is directed to crystalline (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide tetrahydrofuran solvate (Compound I Form XIV). Compound I Form XIV is characterized by an X-ray powder diffractogram comprising the following peaks (±0.2°): at 11.2, 15.7, and 17.9 °2θ, as determined on a diffractometer using Cu—Kα radiation.

Another embodiment is directed to crystalline (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide 2-methyltetrahydrofuran solvate (Compound I Form XV). Compound I Form XV is characterized by an X-ray powder diffractogram comprising the following peaks (±0.2°): at 9.7, 11.0, and 15.5 °2θ, as determined on a diffractometer using Cu—Kα radiation.

Another embodiment is directed to crystalline (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide toluene solvate (Compound I Form XVI). Compound I Form XVI is characterized by an X-ray powder diffractogram comprising the following peaks (±0.2°): at 5.8, 7.8, and 18.8 °2θ, as determined on a diffractometer using Cu—Kα radiation.

Another embodiment is directed to crystalline (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14- methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide toluene solvate (Compound I Form XVII). Compound I Form XVII is characterized by an X-ray powder diffractogram comprising the following peaks (±0.2°): at 7.9, 18.9, and 20.3 °2θ, as determined on a diffractometer using Cu—Kα radiation.

Another embodiment is directed to crystalline (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide methy test butyl ether solvate (Compound I Form XVIII). Compound I Form XVIII is characterized by an X-ray powder diffractogram comprising the following peaks (±0.2°): at 5.6, 6.4, and 7.5 °2θ, as determined on a diffractometer using Cu—Kα radiation.

Another embodiment is directed to crystalline (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide methy tert butyl ether solvate (Compound I Form XIX). Compound I Form XIX is characterized by an X-ray powder diffractogram comprising the following peaks (±0.2°): at 11.1, 15.5, and 19.8 °2θ, as determined on a diffractometer using Cu—Kα radiation.

Another embodiment is directed to crystalline (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide dimethylacetamide solvate (Compound I Form XX). Compound I Form XX is characterized by an X-ray powder diffractogram comprising the following peaks (±0.2°): at 11.9, 14.5, and 19.1 °2θ, as determined on a diffractometer using Cu—Kα radiation.

Another embodiment is directed to crystalline (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide dimethylformamide solvate (Compound I Form XXI). Compound I Form XXI is characterized by an X-ray powder diffractogram comprising the following peaks (±0.2°): at 11.7, 12.2, and 14.4 °2θ, as determined on a diffractometer using Cu—Kα radiation.

Some embodiments provided herein relate to crystalline forms of salts or co-crystals of Compound I.

Thus, one embodiment is directed to crystalline (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide sodium (Compound I sodium Form I). Compound I sodium Form I is characterized by an X-ray powder diffractogram comprising the following peaks (±0.2°): at 5.6, 7.8, and 11.2 °2θ, as determined on a diffractometer using Cu—Kα radiation.

Another embodiment is directed to crystalline (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide sodium (Compound I sodium Form II). Compound I sodium Form II is characterized by an X-ray powder diffractogram comprising the following peaks (±0.2°): at 5.8, 7.3, and 11.1 °2θ, as determined on a diffractometer using Cu—Kα radiation.

Another embodiment is directed to crystalline (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide sodium (Compound I sodium Form III). Compound I sodium Form III is characterized by an X-ray powder diffractogram comprising the following peaks (±0.2°): at 5.4, 7.7, and 10.8 °2θ, as determined on a diffractometer using Cu—Kα radiation.

Another embodiment is directed to crystalline (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide sodium (Compound I sodium Form IV). Compound I sodium Form IV is characterized by an X-ray powder diffractogram comprising the following peaks (±0.2°): at 10.4, 12.1, and 16.6 °2θ, as determined on a diffractometer using Cu—Kα radiation.

Another embodiment is directed to crystalline (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide meglumine (Compound I meglumine Form I). Compound I meglumine Form I is characterized by an X-ray powder diffractogram comprising the following peaks (±0.2°): at 3.6, 5.1, and 8.9 °2θ, as determined on a diffractometer using Cu—Kα radiation.

Another embodiment is directed to crystalline (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide piperazine (Compound I piperazine Form I). Compound I piperazine Form I is characterized by an X-ray powder diffractogram comprising the following peaks (±0.2°): at 4.9, 7.2, and 8.2 °2θ, as determined on a diffractometer using Cu—Kα radiation.

Another embodiment is directed to crystalline (1aR,5S,8S,9S,10R,22aR)-5-tert-butyl-N-[(1R,2R)-2-(difluoromethyl)-1-{[(1-methylcyclopropyl)sulfonyl]

carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide choline (Compound I choline Form I). Compound I choline Form I is characterized by an X-ray powder diffractogram comprising the following peaks (±0.2°): at 7.4, 15.5, and 20.9 °2θ, as determined on a diffractometer using Cu—Kα radiation.

Another embodiment is directed to crystalline (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide deanol (Compound I deanol Form I). "Deanol" refers to dimethylaminoethanol. Compound I deanol Form I is characterized by an X-ray powder diffractogram comprising the following peaks (±0.2°): at 7.4, 10.7, and 15.2 °2θ, as determined on a diffractometer using Cu—Kα radiation.

Another embodiment is directed to crystalline (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide 1-(2-hydroxyethyl)-pyrrolidine (HEP) (Compound I 1-(2-hydroxyethyl)-pyrrolidine (HEP) Form I). Compound I 1-(2-hydroxyethyl)-pyrrolidine (HEP) Form I is characterized by an X-ray powder diffractogram comprising the following peaks (±0.2°): at 8.2, 10.8, and 19.9 °2θ, as determined on a diffractometer using Cu—Kα radiation.

Another embodiment is directed to crystalline (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide 1-(2-hydroxyethyl)-pyrrolidine (HEP) (Compound I 1-(2-hydroxyethyl)-pyrrolidine (HEP) Form II). Compound I 1-(2-hydroxyethyl)-pyrrolidine (HEP) Form II is characterized by an X-ray powder diffractogram comprising the following peaks (±0.2°): at 7.7, 8.3, and 15.5 °2θ, as determined on a diffractometer using Cu—Kα radiation.

Another embodiment is directed to crystalline (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide 1-(2-hydroxyethyl)-pyrrolidine (HEP) (Compound I 1-(2-hydroxyethyl)-pyrrolidine (HEP) Form III). Compound I 1-(2-hydroxyethyl)-pyrrolidine (HEP) Form III is characterized by an X-ray powder diffractogram comprising the following peaks (±0.2°): at 7.1, 8.0, and 10.7 °2θ, as determined on a diffractometer using Cu—Kα radiation.

Another embodiment is directed to crystalline (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide lysine (Compound I lysine Form I). Compound I lysine Form I is characterized by an X-ray powder diffractogram comprising the following peaks (±0.2°): at 8.2, 10.8, and 19.9 °2θ, as determined on a diffractometer using Cu—Kα radiation.

Another embodiment is directed to crystalline (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide arginine (Compound I arginine Form I). Compound I arginine Form I is characterized by an X-ray powder diffractogram comprising the following peaks (±0.2°): at 8.2, 10.8, and 19.9 °2θ, as determined on a diffractometer using Cu—Kα radiation.

Another embodiment is directed to crystalline (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide potassium (Compound I potassium Form I). Compound I potassium Form I is characterized by an X-ray powder diffractogram comprising the following peaks (±0.2°): at 6.4, 8.6, and 15.8 °2θ, as determined on a diffractometer using Cu—Kα radiation.

One embodiment is a composition comprising at least two of Compound I Form I, Compound I Form II, Compound I Form III, Compound I Form IV, Compound I Form V, Compound I Form VI, Compound I Form VII, and Compound I Form VIII, Compound I Form IX, Compound I Form X, Compound I Form XI, Compound I Form XII, Compound I Form XIII, Compound I Form XIV, Compound I Form XV, Compound I Form XVI, Compound I Form XVII, Compound I Form XVIII, Compound I Form XIX, Compound I Form XX, and Compound I Form XXI. Additionally, the disclosure provides in one embodiment a method for treating a subject suffering from hepatitis C virus (HCV). The method comprises administering to the subject a therapeutically effective amount of any one of Compound I Forms I-XXI, as described generally throughout.

Still an additional embodiment includes, optionally in combination with any other embodiment described herein, is the use of any one of Compound I Forms I-XXI and in the manufacture of a medicament for treating HCV in a subject suffering therefrom.

In another embodiment, the disclosure provides a process for making Compound I Form I comprising the step of contacting (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide with ethanol, whereby Compound I Form I is formed.

In another embodiment, the disclosure provides a process for making Compound I Form II comprising the step of contacting (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14- methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide with ethyl acetate, whereby Compound I Form II is formed.

In another embodiment, the disclosure provides a process for making Compound I Form III comprising the step of contacting (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide with isopropanol, whereby Compound I Form III is formed.

In another embodiment, the disclosure provides a process for making Compound I Form IV comprising the step of placing (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide ethanol solvate (Compound I Form I) at about 40° C. and about 75% relative humidity (R.H.), whereby Compound I Form IV is formed.

In another embodiment, the disclosure provides a process for making Compound I Form V comprising the step of contacting (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide with methanol, whereby Compound I Form V is formed.

In another embodiment, the disclosure provides a process for making Compound I Form VI comprising the step of heating crystalline (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide methanol solvate (Compound I Form V) to about 70° C., whereby Compound I Form VI is formed.

In another embodiment, the disclosure provides a process for making Compound I Form VII comprising the step of heating crystalline (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide ethanol solvate, to about 240° C., whereby Compound I Form VII is formed.

In another embodiment, the disclosure provides a process for making Compound I Form VIII comprising the steps of (1) contacting crystalline (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide (anhydrous, Compound I Form VI) with water and heating at about 85° C. in a container; and (2) adding crystalline (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide methanol solvate, in a mixture of acetone and water (1:4 by volume) to the container of step (1) and heating at about 85° C., whereby Compound I Form VIII is formed.

In another embodiment, the disclosure provides a process for making Compound I Form IX comprising the step of contacting (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide with 1:1 heptane/toluene at about 60° C., whereby Compound I Form IX is formed.

In another embodiment, the disclosure provides a process for making Compound I Form X comprising the steps of contacting (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide with water and heating to about 80° C., whereby Compound I Form X is formed.

In another embodiment, the disclosure provides a process for making Compound I Form XI comprising the steps of contacting (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide with either 1:1, 6:4, or 7:3 (v/v) EtOH:water, whereby Compound I Form XI is formed.

In another embodiment, the disclosure provides a process for making Compound I Form XII comprising the steps of contacting (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide with 4:6 or 1:1 (v/v) EtOH:water and slurring at room temperature, or 2:8, 3:7 or 4:6 acetonitrile:water and slurring at room temperature, or 2:8, 3:7, 4:6 or 1:1 (v/v) acetone:water and slurring at room temperature, whereby Compound I Form XII is formed.

In another embodiment, the disclosure provides a process for making Compound I Form XIII comprising the step of contacting (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide with IPAc, whereby Compound I Form XIII is formed.

In another embodiment, the disclosure provides a process for making Compound I Form XIV comprising the step of contacting (1aR,5S,8S,9S,10R,22aR)-5-tert-butyl-N-[(1R,2R)-2-(difluoromethyl)-1-{[(1-methylcyclopropyl)sulfonyl]

carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide with 1:9, 2:8 or 3:7 (v/v) THF:water and slurring at room temperature, whereby Compound I Form XIV is formed.

In another embodiment, the disclosure provides a process for making Compound I Form XV comprising the step of contacting (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide with 2-Me-THF, whereby Compound I Form XV is formed.

In another embodiment, the disclosure provides a process for making Compound I Form XVI comprising the step of contacting (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide with 8:2 toluene:heptane, whereby Compound I Form XVI is formed.

In another embodiment, the disclosure provides a process for making Compound I Form XVII comprising the step of contacting (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide with toluene, whereby Compound I Form XVII is formed.

In another embodiment, the disclosure provides a process for making Compound I Form XVIII comprising the step of contacting (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide with MTBE, whereby Compound I Form XVIII is formed.

In another embodiment, the disclosure provides a process for making Compound I Form XIX comprising the step of contacting (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide with 5 volumes of MTBE and 10 volumes of heptane, whereby Compound I Form XIX is formed.

In another embodiment, the disclosure provides a process for making Compound I Form XX comprising the step of contacting (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide with DMAc, whereby Compound I Form XX is formed.

In another embodiment, the disclosure provides a process for making Compound I Form XXI comprising the step of contacting (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide with DMF, whereby Compound I Form XXI is formed.

In other embodiments, the process of making salts and co-crystals was performed by reacting Compound I with a stoichiometric amount of a salt of co-crystal former in a solvent to yield a product.

In another embodiment, the disclosure provides a process for making Compound I sodium Form I comprising the step of contacting (1 aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide sodium with EtOH, whereby Compound I sodium Form I is formed.

In another embodiment, the disclosure provides a process for making Compound I sodium Form II comprising the step of contacting (1 aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide sodium with condition of <40% relative humidity, whereby Compound I sodium Form II is formed.

In another embodiment, the disclosure provides a process for making Compound I sodium Form III comprising the step of contacting (1 aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide sodium with IPA, whereby Compound I sodium Form III is formed.

In another embodiment, the disclosure provides a process for making Compound I sodium Form IV comprising the step of contacting (1 aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide sodium with IPAc, whereby Compound I sodium Form IV is formed.

In another embodiment, the disclosure provides a process for making Compound I meglumine Form I comprising the step of contacting (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide meglumine with 1:1 toluene:heptane, whereby Compound I meglumine Form I is formed.

In another embodiment, the disclosure provides a process for making Compound I piperazine Form I comprising the step of contacting (1aR,5S,8S,9S,10R,22aR)-5-tert-butyl-N-

[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide piperazine with 1:1 ethanol:water, whereby Compound I piperazine Form I is formed.

In another embodiment, the disclosure provides a process for making Compound I choline Form I comprising the step of contacting (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide choline with 1:1 toluene:heptane, whereby Compound I choline Form I is formed.

In another embodiment, the disclosure provides a process for making Compound I deanol Form I comprising the step of contacting (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide deanol with diethyl ether, whereby Compound I deanol Form I is formed.

In another embodiment, the disclosure provides a process for making Compound I 1-(2-hydroxyethyl)-pyrrolidine Form I comprising the step of contacting (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide 1-(2-hydroxyethyl)-pyrrolidine with 18:83 ethyl acetate:methanol, whereby Compound I 1-(2-hydroxyethyl)-pyrrolidine Form I is formed.

In another embodiment, the disclosure provides a process for making Compound I 1-(2-hydroxyethyl)-pyrrolidine Form II comprising the step of vacuum drying (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide 1-(2-hydroxyethyl)-pyrrolidine, whereby Compound I 1-(2-hydroxyethyl)-pyrrolidine Form II is formed.

In another embodiment, the disclosure provides a process for making Compound I 1-(2-hydroxyethyl)-pyrrolidine Form III comprising the step of contacting (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide 1-(2-hydroxyethyl)-pyrrolidine with 1:1 methyl-tert-butyl ether:toluene, whereby Compound I 1-(2-hydroxyethyl)-pyrrolidine Form III is formed.

In another embodiment, the disclosure provides a process for making Compound I lysine Form I comprising the step of contacting (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide lysine with 80:20 ethanol:water, whereby Compound I lysine Form I is formed.

In another embodiment, the disclosure provides a process for making Compound I arginine Form I comprising the step of contacting (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide arginine with 80:20 isopropyl alcohol:water, whereby Compound I arginine Form I is formed.

In another embodiment, the disclosure provides a process for making Compound I potassium Form I comprising the step of contacting (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide potassium with isopropyl alcohol, whereby Compound I 1-(2-hydroxyethyl)-potassium Form I is formed.

BRIEF DESCRIPTION OF THE DRAWINGS

FIG. 120 is an X-ray powder diffraction pattern of Compound I lysine Form I.

FIG. 121 is an X-ray powder diffraction pattern of Compound I arginine Form I.

FIG. 122 is an X-ray powder diffraction pattern of Compound I potassium Form I.

FIG. 123 is differential scanning calorimetry (DSC) curve of Compound I potassium Form I.

FIG. 124 is thermogravimetric analysis (TGA) of Compound I potassium Form I.

FIG. 125 is dynamic vapor sorption (DVS) curve of Compound I potassium Form I.

DETAILED DESCRIPTION

Figure 1:
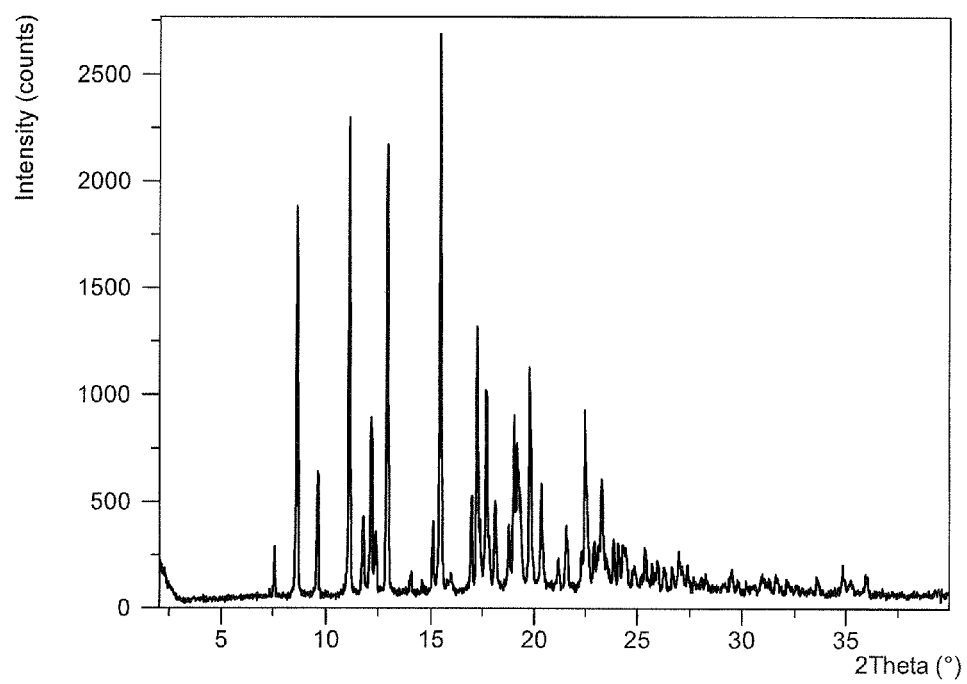
FIG. 1 is an X-ray powder diffraction pattern of Compound I Form I.

Compound named (1 aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide, is a selective and potent inhibitor of HCV NS3 and has the structure as follows:

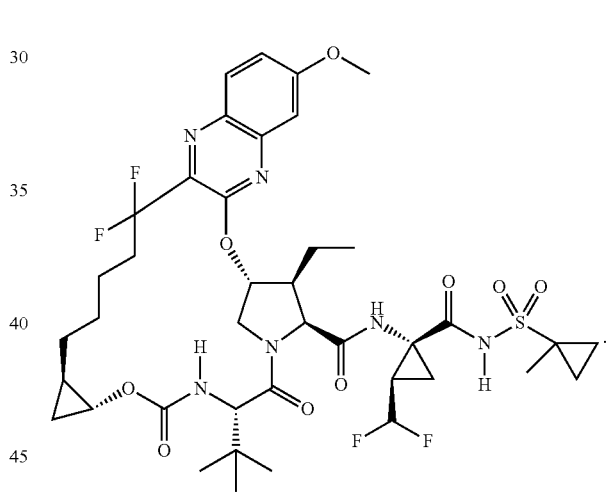

The present disclosure relates to various crystalline forms of Compound I, and processes for making the crystalline forms. Compound I also provides forms further described herein as "Compound I Form I," "Compound I Form II," "Compound I Form III," "Compound I Form IV," "Compound I Form V," "Compound I Form VI," "Compound I Form VII," "Compound I Form VIII," "Compound I Form IX," "Compound I Form X," "Compound I Form XI," "Compound I Form XII," "Compound I Form XIII," "Compound I Form XIV," "Compound I Form XV," "Compound I Form XVI," "Compound I Form XVII," "Compound I Form XVIII," "Compound I Form XIX," "Compound I Form XX," "Compound I Form XXI," In some embodiments, such forms of Compound I may be a solvate.

Additional crystalline forms of Compound I are also further described herein. In some embodiments, crystalline forms of Compound I may include salts or co-crystals of Compound I. Salts or co-crystals of Compound I may have the following formula:

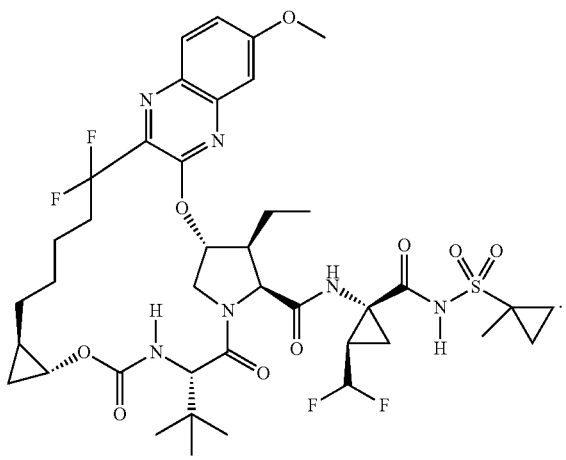

In some embodiments, Y may be sodium, meglumine, piperazine, choline, deanol, 1-(2-hydroxyethyl)-pyrrolidine, lysine or arginine. The following exemplary forms are further described herein: "Compound I sodium Form I," "Compound I sodium Form II," "Compound I sodium Form III," "Compound I sodium Form IV," "Compound I meglumine Form I," "Compound I piperazine Form I," "Compound I choline Form I," "Compound I deanol Form I," "Compound I 1-(2-hydroxyethyl)-pyrrolidine Form I," "Compound I 1-(2-hydroxyethyl)-pyrrolidine Form II," "Compound I 1-(2-hydroxyethyl)-pyrrolidine Form III," "Compound I lysine Form I," "Compound I arginine Form I," and "Compound I potassium Form I."

DEFINITIONS

As used in the present specification, the following words and phrases are generally intended to have the meanings as set forth below, except to the extent that the context in which they are used indicates otherwise.

The term "solvate" refers to a complex formed by the combining of Compound I and a solvent.

The term "desolvated" refers to a Compound I form that is a solvate as described herein, and from which solvent molecules have been partially or completely removed. Desolvation techniques to produce desolvated forms include, without limitation, exposure of a Compound I form (solvate) to a vacuum, subjecting the solvate to elevated temperature, exposing the solvate to a stream of gas, such as air or nitrogen, or any combination thereof. Thus, a desolvated Compound I form can be anhydrous, i.e., completely without solvent molecules, or partially solvated wherein solvent molecules are present in stoichiometric or non-stoichiometric amounts.

The term "therapeutically effective amount" refers to an amount that is sufficient to effect treatment, as defined below, when administered to a mammal in need of such treatment. The therapeutically effective amount will vary depending upon the subject being treated, the weight and age of the subject, the severity of the disease condition, the manner of administration and the like, which can readily be determined by one of ordinary skill in the art.

The term "about" refers to a range of ±10%, unless otherwise specified.

The term "co-crystal" refers to a crystalline material formed by combining a compound of Formula I, or any Formula disclosed herein and one or more co-crystal formers (i.e., a molecule, ion or atom). In certain instances, co-crystals may have improved properties as compared to the parent form (i.e., the free molecule, zwitterion, etc.) or a salt of the parent compound. Improved properties can be increased solubility, increased dissolution, increased bioavailability, increased dose response, decreased hygroscopicity, a crystalline form of a normally amorphous compound, a crystalline form of a difficult to salt or unsaltable compound, decreased form diversity, more desired morphology, and the like. Methods for making and characterizing co-crystals are known to those of skill in the art.

Salts of the compounds disclosed herein can be base addition salts or acid addition salts depending on the reactivity of the functional groups present on the specific compound. Base addition salts can be derived from inorganic or organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Amines are of general structure $N(R^{30})(R^{31})(R^{32})$, wherein mono-substituted amines have 2 of the three substituents on nitrogen ($R^{30}$, $R^{31}$ and $R^{32}$) as hydrogen, di-substituted amines have 1 of the three substituents on nitrogen ($R^{30}$, $R^{31}$ and $R^{32}$) as hydrogen, whereas tri-substituted amines have none of the three substituents on nitrogen ($R^{30}$, $R^{31}$ and $R^{32}$) as hydrogen. $R^{30}$, $R^{31}$ and $R^{32}$ are selected from a variety of substituents such as hydrogen, optionally substituted alkyl, aryl, heteroaryl, cycloalkyl, cycloalkenyl, heterocyclyl and the like. The above-mentioned amines refer to the compounds wherein either one, two or three substituents on the nitrogen are as listed in the name. For example, the term "cycloalkenyl amine" refers to cycloalkenyl-$NH_2$, wherein "cycloalkenyl" is as defined herein. The term "diheteroarylamine" refers to NH(heteroaryl)$_2$, wherein "heteroaryl" is as defined herein and so on.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Acid addition salts can be derived from inorganic or organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

Any of the salts disclosed herein may be optionally pharmaceutically acceptable. The term "pharmaceutically acceptable salt" of a given compound refers to salts that retain the biological effectiveness and properties of the given compound, and which are not biologically or otherwise undesirable. See: P. Heinrich Stahl and Camille G. Wermuth (Eds.) Pharmaceutical Salts: Properties, Selection, and Use (International Union of Pure and Applied Chemistry), Wiley-VCH; 2nd Revised Edition (May 16, 2011). Pharmaceutically acceptable base addition salts can be prepared from inorganic and organic bases.

Pharmaceutically acceptable base addition salts may be salts prepared from inorganic and organic bases and pharmaceutically acceptable acid addition salts may be salts prepared from inorganic and organic acids.

The term "alkyl" refers to a monoradical branched or unbranched saturated hydrocarbon chain having from 1 to 20 carbon atoms. In some embodiments, the alkyl has 1 to 15 carbon atoms, or from 1 to 10 carbon atoms, or from 1 to 8 carbon atoms, or from 1 to 6 carbon atoms, or from 1 to 4 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:
1) an alkyl group as defined above, having 1, 2, 3, 4 or 5 substituents, (in some embodiments, 1, 2 or 3 substituents) selected from the group consisting of alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)—cycloalkyl, —S(O)-heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2; or
2) an alkyl group as defined above that is interrupted by 1-10 atoms (e.g. 1, 2, 3, 4 or 5 atoms) independently chosen from oxygen, sulfur and NR$^a$, where R$^a$ is chosen from hydrogen, alkyl, cycloalkyl, alkenyl, cycloalkenyl, alkynyl, aryl, heteroaryl and heterocyclyl. All substituents may be optionally further substituted by alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2; or
3) an alkyl group as defined above that has both 1, 2, 3, 4 or 5 substituents as defined above and is also interrupted by 1-10 atoms (e.g. 1, 2, 3, 4 or 5 atoms) as defined above.

As used herein, the term "interrupted by" means a carbon atom of a group (e.g. an alkyl group) is replaced by a heteroatom.

The term "lower alkyl" refers to a monoradical branched or unbranched saturated hydrocarbon chain having 1, 2, 3, 4, 5 or 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents (in some embodiments, 1, 2 or 3 substituents), as defined for substituted alkyl or a lower alkyl group as defined above that is interrupted by 1, 2, 3, 4 or 5 atoms as defined for substituted alkyl or a lower alkyl group as defined above that has both 1, 2, 3, 4 or 5 substituents as defined above and is also interrupted by 1, 2, 3, 4 or 5 atoms as defined above.

The term "alkylene" refers to a diradical of a branched or unbranched saturated hydrocarbon chain, in some embodiments, having from 1 to 20 carbon atoms (e.g. 1-10 carbon atoms or 1, 2, 3, 4, 5 or 6 carbon atoms). This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—), and the like.

The term "lower alkylene" refers to a diradical of a branched or unbranched saturated hydrocarbon chain, in some embodiments, having 1, 2, 3, 4, 5 or 6 carbon atoms.

The term "substituted alkylene" refers to an alkylene group as defined above having 1 to 5 substituents (in some embodiments, 1, 2 or 3 substituents) as defined for substituted alkyl.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "aralkyloxy" refers to the group —O-aralkyl. "Optionally substituted aralkyloxy" refers to an optionally substituted aralkyl group covalently linked to an optionally substituted alkylene group. Such aralkyl groups are exemplified by benzyloxy, phenylethyloxy, and the like.

The term "alkenyl" refers to a monoradical of a branched or unbranched unsaturated hydrocarbon group having from 2 to 20 carbon atoms (in some embodiments, from 2 to 10 carbon atoms, e.g. 2 to 6 carbon atoms) and having from 1 to 6 carbon-carbon double bonds, e.g. 1, 2 or 3 carbon-carbon double bonds. In some embodiments, alkenyl groups include ethenyl (or vinyl, i.e. —CH═CH$_2$), 1-propylene (or allyl, i.e. —CH$_2$CH═CH$_2$), isopropylene (—C(CH$_3$)═CH$_2$), and the like.

The term "lower alkenyl" refers to alkenyl as defined above having from 2 to 6 carbon atoms.

The term "substituted alkenyl" refers to an alkenyl group as defined above having 1 to 5 substituents (in some embodiments, 1, 2 or 3 substituents) as defined for substituted alkyl.

The term "alkenylene" refers to a diradical of a branched or unbranched unsaturated hydrocarbon group having from 2 to 20 carbon atoms (in some embodiments, from 2 to 10 carbon atoms, e.g. 2 to 6 carbon atoms) and having from 1 to 6 carbon-carbon double bonds, e.g. 1, 2 or 3 carbon-carbon double bonds.

The term "alkynyl" refers to a monoradical of an unsaturated hydrocarbon, in some embodiments, having from 2 to 20 carbon atoms (in some embodiments, from 2 to 10 carbon atoms, e.g. 2 to 6 carbon atoms) and having from 1 to 6 carbon-carbon triple bonds e.g. 1, 2 or 3 carbon-carbon triple bonds. In some embodiments, alkynyl groups include ethynyl (—C≡CH), propargyl (or propynyl, i.e. —C≡CCH$_3$), and the like.

The term "substituted alkynyl" refers to an alkynyl group as defined above having 1 to 5 substituents (in some embodiments, 1, 2 or 3 substituents) as defined for substituted alkyl.

The term "alkynylene" refers to a diradical of an unsaturated hydrocarbon, in some embodiments, having from 2 to 20 carbon atoms (in some embodiments, from 2 to 10 carbon atoms, e.g. 2 to 6 carbon atoms) and having from 1 to 6 carbon-carbon triple bonds e.g. 1, 2 or 3 carbon-carbon triple bonds.

The term "hydroxy" or "hydroxyl" refers to a group —OH.

The term "alkoxy" refers to the group R—O—, where R is alkyl or —Y—Z, in which Y is alkylene and Z is alkenyl or alkynyl, where alkyl, alkenyl and alkynyl are as defined herein. In some embodiments, alkoxy groups are alkyl-O— and includes, by way of example, methoxy, ethoxy, n-propoxy, iso-propoxy, n-butoxy, tert-butoxy, sec-butoxy, n-pentoxy, n-hexyloxy, 1,2-dimethylbutoxy, and the like.

The term "lower alkoxy" refers to the group R—O— in which R is optionally substituted lower alkyl. This term is exemplified by groups such as methoxy, ethoxy, n-propoxy, iso-propoxy, n-butoxy, iso-butoxy, t-butoxy, n-hexyloxy, and the like.

The term "substituted alkoxy" refers to the group R—O—, where R is substituted alkyl or —Y—Z, in which Y is substituted alkylene and Z is substituted alkenyl or substituted alkynyl, where substituted alkyl, substituted alkenyl and substituted alkynyl are as defined herein.

The term "C$_{1-3}$ haloalkyl" refers to an alkyl group having from 1 to 3 carbon atoms covalently bonded to from 1 to 7, or from 1 to 6, or from 1 to 3, halogen(s), where alkyl and halogen are defined herein. In some embodiments, C$_{1-3}$ haloalkyl includes, by way of example, trifluoromethyl, difluoromethyl, fluoromethyl, 2,2,2-trifluoroethyl, 2,2-difluoroethyl, 2-fluoroethyl, 3,3,3-trifluoropropyl, 3,3-difluoropropyl, 3-fluoropropyl.

The term "cycloalkyl" refers to cyclic alkyl groups of from 3 to 20 carbon atoms, or from 3 to 10 carbon atoms, having a single cyclic ring or multiple condensed rings. Such cycloalkyl groups include, by way of example, single ring structures such as cyclopropyl, cyclobutyl, cyclopentyl, cyclooctyl and the like or multiple ring structures such as adamantanyl and bicyclo[2.2.1]heptanyl or cyclic alkyl groups to which is fused an aryl group, for example indanyl, and the like, provided that the point of attachment is through the cyclic alkyl group.

The term "cycloalkenyl" refers to cyclic alkyl groups of from 3 to 20 carbon atoms having a single cyclic ring or multiple condensed rings and having at least one double bond and in some embodiments, from 1 to 2 double bonds.

The terms "substituted cycloalkyl" and "substituted cycloalkenyl" refer to cycloalkyl or cycloalkenyl groups having 1, 2, 3, 4 or 5 substituents (in some embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)-heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. The term "substituted cycloalkyl" also includes cycloalkyl groups wherein one or more of the annular carbon atoms of the cycloalkyl group has an oxo group bonded thereto. In addition, a substituent on the cycloalkyl or cycloalkenyl may be attached to the same carbon atom as, or is geminal to, the attachment of the substituted cycloalkyl or cycloalkenyl to the 6,7-ring system. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "cycloalkoxy" refers to the group cycloalkyl-O—.

The term "substituted cycloalkoxy" refers to the group substituted cycloalkyl-O—.

The term "cycloalkenyloxy" refers to the group cycloalkenyl-O—.

The term "substituted cycloalkenyloxy" refers to the group substituted cycloalkenyl-O—.

The term "aryl" refers to an aromatic carbocyclic group of 6 to 20 carbon atoms having a single ring (e.g., phenyl) or multiple rings (e.g., biphenyl) or multiple condensed (fused) rings (e.g., naphthyl, fluorenyl and anthryl). In some embodiments, aryls include phenyl, fluorenyl, naphthyl, anthryl, and the like.

Unless otherwise constrained by the definition for the aryl substituent, such aryl groups can optionally be substituted with 1, 2, 3, 4 or 5 substituents (in some embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)-heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "heterocyclyl," "heterocycle," or "heterocyclic" refers to a monoradical saturated group having a single ring or multiple condensed rings, having from 1 to 40 carbon atoms and from 1 to 10 hetero atoms (in some embodiments from 1 to 4 heteroatoms), selected from nitrogen, sulfur, phosphorus, and/or oxygen within the ring. In some embodiments, the "heterocyclyl," "heterocycle," or "heterocyclic" group is linked to the remainder of the molecule through one of the heteroatoms within the ring.

Unless otherwise constrained by the definition for the heterocyclic substituent, such heterocyclic groups can be optionally substituted with 1 to 5 substituents (in some embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)— heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. In addition, a substituent on the heterocyclic group may be attached to the same carbon atom as, or is geminal to, the attachment of the substituted heterocyclic group to the 6,7-ring system. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2. Examples of heterocyclics include tetrahydrofuranyl, morpholino, piperidinyl, and the like.

The term "heterocyclooxy" refers to the group —O-heterocyclyl.

The term "heteroaryl" refers to a group comprising single or multiple rings comprising 1 to 15 carbon atoms and 1 to 4 heteroatoms selected from oxygen, nitrogen and sulfur within at least one ring. The term "heteroaryl" is generic to the terms "aromatic heteroaryl" and "partially saturated heteroaryl". The term "aromatic heteroaryl" refers to a heteroaryl in which at least one ring is aromatic, regardless of the point of attachment. Examples of aromatic heteroaryls include pyrrole, thiophene, pyridine, quinoline, pteridine.

The term "partially saturated heteroaryl" refers to a heteroaryl having a structure equivalent to an underlying aromatic heteroaryl which has had one or more double bonds in an aromatic ring of the underlying aromatic heteroaryl saturated. Examples of partially saturated heteroaryls include dihydropyrrole, dihydropyridine, chroman, 2-oxo-1,2-dihydropyridin-4-yl, and the like.

Unless otherwise constrained by the definition for the heteroaryl substituent, such heteroaryl groups can be optionally substituted with 1 to 5 substituents (in some embodiments, 1, 2 or 3 substituents) selected from the group consisting alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)-heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2. Such heteroaryl groups can have a single ring (e.g., pyridyl or furyl) or multiple condensed rings (e.g., indolizinyl, benzothiazole or benzothienyl). Examples of nitrogen heterocyclyls and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroaryloxy" refers to the group heteroaryl-O—.

The term "amino" refers to the group —NH$_2$.

The term "substituted amino" refers to the group —NRR where each R is independently selected from the group consisting of hydrogen, alkyl, cycloalkyl, aryl, heteroaryl and heterocyclyl provided that both R groups are not hydrogen or a group —Y—Z, in which Y is optionally substituted alkylene and Z is alkenyl, cycloalkenyl or alkynyl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "alkyl amine" refers to R—NH$_2$ in which R is optionally substituted alkyl.

The term "dialkyl amine" refers to R—NHR in which each R is independently an optionally substituted alkyl.

The term "trialkyl amine" refers to NR$_3$ in which each R is independently an optionally substituted alkyl.

The term "cyano" refers to the group —CN.

The term "azido" refers to a group

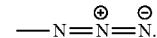

The term "keto" or "oxo" refers to a group =O.

The term "carboxy" refers to a group —C(O)—OH.

The term "ester" or "carboxyester" refers to the group —C(O)OR, where R is alkyl, cycloalkyl, aryl, heteroaryl or heterocyclyl, which may be optionally further substituted by alkyl, alkoxy, halogen, CF$_3$, amino, substituted amino, cyano or —S(O)$_n$R$^a$, in which R$^a$ is alkyl, aryl or heteroaryl and n is 0, 1 or 2.

The term "acyl" denotes the group —C(O)R, in which R is hydrogen, alkyl, cycloalkyl, heterocyclyl, aryl or heteroaryl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "carboxyalkyl" refers to the groups —C(O)O-alkyl or —C(O)O-cycloalkyl, where alkyl and cycloalkyl are as defined herein, and may be optionally further substituted by alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —$S(O)_nR^a$, in which $R^a$ is alkyl, aryl or heteroaryl and n is 0, 1 or 2.

The term "aminocarbonyl" refers to the group —C(O)NRR where each R is independently hydrogen, alkyl, cycloalkyl, aryl, heteroaryl, or heterocyclyl, or where both R groups are joined to form a heterocyclic group (e.g., morpholino). Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —$S(O)_nR^a$, in which $R^a$ is alkyl, aryl or heteroaryl and n is 0, 1 or 2.

The term "acyloxy" refers to the group —OC(O)—R, in which R is alkyl, cycloalkyl, heterocyclyl, aryl or heteroaryl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —$S(O)_nR^a$, in which $R^a$ is alkyl, aryl or heteroaryl and n is 0, 1 or 2.

The term "acylamino" refers to the group —NRC(O)R where each R is independently hydrogen, alkyl, cycloalkyl, aryl, heteroaryl or heterocyclyl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —$S(O)_nR^a$, in which $R^a$ is alkyl, aryl or heteroaryl and n is 0, 1 or 2.

The term "alkoxycarbonylamino" refers to the group —$N(R^d)C(O)OR$ in which R is alkyl and $R^d$ is hydrogen or alkyl. Unless otherwise constrained by the definition, each alkyl may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —$S(O)_nR^a$, in which $R^a$ is alkyl, aryl or heteroaryl and n is 0, 1 or 2.

The term "aminocarbonylamino" refers to the group —$NR^cC(O)NRR$, wherein $R^c$ is hydrogen or alkyl and each R is hydrogen, alkyl, cycloalkyl, aryl, heteroaryl or heterocyclyl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —$S(O)_nR^a$, in which $R^a$ is alkyl, aryl or heteroaryl and n is 0, 1 or 2.

The term "thiol" refers to the group —SH.

The term "thiocarbonyl" refers to a group =S.

The term "alkylthio" refers to the group —S-alkyl.

The term "substituted alkylthio" refers to the group —S-substituted alkyl.

The term "heterocyclylthio" refers to the group —S-heterocyclyl.

The term "arylthio" refers to the group —S-aryl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, cycloalkyl, heterocyclyl, aryl or heteroaryl. "Substituted sulfoxide" refers to a group —S(O)R, in which R is substituted alkyl, substituted cycloalkyl, substituted heterocyclyl, substituted aryl or substituted heteroaryl, as defined herein.

The term "sulfone" refers to a group —$S(O)_2R$, in which R is alkyl, cycloalkyl, heterocyclyl, aryl or heteroaryl. "Substituted sulfone" refers to a group —$S(O)_2R$, in which R is substituted alkyl, substituted cycloalkyl, substituted heterocyclyl, substituted aryl or substituted heteroaryl, as defined herein.

The term "aminosulfonyl" refers to the group —$S(O)_2NRR$, wherein each R is independently hydrogen, alkyl, cycloalkyl, aryl, heteroaryl or heterocyclyl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —$S(O)_nR^a$, in which $R^a$ is alkyl, aryl or heteroaryl and n is 0, 1 or 2.

The term "hydroxyamino" refers to the group —NHOH.

The term "alkoxyamino" refers to the group —NHOR in which R is optionally substituted alkyl.

The term "halogen" or "halo" refers to fluoro, bromo, chloro and iodo.

"Optional" or "optionally" means that the subsequently described event or circumstance may or may not occur, and that the description includes instances where said event or circumstance occurs and instances in which it does not.

A "substituted" group includes embodiments in which a monoradical substituent is bound to a single atom of the substituted group (e.g. forming a branch), and also includes embodiments in which the substituent may be a diradical bridging group bound to two adjacent atoms of the substituted group, thereby forming a fused ring on the substituted group.

Where a given group (moiety) is described herein as being attached to a second group and the site of attachment is not explicit, the given group may be attached at any available site of the given group to any available site of the second group. For example, a "lower alkyl-substituted phenyl", where the attachment sites are not explicit, may have any available site of the lower alkyl group attached to any available site of the phenyl group. In this regard, an "available site" is a site of the group at which a hydrogen of the group may be replaced with a substituent.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. Also not included are infinite numbers of substituents, whether the substituents are the same or different. In such cases, the maximum number of such substituents is three. Each of the above definitions is thus constrained by a limitation that, for example, substituted aryl groups are limited to -substituted aryl-(substituted aryl)-substituted aryl.

All or most of the XRPD patterns of various forms of Compound I were collected with a PANalytical X'Pert PRO MPD diffractometer using the following experimental setting: 45 kV, 40 mA, Kα1=1.5406 Å, scan range 2-40 °2θ, step size 0.0167 °2θ, counting time: 15.875 s or 48.260 s. The DSC analysis was conducted on a TA Instruments Q2000 differential scanning calorimeter using approximately 2-3 mg of material, 10° C./min heating rate over a typical range of (−30° C.)-300° C. or 20° C.-350° C. The TGA data were obtained on a TA Instruments 2950 and Q5000 thermogravimetric analyzers using approximately 2-5 mg of material, 10° C./min heating rate over a typical range of 25-350° C.

In addition, abbreviations as used herein have respective meanings as follows:

| | |
|---|---|
| δ | Chemical shift |
| 2-Me - THF or MeTHF | 2-methyltetrahydrofuran |
| amu | Atomic mass unit |
| atm | Standard atmosphere |
| Ac | acetate |
| Boc | tert-butoxycarbonyl |
| br | broad |
| CPME | Cyclopentyl methyl ether |
| Cy | cylcohexyl |
| d | doublet |
| dd | doublet of doublets |
| ddd | doublet of doublet of doublets |
| DCM | dichloromethane |
| DMA or DMAc | N,N-dimethylacetamide |
| DMF | dimethylformamide |
| dq | doublet of quartets |
| dt | doublet of triplets |
| DSC | differential scanning calorimetry |
| DVS | Dynamic vapor sorption |
| EDC•HCl | N-(3-Dimethylaminopropyl)-N'-ethylcarbodiimide hydrochloride |
| EDTA | Ethylenediaminetetraacetic acid |
| equiv or eq. | equivalents |
| Et | ethyl |
| EtOAc | ethyl acetate |
| EtOH | ethanol |
| g | gram |
| h/hrs | hour(s) |
| HEP | 1-(2-hydroxyethyl)-pyrrolidine |
| HOBt | 1-hydroxybenzotriazole hydrate |
| Hz | hertz |
| IPA | isopropanol |
| IPAc | isopropyl acetate |
| iPr | isopropyl |
| J | Coupling constant |
| L | liter |
| LC | Liquid chromatography |
| LCMS | Liquid chromatography mass spectrometry |
| M | molar |
| m | multiplet |
| m/z | Mass to charge |
| Me | methyl |
| MEK | methyl ethyl ketone |
| MeOH | methanol |
| mg | milligram |
| MIBK | methyl isobutyl ketone |
| MHz | megahertz |
| mL | milliliter |
| mmol | millimole |
| mol | mole |
| MS | mass spectroscopy |
| MTBE | Methyl tert-butyl ether |
| N | Normal |
| NMM | N-methylmorpholine |
| NMR | nuclear magnetic resonance |
| Ph | phenyl |
| ppm | parts per million |
| psig | pounds per square inch |
| q | quartet |
| R.H. or RH | Relative humidity |
| s | singlet |
| t | triplet |
| td | Triplet of doublets |
| tdd | Triplet of doublet of doublets |
| tBu | tert-butyl |
| TGA | thermogravimetric analysis |
| Ts | tosyl |
| THF | tetrahydrofuran |
| UPLC | ultra performance liquid chromatography |
| μL | microliter |
| μg | microgram |
| vol | volume |
| v/v | volume to volume |
| w/w or wt/wt | weight to weight |
| wt. | weight |
| XRPD | X-ray powder diffraction |

Crystalline Forms of Compound I

As described generally above, the present disclosure provides crystalline forms of Compound I and Compound I salts/co-crystals, which are disclosed herein.

Compound I Form I is characterized by an X-ray powder diffractogram comprising peaks at 8.6, 11.1, and 15.5 °2θ±0.2 °2θ, as determined on a diffractometer using Cu—Kα radiation. The diffractogram comprises an additional peak at 12.9 °2θ±0.2 °2θ. Form I is also characterized by its full X-ray powder diffractogram as substantially shown in FIG. 1.

Figure 2:
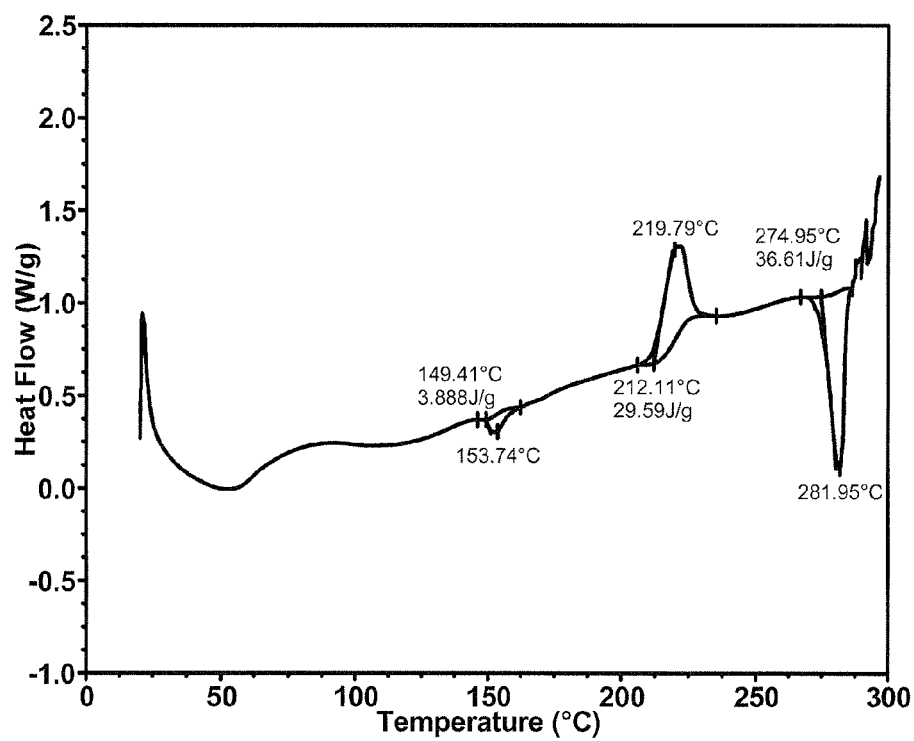
FIG. 2 is differential scanning calorimetry (DSC) curve of Compound I Form I.

In some embodiments, Form I is also characterized by its differential scanning calorimetry (DSC) curve substantially as shown in FIG. 2.

Figure 3:
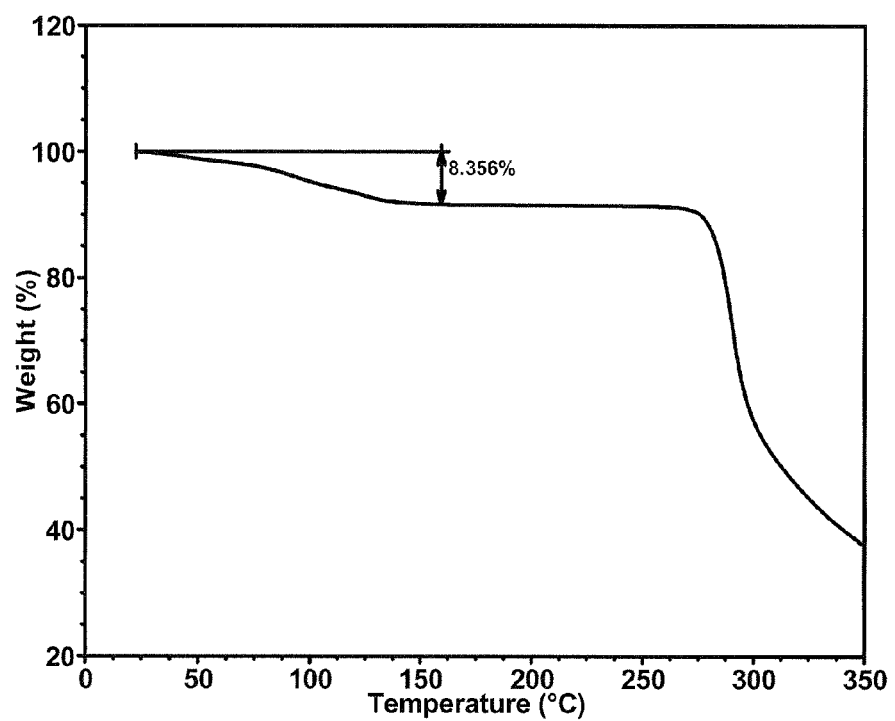
FIG. 3 is thermogravimetric analysis (TGA) of Compound I Form I.

In some embodiments, Form I is also characterized by thermogravimetric analysis (TGA) comprising a thermogram substantially as shown in FIG. 3.

Figure 4:
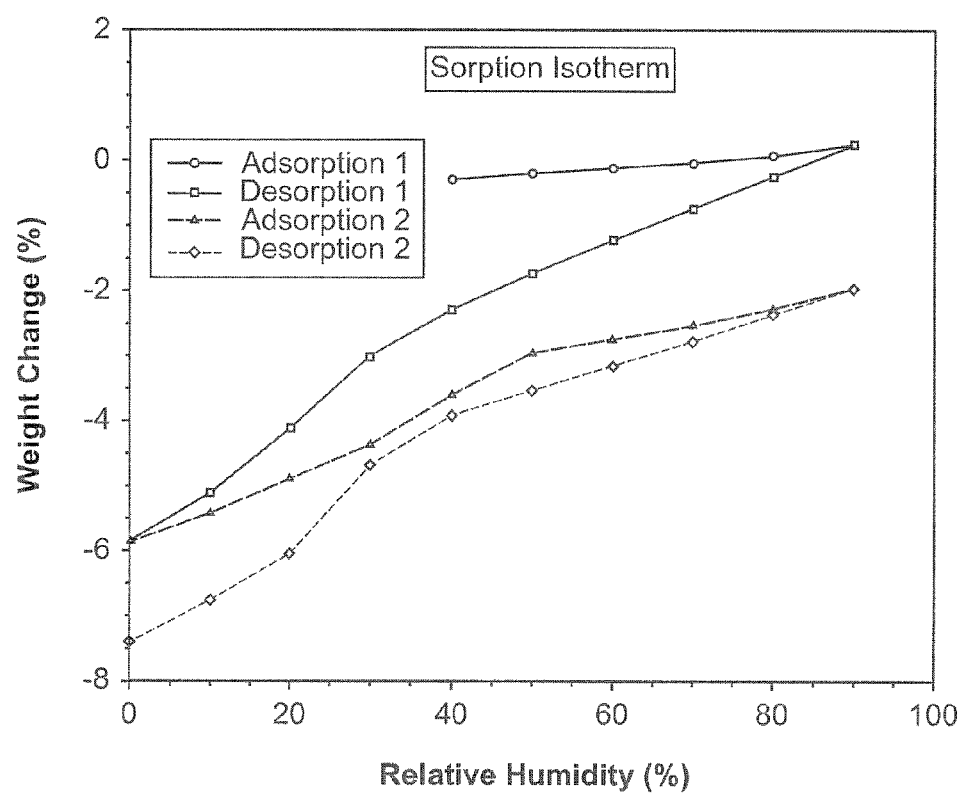
FIG. 4 is dynamic vapor sorption (DVS) curve of Compound I Form I.

In some embodiments, Form I is also characterized by a dynamic vapor sorption (DVS) curve substantially as shown in FIG. 4.

Figure 5:
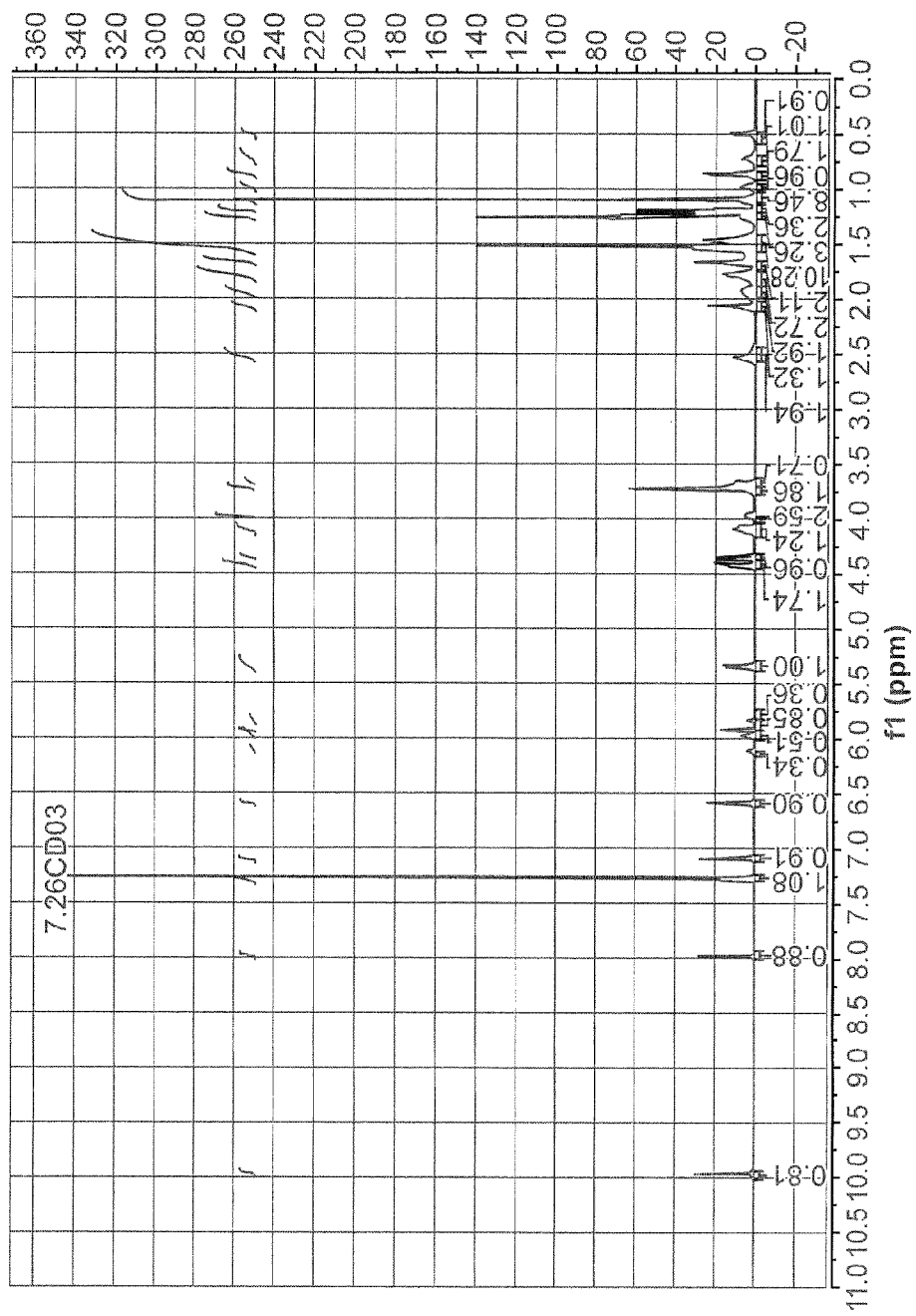
FIG. 5 is a nuclear magnetic resonance spectrum ($^1$H NMR) of Compound I Form I.

In some embodiments, Form I is also characterized by a nuclear magnetic resonance spectrum ($^1$H NMR) substantially as shown in FIG. 5.

In one embodiment, Form I comprises about 1.7 mole equivalents of ethanol.

Compound I Form II is characterized by an X-ray powder diffractogram comprising peaks at 8.7, 13.0, and 17.4 °2θ±0.2 °2θ, as determined on a diffractometer using Cu—Kα radiation. The diffractogram comprises an additional peak at 15.4 °2θ±0.2 °2θ. Form II is also characterized by its full X-ray powder diffractogram as substantially shown in FIG. 6.

Figure 7:
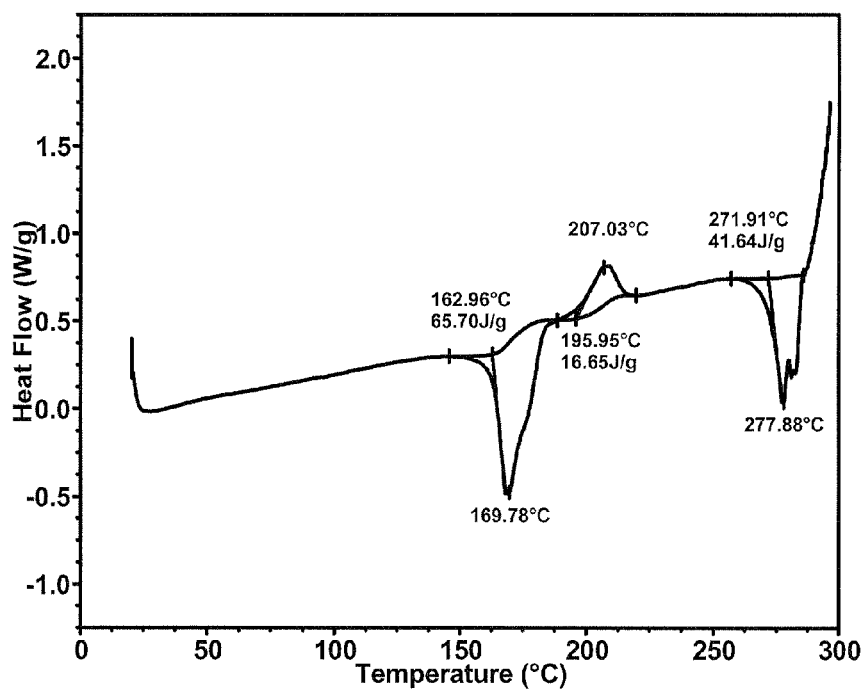
FIG. 7 is differential scanning calorimetry (DSC) curve of Compound I Form II.

In some embodiments, Form II is also characterized by its differential scanning calorimetry (DSC) curve substantially as shown in FIG. 7.

Figure 8:
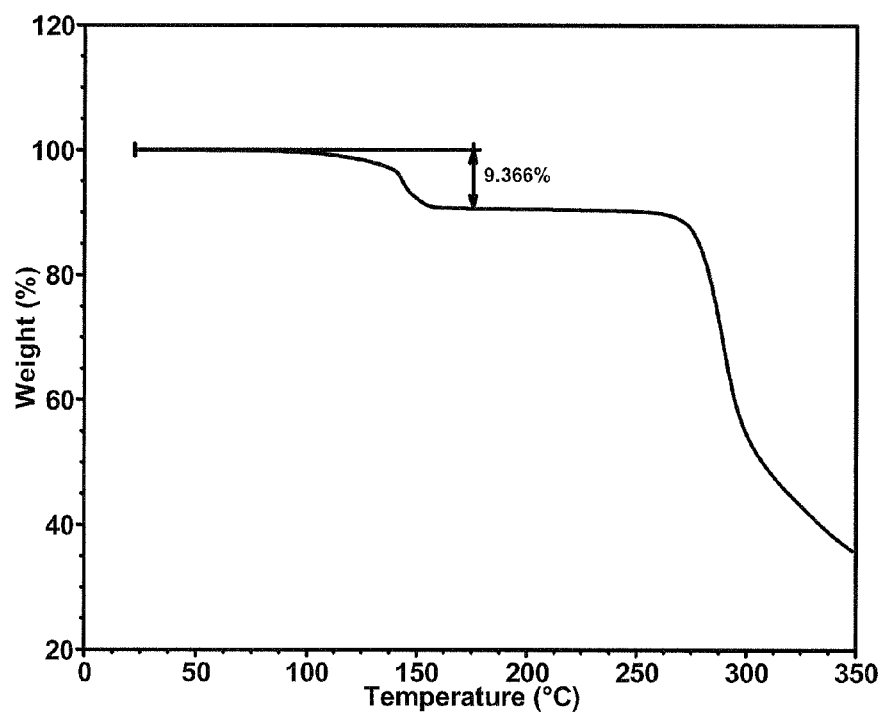
FIG. 8 is thermogravimetric analysis (TGA) of Compound I Form II.

In some embodiments, Form II is also characterized by thermogravimetric analysis (TGA) comprising a thermogram substantially as shown in FIG. 8.

Figure 9:
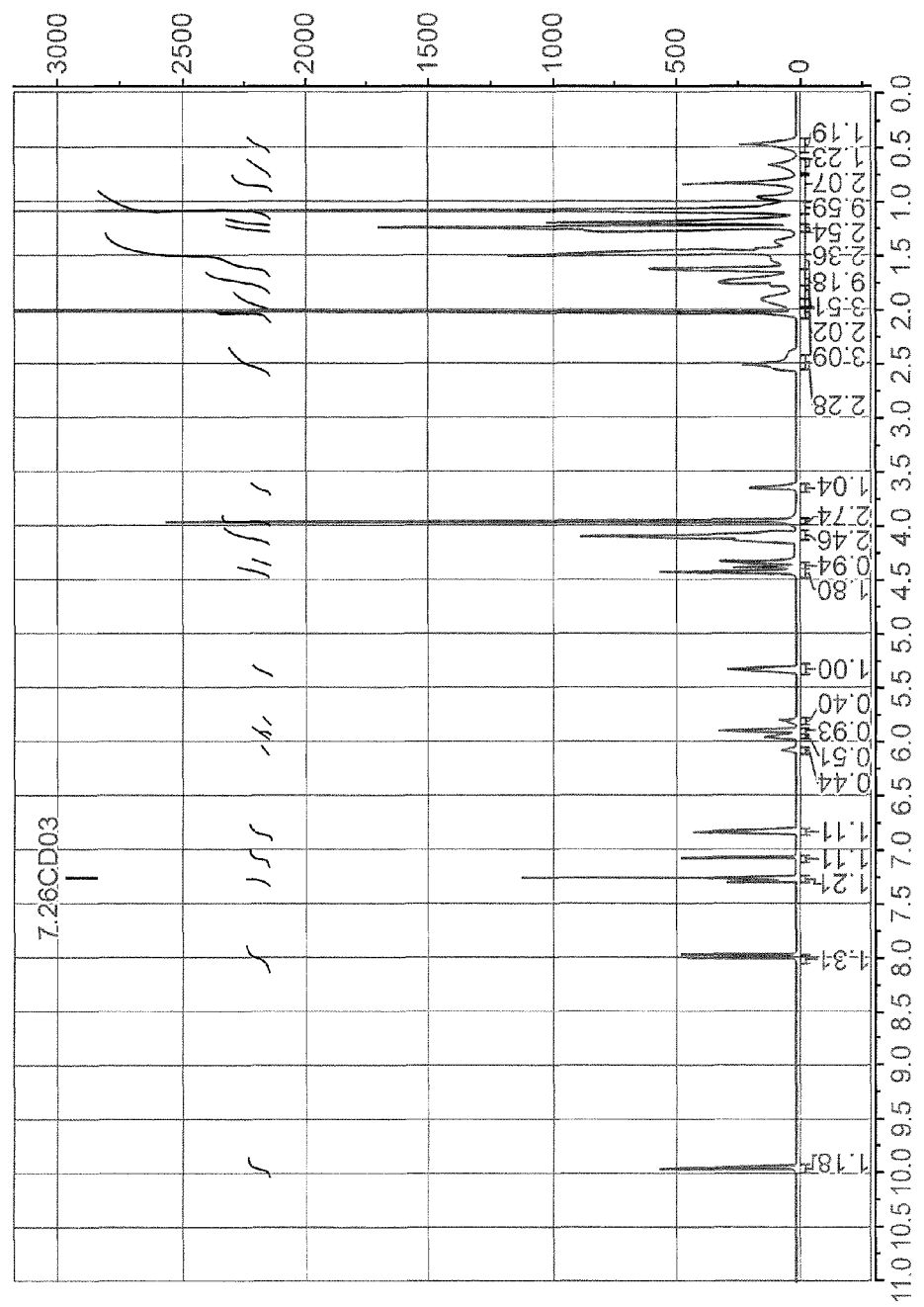
FIG. 9 is a nuclear magnetic resonance spectrum ($^1$H NMR) of Compound I Form II.

In some embodiments, Form II is also characterized by a nuclear magnetic resonance spectrum ($^1$H NMR) substantially as shown in FIG. 9.

Figure 10:
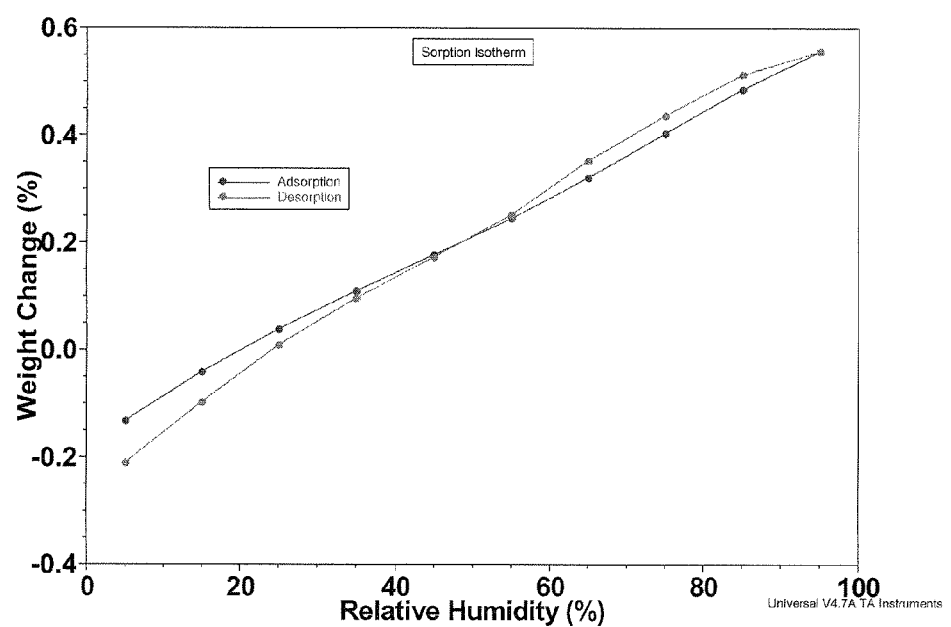
FIG. 10 is dynamic vapor sorption (DVS) curve of Compound I Form II.

In some embodiments, Form II is also characterized by a dynamic vapor sorption (DVS) curve substantially as shown in FIG. 10.

In one embodiment, Form II comprises about 1 mole equivalent of ethyl acetate.

Compound I Form III is characterized by an X-ray powder diffractogram comprising peaks at 11.1, 12.8, and 19.7 °2θ±0.2 °2θ, as determined on a diffractometer using Cu—Kα radiation. The diffractogram comprises an additional peak at 15.5 °2θ±0.2 °2θ. Form III is also characterized by its full X-ray powder diffractogram as substantially shown in FIG. 12.

Figure 13:
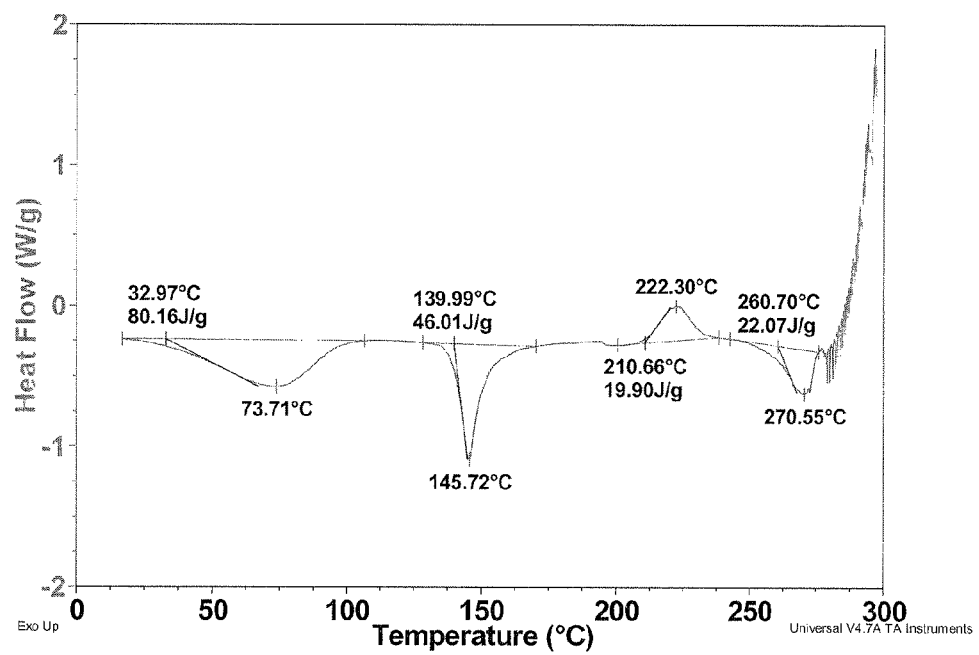
FIG. 13 is differential scanning calorimetry (DSC) curve of Compound I Form III.

In some embodiments, Form III is also characterized by its differential scanning calorimetry (DSC) curve substantially as shown in FIG. 13.

Figure 14:
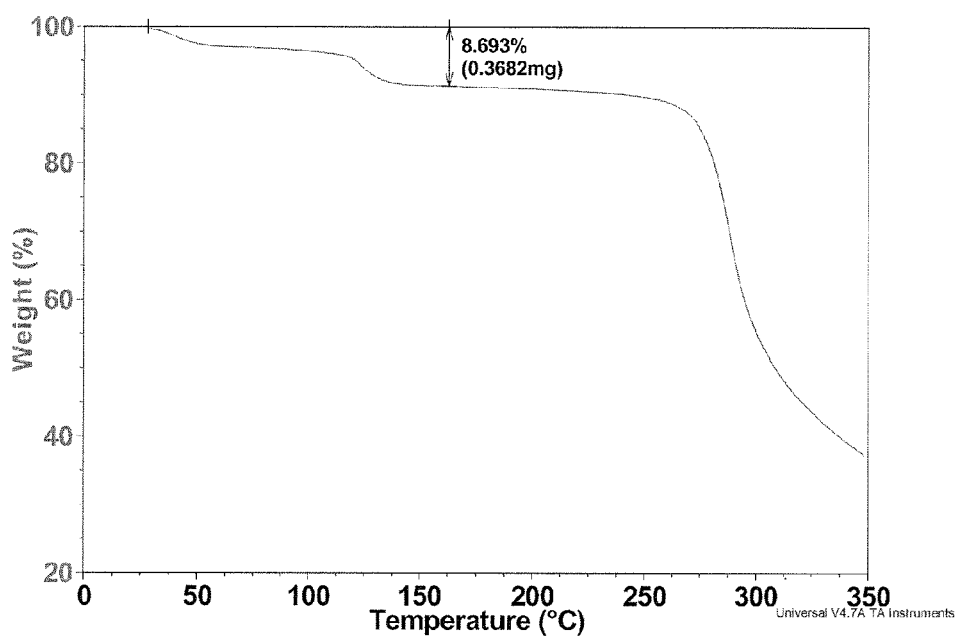
FIG. 14 is thermogravimetric analysis (TGA) of Compound I Form III.

In some embodiments, Form III is also characterized by thermogravimetric analysis (TGA) comprising a thermogram substantially as shown in FIG. 14.

Figure 15:
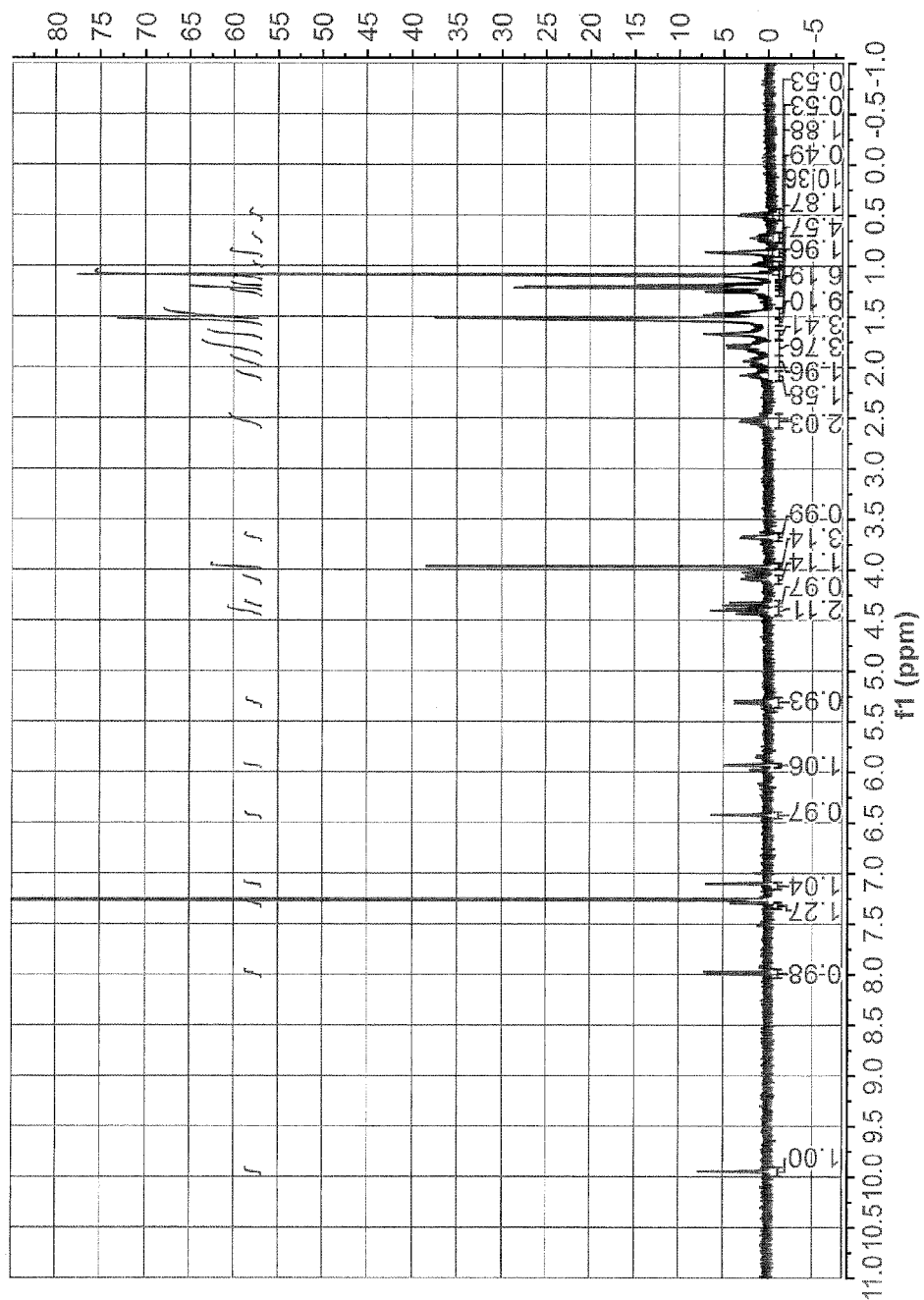
FIG. 15 is a nuclear magnetic resonance spectrum ($^1$H NMR) of Compound I Form III.
Figure 16:
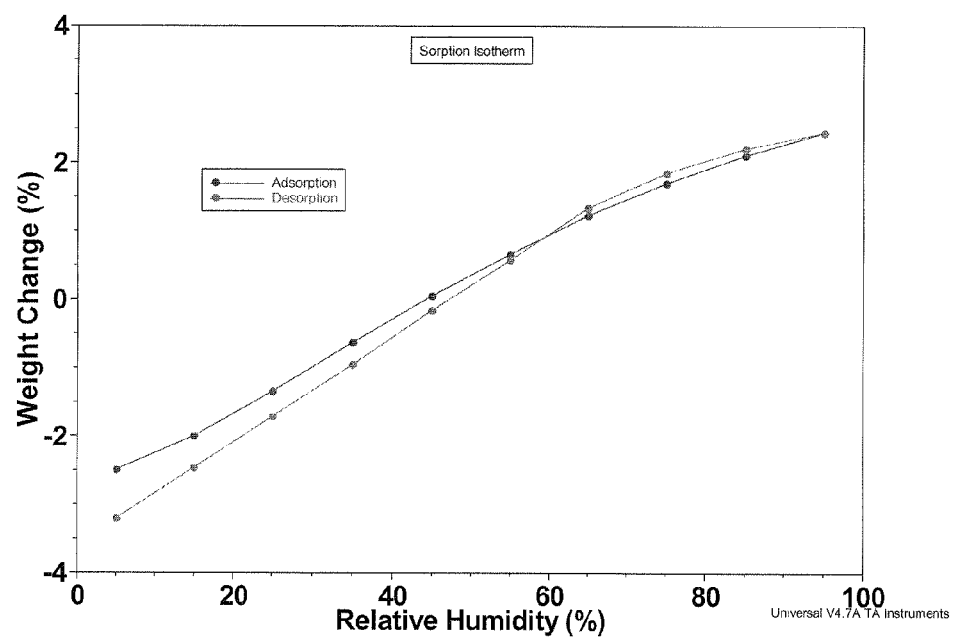
FIG. 16 is dynamic vapor sorption (DVS) curve of Compound I Form III.

In some embodiments, Form III is also characterized by a nuclear magnetic resonance spectrum ($^1$H NMR) substantially as shown in FIG. 15. In some embodiments, Form III is also characterized by a dynamic vapor sorption (DVS) curve substantially as shown in FIG. 16.

In one embodiment, Form III comprises about 1.4 mole equivalents of isopropanol.

Compound I Form IV is characterized by an X-ray powder diffractogram comprising peaks at 8.7, 8.9, and 16.0 °2θ±0.2 °2θ, as determined on a diffractometer using Cu—Kα radiation. The diffractogram comprises an additional peak at 13.0 °2θ±0.2 °2θ. Form IV is also characterized by its full X-ray powder diffractogram as substantially shown in FIG. 17.

Figure 18:
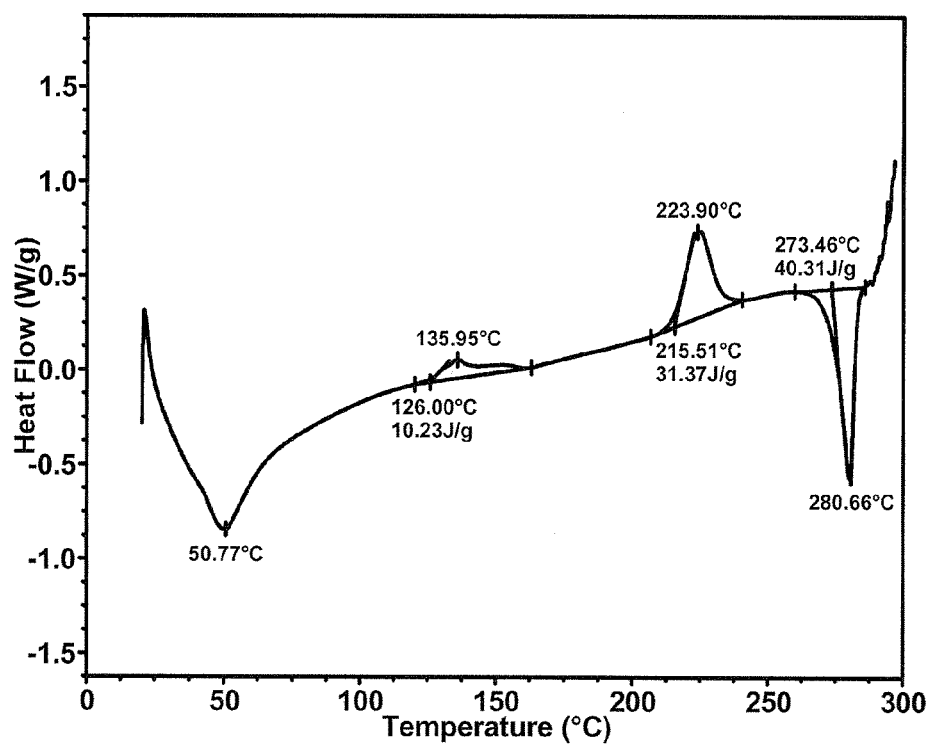
FIG. 18 is differential scanning calorimetry (DSC) curve of Compound I Form IV.

In some embodiments, Form IV is also characterized by its differential scanning calorimetry (DSC) curve substantially as shown in FIG. 18.

Figure 19:
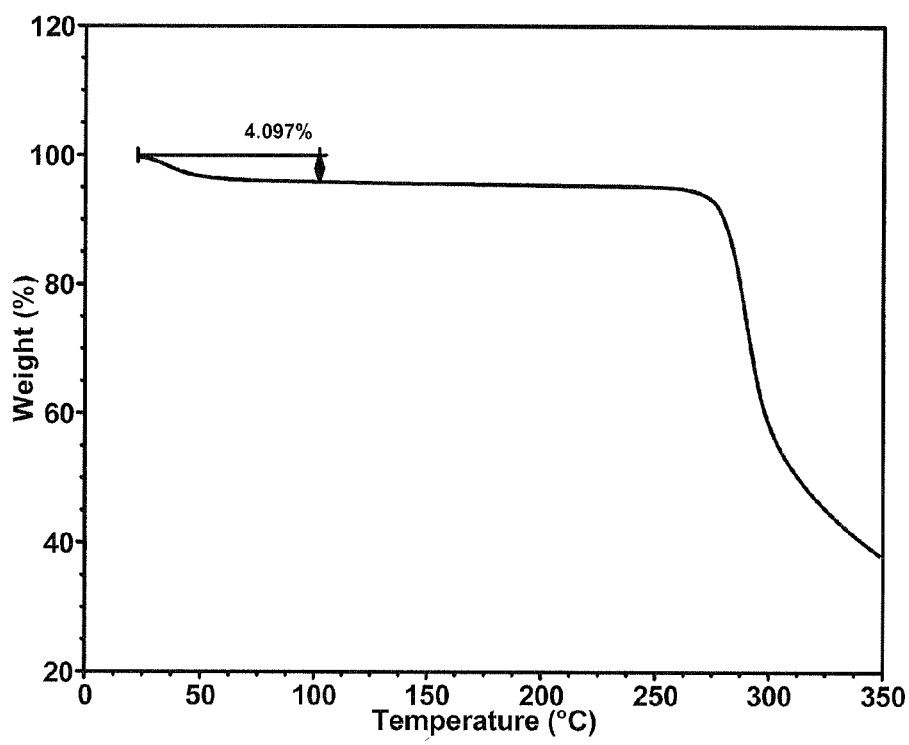
FIG. 19 is thermogravimetric analysis (TGA) of Compound I Form IV.

In some embodiments, Form IV is also characterized by thermogravimetric analysis (TGA) comprising a thermogram substantially as shown in FIG. 19.

Figure 20:
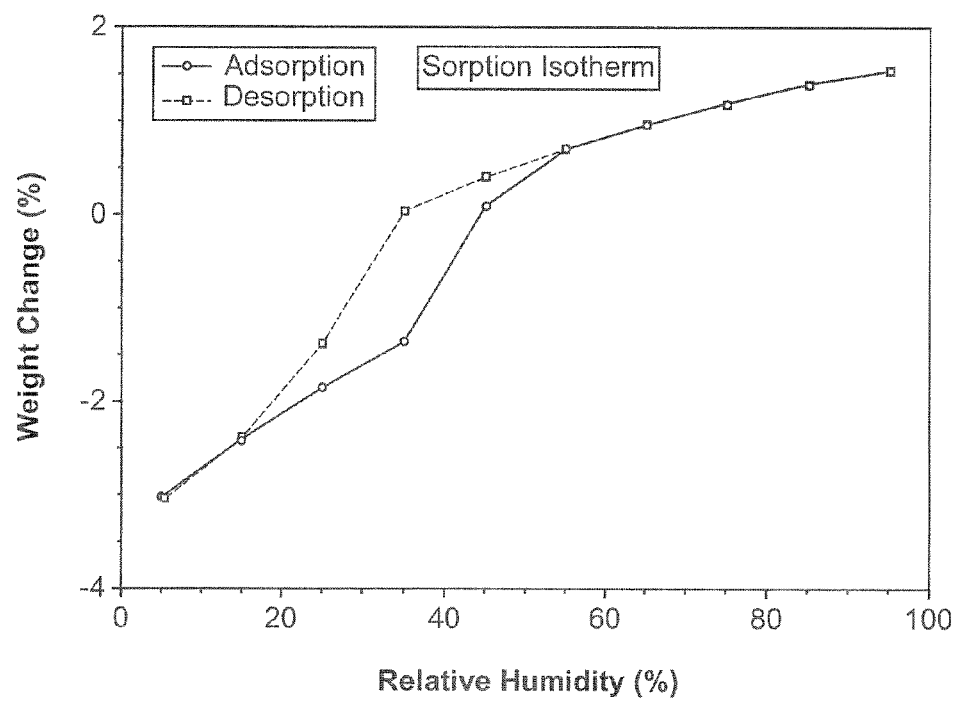
FIG. 20 is dynamic vapor sorption (DVS) curve of Compound I Form IV.

In some embodiments, Form IV is also characterized by a dynamic vapor sorption (DVS) curve substantially as shown in FIG. 20.

In one embodiment, Form IV comprises about 2.2 mole equivalents of water.

Figure 21:
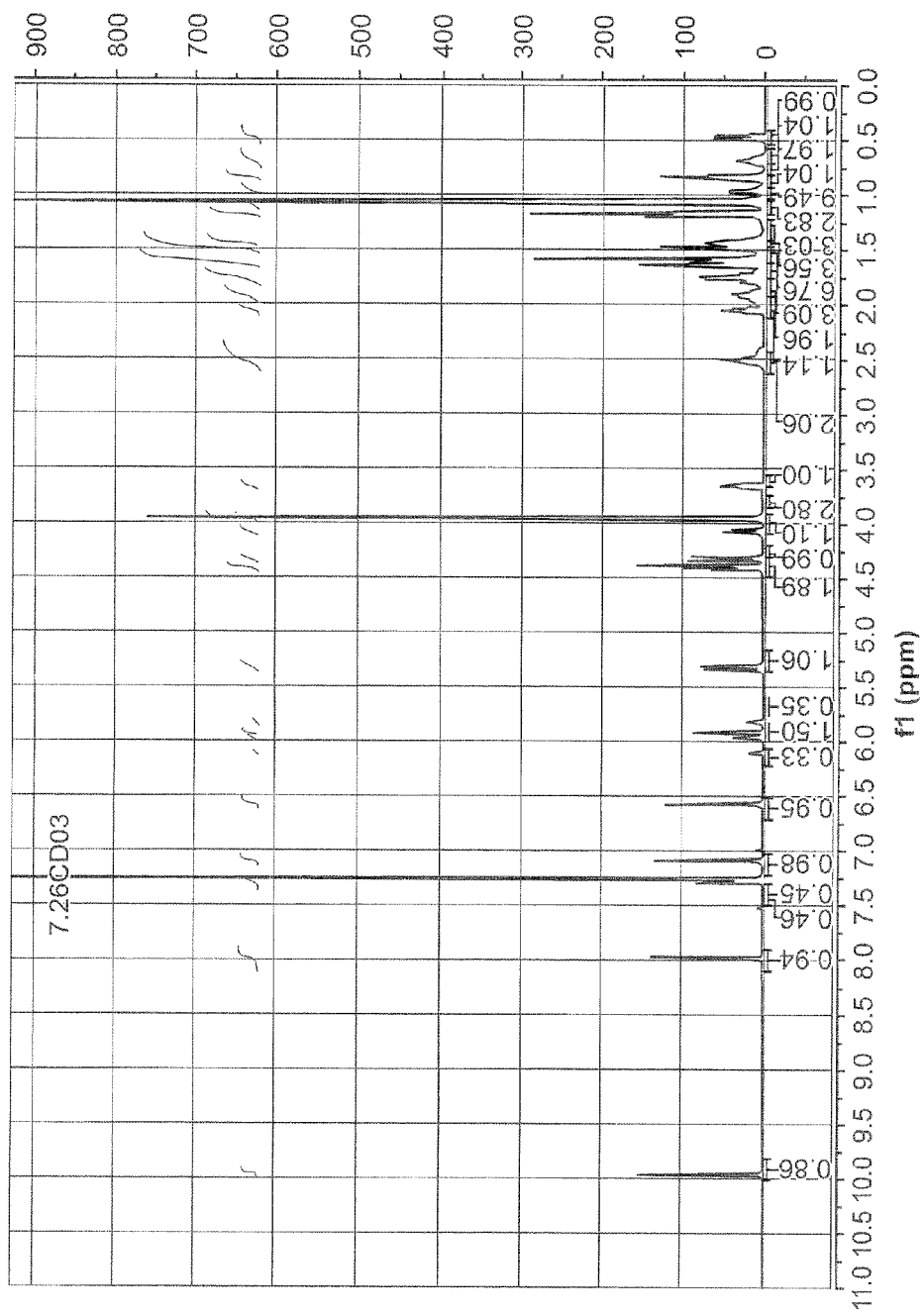
FIG. 21 is a nuclear magnetic resonance spectrum ($^1$H NMR) of Compound I Form IV.

In some embodiments, Form IV is also characterized by a nuclear magnetic resonance spectrum ($^1$H NMR) substantially as shown in FIG. 21.

Compound I Form V is characterized by an X-ray powder diffractogram comprising peaks at 6.2, 12.4, and 19.6 °2θ±0.2 °2θ, as determined on a diffractometer using Cu—Kα radiation. The diffractogram comprises an additional peak at 13.7 °2θ±0.2 °2θ. Form V is also characterized by its full X-ray powder diffractogram as substantially shown in FIG. 22.

Figure 23:
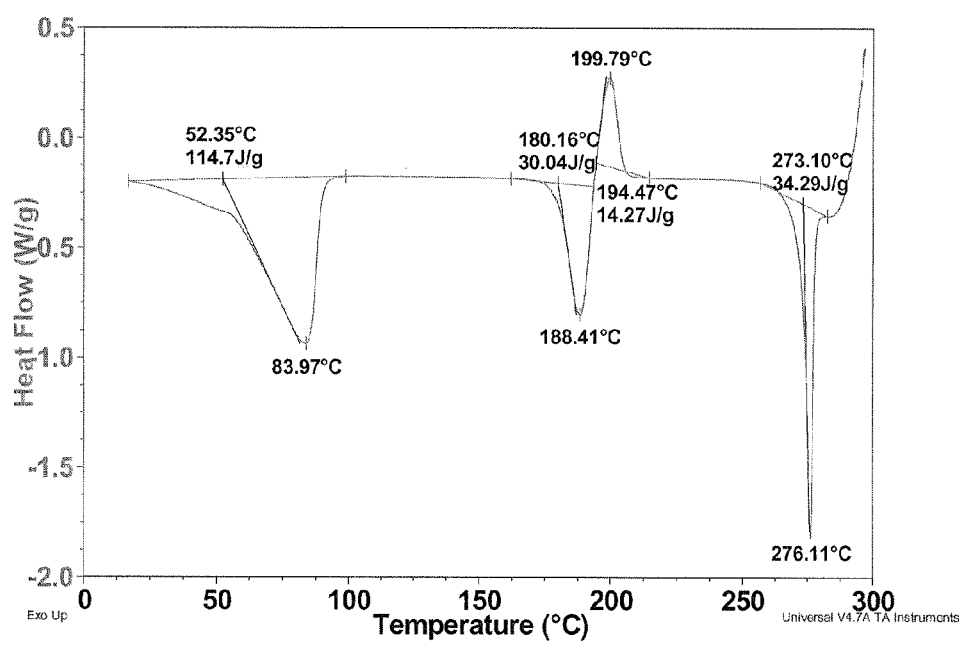
FIG. 23 is differential scanning calorimetry (DSC) curve of Compound I Form V.

In some embodiments, Form V is characterized by its differential scanning calorimetry (DSC) curve substantially as shown in FIG. 23.

Figure 24:
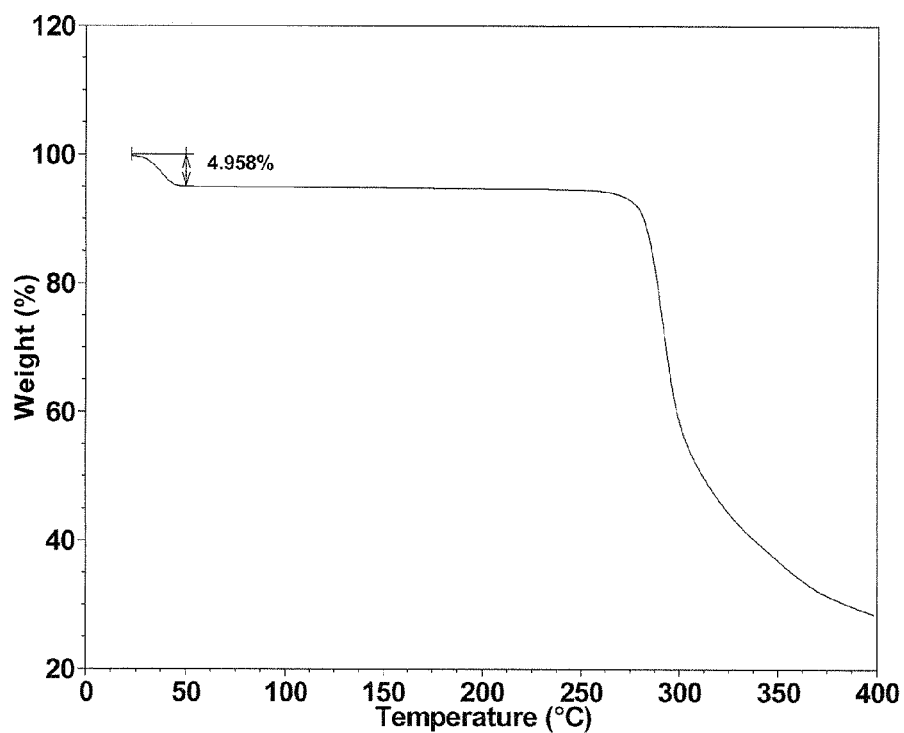
FIG. 24 is thermogravimetric analysis (TGA) of Compound I Form V.

In some embodiments, Form V is also characterized by thermogravimetric analysis (TGA) comprising a thermogram substantially as shown in FIG. 24.

Figure 25:
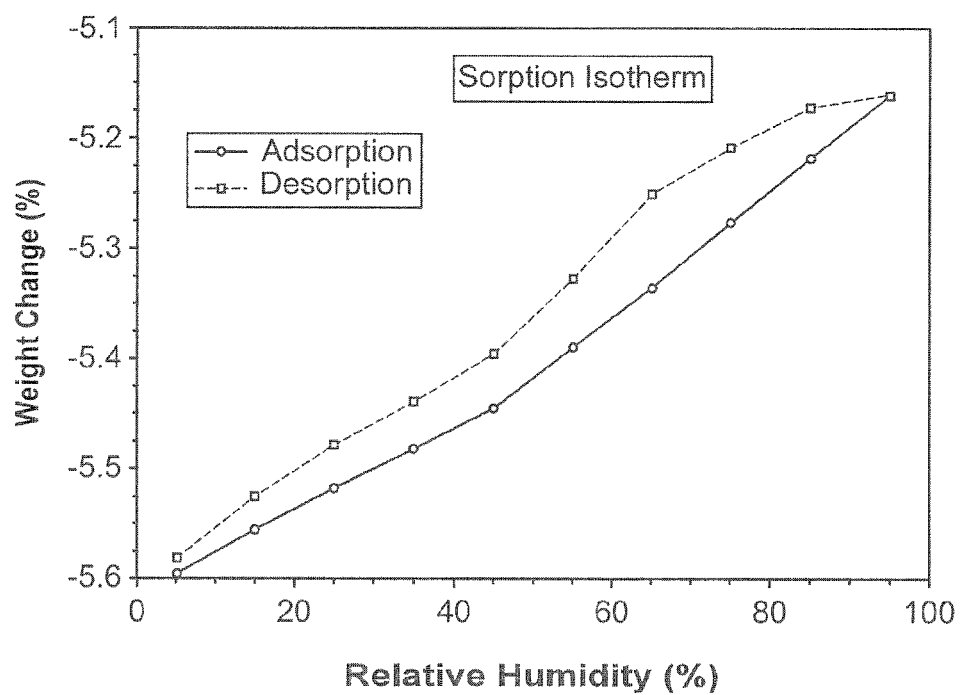
FIG. 25 is dynamic vapor sorption (DVS) curve of Compound I Form V.

In some embodiments, Form V is also characterized by a dynamic vapor sorption (DVS) curve substantially as shown in FIG. 25.

In one embodiment, Form V comprises from about >1 to about 2.5 mole equivalents of methanol. In another embodiment, Form V comprises about 2.5 mole equivalents of methanol.

Compound I Form VI is characterized by an X-ray powder diffractogram comprising peaks at 14.6, 15.4, and 20.0 °2θ±0.2 °2θ, as determined on a diffractometer using Cu—Kα radiation. The diffractogram comprises an additional peak at 18.1 °2θ±0.2 °2θ. Form VI is also characterized by its full X-ray powder diffractogram as substantially shown in FIG. 27.

Figure 28:
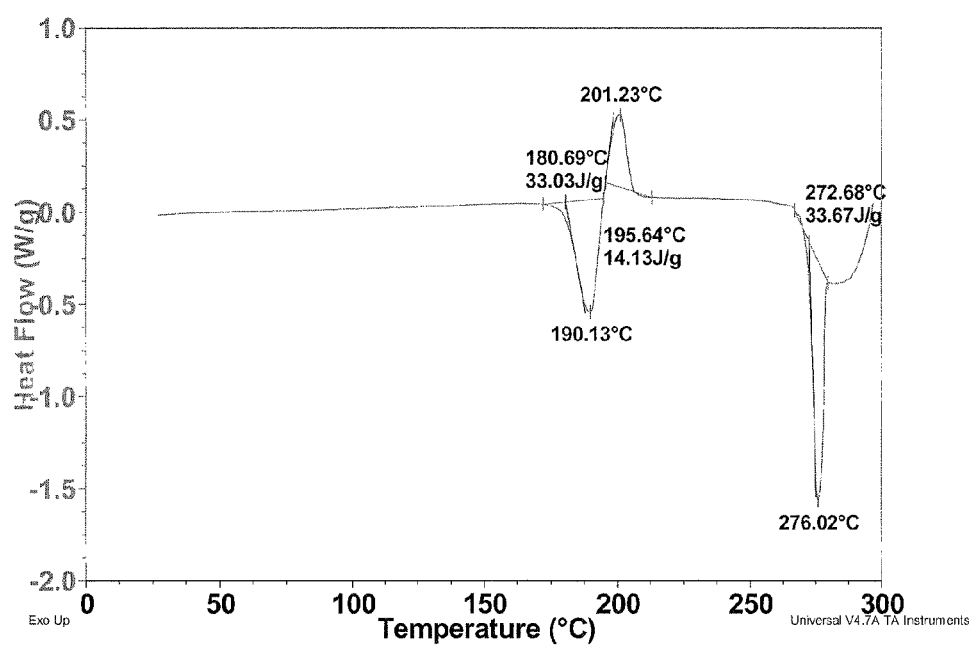
FIG. 28 is differential scanning calorimetry (DSC) curve of Compound I Form VI.

In some embodiments, Form VI is also characterized by its differential scanning calorimetry (DSC) curve substantially as shown in FIG. 28.

Figure 29:
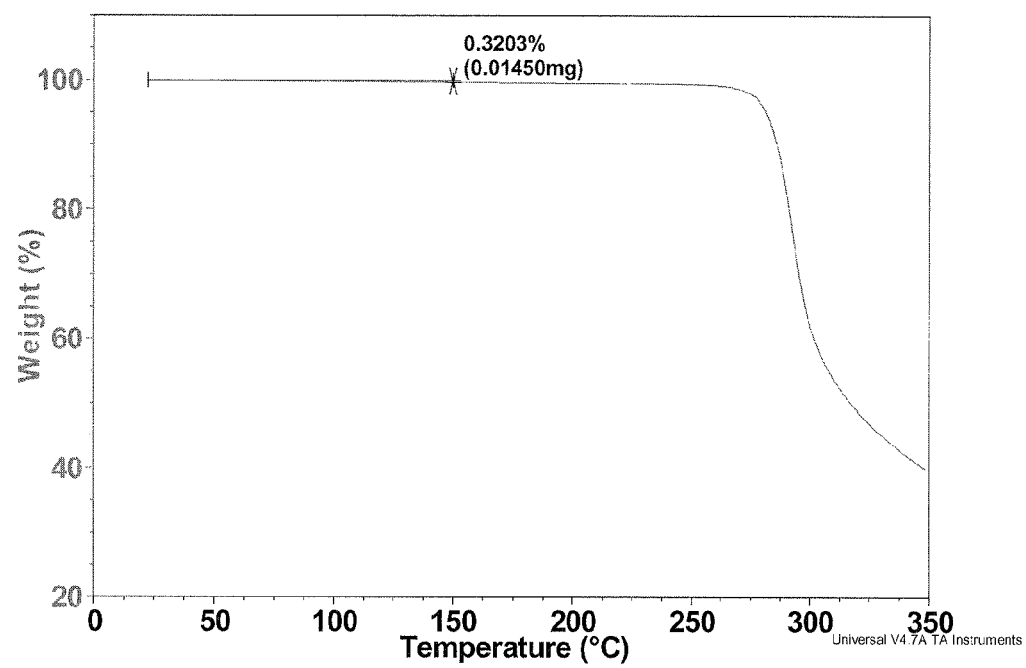
FIG. 29 is thermogravimetric analysis (TGA) of Compound I Form VI.

In some embodiments, Form VI is also characterized by thermogravimetric analysis (TGA) comprising a thermogram substantially as shown in FIG. 29.

Figure 30:
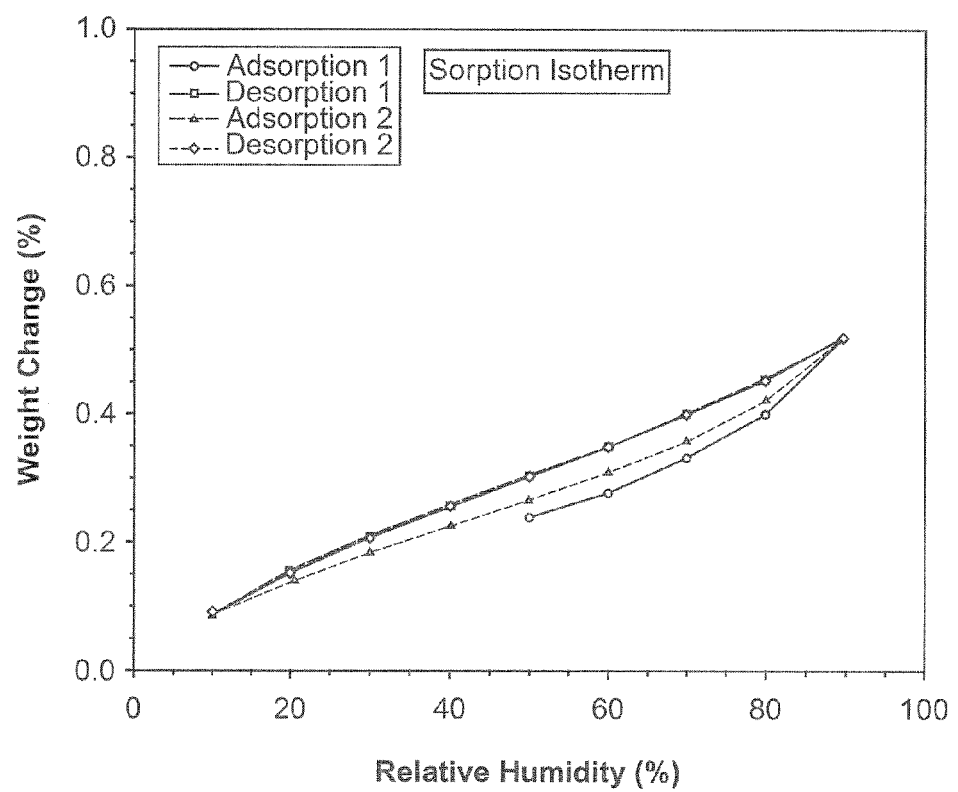
FIG. 30 is dynamic vapor sorption (DVS) curve of Compound I Form VI.

In some embodiments, Form VI is also characterized by a dynamic vapor sorption (DVS) curve substantially as shown in FIG. 30.

Compound I Form VII is characterized by an X-ray powder diffractogram comprising peaks at 6.5, 8.5, and 18.7 °2θ±0.2 °2θ, as determined on a diffractometer using Cu—Kα radiation. The diffractogram comprises an additional peak at 17.5 °2θ±0.2 °2θ. Form VII is also characterized by its full X-ray powder diffractogram as substantially shown in FIG. 31.

Figure 32:
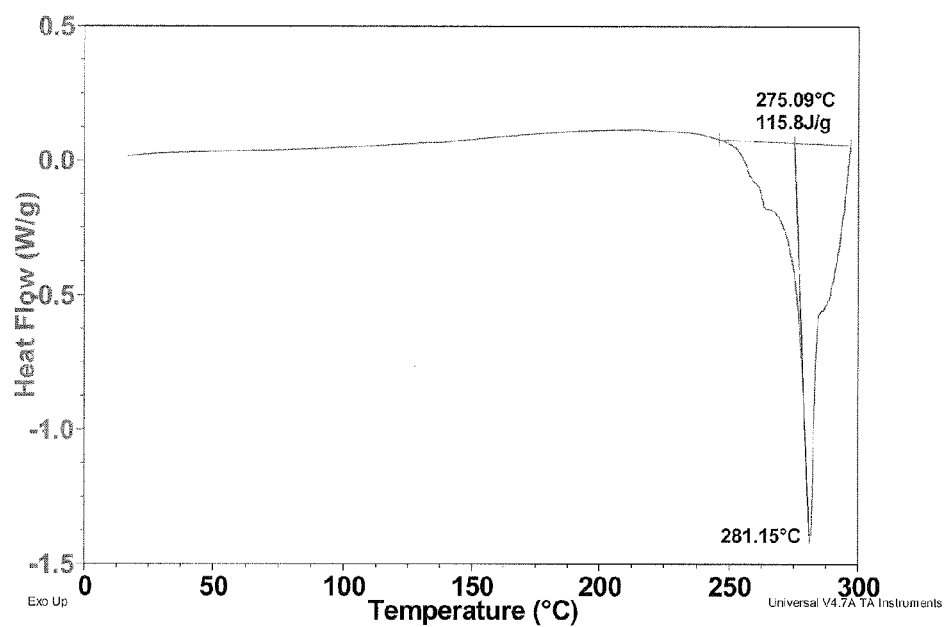
FIG. 32 is differential scanning calorimetry (DSC) curve of Compound I Form VII.

In some embodiments, Form VII is also characterized by its differential scanning calorimetry (DSC) curve substantially as shown in FIG. 32.

Figure 33:
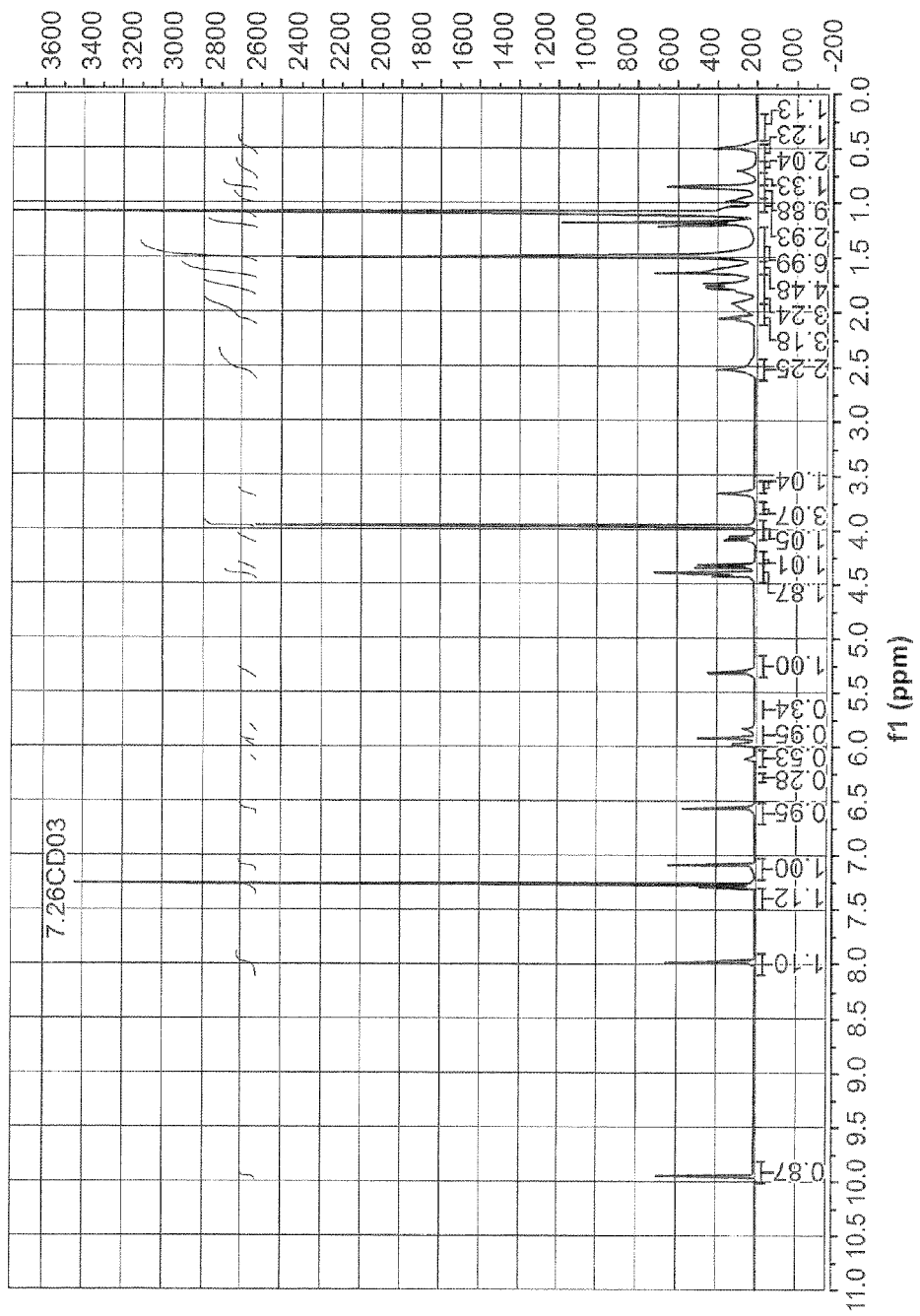
FIG. 33 is a nuclear magnetic resonance spectrum ($^1$H NMR) of Compound I Form VII.
Figure 34:
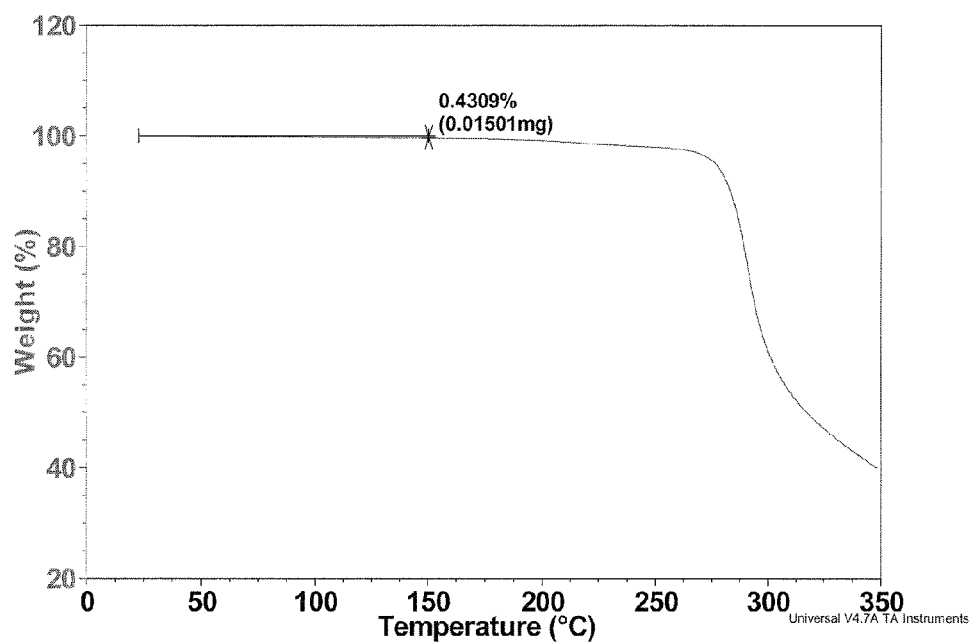
FIG. 34 is thermogravimetric analysis (TGA) of Compound I Form VII.

In some embodiments, Form VII is also characterized by a nuclear magnetic resonance spectrum ($^1$H NMR) substantially as shown in FIG. 33. In some embodiments, Form VII is also characterized by thermogravimetric analysis (TGA) comprising a thermogram substantially as shown in FIG. 34.

Figure 35:
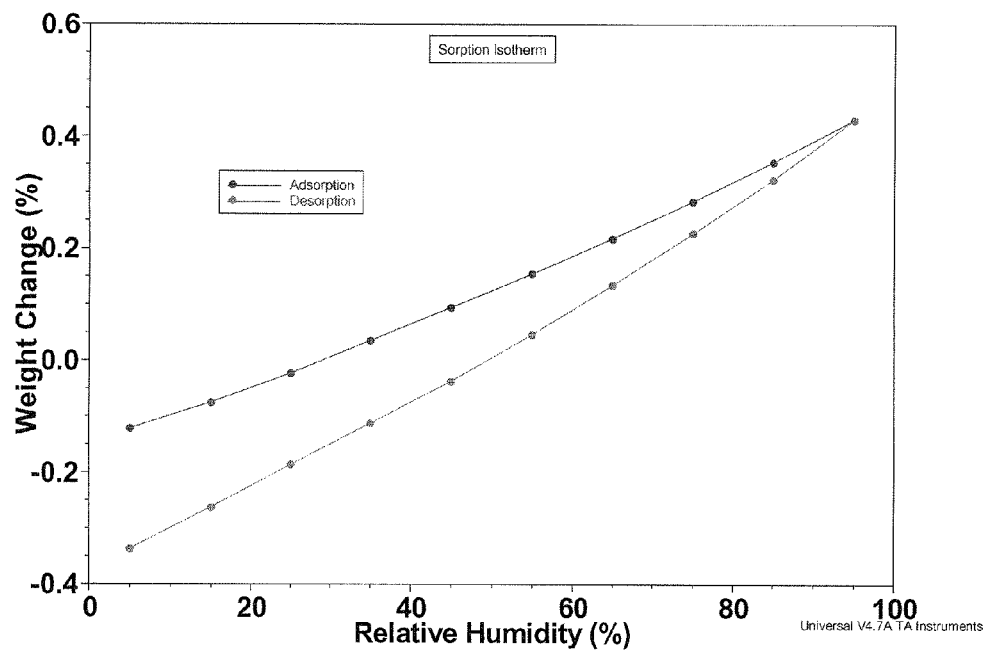
FIG. 35 is dynamic vapor sorption (DVS) curve of Compound I Form VII.

In some embodiments, Form VII is also characterized by a dynamic vapor sorption (DVS) curve substantially as shown in FIG. 35.

Compound I Form VIII is characterized by an X-ray powder diffractogram comprising peaks at 7.8, 8.2, and 20.2 °2θ±0.2 °2θ, as determined on a diffractometer using Cu—Kα radiation. The diffractogram comprises an additional peak at 16.5 °2θ±0.2 °2θ. Form VIII is also characterized by its full X-ray powder diffractogram as substantially shown in FIG. 36.

Figure 37:
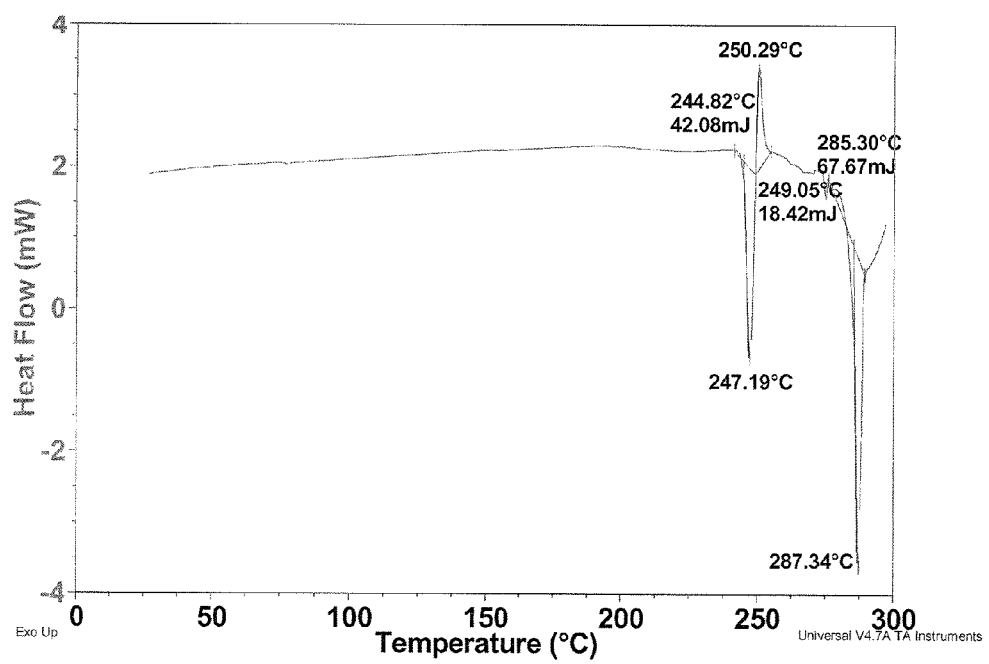
FIG. 37 is differential scanning calorimetry (DSC) curve of Compound I Form VIII.

In some embodiments, Form VIII is also characterized by its differential scanning calorimetry (DSC) curve substantially as shown in FIG. 37.

Figure 38:
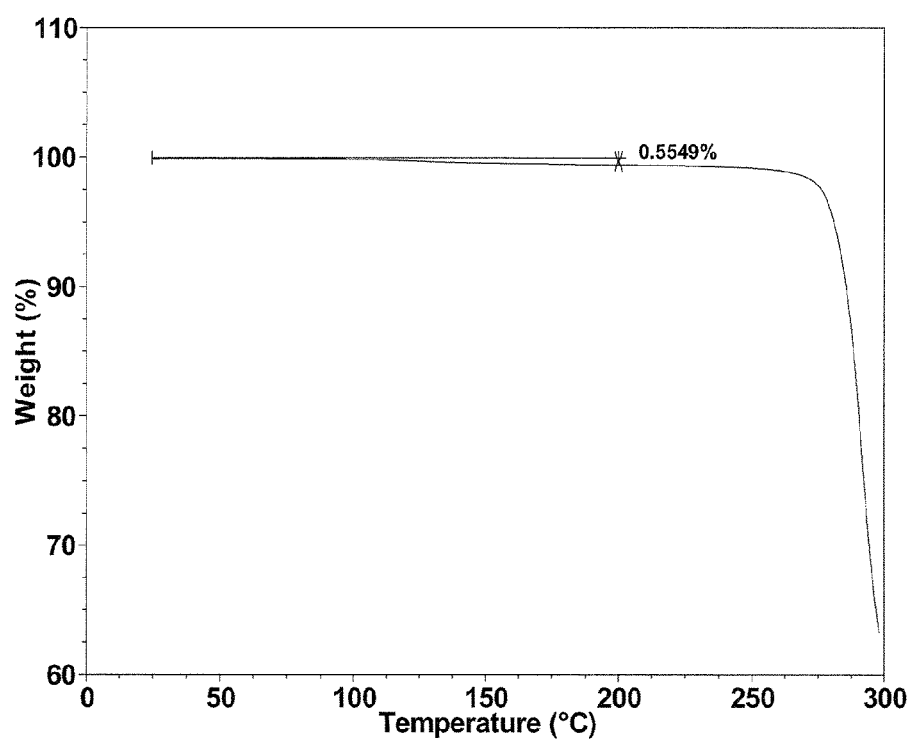
FIG. 38 is thermogravimetric analysis (TGA) of Compound I Form VIII.

In some embodiments, Form VIII is also characterized by thermogravimetric analysis (TGA) comprising a thermogram substantially as shown in FIG. 38.

Figure 39:
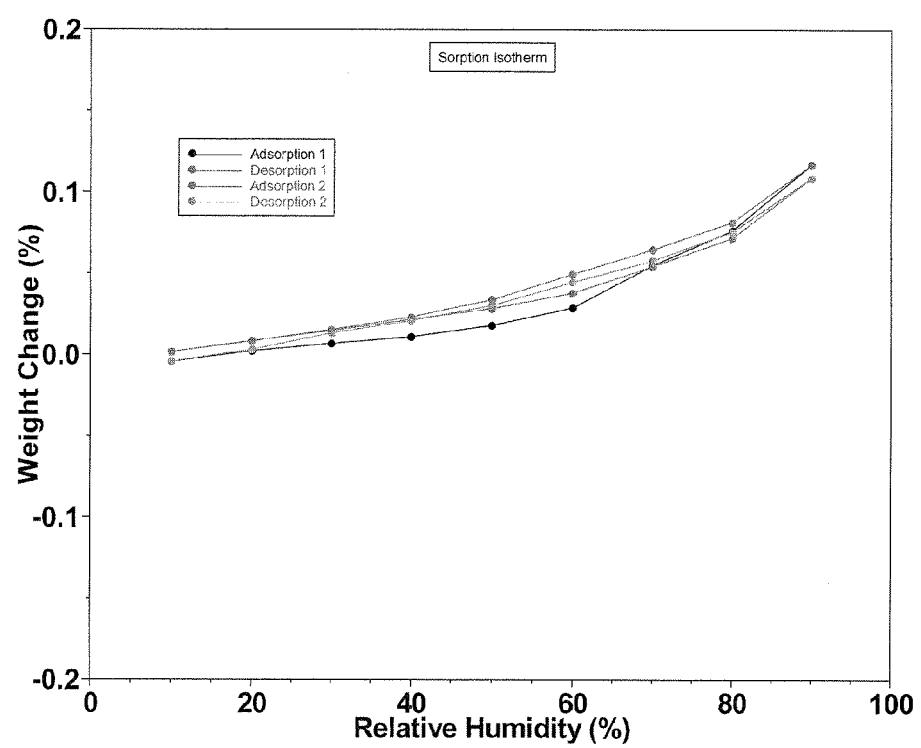
FIG. 39 is dynamic vapor sorption (DVS) curve of Compound I Form VIII.

In some embodiments, Form VIII is also characterized by a dynamic vapor sorption (DVS) curve substantially as shown in FIG. 39.

Compound I Form IX is characterized by an X-ray powder diffractogram comprising peaks at 6.1, 9.5, and 19.4 °2θ±0.2 °2θ, as determined on a diffractometer using Cu—Kα radiation. The diffractogram comprises an additional peak at 20.8 °2θ±0.2 °2θ. Form IX is also characterized by its full X-ray powder diffractogram as substantially shown in FIG. 40.

Figure 41:
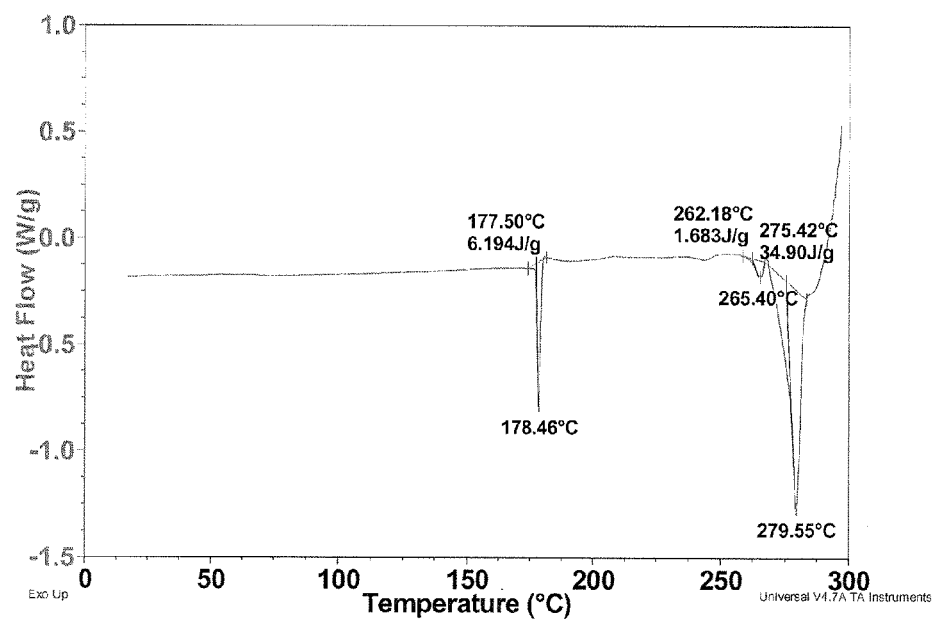
FIG. 41 is differential scanning calorimetry (DSC) curve of Compound I Form IX.

In some embodiments, Form IX is also characterized by its differential scanning calorimetry (DSC) curve substantially as shown in FIG. 41.

Figure 42:
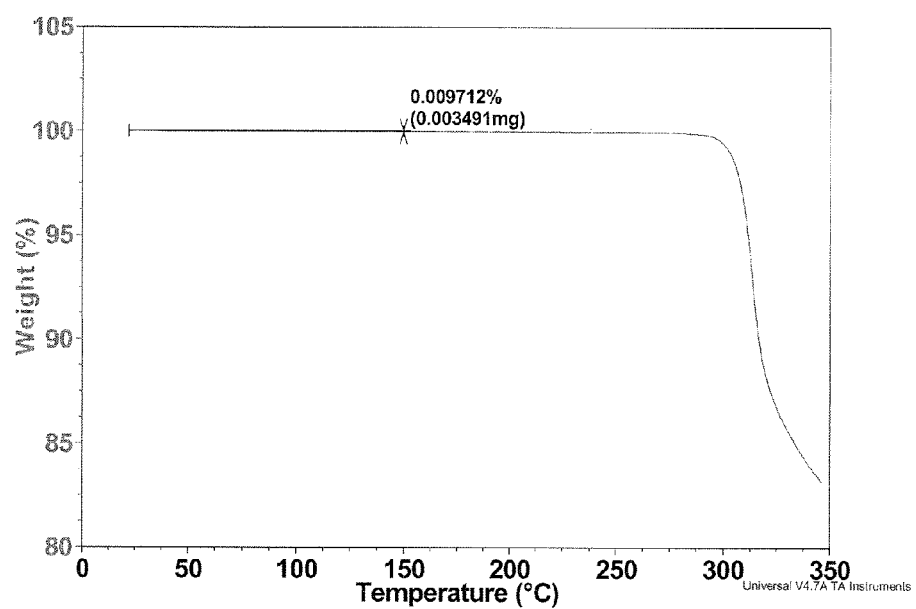
FIG. 42 is thermogravimetric analysis (TGA) of Compound I Form IX.

In some embodiments, Form IX is also characterized by thermogravimetric analysis (TGA) comprising a thermogram substantially as shown in FIG. 42.

Figure 43:
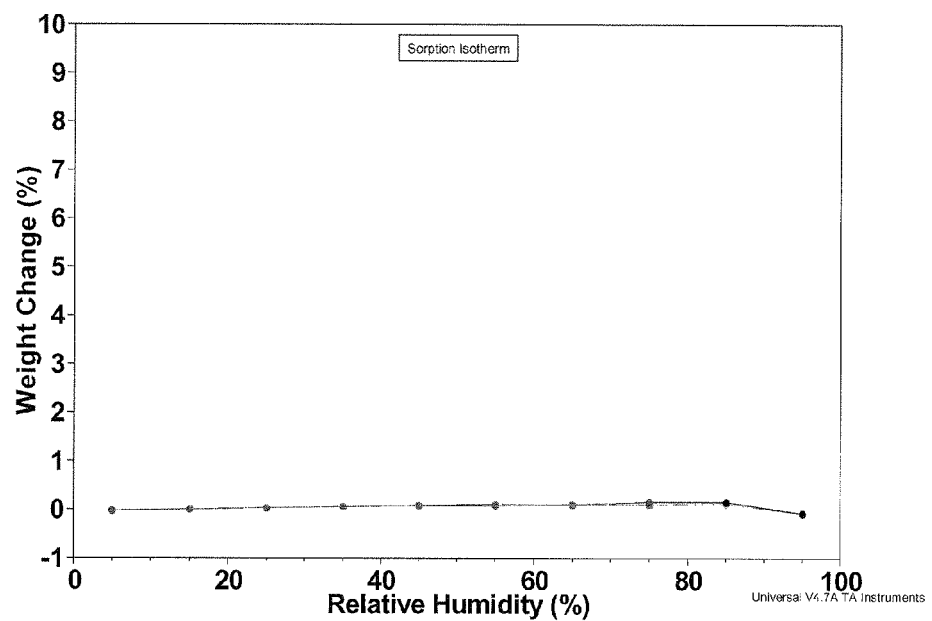
FIG. 43 is dynamic vapor sorption (DVS) curve of Compound I Form IX.

In some embodiments, Form IX is also characterized by a dynamic vapor sorption (DVS) curve substantially as shown in FIG. 43.

Compound I Form X is characterized by an X-ray powder diffractogram comprising peaks at 8.0, 19.0, and 20.4 °2θ±0.2 °2θ, as determined on a diffractometer using Cu—Kα radiation. The diffractogram comprises an additional peak at 13.9 °2θ±0.2 °2θ. Form X is also characterized by its full X-ray powder diffractogram as substantially shown in FIG. 44.

Figure 45:
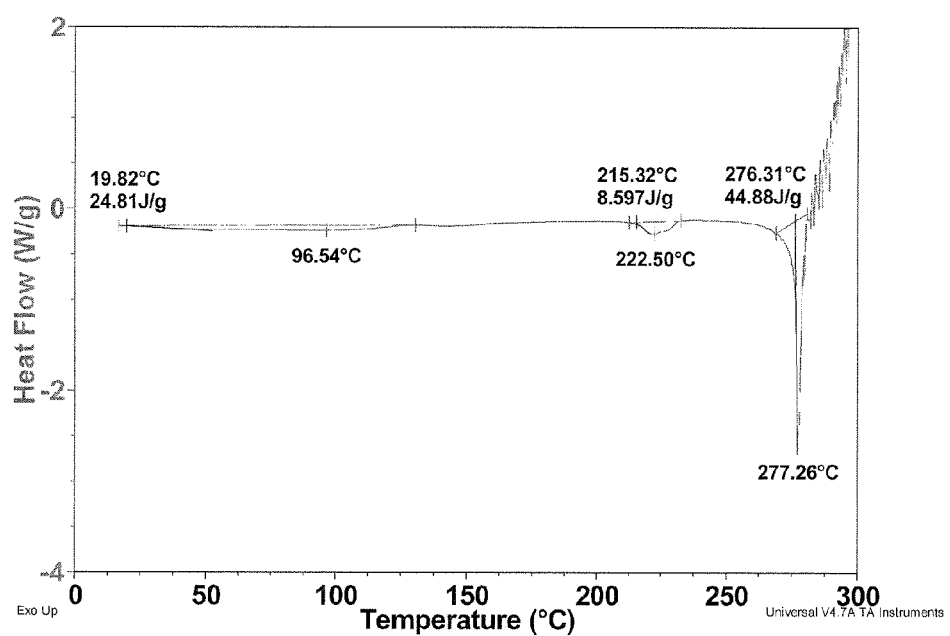
FIG. 45 is differential scanning calorimetry (DSC) curve of Compound I Form X.

In some embodiments, Form X is also characterized by its differential scanning calorimetry (DSC) curve substantially as shown in FIG. 45.

Figure 46:
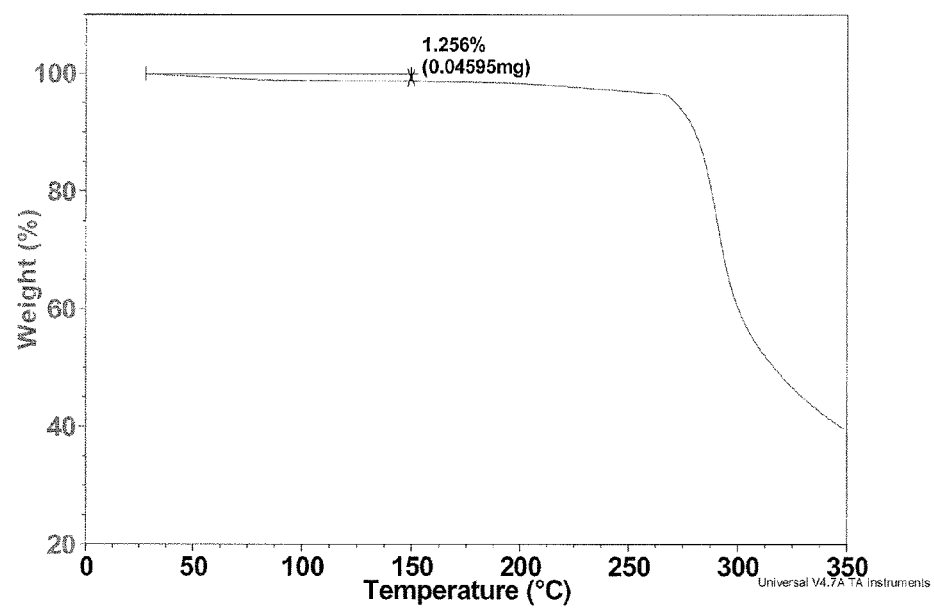
FIG. 46 is thermogravimetric analysis (TGA) of Compound I Form X.

In some embodiments, Form X is also characterized by thermogravimetric analysis (TGA) comprising a thermogram substantially as shown in FIG. 46.

Figure 47:
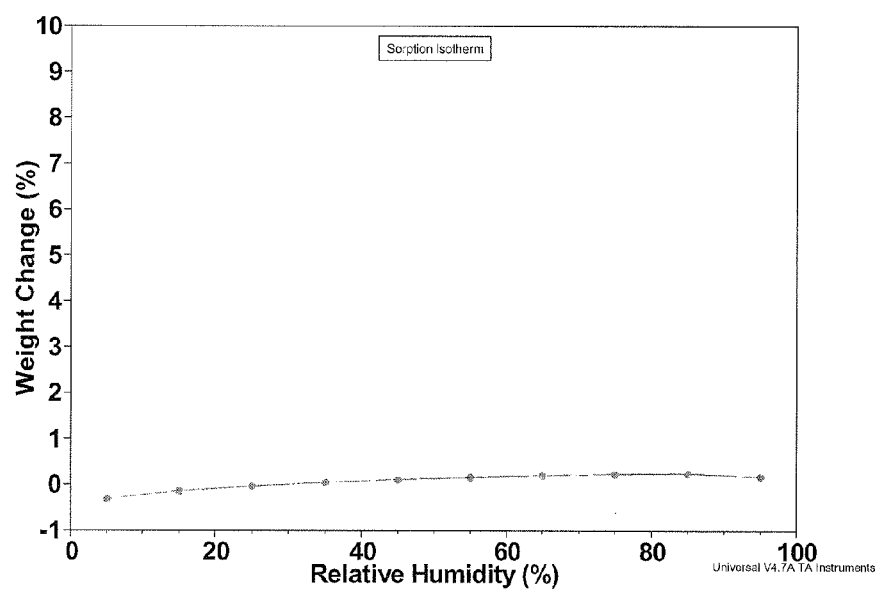
FIG. 47 is dynamic vapor sorption (DVS) curve of Compound I Form X.

In some embodiments, Form X is also characterized by a dynamic vapor sorption (DVS) curve substantially as shown in FIG. 47.

In one embodiment, Form X comprises about 0.58 mole equivalents of water.

Compound I Form XI is characterized by an X-ray powder diffractogram comprising peaks at 11.0, 13.9, and 20.9 °2θ±0.2 °2θ, as determined on a diffractometer using Cu—Kα radiation. The diffractogram comprises an additional peak at 15.2 °2θ±0.2 °2θ. Form XI is also characterized by its full X-ray powder diffractogram as substantially shown in FIG. 48.

Figure 49:
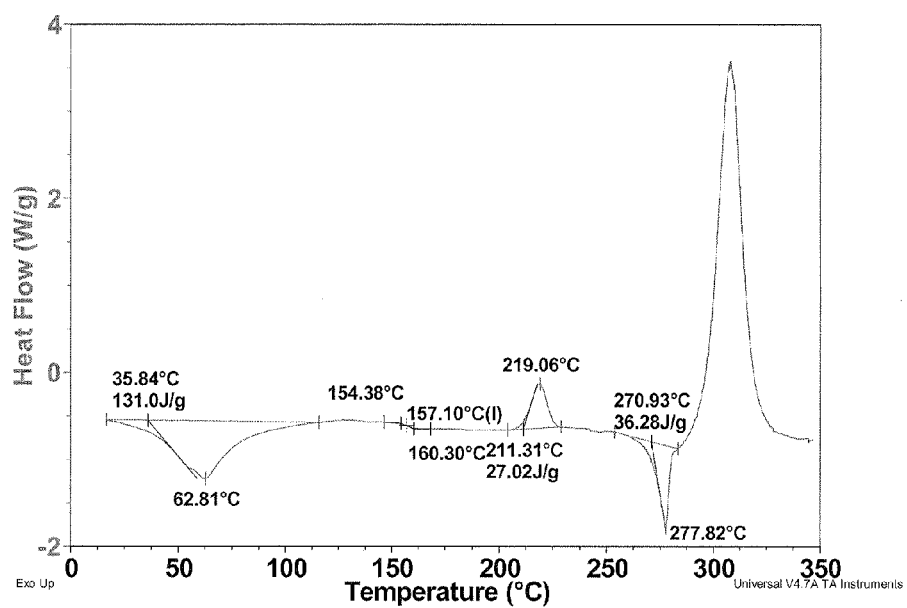
FIG. 49 is differential scanning calorimetry (DSC) curve of Compound I Form XI.

In some embodiments, Form XI is also characterized by its differential scanning calorimetry (DSC) curve substantially as shown in FIG. 49.

Figure 50:
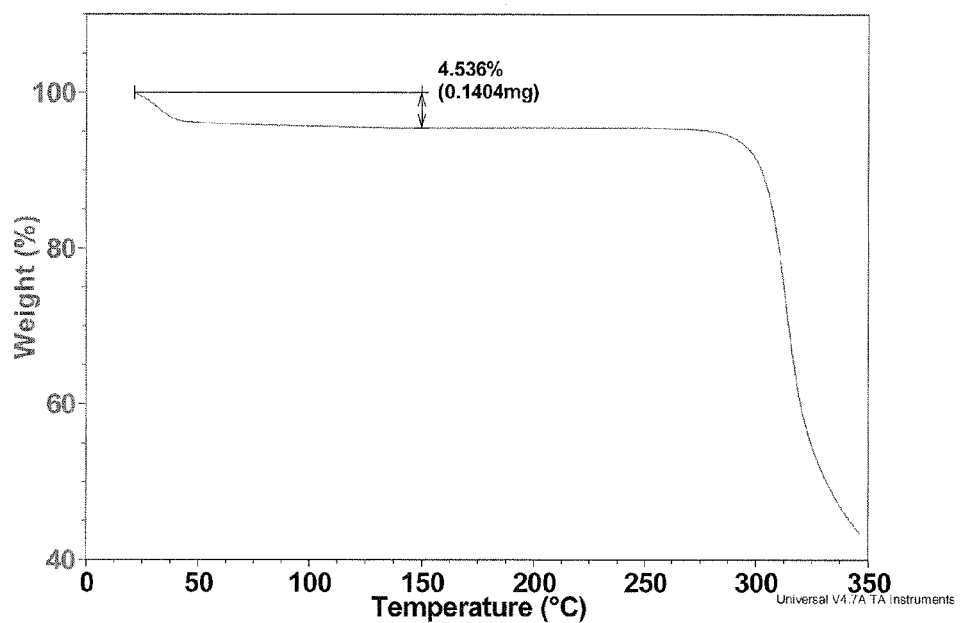
FIG. 50 is thermogravimetric analysis (TGA) of Compound I Form XI.

In some embodiments, Form XI is also characterized by thermogravimetric analysis (TGA) comprising a thermogram substantially as shown in FIG. 50.

Figure 51:
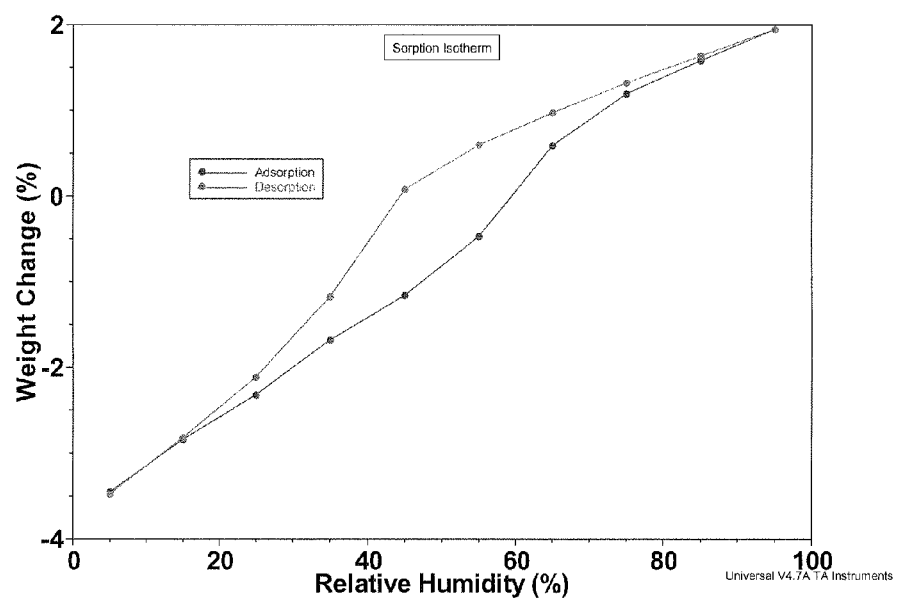
FIG. 51 is dynamic vapor sorption (DVS) curve of Compound I Form XI.

In some embodiments, Form XI is also characterized by a dynamic vapor sorption (DVS) curve substantially as shown in FIG. 51.

In one embodiment, Form XI comprises about 2.3 mole equivalents of water.

Compound I Form XII is characterized by an X-ray powder diffractogram comprising peaks at 12.4, 14.6, and 19.3 °2θ±0.2 °2θ, as determined on a diffractometer using Cu—Kα radiation. The diffractogram comprises an additional peak at 15.4 °2θ±0.2 °2θ. Form XII is also characterized by its full X-ray powder diffractogram as substantially shown in FIG. 52.

Figure 53:
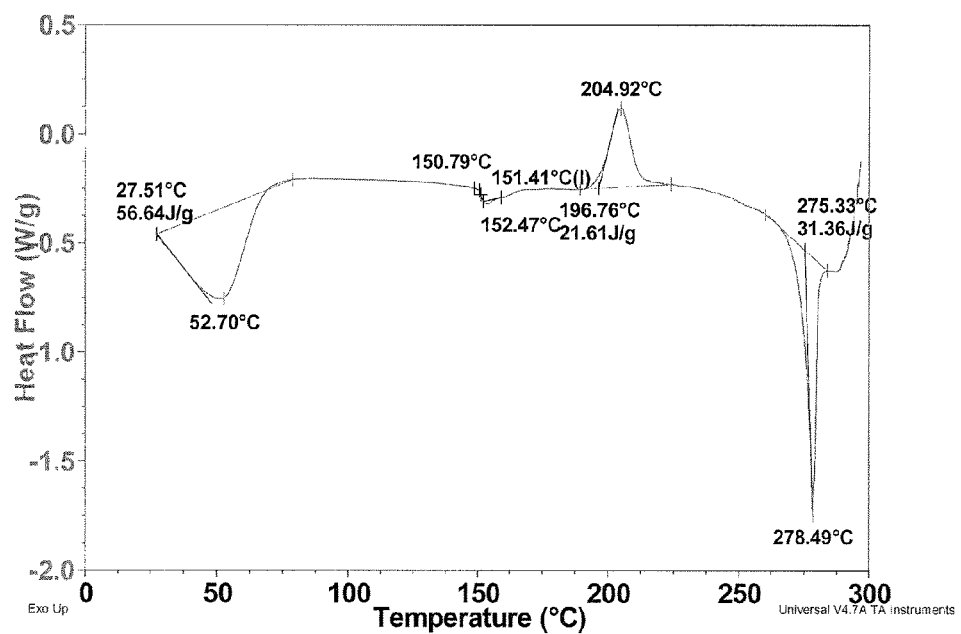
FIG. 53 is differential scanning calorimetry (DSC) curve of Compound I Form XII.

In some embodiments, Form XII is also characterized by its differential scanning calorimetry (DSC) curve substantially as shown in FIG. 53.

Figure 54:
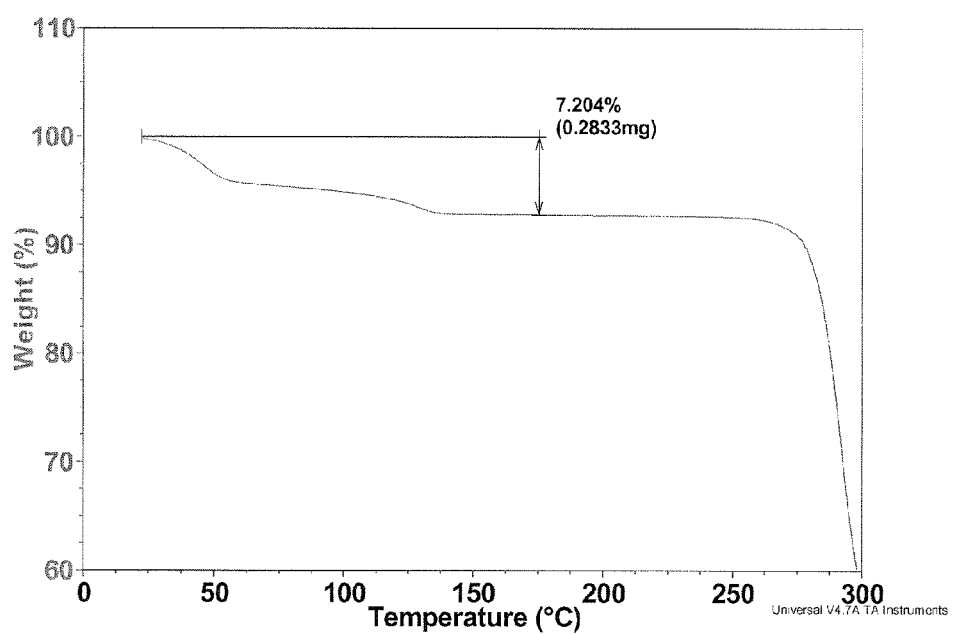
FIG. 54 is thermogravimetric analysis (TGA) of Compound I Form XII.

In some embodiments, Form XII is also characterized by thermogravimetric analysis (TGA) comprising a thermogram substantially as shown in FIG. 54.

Figure 55:
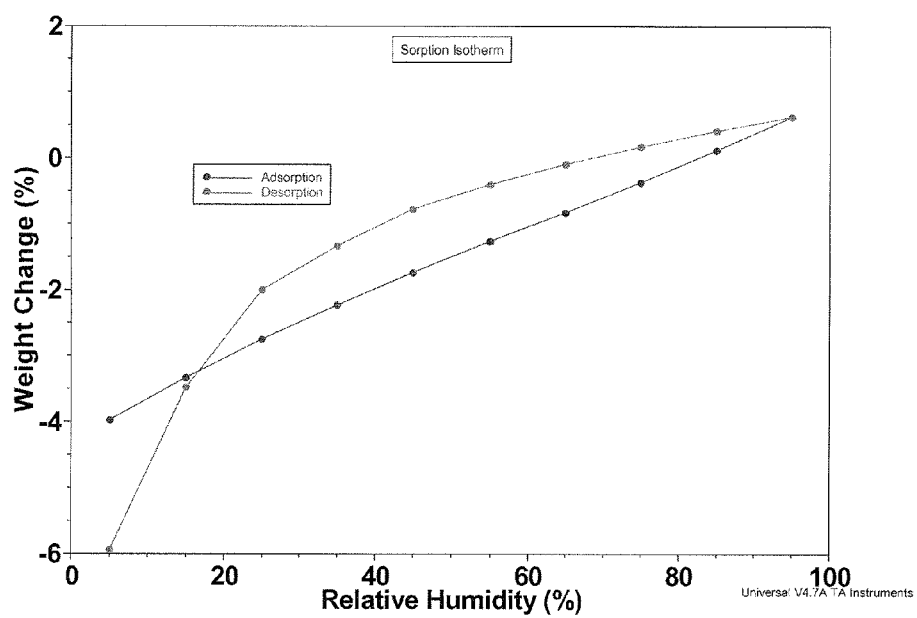
FIG. 55 is dynamic vapor sorption (DVS) curve of Compound I Form XII.

In some embodiments, Form XII is also characterized by a dynamic vapor sorption (DVS) curve substantially as shown in FIG. 55.

In one embodiment, Form XII comprises about 3.7 mole equivalents of water.

Compound I Form XIII is characterized by an X-ray powder diffractogram comprising peaks at 8.5, 11.0, and 15.4 °2θ±0.2 °2θ, as determined on a diffractometer using Cu—Kα radiation. The diffractogram comprises an additional peak at 22.2 °2θ±0.2 °2θ. Form XIII is also characterized by its full X-ray powder diffractogram as substantially shown in FIG. 56.

Figure 57:
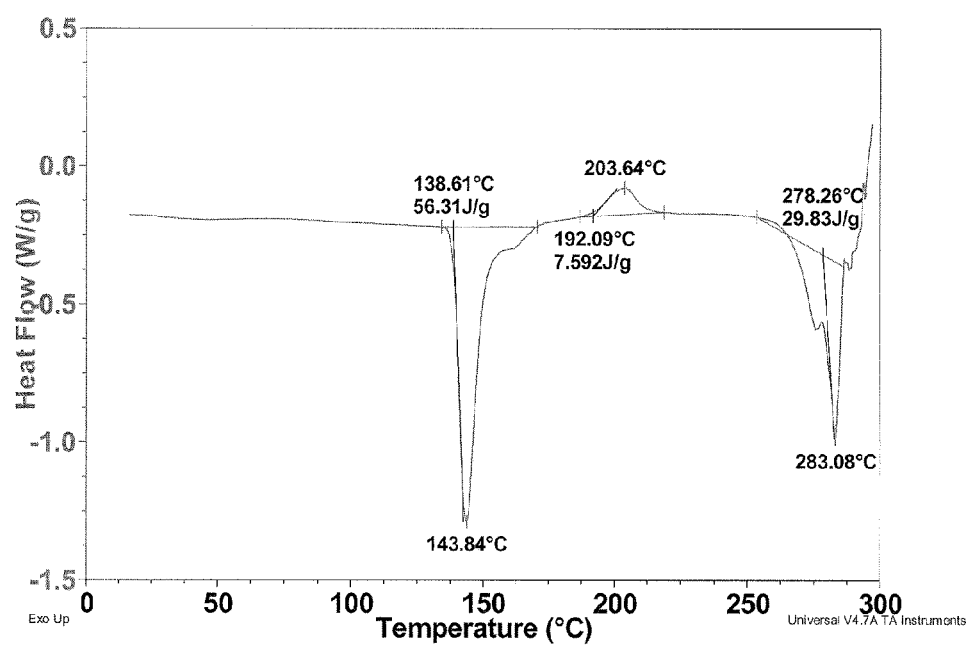
FIG. 57 is differential scanning calorimetry (DSC) curve of Compound I Form XIII.

In some embodiments, Form XIII is also characterized by its differential scanning calorimetry (DSC) curve substantially as shown in FIG. 57.

Figure 58:
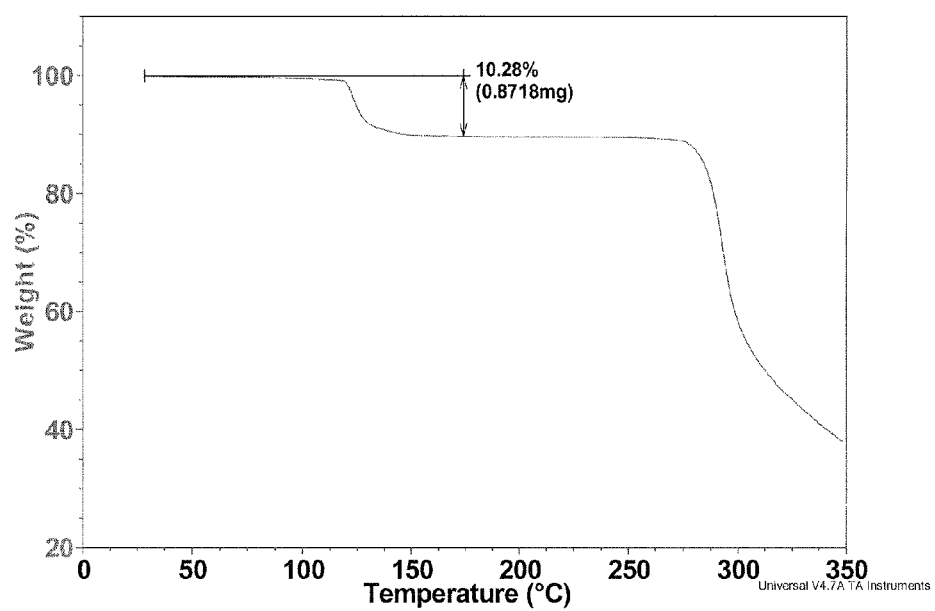
FIG. 58 is thermogravimetric analysis (TGA) of Compound I Form XIII.

In some embodiments, Form XIII is also characterized by thermogravimetric analysis (TGA) comprising a thermogram substantially as shown in FIG. 58.

Figure 59:
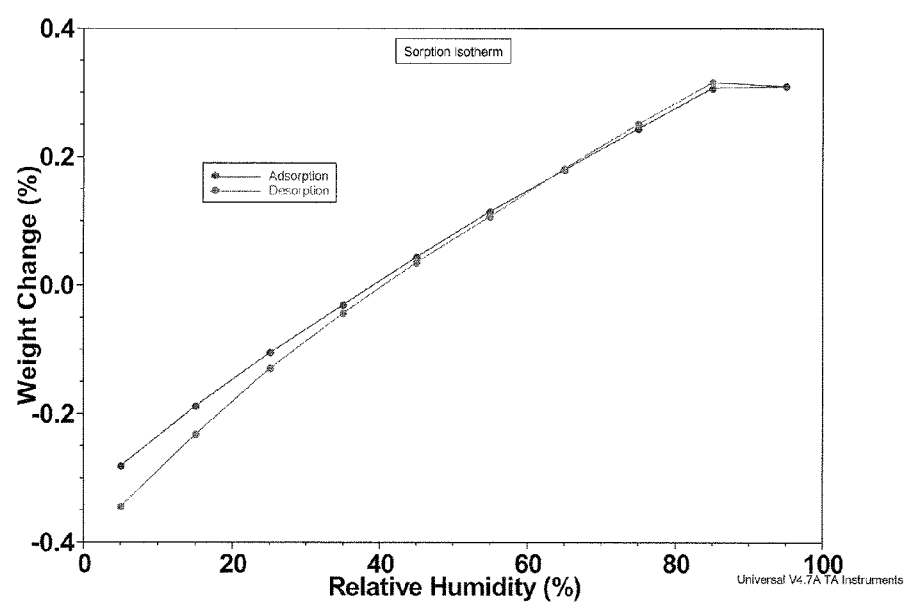
FIG. 59 is dynamic vapor sorption (DVS) curve of Compound I Form XIII.

In some embodiments, Form XIII is also characterized by a dynamic vapor sorption (DVS) curve substantially as shown in FIG. 59.

Compound I Form XIV is characterized by an X-ray powder diffractogram comprising peaks at 11.2, 15.7, and 17.9 °2θ±0.2 °2θ, as determined on a diffractometer using Cu—Kα radiation. The diffractogram comprises an additional peak at 23.1 °2θ±0.2 °2θ. Form XIV is also characterized by its full X-ray powder diffractogram as substantially shown in FIG. 60.

Figure 61:
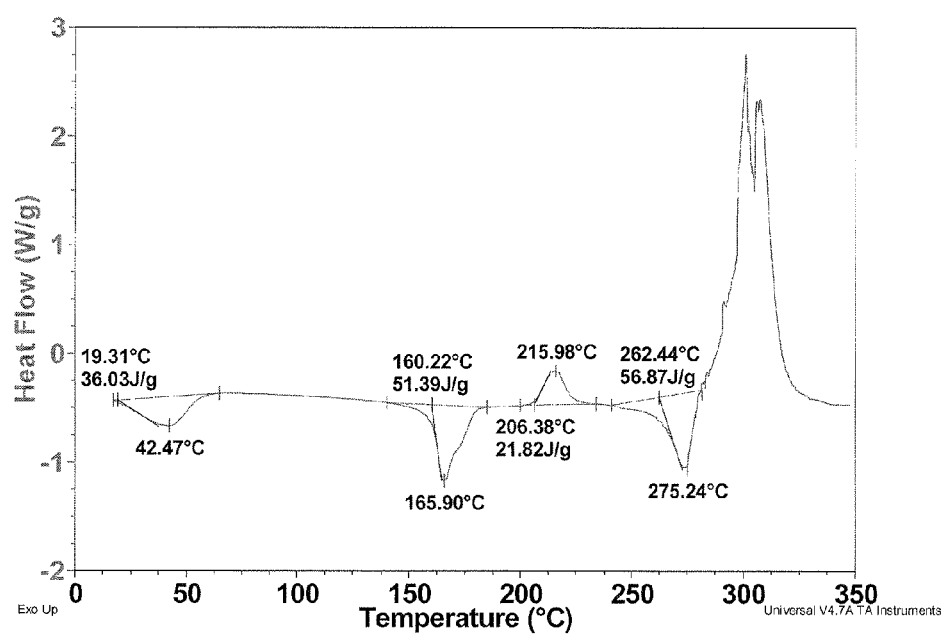
FIG. 61 is differential scanning calorimetry (DSC) curve of Compound I Form XIV.

In some embodiments, Form XIV is also characterized by its differential scanning calorimetry (DSC) curve substantially as shown in FIG. 61.

Figure 62:
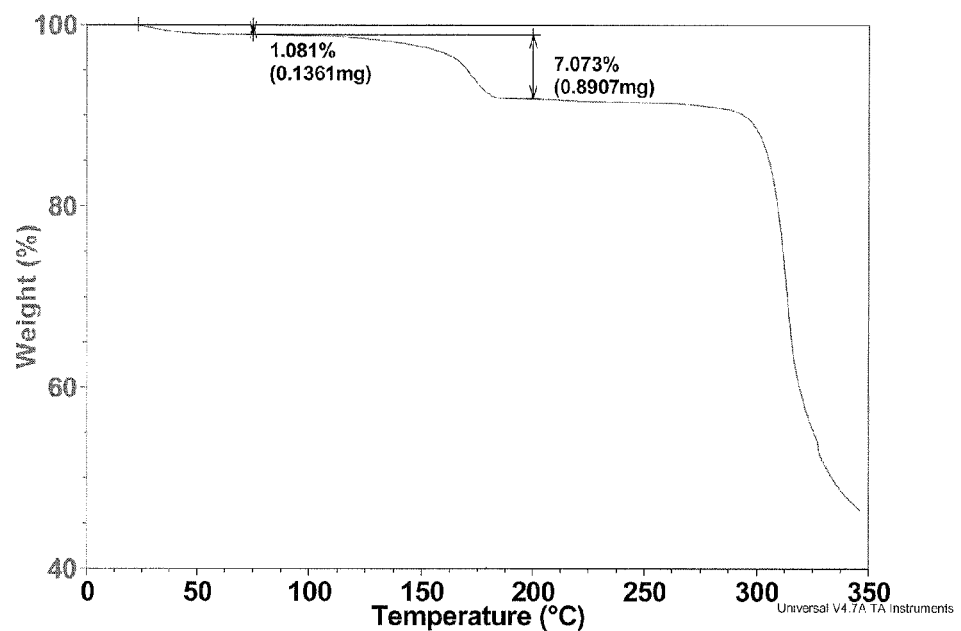
FIG. 62 is thermogravimetric analysis (TGA) of Compound I Form XIV.

In some embodiments, Form XIV is also characterized by thermogravimetric analysis (TGA) comprising a thermogram substantially as shown in FIG. 62.

Figure 63:
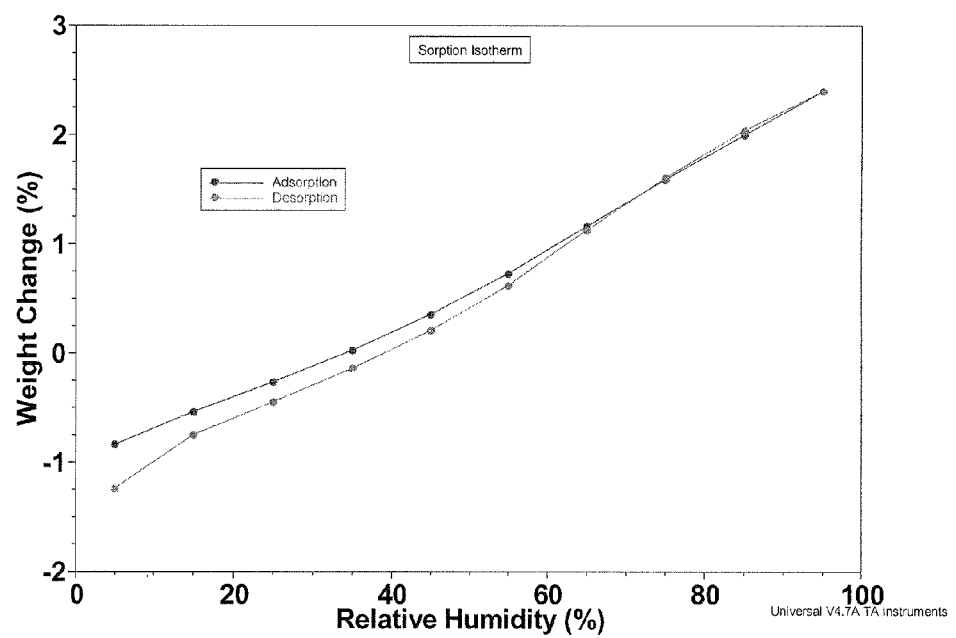
FIG. 63 is dynamic vapor sorption (DVS) curve of Compound I Form XIV.

In some embodiments, Form XIV is also characterized by a dynamic vapor sorption (DVS) curve substantially as shown in FIG. 63.

Compound I Form XV is characterized by an X-ray powder diffractogram comprising peaks at 9.7, 11.0, and 15.5 °2θ±0.2 °2θ, as determined on a diffractometer using Cu—Kα radiation. The diffractogram comprises an additional peak at 19.7 °2θ±0.2 °2θ. Form XV is also characterized by its full X-ray powder diffractogram as substantially shown in FIG. 64.

Figure 65:
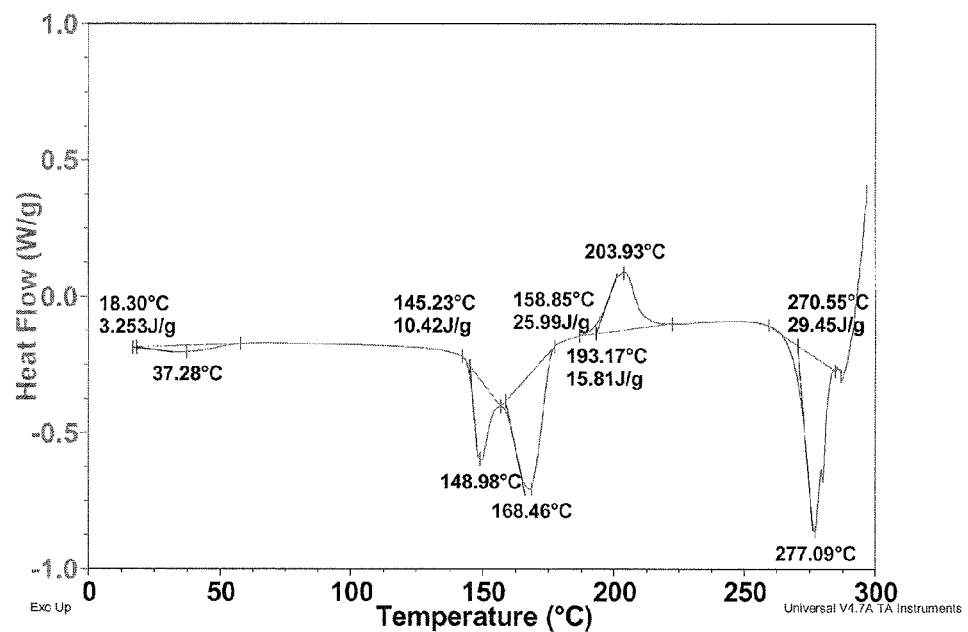
FIG. 65 is differential scanning calorimetry (DSC) curve of Compound I Form XV.

In some embodiments, Form XV is also characterized by its differential scanning calorimetry (DSC) curve substantially as shown in FIG. 65.

Figure 66:
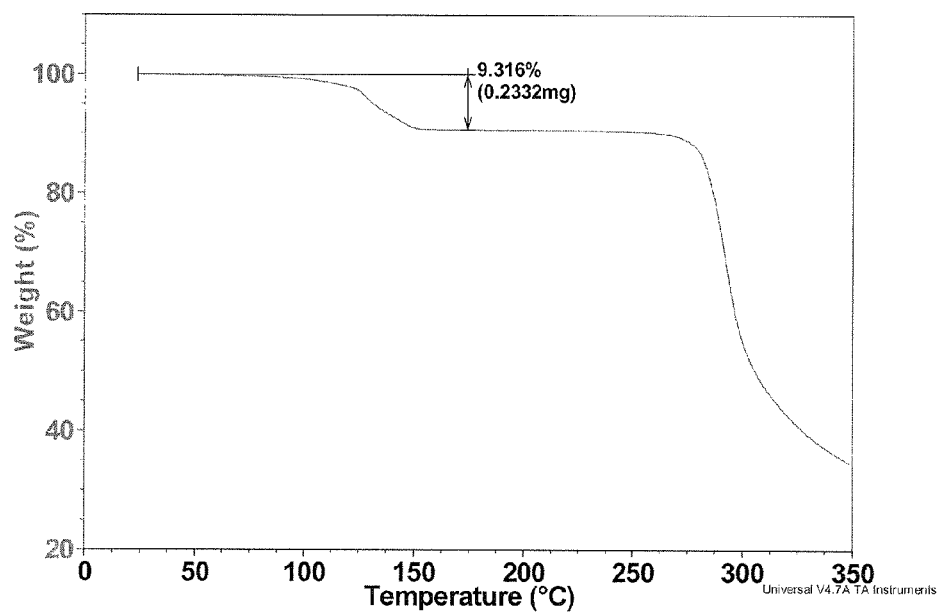
FIG. 66 is thermogravimetric analysis (TGA) of Compound I Form XV.

In some embodiments, Form XV is also characterized by thermogravimetric analysis (TGA) comprising a thermogram substantially as shown in FIG. 66.

Figure 67:
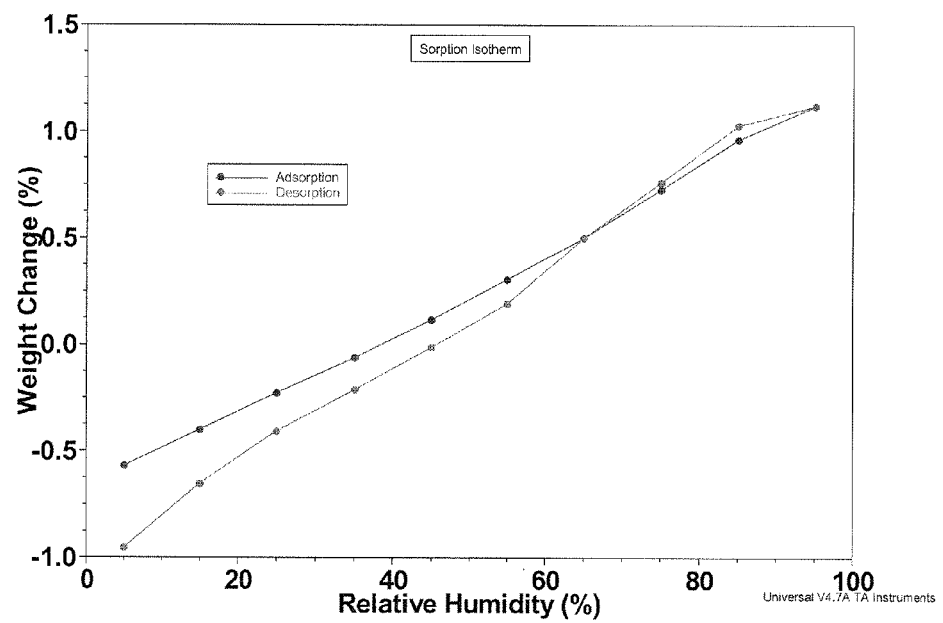
FIG. 67 is dynamic vapor sorption (DVS) curve of Compound I Form XV.

In some embodiments, Form XV is also characterized by a dynamic vapor sorption (DVS) curve substantially as shown in FIG. 67.

Compound I Form XVI is characterized by an X-ray powder diffractogram comprising peaks at 5.8, 7.8, and 18.8 °2θ±0.2 °2θ, as determined on a diffractometer using Cu—Kα radiation. The diffractogram comprises an additional peak at 25.0 °2θ±0.2 °2θ. Form XVI is also characterized by its full X-ray powder diffractogram as substantially shown in FIG. 68.

Figure 69:
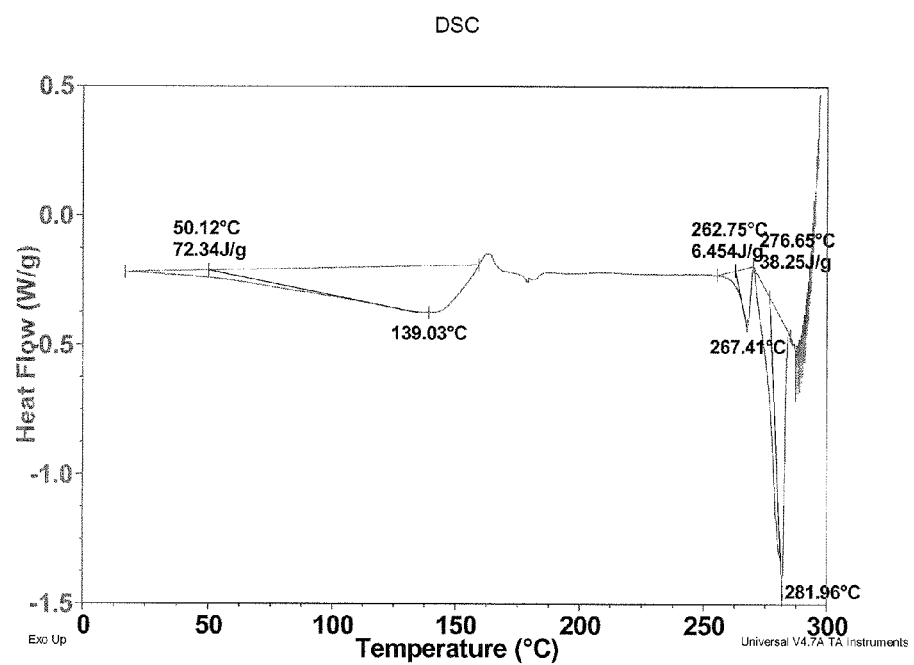
FIG. 69 is differential scanning calorimetry (DSC) curve of Compound I Form XVI.

In some embodiments, Form XVI is also characterized by its differential scanning calorimetry (DSC) curve substantially as shown in FIG. 69.

Figure 70:
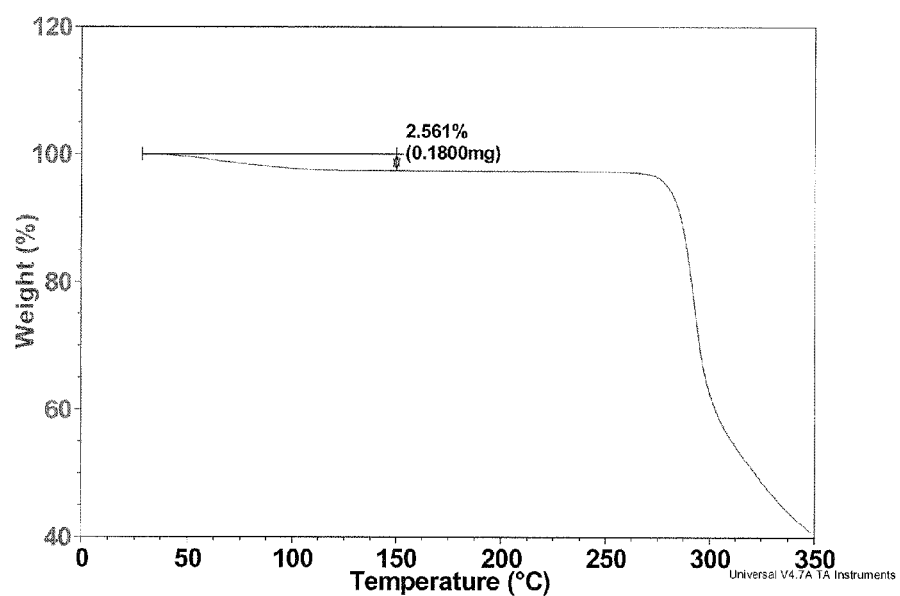
FIG. 70 is thermogravimetric analysis (TGA) of Compound I Form XVI.

In some embodiments, Form XVI is also characterized by thermogravimetric analysis (TGA) comprising a thermogram substantially as shown in FIG. 70.

Compound I Form XVII is characterized by an X-ray powder diffractogram comprising peaks at 7.9, 18.9, and 20.3 °2θ±0.2 °2θ, as determined on a diffractometer using Cu—Kα radiation. The diffractogram comprises an additional peak at 21.5 °2θ±0.2 °2θ. Form XVII is also characterized by its full X-ray powder diffractogram as substantially shown in FIG. 71.

Figure 72:
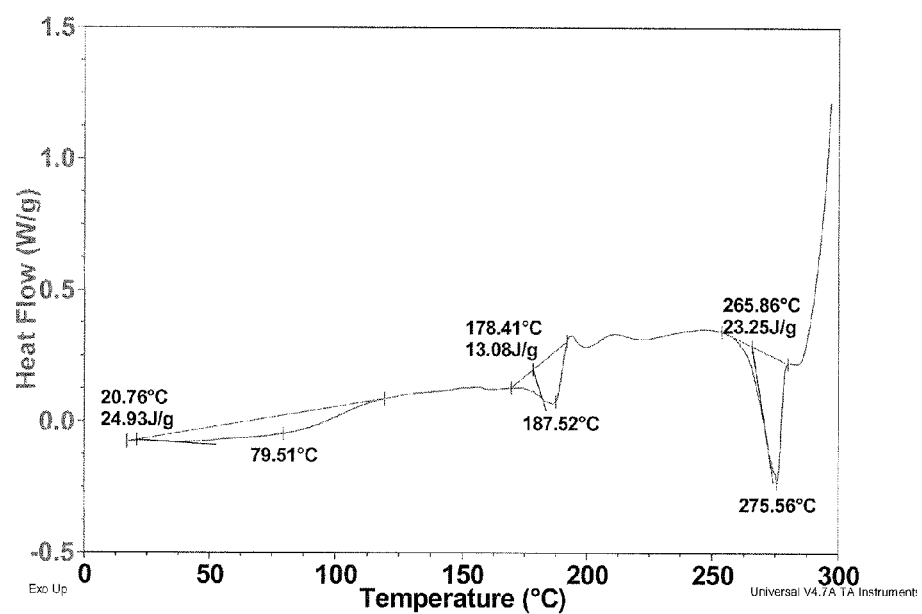
FIG. 72 is differential scanning calorimetry (DSC) curve of Compound I Form XVII.

In some embodiments, Form XVII is also characterized by its differential scanning calorimetry (DSC) curve substantially as shown in FIG. 72.

Figure 73:
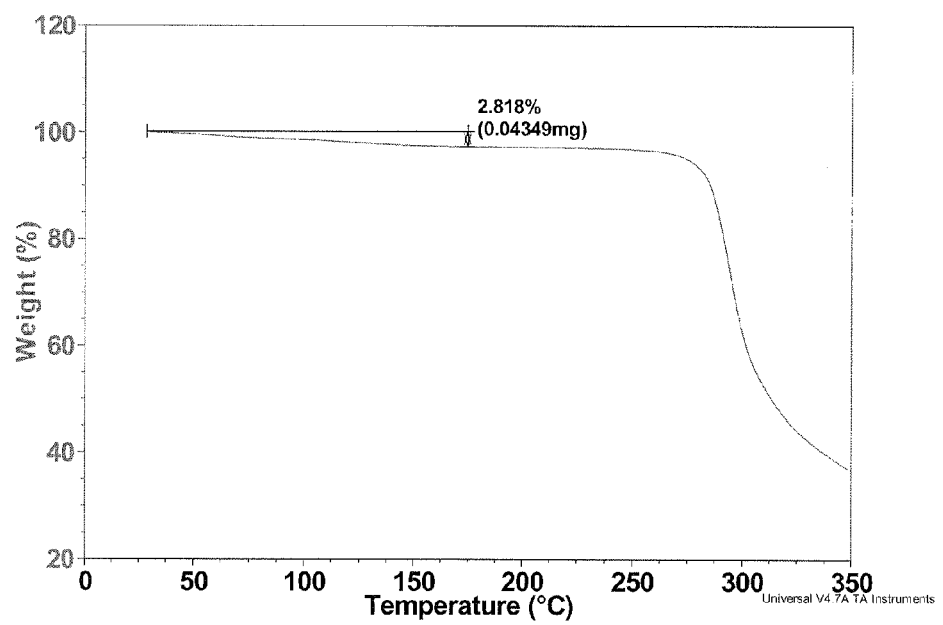
FIG. 73 is thermogravimetric analysis (TGA) of Compound I Form XVII.

In some embodiments, Form XVII is also characterized by thermogravimetric analysis (TGA) comprising a thermogram substantially as shown in FIG. 73.

Compound I Form XVIII is characterized by an X-ray powder diffractogram comprising peaks at 5.6, 6.4, and 7.5 °2θ±0.2 °2θ, as determined on a diffractometer using Cu—Kα radiation. The diffractogram comprises an additional peak at 16.6 °2θ±0.2 °2θ. Form XVIII is also characterized by its full X-ray powder diffractogram as substantially shown in FIG. 74.

Figure 75:
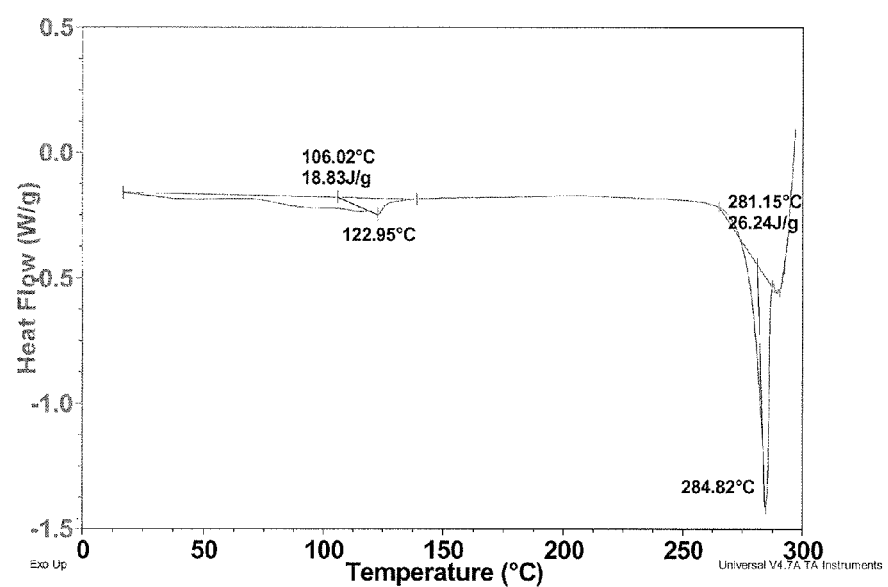
FIG. 75 is differential scanning calorimetry (DSC) curve of Compound I Form XVIII.

In some embodiments, Form XVIII is also characterized by its differential scanning calorimetry (DSC) curve substantially as shown in FIG. 75.

Figure 76:
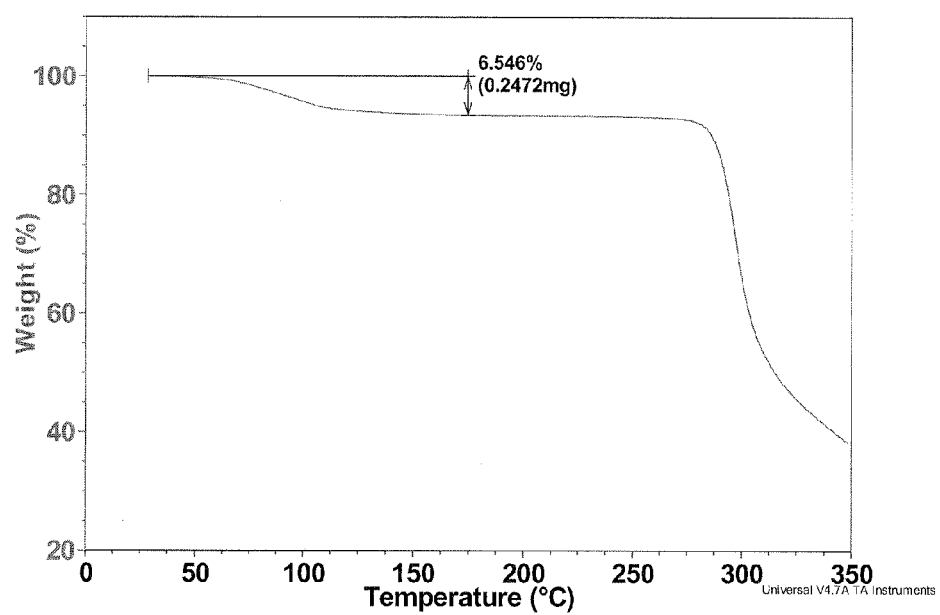
FIG. 76 is thermogravimetric analysis (TGA) of Compound I Form XVIII.

In some embodiments, Form XVIII is also characterized by thermogravimetric analysis (TGA) comprising a thermogram substantially as shown in FIG. 76.

Figure 77:
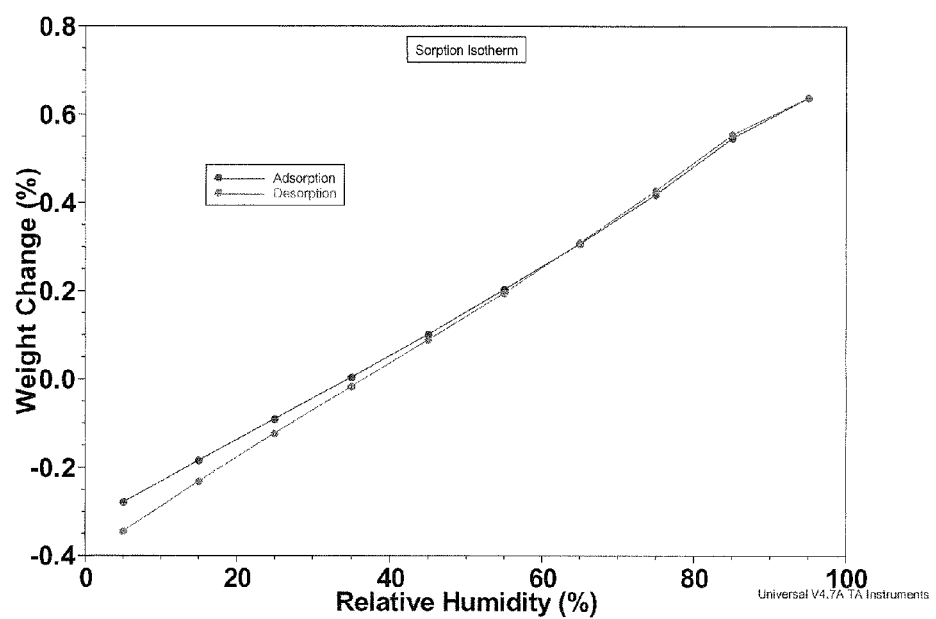
FIG. 77 is dynamic vapor sorption (DVS) curve of Compound I Form XVIII.

In some embodiments, Form XVIII is also characterized by a dynamic vapor sorption (DVS) curve substantially as shown in FIG. 77.

Figure 78:
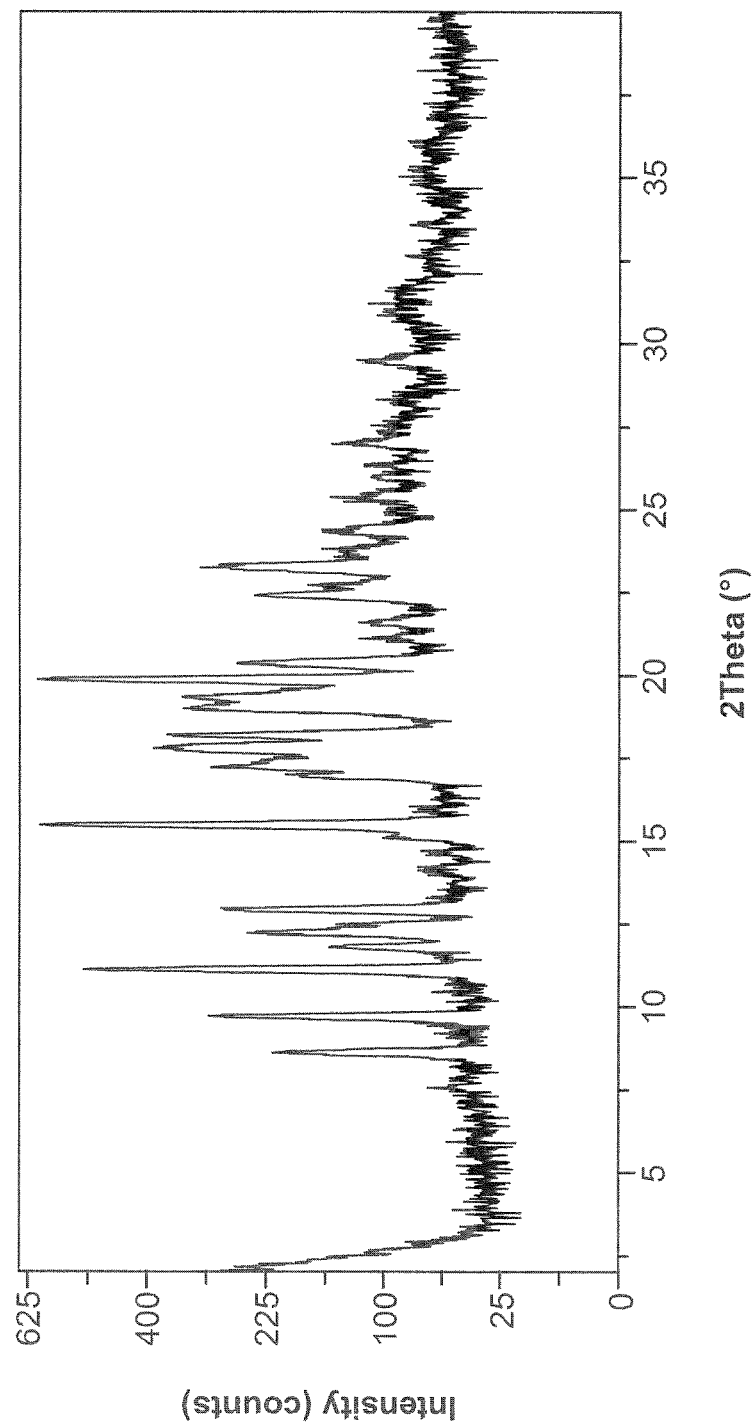
FIG. 78 is an X-ray powder diffraction pattern of Compound I Form XIX.

Compound I Form XIX is characterized by an X-ray powder diffractogram comprising peaks at 11.1, 15.5, and 19.8 °2θ±0.2 °2θ, as determined on a diffractometer using Cu—Kα radiation. The diffractogram comprises an additional peak at 23.3 °2θ±0.2 °2θ. Form XIX is also characterized by its full X-ray powder diffractogram as substantially as shown in FIG. 78.

Figure 79:
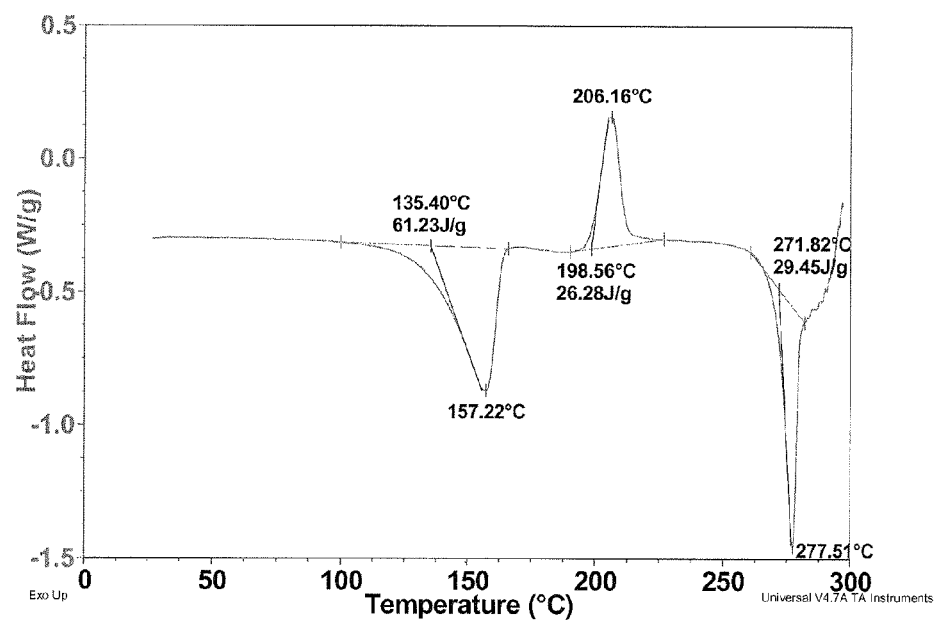
FIG. 79 is differential scanning calorimetry (DSC) curve of Compound I Form XIX.

In some embodiments, Form XIX is also characterized by its differential scanning calorimetry (DSC) curve substantially as shown in FIG. 79.

Figure 80:
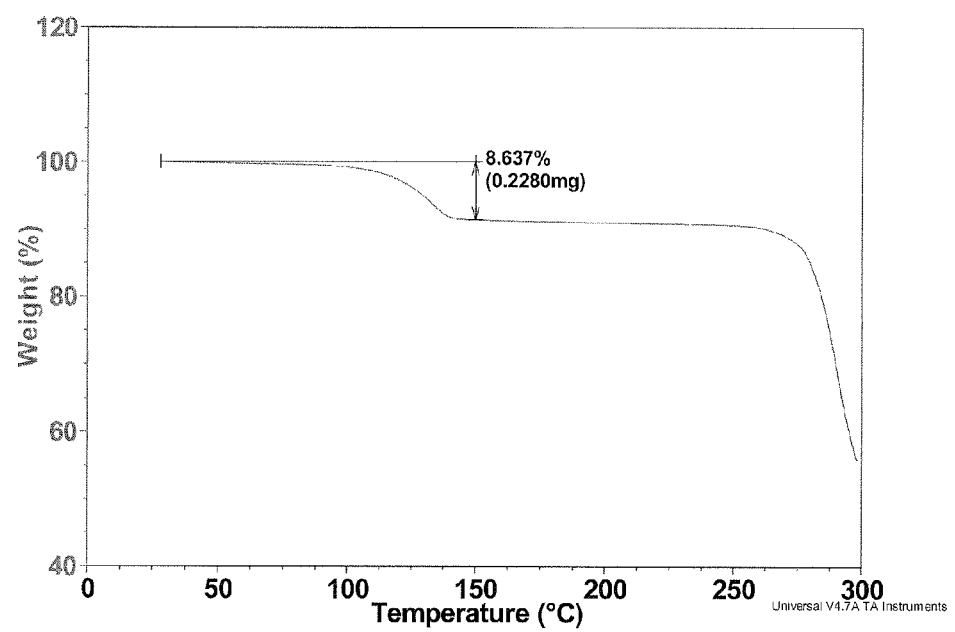
FIG. 80 is thermogravimetric analysis (TGA) of Compound I Form XIX.

In some embodiments, Form XIX is also characterized by thermogravimetric analysis (TGA) comprising a thermogram substantially as shown in FIG. 80.

Figure 81:
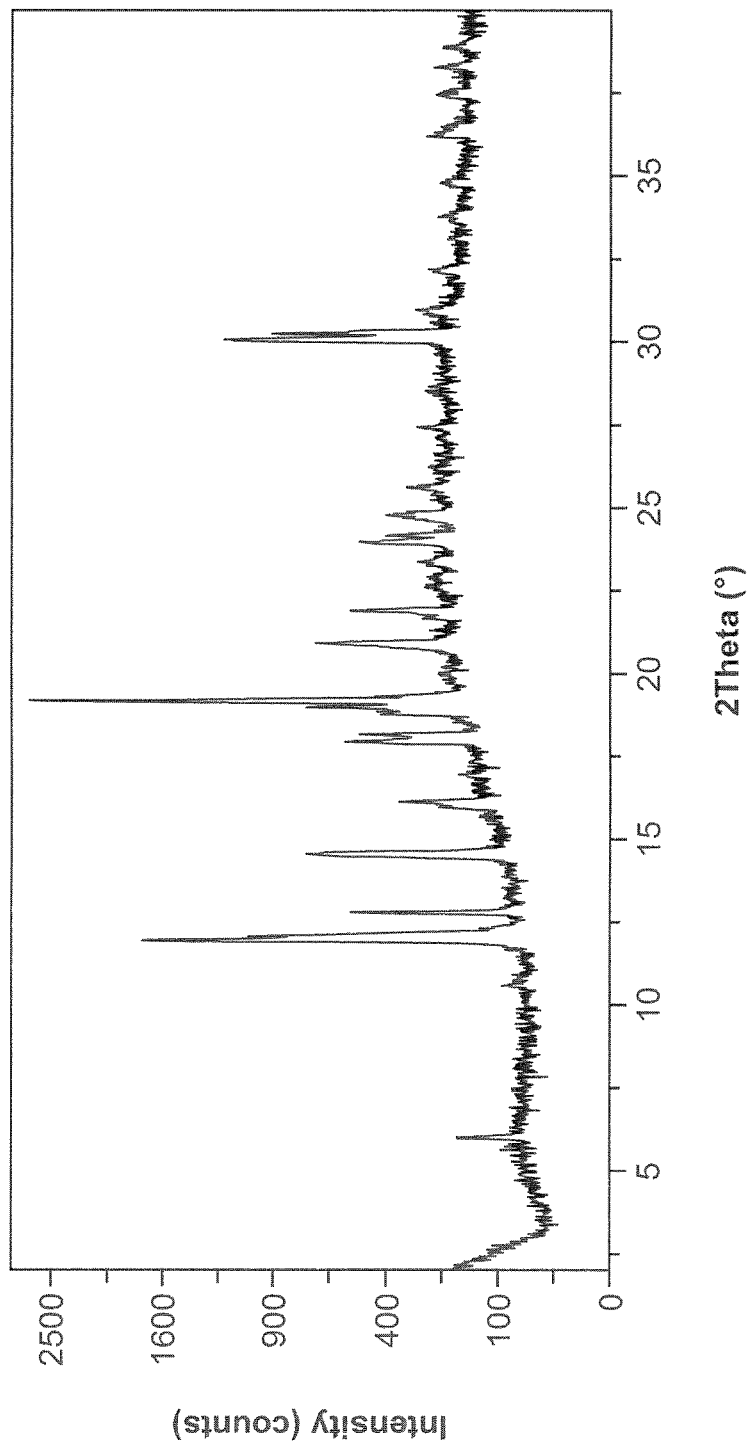
FIG. 81 is an X-ray powder diffraction pattern of Compound I Form XX.

Compound I Form XX is characterized by an X-ray powder diffractogram comprising peaks at 11.9, 14.5, and 19.1 °2θ±0.2 °2θ, as determined on a diffractometer using Cu—Kα radiation. The diffractogram comprises an additional peak at 30.0 °2θ±0.2 °2θ. Form XX is also characterized by its full X-ray powder diffractogram as substantially as shown in FIG. 81.

Figure 82:
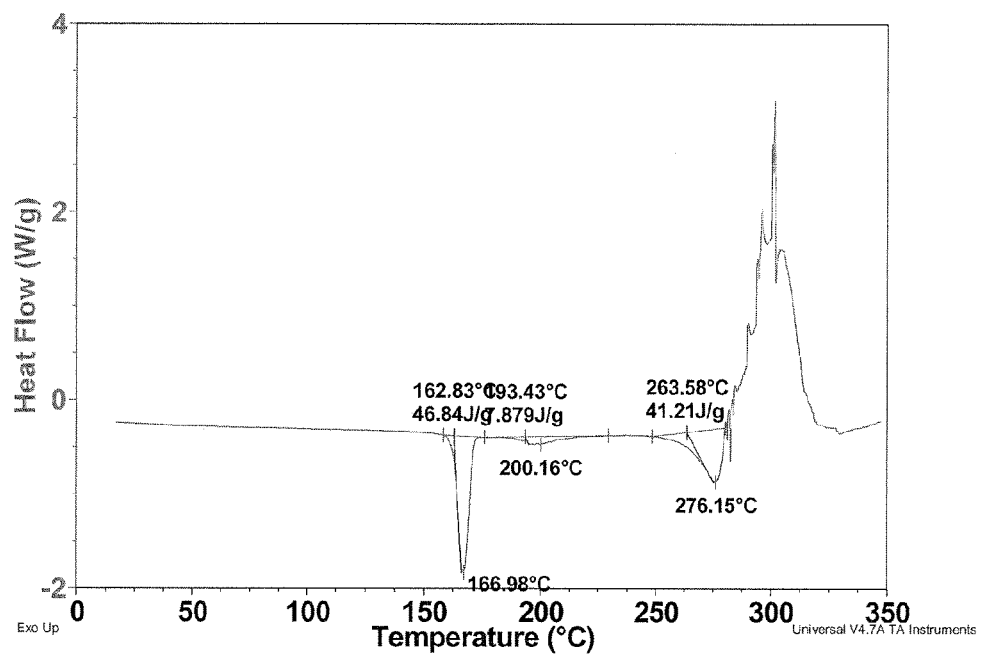
FIG. 82 is differential scanning calorimetry (DSC) curve of Compound I Form XX.

In some embodiments, Form XX is also characterized by its differential scanning calorimetry (DSC) curve substantially as shown in FIG. 82.

Figure 83:
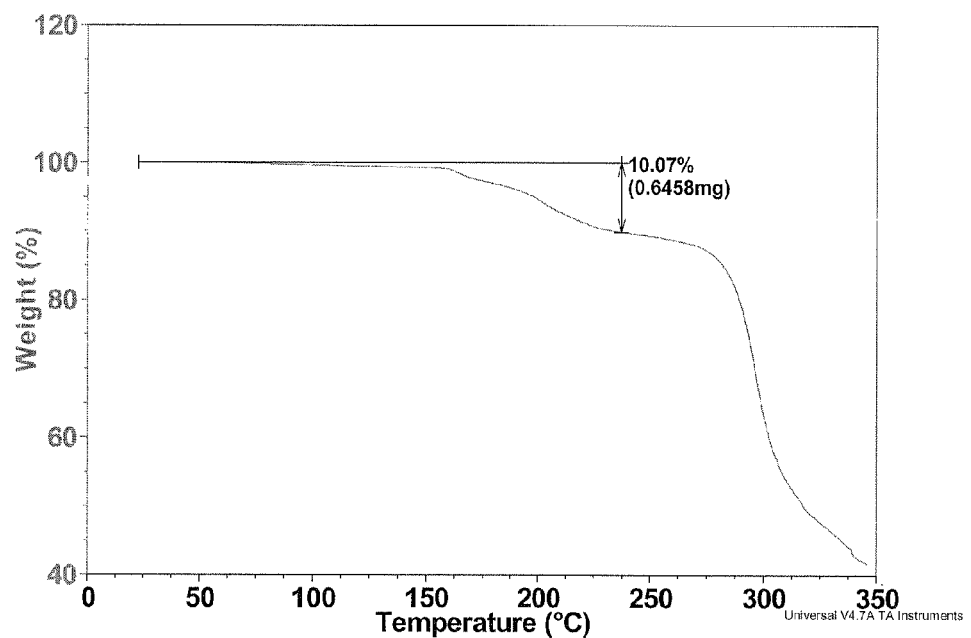
FIG. 83 is thermogravimetric analysis (TGA) of Compound I Form XX.

In some embodiments, Form XX is also characterized by thermogravimetric analysis (TGA) comprising a thermogram substantially as shown in FIG. 83.

Figure 84:
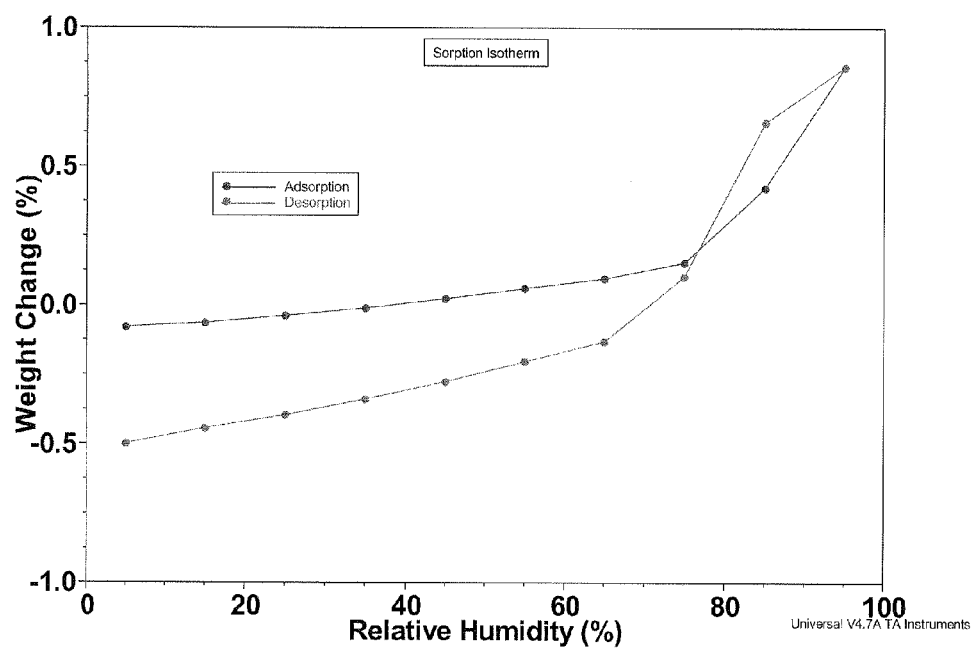
FIG. 84 is dynamic vapor sorption (DVS) curve of Compound I Form XX.

In some embodiments, Form XX is also characterized by a dynamic vapor sorption (DVS) curve substantially as shown in FIG. 84.

Figure 85:
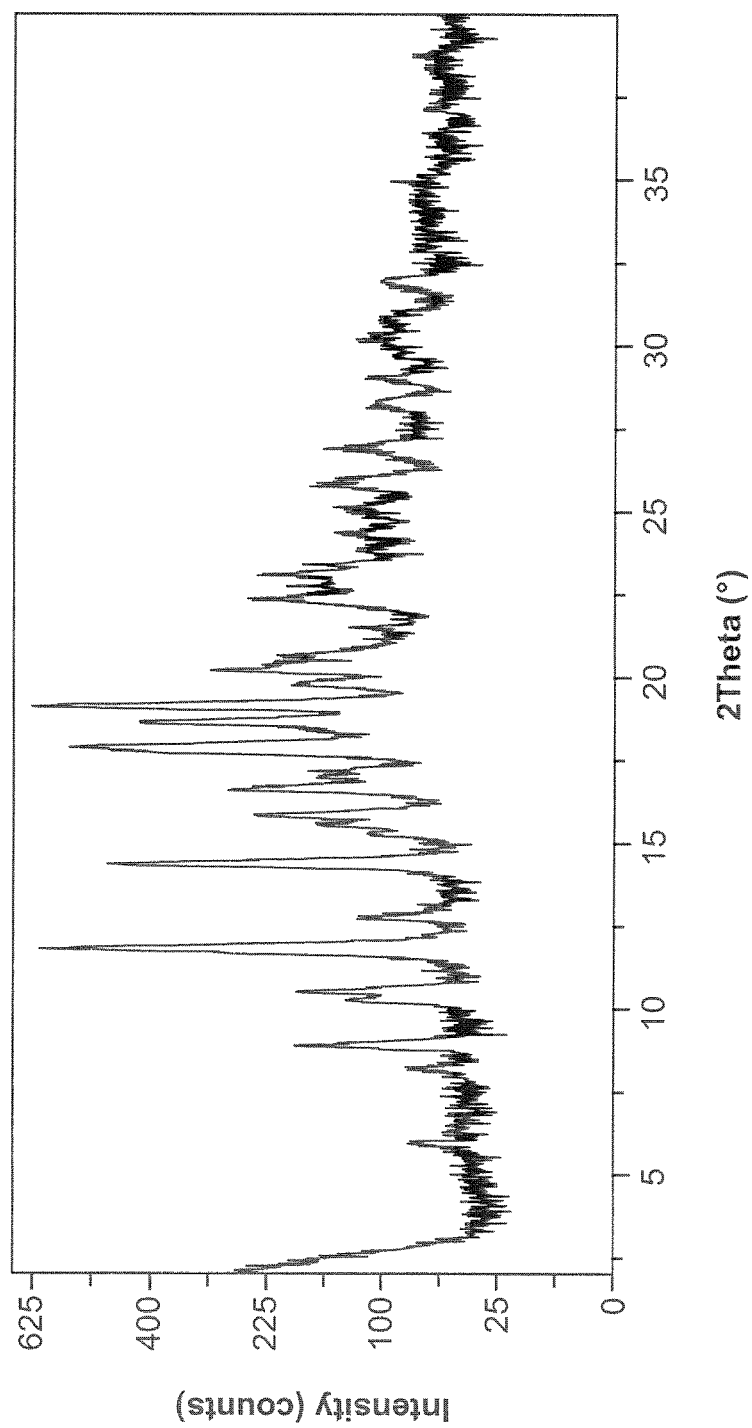
FIG. 85 is an X-ray powder diffraction pattern of Compound I Form XXI.

Compound I Form XXI is characterized by an X-ray powder diffractogram comprising peaks at 11.9, 12.2, and 14.4 °2θ±0.2 °2θ, as determined on a diffractometer using Cu—Kα radiation. The diffractogram comprises an additional peak at 19.1 °2θ±0.2 °2θ. Form XXI is also characterized by its full X-ray powder diffractogram as substantially as shown in FIG. 85.

Figure 86:
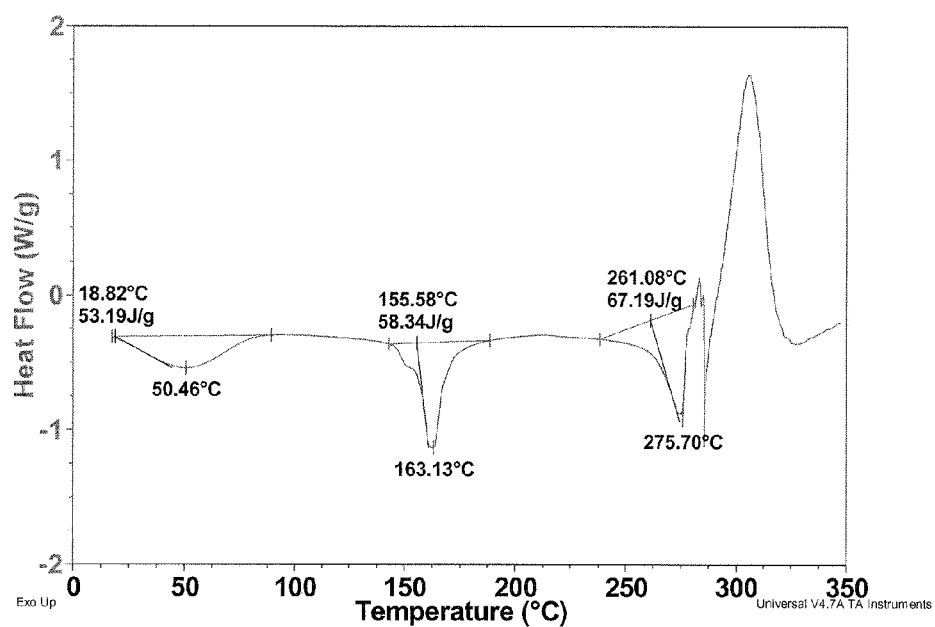
FIG. 86 is differential scanning calorimetry (DSC) curve of Compound I Form XXI.

In some embodiments, Form XXI is also characterized by its differential scanning calorimetry (DSC) curve substantially as shown in FIG. 86.

Figure 87:
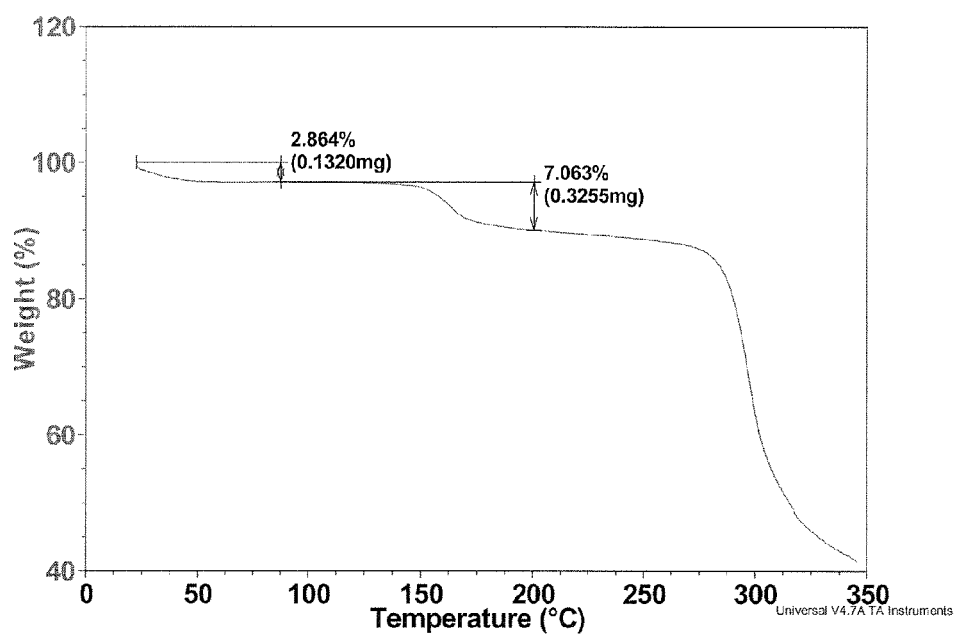
FIG. 87 is thermogravimetric analysis (TGA) of Compound I Form XXI.

In some embodiments, Form XXI is also characterized by thermogravimetric analysis (TGA) comprising a thermogram substantially as shown in FIG. 87.

Figure 88:
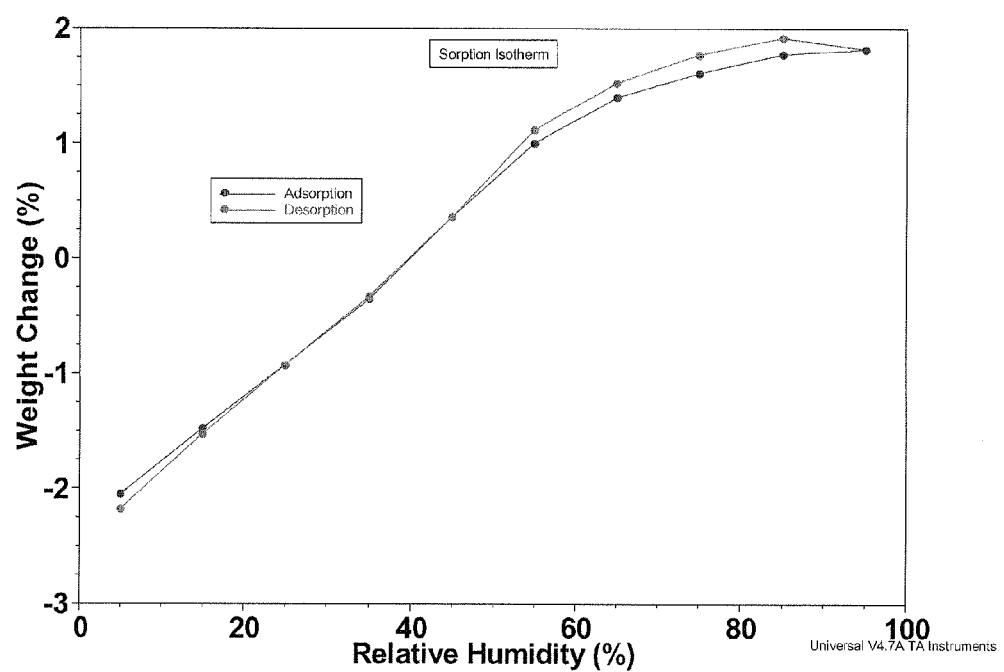
FIG. 88 is dynamic vapor sorption (DVS) curve of Compound I Form XXI.

In some embodiments, Form XXI is also characterized by a dynamic vapor sorption (DVS) curve substantially as shown in FIG. 88.

Figure 89:
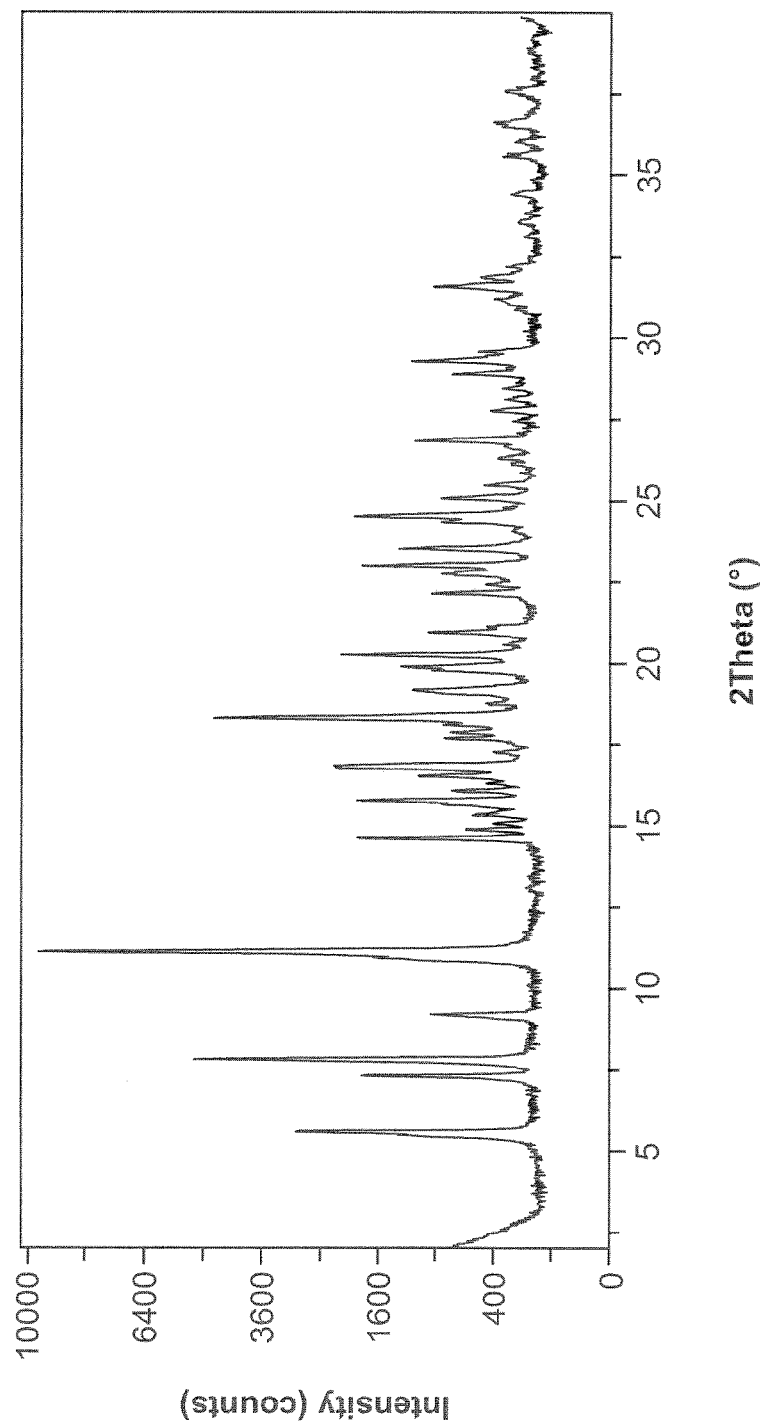
FIG. 89 is an X-ray powder diffraction pattern of Compound I sodium Form I.

Compound I sodium Form I is characterized by an X-ray powder diffractogram comprising peaks at 5.6, 7.8, and 11.2 °2θ±0.2 °2θ, as determined on a diffractometer using Cu—Kα radiation. The diffractogram comprises an additional peak at 18.4 °2θ±0.2 °2θ. Compound I sodium Form I is also characterized by its full X-ray powder diffractogram as substantially as shown in FIG. 89.

Figure 90:
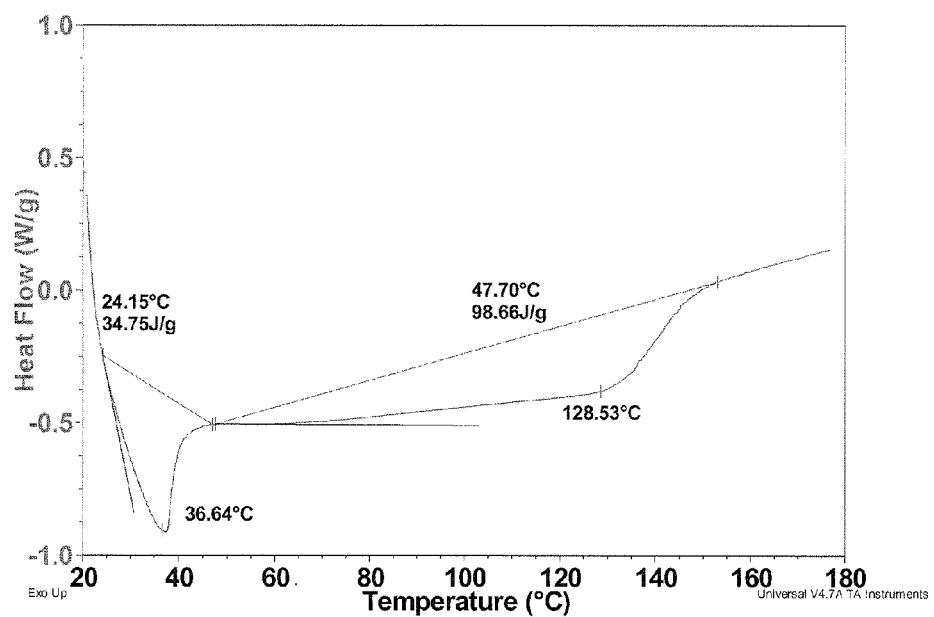
FIG. 90 is differential scanning calorimetry (DSC) curve of Compound I sodium Form I.

In some embodiments, Compound I sodium Form I is also characterized by its differential scanning calorimetry (DSC) curve substantially as shown in FIG. 90.

Figure 91:
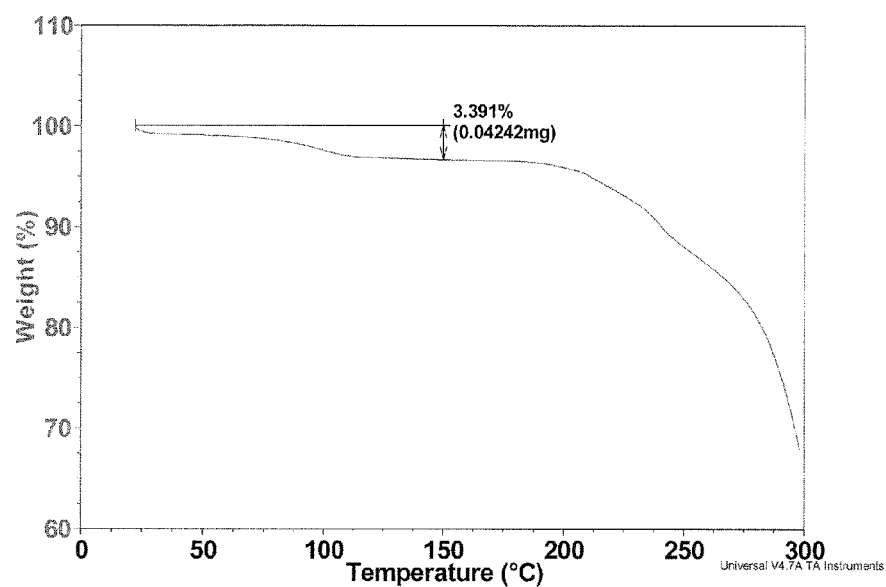
FIG. 91 is thermogravimetric analysis (TGA) of Compound I sodium Form I.

In some embodiments, Compound I sodium Form I is also characterized by thermogravimetric analysis (TGA) comprising a thermogram substantially as shown in FIG. 91.

Figure 92:
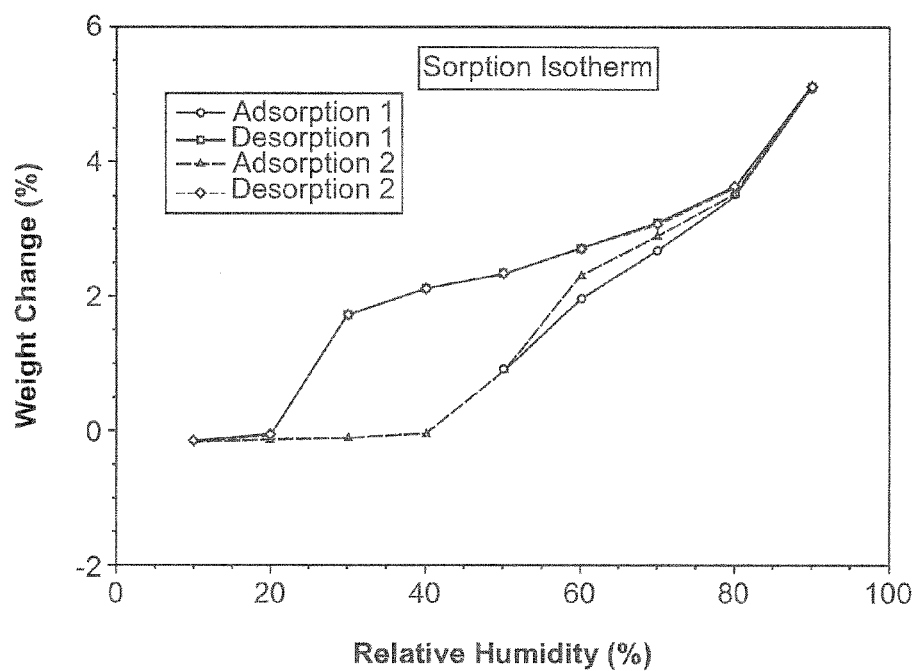
FIG. 92 is dynamic vapor sorption (DVS) curve of Compound I sodium Form I.

In some embodiments, Compound I sodium Form I is also characterized by a dynamic vapor sorption (DVS) curve substantially as shown in FIG. 92.

Compound I sodium Form II is characterized by an X-ray powder diffractogram comprising peaks at 5.8, 7.3, and 11.1 °2θ±0.2 °2θ, as determined on a diffractometer using Cu—Kα radiation. The diffractogram comprises an additional peak at 19.0 °2θ±0.2 °2θ. Compound I sodium Form II is also characterized by its full X-ray powder diffractogram as substantially shown in FIG. 93.

Figure 94:
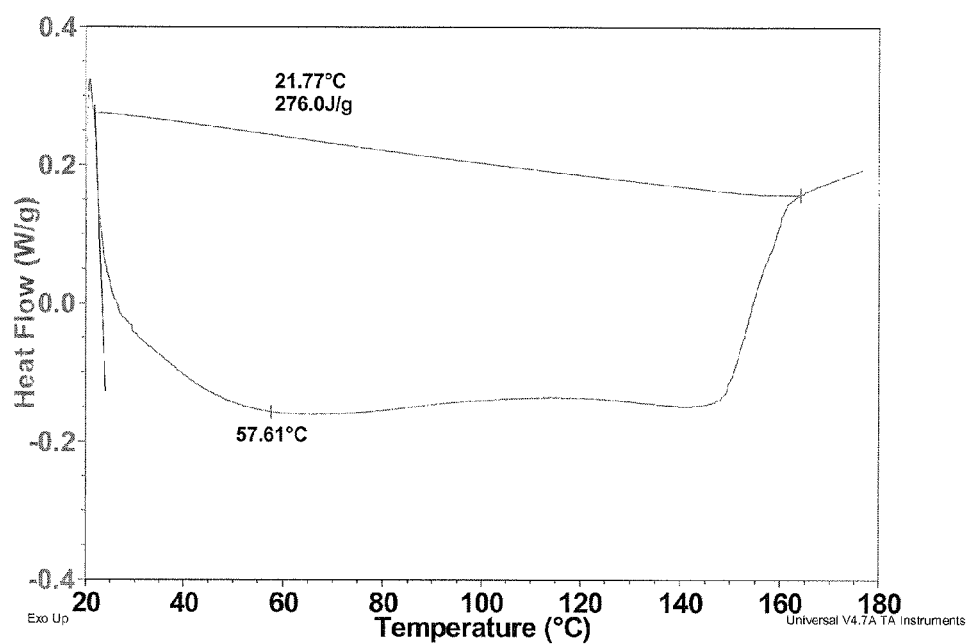
FIG. 94 is differential scanning calorimetry (DSC) curve of Compound I sodium Form II.

In some embodiments, Compound I sodium Form II is also characterized by its differential scanning calorimetry (DSC) curve substantially as shown in FIG. 94.

Figure 95:
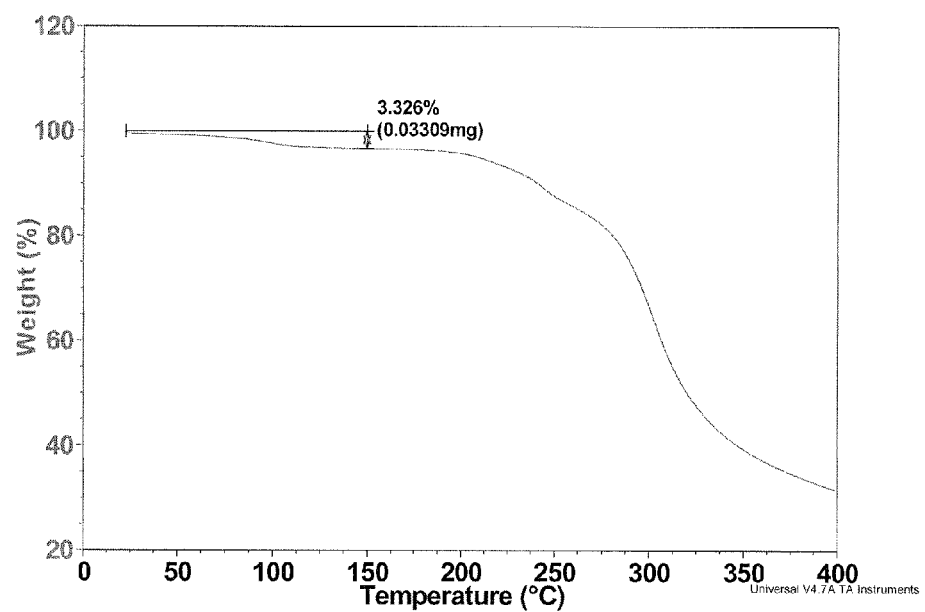
FIG. 95 is thermogravimetric analysis (TGA) of Compound I sodium Form II.

In some embodiments, Compound I sodium Form II is also characterized by thermogravimetric analysis (TGA) comprising a thermogram substantially as shown in FIG. 95.

Figure 96:
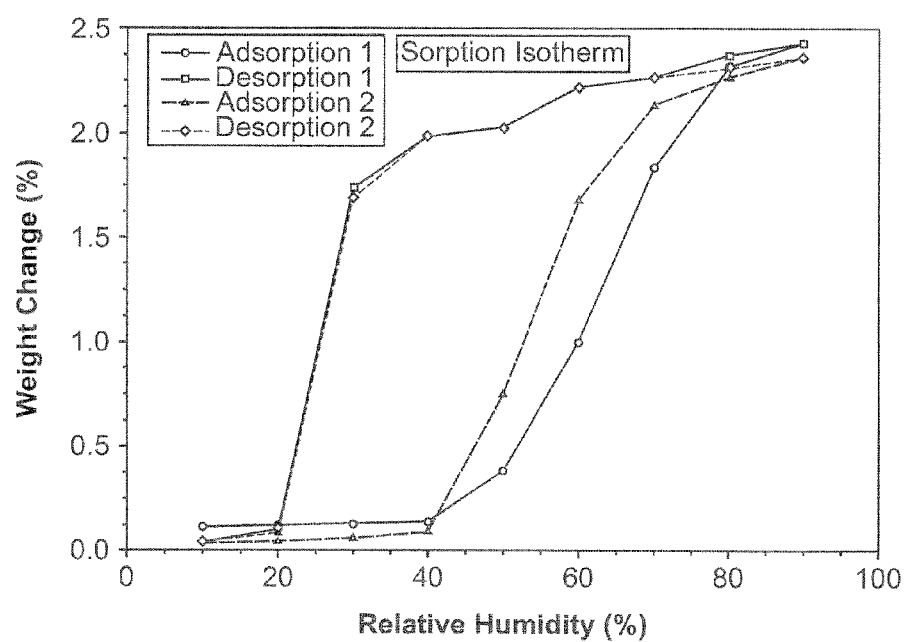
FIG. 96 is dynamic vapor sorption (DVS) curve of Compound I sodium Form II.

In some embodiments, Compound I sodium Form II is also characterized by a dynamic vapor sorption (DVS) curve substantially as shown in FIG. 96.

Compound I sodium Form III is characterized by an X-ray powder diffractogram comprising peaks at 5.4, 7.7, and 10.8 °2θ±0.2 °2θ, as determined on a diffractometer using Cu—Kα radiation. The diffractogram comprises an additional peak at 17.7 °2θ±0.2 °2θ. Compound I sodium Form III is also characterized by its full X-ray powder diffractogram as substantially shown in FIG. 97.

Figure 98:
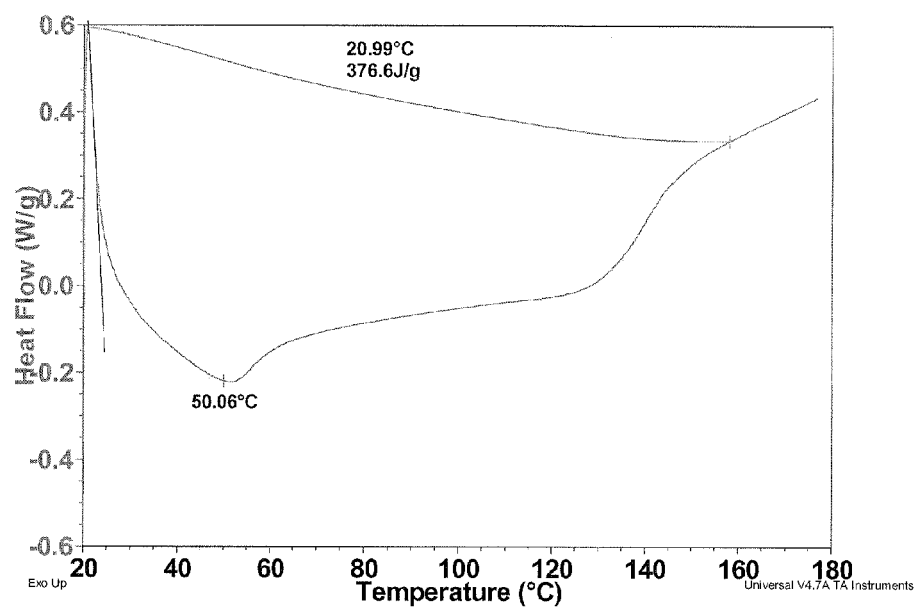
FIG. 98 is differential scanning calorimetry (DSC) curve of Compound I sodium Form III.

In some embodiments, Compound I sodium Form III is also characterized by its differential scanning calorimetry (DSC) curve substantially as shown in FIG. 98.

Figure 99:
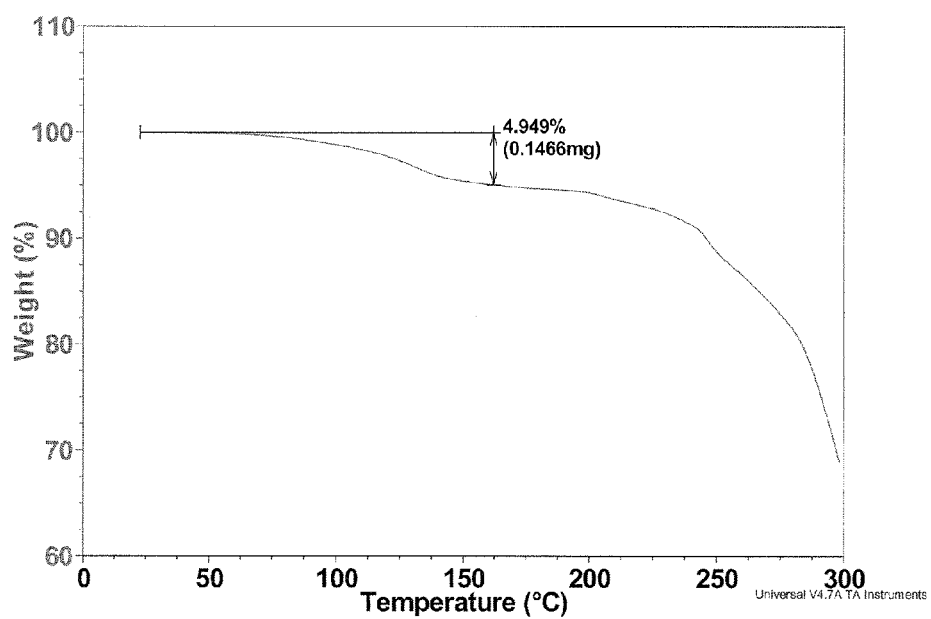
FIG. 99 is thermogravimetric analysis (TGA) of Compound I sodium Form III.

In some embodiments, Compound I sodium Form III is also characterized by thermogravimetric analysis (TGA) comprising a thermogram substantially as shown in FIG. 99.

Figure 100:
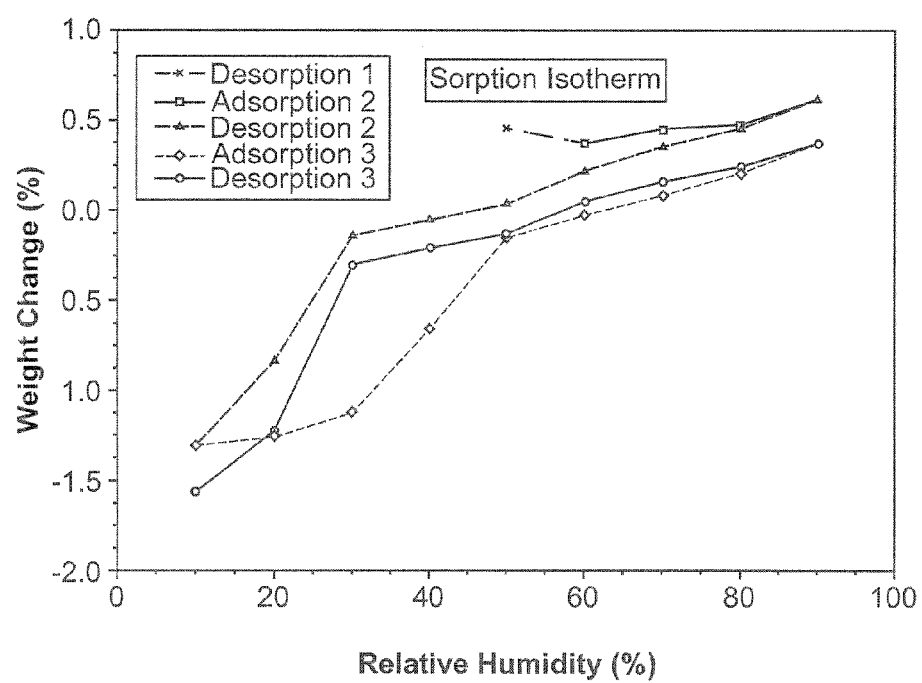
FIG. 100 is dynamic vapor sorption (DVS) curve of Compound I sodium Form III.

In some embodiments, Compound I sodium Form III is also characterized by a dynamic vapor sorption (DVS) curve substantially as shown in FIG. 100.

Compound I sodium Form IV is characterized by an X-ray powder diffractogram comprising peaks at 10.4, 12.1, and 16.6 °2θ±0.2 °2θ, as determined on a diffractometer using Cu—Kα radiation. The diffractogram comprises an additional peak at 19.4 °2θ±0.2 °2θ. Compound I sodium Form IV is also characterized by its full X-ray powder diffractogram as substantially shown in FIG. 101.

Figure 102:
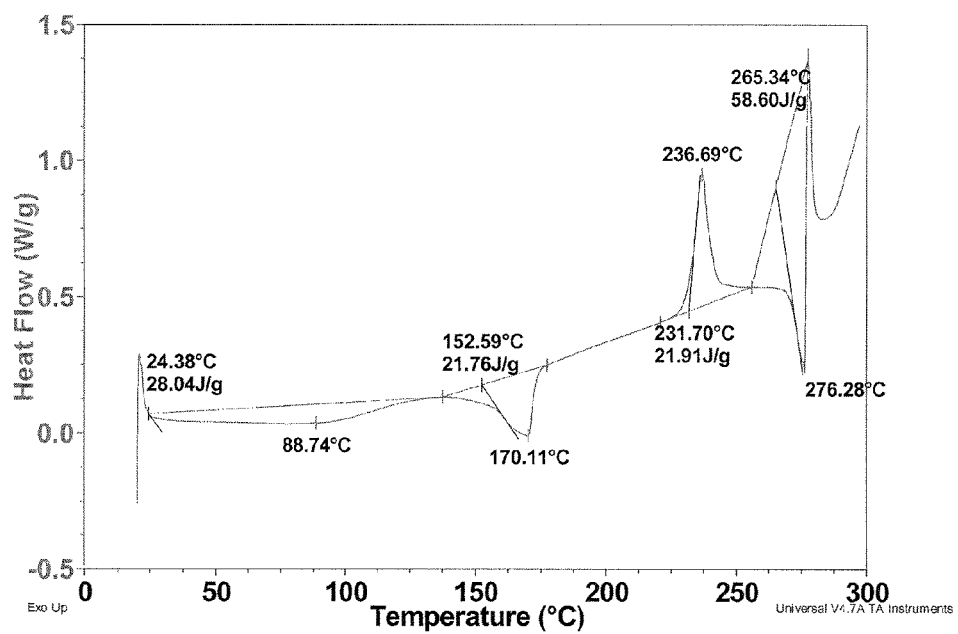
FIG. 102 is differential scanning calorimetry (DSC) curve of Compound I sodium Form IV.

In some embodiments, Compound I sodium Form IV is also characterized by its differential scanning calorimetry (DSC) curve substantially as shown in FIG. 102.

Figure 103:
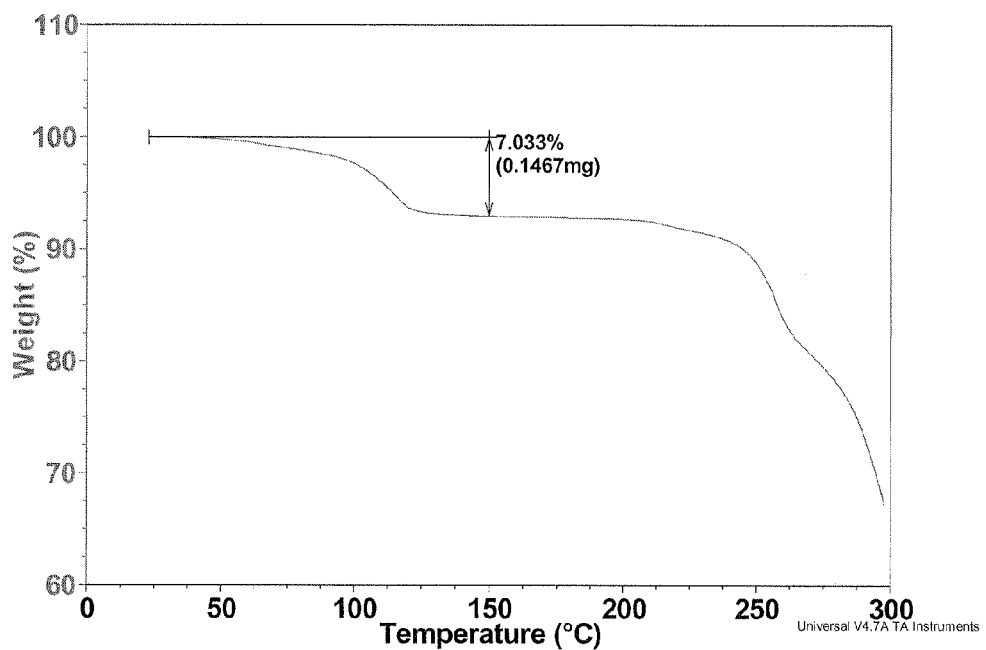
FIG. 103 is thermogravimetric analysis (TGA) of Compound I sodium Form IV.

In some embodiments, Compound I sodium Form IV is also characterized by thermogravimetric analysis (TGA) comprising a thermogram substantially as shown in FIG. 103.

Figure 104:
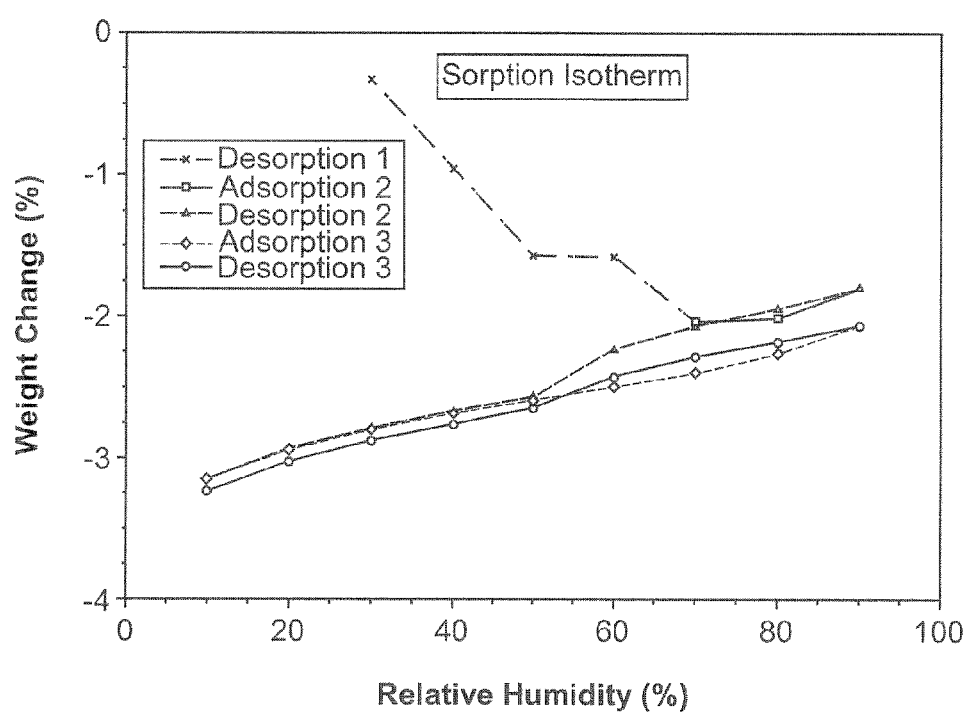
FIG. 104 is dynamic vapor sorption (DVS) curve of Compound I sodium Form IV.

In some embodiments, Compound I sodium Form IV is also characterized by a dynamic vapor sorption (DVS) curve substantially as shown in FIG. 104.

Compound I meglumine Form I is characterized by an X-ray powder diffractogram comprising peaks at 3.6, 5.1, and 8.9 °2θ±0.2 °2θ, as determined on a diffractometer using Cu—Kα radiation. The diffractogram comprises an additional peak at 18.2 °2θ±0.2 °2θ. Compound I meglumine Form I is also characterized by its full X-ray powder diffractogram as substantially shown in FIG. 105.

Figure 106:
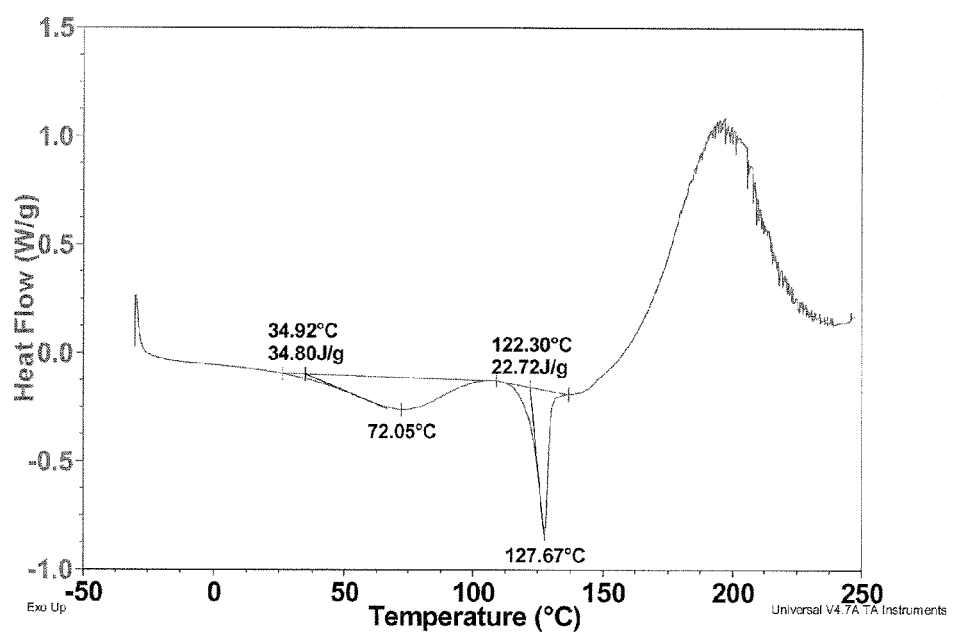
FIG. 106 is differential scanning calorimetry (DSC) curve of Compound I meglumine Form I.

In some embodiments, Compound I meglumine Form I is also characterized by its differential scanning calorimetry (DSC) curve substantially as shown in FIG. 106.

Figure 107:
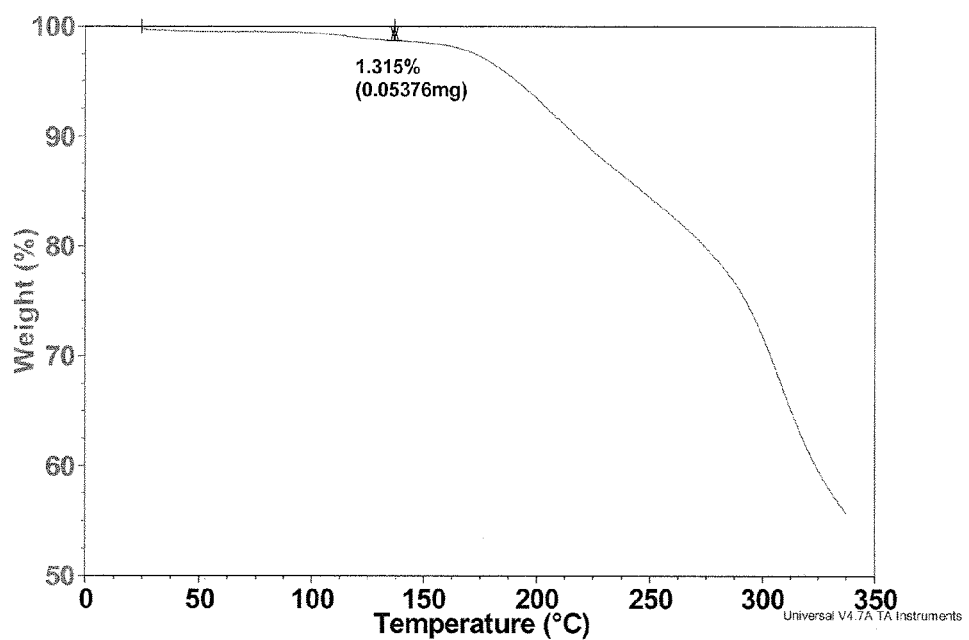
FIG. 107 is thermogravimetric analysis (TGA) of Compound I meglumine Form I.

In some embodiments, Compound I meglumine Form I is also characterized by thermogravimetric analysis (TGA) comprising a thermogram substantially as shown in FIG. 107.

Compound I piperazine Form I is characterized by an X-ray powder diffractogram comprising peaks at 4.9, 7.2, and 8.2 °2θ±0.2 °2θ, as determined on a diffractometer using Cu—Kα radiation. The diffractogram comprises an additional peak at 10.9 °2θ±0.2 °2θ. Compound I piperazine Form I is also characterized by its full X-ray powder diffractogram as substantially shown in FIG. 108.

Figure 109:
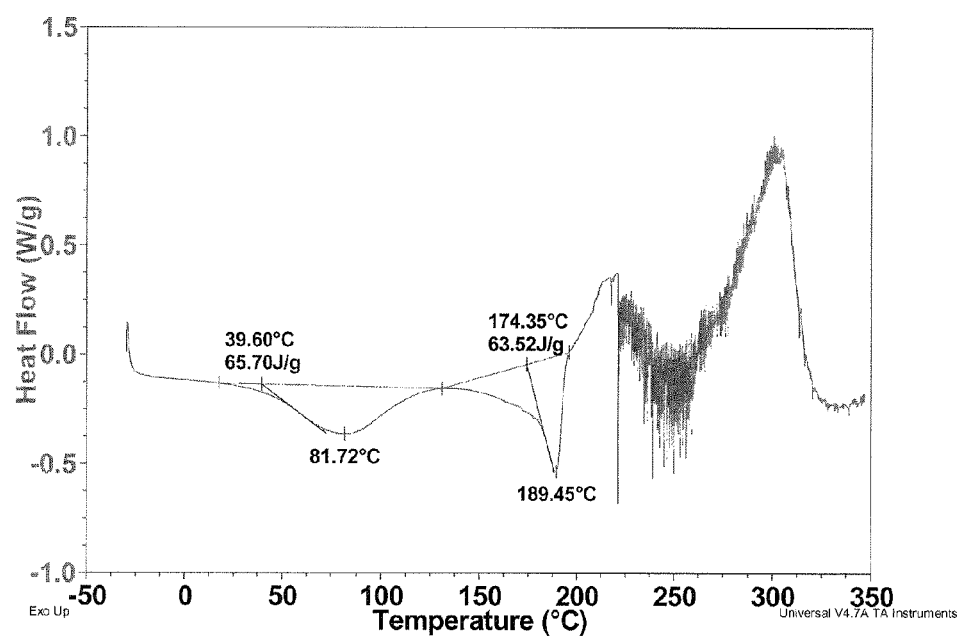
FIG. 109 is differential scanning calorimetry (DSC) curve of Compound I piperazine Form I.

In some embodiments, Compound I piperazine Form I is also characterized by its differential scanning calorimetry (DSC) curve substantially as shown in FIG. 109.

Figure 110:
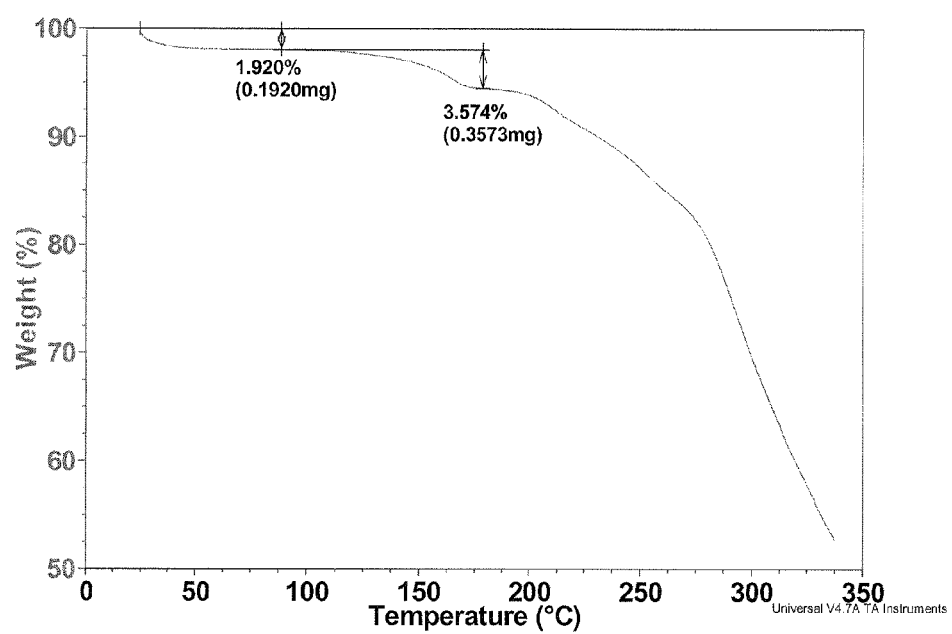
FIG. 110 is thermogravimetric analysis (TGA) of Compound I piperazine Form I.

In some embodiments, Compound I piperazine Form I is also characterized by thermogravimetric analysis (TGA) comprising a thermogram substantially as shown in FIG. 110.

Compound I choline Form I is characterized by an X-ray powder diffractogram comprising peaks at 7.4, 15.5, and 20.9 °2θ±0.2 °2θ, as determined on a diffractometer using Cu—Kα radiation. The diffractogram comprises an additional peak at 23.5 °2θ±0.2 °2θ. Compound I choline Form I is also characterized by its full X-ray powder diffractogram as substantially shown in FIG. 111.

Figure 112:
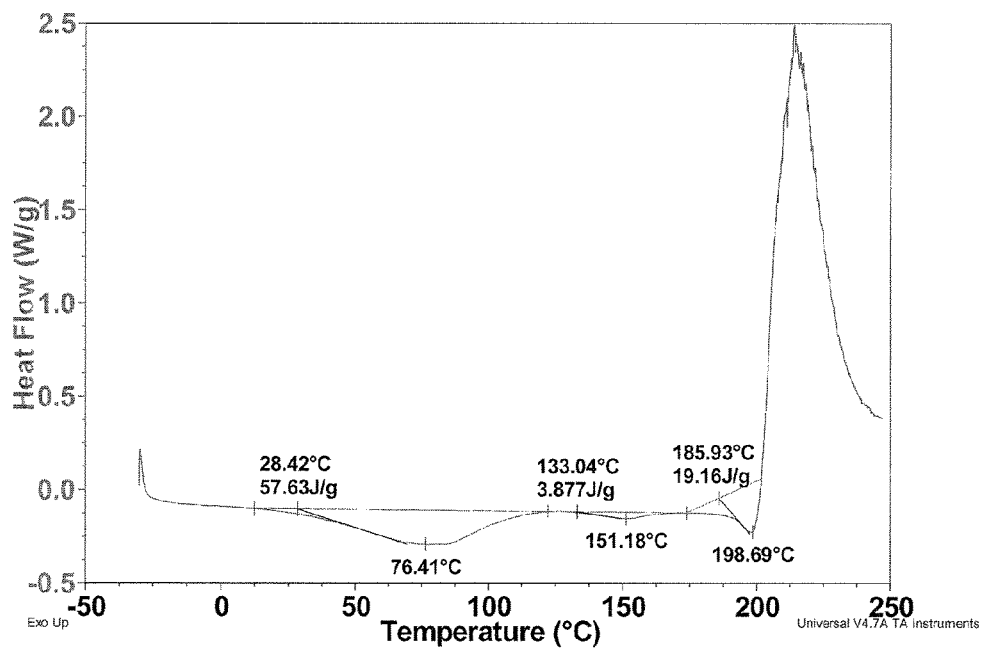
FIG. 112 is differential scanning calorimetry (DSC) curve of Compound I choline Form I.

In some embodiments, Compound I choline Form I is also characterized by its differential scanning calorimetry (DSC) curve substantially as shown in FIG. 112.

Figure 113:
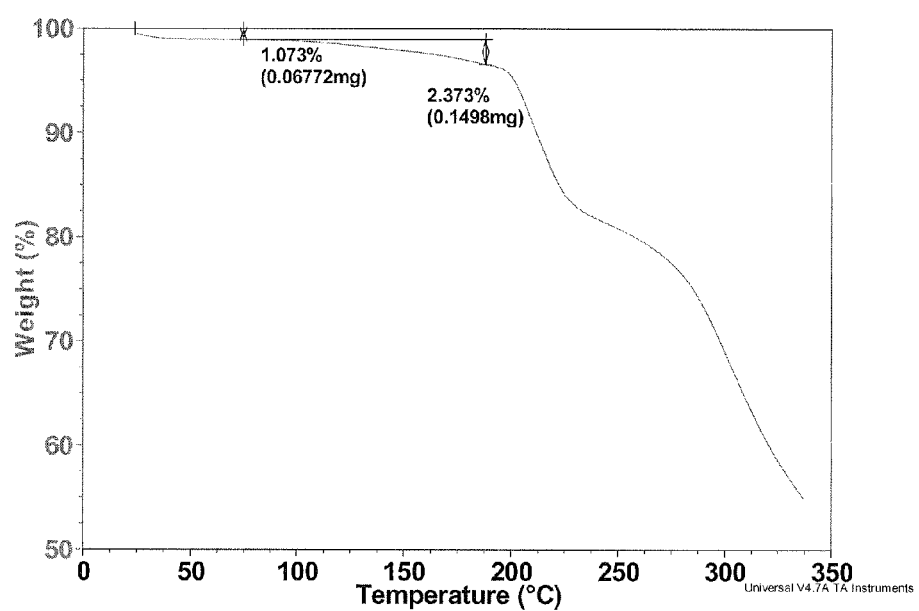
FIG. 113 is thermogravimetric analysis (TGA) of Compound I choline Form I.

In some embodiments, Compound I choline Form I is also characterized by thermogravimetric analysis (TGA) comprising a thermogram substantially as shown in FIG. 113.

Compound I deanol Form I is characterized by an X-ray powder diffractogram comprising peaks at 7.4, 10.7, and 15.2 °2θ±0.2 °2θ, as determined on a diffractometer using Cu—Kα radiation. The diffractogram comprises an additional peak at 20.8 °2θ±0.2 °2θ. Compound I deanol Form I is also characterized by its full X-ray powder diffractogram as substantially shown in FIG. 114.

Compound I 1-(2-hydroxyethyl)-pyrrolidine Form I is characterized by an X-ray powder diffractogram comprising peaks at 8.2, 10.8, and 19.9 °2θ±0.2 °2θ, as determined on a diffractometer using Cu—Kα radiation. The diffractogram comprises an additional peak at 21.1 ° 2θ±0.2 °2θ. Compound I 1-(2-hydroxyethyl)-pyrrolidine Form I is also characterized by its full X-ray powder diffractogram as substantially shown in FIG. 115.

Figure 116:
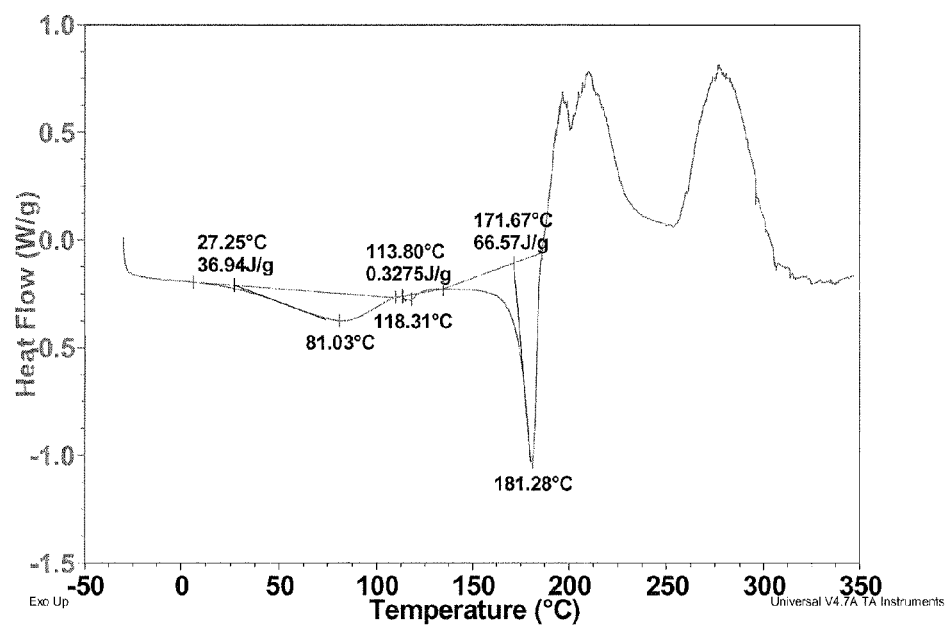
FIG. 116 is differential scanning calorimetry (DSC) curve of Compound I 1-(2-hydroxyethyl)-pyrrolidine (HEP) Form I.

In some embodiments, Compound I 1-(2-hydroxyethyl)-pyrrolidine Form I is also characterized by its differential scanning calorimetry (DSC) curve substantially as shown in FIG. 116.

Figure 117:
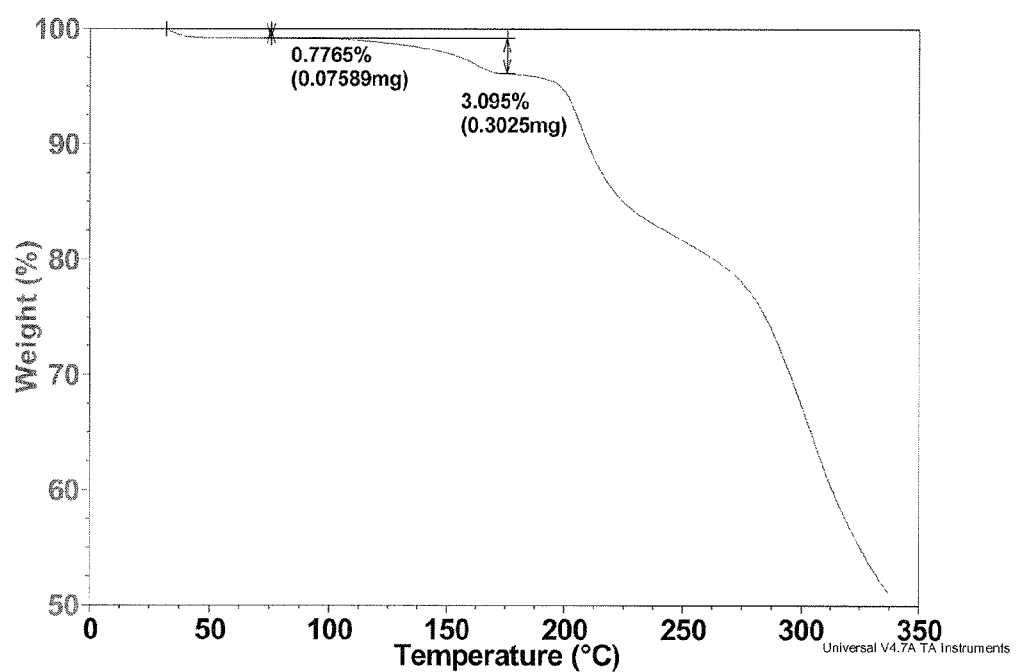
FIG. 117 is thermogravimetric analysis (TGA) of Compound I 1-(2-hydroxyethyl)-pyrrolidine (HEP) Form I.

In some embodiments, Compound I 1-(2-hydroxyethyl)-pyrrolidine Form I is also characterized by thermogravimetric analysis (TGA) comprising a thermogram substantially as shown in FIG. 117.

Compound I 1-(2-hydroxyethyl)-pyrrolidine Form II is characterized by an X-ray powder diffractogram comprising peaks at 7.7, 8.3, and 15.5 °2θ±0.2 °2θ, as determined on a diffractometer using Cu—Kα radiation. The diffractogram comprises an additional peak at 20.9 °2θ±0.2 °2θ. Compound I 1-(2-hydroxyethyl)-pyrrolidine Form II is also characterized by its full X-ray powder diffractogram as substantially shown in FIG. 118.

Compound I 1-(2-hydroxyethyl)-pyrrolidine Form III is characterized by an X-ray powder diffractogram comprising peaks at 7.1, 8.0, and 10.7 °2θ±0.2 °2θ, as determined on a diffractometer using Cu—Kα radiation. The diffractogram comprises an additional peak at 21.4 °2θ±0.2 °2θ. Compound I 1-(2-hydroxyethyl)-pyrrolidine Form III is also characterized by its full X-ray powder diffractogram as substantially shown in FIG. 119.

Compound I lysine Form I is characterized by an X-ray powder diffractogram comprising peaks at 4.2, 8.3, and 9.5 °2θ±0.2 °2θ, as determined on a diffractometer using Cu—Kα radiation. The diffractogram comprises an additional peak at 22.0 °2θ±0.2 °2θ. Compound I lysine Form I is also characterized by its full X-ray powder diffractogram as substantially shown in FIG. 120.

Compound I arginine Form I is characterized by an X-ray powder diffractogram comprising peaks at 7.1, 8.1, and 9.5 °2θ±0.2 °2θ, as determined on a diffractometer using Cu—Kα radiation. The diffractogram comprises an additional peak at 10.8 °2θ±0.2 °2θ. Compound I arginine Form I is also characterized by its full X-ray powder diffractogram as substantially shown in FIG. 121.

Compound I potassium Form I is characterized by an X-ray powder diffractogram comprising peaks at 6.4, 8.6, and 15.8 °2θ±0.2 °2θ, as determined on a diffractometer using Cu—Kα radiation. The diffractogram comprises an additional peak at 20.4 °2θ±0.2 °2θ. Compound I potassium Form I is also characterized by its full X-ray powder diffractogram as substantially shown in FIG. 122.

Figure 123:
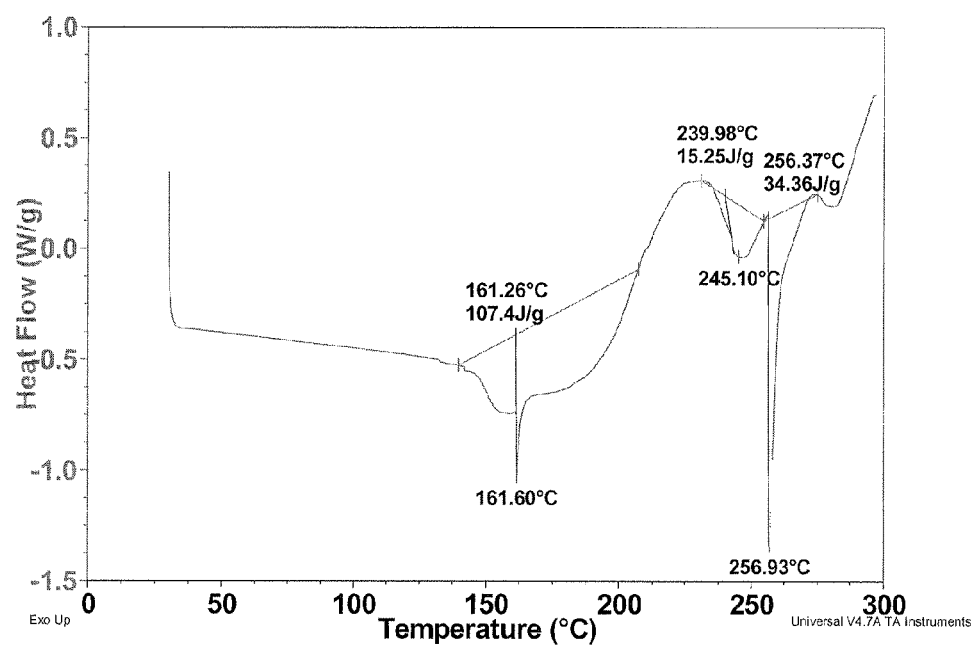

In some embodiments, Compound I potassium Form I is also characterized by its differential scanning calorimetry (DSC) curve substantially as shown in FIG. 123.

Figure 124:
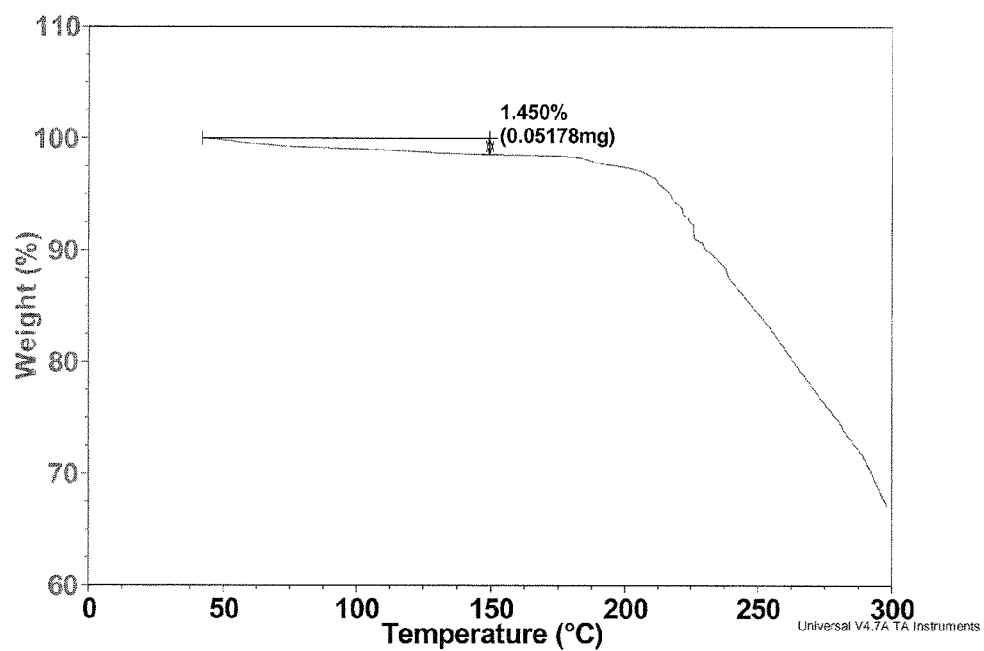

In some embodiments, Compound I potassium Form I is also characterized by thermogravimetric analysis (TGA) comprising a thermogram substantially as shown in FIG. 124.

Figure 125:
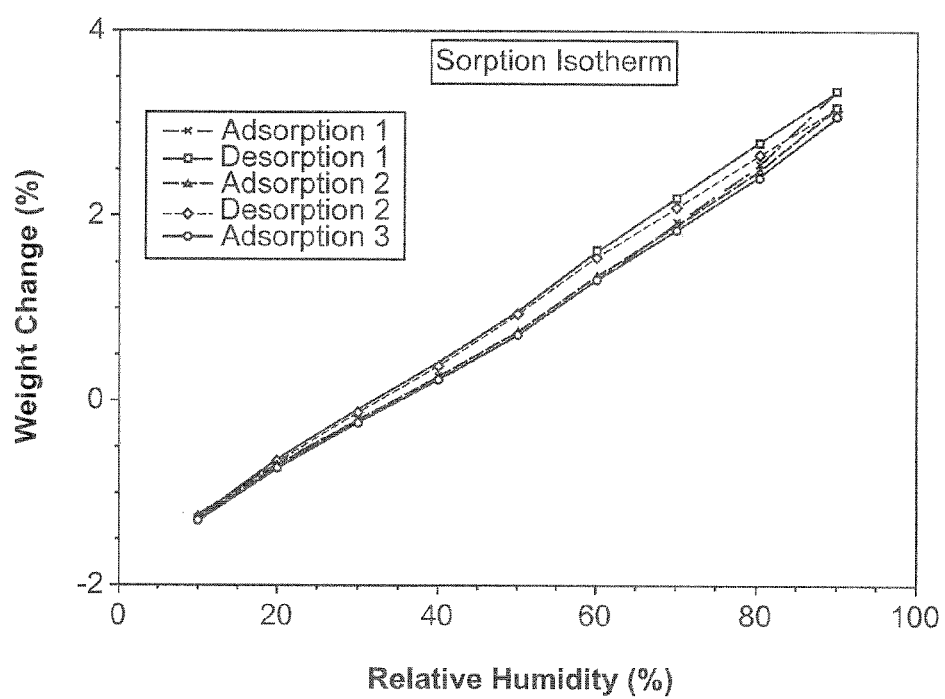

In some embodiments, Compound I potassium Form I is also characterized by a dynamic vapor sorption (DVS) curve substantially as shown in FIG. 125.

Pharmaceutical Formulations

The Compound I forms of this disclosure are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as, for example, those set forth in the Handbook of Pharmaceutical Excipients (1986). Excipients include ascorbic acid and other antioxidants, chelating agents such as, for example, EDTA, carbohydrates such as, for example, dextrin, hydroxyalkylcellulose, hydroxyalkylmethylcellulose, stearic acid and the like. The pH of the formulations ranges from about 3 to about 11, but is ordinarily about 7 to 10. It is contemplated that the Compound I form may be administered once, twice or three times a day.

While it is possible for the active ingredients to be administered alone it may be preferable to present them as pharmaceutical formulations. The formulations, both for veterinary and for human use, of the disclosure comprise at least one active ingredient, as above defined, together with one or more acceptable carriers therefore and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present disclosure suitable for oral administration may be presented as discrete units such as, for example, capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as, for example, a powder or granules, optionally mixed with a binder, lubricant, inert diluent, or preservative. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as, for example, 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as, for example, propylene glycol, butane 1,3-diol, mannitol, sorbitol, glycerol and polyethylene glycol (including PEG 400) and mixtures thereof. The topical formulations may desirably include a Compound I form which enhances absorption or penetration of the active ingredient through the skin or other affected areas. Examples of such dermal penetration enhancers include dimethyl sulphoxide and related analogs.

The oily phase of the emulsions of this disclosure may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the disclosure include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as, for example, di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as, for example, white soft paraffin and/or liquid paraffin or other mineral oils are used.

Pharmaceutical formulations according to the present disclosure comprise one or more Compound I forms of the disclosure together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as, for example, calcium or sodium carbonate, lactose, lactose monohydrate, croscarmellose sodium, povidone, calcium or sodium phosphate; granulating and disintegrating agents, such as, for example, maize starch, or alginic acid; binding agents, such as, for example, cellulose, microcrystalline cellulose, starch, gelatin or acacia; and lubricating agents, such as, for example, magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as, for example, glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as, for example, peanut oil, liquid paraffin or olive oil.

Aqueous suspensions of the disclosure contain the active materials in admixture with excipients suitable for the manufacture of aqueous suspensions. Such excipients include a suspending agent, such as, for example, sodium carboxymethylcellulose, methylcellulose, hydroxypropyl methylcelluose, sodium alginate, polyvinylpyrrolidone, gum tragacanth and gum acacia, and dispersing or wetting agents such as, for example, a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as, for example, ethyl or n-propyl p-hydroxy-benzoate, one or more coloring agents, one or more flavoring agents and one or more sweetening agents, such as, for example, sucrose or saccharin.

Oil suspensions may be formulated by suspending the active ingredient in a vegetable oil, such as, for example, arachis oil, olive oil, sesame oil or coconut oil, or in a mineral oil such as, for example, liquid paraffin. The oral suspensions may contain a thickening agent, such as, for example, beeswax, hard paraffin or cetyl alcohol. Sweetening agents, such as, for example, those set forth above, and flavoring agents may be added to provide a palatable oral preparation. These compositions may be preserved by the addition of an antioxidant such as, for example, ascorbic acid.

Granules of the disclosure suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the disclosure may also be in the form of oil-in-water emulsions. The oily phase may be a vegetable oil, such as, for example, olive oil or arachis oil, a mineral oil, such as, for example, liquid paraffin, or a mixture of these. Suitable emulsifying agents include naturally-occurring gums, such as, for example, gum acacia and gum tragacanth, naturally occurring phosphatides, such as, for example, soybean lecithin, esters or partial esters derived from fatty acids and hexitol anhydrides, such as, for example, sorbitan monooleate, and condensation products of these partial esters with ethylene oxide, such as, for example, polyoxyethylene sorbitan monooleate. The emulsion may also contain sweetening and flavoring agents. Syrups and elixirs may be formulated with sweetening agents, such as, for example, glycerol, sorbitol or sucrose. Such formulations may also contain a demulcent, a preservative, a flavoring or a coloring agent.

The pharmaceutical compositions of the disclosure may be in the form of a sterile injectable preparation, such as, for example, a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as, for example, a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as, for example, oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). In some embodiments, the pharmaceutical compositions described herein contain about 1 to 800 mg, 1 to 600 mg, 1 to 400 mg, 1-300 mg, 1 to 200 mg, 1 to 100 mg or 1 to 50 mg of a Compound I Form (such as Forms I-XXI). In some embodiments, the pharmaceutical compositions described herein contain not more than about 400 mg, preferably not more than about 300 mg, of Compound I Form (such as Forms I-XXI). In some embodiments, the pharmaceutical compositions described herein contain about 10, 25, or 50 mg of Compound I Form (such as Forms I-XXI). In other embodiments, the pharmaceutical compositions described herein contain about 100 mg of a Compound I Form (such as Forms I-XXI).

The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10%, particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as, for example, gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as, for example, 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as, for example, compounds heretofore used in the treatment or prophylaxis of conditions associated with HCV activity.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this disclosure may include other agents conventional in the art having regard to the type of formulation in question, for example those suitable for oral administration may include flavoring agents.

The disclosure further provides veterinary compositions comprising at least one active ingredient as above defined together with a veterinary carrier therefore.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compound I forms of the disclosure can also be formulated to provide controlled release of the active ingredient to allow less frequent dosing or to improve the pharmacokinetic or toxicity profile of the active ingredient. Accordingly, the disclosure also provides compositions comprising one or more Compound I forms of the disclosure formulated for sustained or controlled release.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies.

In one embodiment, the present disclosure provides a pharmaceutical composition comprising a compound selected from the group consisting of Compound I Form I, Compound I Form II, Compound I Form III, Compound I Form IV, Compound I Form V, Compound I Form VI, Compound I Form VII, Compound I Form VIII, Compound I Form IX, Compound I Form X, Compound I Form XI, Compound I Form XII, Compound I Form XIII, Compound I Form XIV, Compound I Form XV, Compound I Form XVI, Compound I Form XVII, Compound I Form XVIII, Compound I Form XIX, Compound I Form XX, and Compound I Form XXI and a pharmaceutically acceptable excipient.

Methods of Use

The crystalline forms of Compound I described herein are administered to a subject suffering from hepatitis C virus (HCV) in either single or multiple doses by any of the accepted modes of administration known to those who are skilled in the art. Administration routes include, for example, those described in any patents and patent applications incorporated by reference, such as rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

Oral administration can be carried out by delivering any of the Compound I forms by capsule or enteric coated tablets, or the like.

The Compound I forms also can be administered by transdermal delivery devices ("patches"). Such transdermal patches may be used to provide continuous or discontinuous infusion of the compounds of the present disclosure in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compounds are preferably formulated in a unit dosage form. The term "unit dosage forms" refers to physically discrete units suitable as unitary dosages for human subjects and other mammals, each unit containing a predetermined quantity of active material calculated to produce the desired therapeutic effect. The compounds are generally administered in a pharmaceutically effective amount.

For oral administration, each dosage unit typically contains from 1 mg to 2 g of a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

Combination Therapy

In yet another embodiment, the present application discloses pharmaceutical compositions comprising a Compound I Form (such as Forms I-XXI), in combination with at least one additional therapeutic agent (i.e., active ingredient), and a pharmaceutically acceptable carrier or excipient. In certain embodiments, additional therapeutic agents include additional antiviral agents.

The additional therapeutic agent used in combination with the compounds described herein includes, without limitation, any agent having a therapeutic effect when used in combination with the compound of the present invention. Such combinations are selected based on the condition to be treated, cross-reactivities of ingredients and pharmaco-properties of the combination. For example, in certain embodiments, the therapeutic agent used in combination with the Compound I Form (such as Forms I-XXI) include, without limitation, one of more of the following: interferons, ribavirin analogs, NS3 protease inhibitors, NS5a inhibitors, NS5b inhibitors, alpha-glucosidase 1 inhibitors, hepatoprotectants, non-nucleoside inhibitors of HCV, nucleoside analogues, and other drugs for treating HCV infection. In some embodiments, the additional therapeutic agents include, without limitation, NS3 protease inhibitors, NS5a inhibitors, and/or NS5b inhibitors. In some embodiments, a pharmaceutical composition including a compound I Form and one or more of an NS3 protease inhibitor, an NS5a inhibitor, and/or an NS5b inhibitor is provided. In some embodiments, a pharmaceutical composition including a Compound I Form (such as Forms I-XXI), or a pharmaceutically acceptable salt thereof and one or more of an NS5a inhibitor and/or an NS5b inhibitor is provided. In certain embodiments, pharmaceutical compositions are provided which includes a compound I Form and one or more additional antiviral agents, wherein the additional antiviral agent is not an interferon, ribavirin, or a ribavirin analogue. In further embodiments, pharmaceutical compositions is provided which includes a Compound I Form (such as Forms I-XXI), and one or more additional antiviral agents, wherein the additional antiviral agent is not ribavirin or a ribavirin analogue.

In certain embodiments, the compounds disclosed herein are combined with one or more other active ingredients (e.g., one or more additional antiviral agents) in a unitary dosage form for simultaneous or sequential administration to a patient. The combination therapy may be administered as a simultaneous or sequential regimen. When administered sequentially, the combination is administered in two or more administrations. In certain embodiments, the active ingredients are: (1) co-formulated and administered or delivered simultaneously in a combined pharmaceutical composition; (2) delivered by alternation or in parallel as separate pharmaceutical composition; or (3) by some other regimen.

When delivered in alternation therapy, the active ingredients are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

Exemplary inferferons include, without limitation, pegylated rIFN-alpha 2b (PEG-Intron), pegylated rIFN-alpha 2a (Pegasys), rIFN-alpha 2b (Intron A), rIFN-alpha 2a (Roferon-A), interferon alpha (MOR-22, OPC-18, Alfaferone, Alfanative, Multiferon, subalin), interferon alfacon-1 (Infergen), interferon alpha-n1 (Wellferon), interferon alpha-n3 (Alferon), interferon-beta (Avonex, DL-8234), interferon-omega (omega DUROS, Biomed 510), albinterferon alpha-2b (Albuferon), IFN alpha XL, BLX-883 (Locteron), DA-3021, glycosylated interferon alpha-2b (AVI-005), PEG-Infergen, PEGylated interferon lambda (PEGylated IL-29), or belerofon, IFN alpha-2b XL, rIFN-alpha 2a, consensus IFN alpha, infergen, rebif, pegylated IFN-beta, oral interferon alpha, feron, reaferon, intermax alpha, r-IFN-beta, and infergen+actimmune.

Exemplary ribavarin analogs include, without limitation, ribavirin (Rebetol, Copegus), levovirin VX-497, and taribavirin (Viramidine).

Exemplary NS5A inhibitors include, without limitation, ledipasvir (GS-5885), GS-5816, JNJ-47910382, daclatasvir (BMS-790052), ABT-267, MK-8742, EDP-239, IDX-719, PPI-668, GSK-2336805, ACH-3102, A-831, A-689, AZD-2836 (A-831), AZD-7295 (A-689), and BMS-790052. For example, NS5A inhibitors may be found in U.S. Pat. No. 8,575,135, which patent is incorporated by reference.

Exemplary NS5B inhibitors include, without limitation, polymerase inhibitor is sofosbuvir (GS-7977), tegobuvir (GS-9190), GS-9669, TMC647055, ABT-333, ABT-072, setrobuvir (ANA-598), filibuvir (PF-868554), VX-222, IDX-375, IDX-184, IDX-102, BI-207127, valopicitabine (NM-283), R1626, PSI-6130 (R1656), PSI-7851, BCX-4678, nesbuvir (HCV-796), BILB 1941, MK-0608, NM-107, R7128, VCH-759, GSK625433, XTL-2125, VCH-916, JTK-652, MK-3281, VBY-708, A848837, GL59728, A-63890, A-48773, A-48547, BC-2329, BMS-791325, and BILB-1941. In another embodiment, compounds as described herein may be combined with both an NS5A inhibitor and an NS5B inhibitor as described hereinabove.

Exemplary NS3 protease inhibitors include, without limitation, GS-9451, GS-9256, simeprevir (TMC-435), ABT-450, boceprevir (SCH-503034), narlaprevir (SCH-900518), vaniprevir (MK-7009), MK-5172, danoprevir (ITMN-191), sovaprevir (ACH-1625), neceprevir (ACH-2684), Telaprevir (VX-950), VX-813, VX-500, faldaprevir (BI-201335), asunaprevir (BMS-650032), BMS-605339, VBY-376, PHX-1766, YH5531, BILN-2065, and BILN-2061.

Exemplary alpha-glucosidase 1 inhibitors include, without limitation, celgosivir (MX-3253), Miglitol, and UT-231B.

Exemplary hepatoprotectants include, without limitation, IDN-6556, ME 3738, MitoQ, and LB-84451.

Exemplary non-nucleoside inhibitors of HCV include, without limitation, benzimidazole derivatives, benzo-1,2,4-thiadiazine derivatives, and phenylalanine derivatives.

Exemplary nucleoside analogues include, without limitation, ribavirin, viramidine, levovirin, a L-nucleoside, or isatoribine and said interferon is α-interferon or pegylated interferon.

Exemplary other drugs for treating HCV infection include, without limitation, imiquimod, 852A, GS-9524, ANA-773, ANA-975, AZD-8848 (DSP-3025), PF-04878691, and SM-360320, cyclophillin inhibitors (e.g., DEBIO-025, SCY-635, or NIM811) or HCV IRES inhibitors (e.g., MCI-067); emericasan (IDN-6556), ME-3738, GS-9450 (LB-84451), silibilin, or MitoQ. BAS-100, SPI-452, PF-4194477, TMC-41629, GS-9350, GS-9585, and roxythromycin.

Additional exemplary other drugs for treating HCV infection include, without limitation, zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975 (isatoribine), XTL-6865, ANA 971, NOV-205, tarvacin, EHC-18, and NIM811.

Still further exemplary other drugs for treating HCV infection include, without limitation, thymosin alpha 1 (Zadaxin), nitazoxanide (Alinea, NTZ), BIVN-401 (virostat), PYN-17 (altirex), KPE02003002, actilon (CPG-10101), GS-9525, KRN-tarvacin, EHC-18, VGX-410C, EMZ-702, AVI 4065, BMS-650032, Bavituximab, MDX-1106 (ONO-4538), Oglufanide, FK-788, VX-497 (merimepodib), DEBIO-025, ANA-975 (isatoribine), XTL-6865, or NIMBI 1.

EXAMPLES

Example 1

Preparation of (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide ethanol solvate (Compound I Form I)

The solution containing Compound I, prepared as discussed in Example 36, was solvent swapped into 7 volumes (7× the mass of Compound I used in equivalent mL volume) ethanol and heated to about 55° C. Then, 3.5 volumes of water were added to the solution over about 2 hours at about 55° C. Another 2 volumes of water at about 55° C. were added to the solution. The slurry was cooled to about 20° C. over about 2 hours, aged for about 5 hours, then filtered and washed with 2 volumes of ethanol/water (1:1 vol/vol) to provide Compound I Form I.

The XRPD pattern for Compound I Form I is shown in FIG. 1 and major peaks and their related intensities in the XRPD pattern are shown in Table 1 below.

TABLE 1

Major Peaks in the XRPD Pattern for Compound I Form I

| Pos. [°2Th.] | d-spacing [Å] | Rel. Int. [%] |
|---|---|---|
| 15.4674 | 5.72892 | 100 |
| 11.1347 | 7.9465 | 84.64 |
| 12.9258 | 6.84913 | 82.94 |
| 8.6318 | 10.24425 | 66.31 |

The differential scanning calorimetry (DSC) curve of Form I is shown in FIG. 2. The thermogravimetric analysis (TGA) of Form I comprising a thermogram is shown in FIG. 3. The dynamic vapor sorption (DVS) of Form I is shown in FIG. 4. The nuclear magnetic resonance spectrum ($^1$H NMR) of Form I is shown in shown in FIG. 5.

Example 2

Preparation of (1aR,5S,8S,9S,10R,22aR)-5-tert-butyl-N-[(1R,2R)-2-(difluoromethyl)-1-{[(1-methyl-cyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide ethyl acetate solvate (Compound I Form II)

The solution containing Compound I, prepared as discussed in Example 36, was solvent swapped into 5 volumes of EtOAc and heated to about 50° C. Then, 3 volumes of heptane were added at about 50° C. 7 volumes of heptane were then added to the reactor over about 1 hour at about 50° C. The reactor contents were then cooled to room temperature over about 2 hours and the solids were filtered off to provide Form II.

Figure 6:
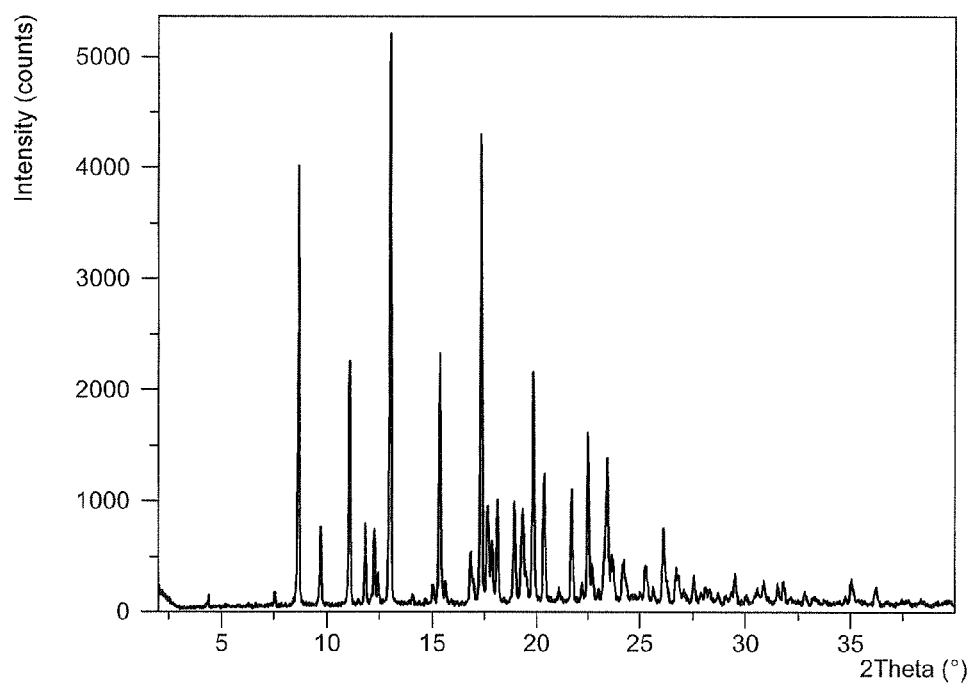
FIG. 6 is an X-ray powder diffraction pattern of Compound I Form II.

The XRPD pattern for Form II is as shown in FIG. 6. Major peaks and their related intensities in the XRPD pattern are shown in Table 2 below.

TABLE 2

Major Peaks in the XRPD Pattern for Compound I Form II

| Pos. [°2Th.] | d-spacing [Å] | Rel. Int. [%] |
| --- | --- | --- |
| 13.0341 | 6.79247 | 100 |
| 17.367 | 5.10635 | 81.26 |
| 8.7099 | 10.15261 | 76.12 |
| 15.3765 | 5.76261 | 44.59 |

Figure 11:
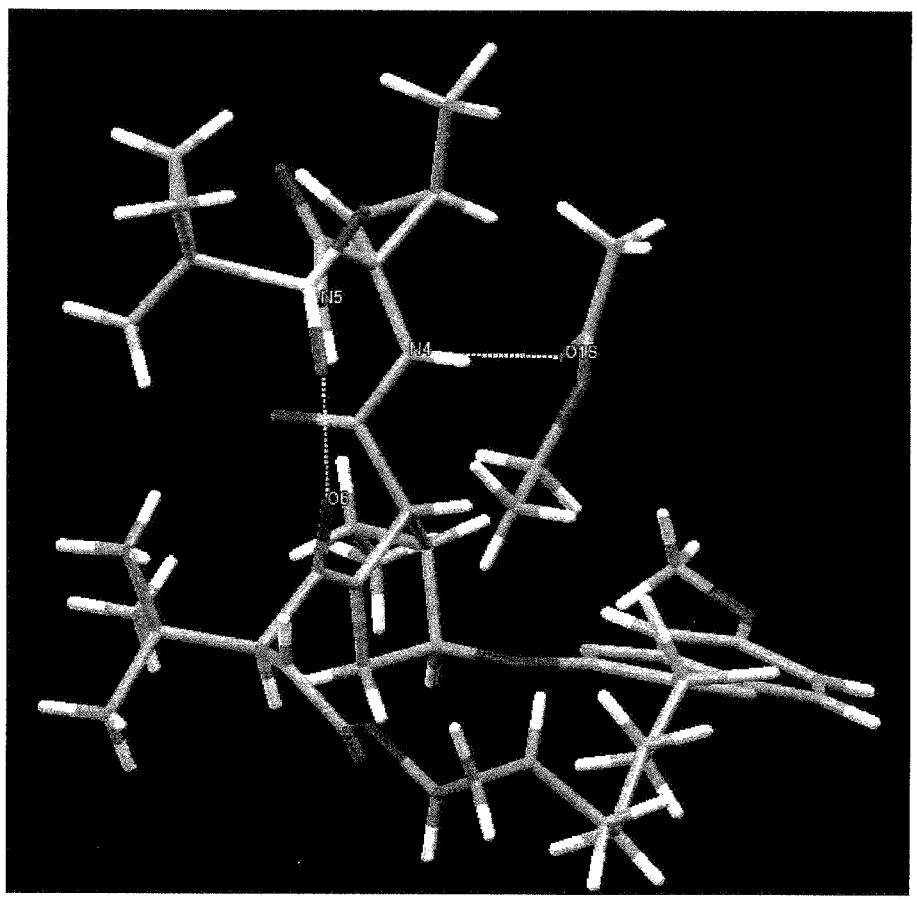
FIG. 11 is single crystal analysis of Compound I Form II.

The differential scanning calorimetry (DSC) curve of Form II is shown in FIG. 7. The thermogravimetric analysis (TGA) of Form II comprising a thermogram is shown in FIG. 8. The nuclear magnetic resonance spectrum ($^1$H NMR) of Form II is shown in FIG. 9. The dynamic vapor sorption (DVS) of Form II is shown in FIG. 10. Single crystal analysis of Form II is shown in FIG. 11, which shows that there is 1 molar equivalent of ethyl acetate for every molecule of Compound I. The unit cell dimensions are given below.

| Crystal system | Monoclinic |
| --- | --- |
| Space group | P2$_1$ |
| Unit cell dimensions | a = 11.7472(2) Å |
| | b = 10.1096(3) Å |
| | c = 20.3398(3) Å |
| | α = 90° |
| | β = 93.3766(16)° |
| | γ = 90° |

Example 3

Preparation of (1aR,5S,8S,9S,10R,22aR)-5-tert-butyl-N-[(1R,2R)-2-(difluoromethyl)-1-{[(1-methyl-cyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide isopropanol solvate (Compound I Form III)

Compound I Form III was prepared by adding ~50 mg of Compound I, prepared as discussed in Example 36, into a vial containing 1 mL of isopropanol and a magnetic stirrer. The contents of the vial were stirred at room temperature for about ~48 hours before the wet solids were isolated to provide Form III.

Figure 12:
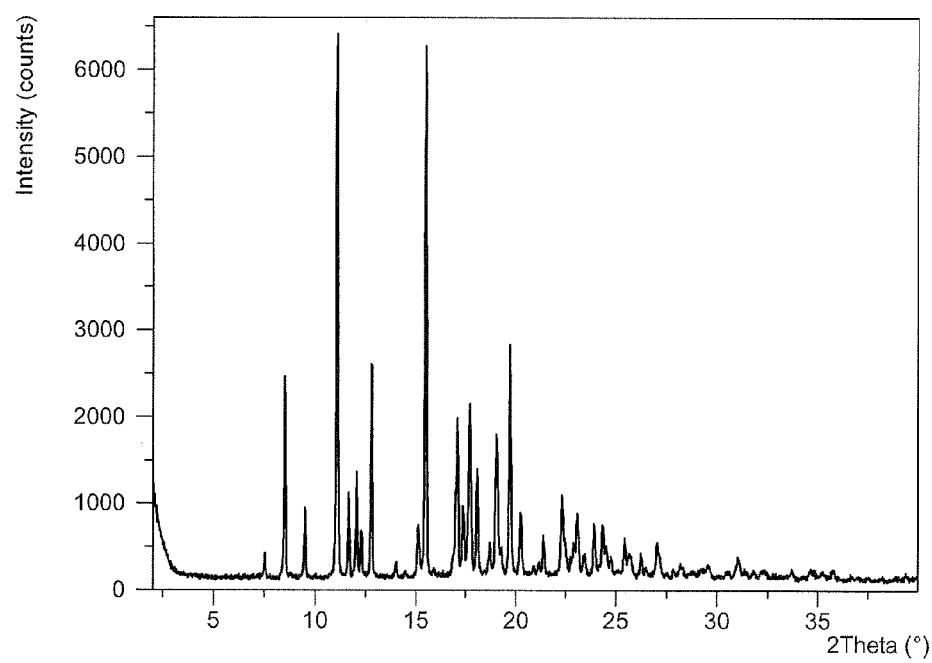
FIG. 12 is an X-ray powder diffraction pattern of Compound I Form III.

The XRPD pattern for Form III is as shown in FIG. 12. Major peaks and their related intensities in the XRPD pattern are shown in Table 3 below.

TABLE 3

Major Peaks in the XRPD Pattern for Compound I Form III

| Pos. [°2Th.] | d-spacing [Å] | Rel. Int. [%] |
| --- | --- | --- |
| 11.1013 | 7.97035 | 100 |
| 15.4961 | 5.7184 | 98.22 |
| 19.724 | 4.50116 | 44.08 |
| 12.7972 | 6.91768 | 41.06 |

The differential scanning calorimetry (DSC) curve of Form III is shown in FIG. 13. The thermogravimetric analysis (TGA) of Form III comprising a thermogram is shown in FIG. 14. The nuclear magnetic resonance spectrum ($^1$H NMR) of Form III is shown in FIG. 15. The dynamic vapor sorption (DVS) of Form III is shown in FIG. 16.

Example 4

Preparation of (1aR,5S,8S,9S,10R,22aR)-5-tert-butyl-N-[(1R,2R)-2-(difluoromethyl)-1-{[(1-methyl-cyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide dihydrate (Compound I Form IV)

Compound I Form IV was prepared by placing Compound I Form I of Example 1 in an accelerated stability chamber set at about 40° C. and 75% R.H. for 2 weeks. After 2 weeks, Form IV was isolated and analyzed.

Figure 17:
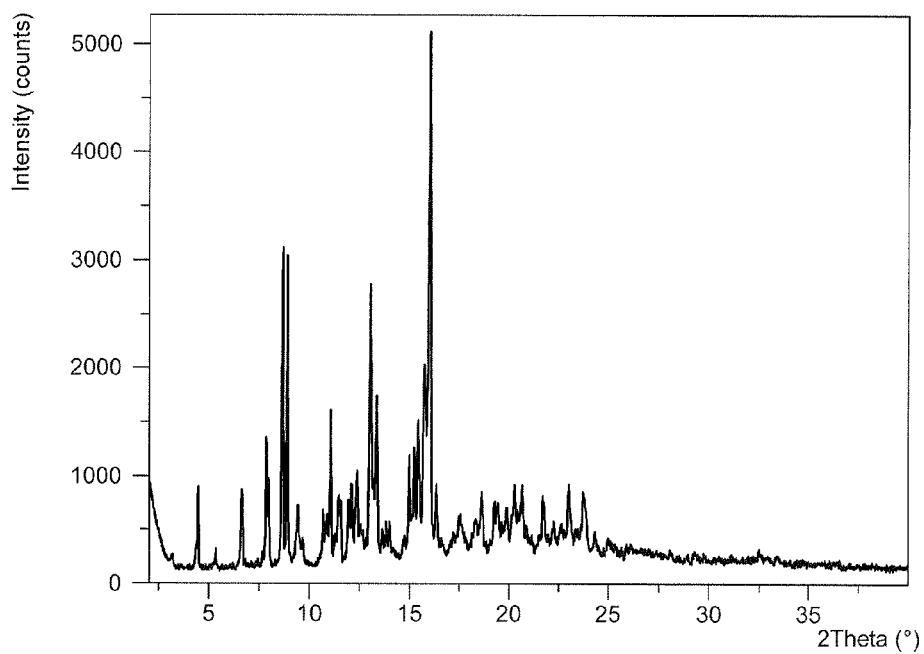
FIG. 17 is an X-ray powder diffraction pattern of Compound I Form IV.

The XRPD pattern for Form IV is as shown in FIG. 17. Major peaks and their related intensities in the XRPD pattern are shown in Table 4 below.

TABLE 4

Major Peaks in the XRPD Pattern for Compound I Form IV

| Pos. [°2Th.] | d-spacing [Å] | Rel. Int. [%] |
| --- | --- | --- |
| 16.0321 | 5.5284 | 100 |
| 8.9039 | 9.93182 | 61.9 |
| 8.6774 | 10.19058 | 60.64 |
| 13.0132 | 6.80335 | 53.85 |

The differential scanning calorimetry (DSC) curve of Form IV is shown in FIG. 18. The thermogravimetric analysis (TGA) of Form IV comprising a thermogram is shown in FIG. 19. The dynamic vapor sorption (DVS) of Form IV is shown in FIG. 20. The nuclear magnetic resonance spectrum ($^1$H NMR) of Form IV is shown in FIG. 21.

Example 5

Preparation of (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide methanol solvate (Compound I Form V)

Compound I Form V was prepared by mixing 400 mg of Compound I, prepared as discussed in Example 36, in an amber vial containing 4 mL of MeOH at room temperature using a magnetic stir bar. The initial solids dissolved and re-crystallized out to provide Compound I Form V.

Figure 22:
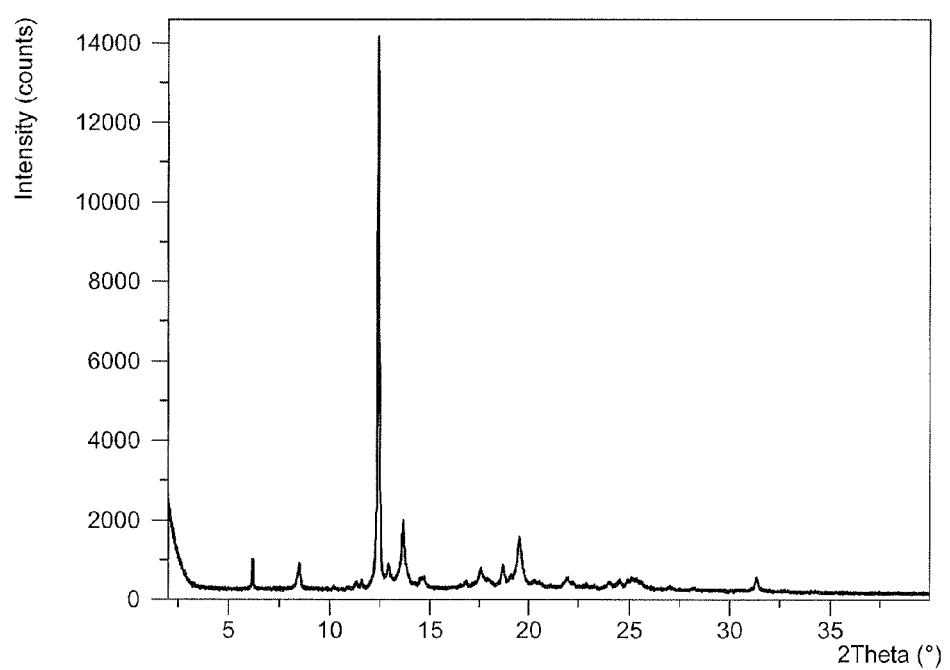
FIG. 22 is an X-ray powder diffraction pattern of Compound I Form V.

The XRPD pattern for Form V is as shown in FIG. 22. Major peaks and their related intensities in the XRPD pattern are shown in Table 5 below.

TABLE 5

Major Peaks in the XRPD Pattern for Compound I Form V

| Pos. [°2Th.] | d-spacing [Å] | Rel. Int. [%] |
| --- | --- | --- |
| 12.4162 | 7.12909 | 100 |
| 13.6778 | 6.4742 | 12.63 |
| 19.5695 | 4.53633 | 8.78 |
| 6.2238 | 14.20129 | 5.36 |

Figure 26:
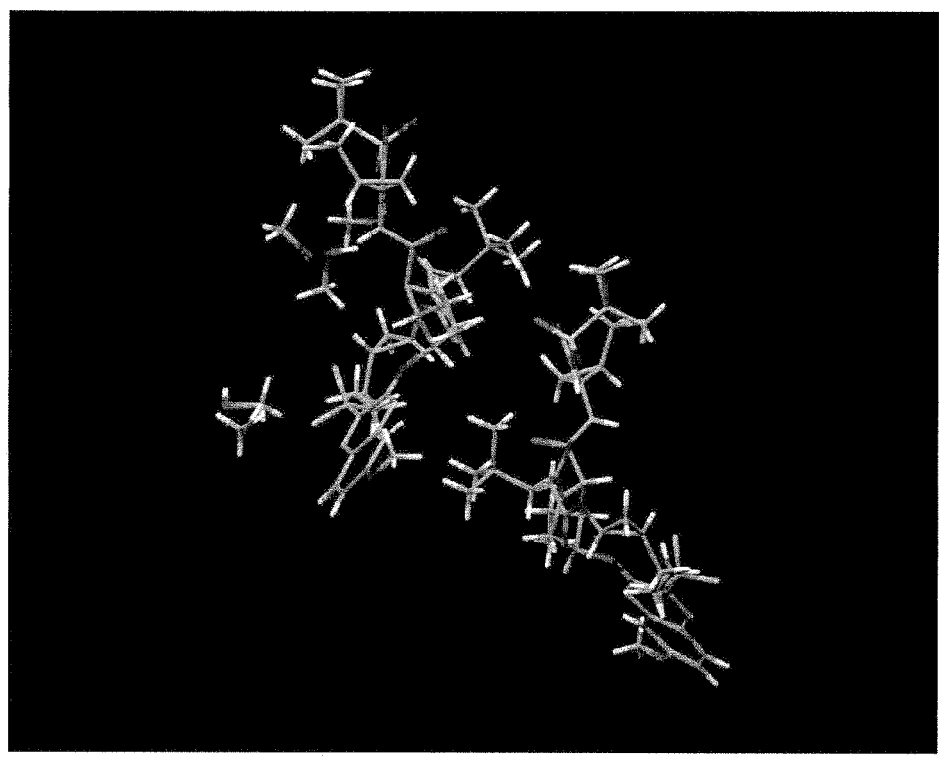
FIG. 26 is single crystal analysis of Compound I Form V.

The differential scanning calorimetry (DSC) curve of Form V is shown in FIG. 23. The thermogravimetric analysis (TGA) of Form V comprising a thermogram is shown in FIG. 24. The dynamic vapor sorption (DVS) of Form V is shown in FIG. 25. Single crystal analysis of Form V is shown in FIG. 26, which shows that there are from about >1 to about 2.5 equivalents of methanol for every molecule of Compound I. The unit cell dimensions are given in Table 6 below.

TABLE 6

Compound I Form V Unit Cell Information

| | |
| --- | --- |
| Crystal System: | Triclinic |
| Space Group: | P1 |
| Volume: | 2435.18(19) Å$^3$ |
| Unit Cell Dimensions: | a = 10.7741(5) Å |
| | b = 15.1017(7) Å |
| | c = 15.6272(7) Å |
| | α = 82.914(2)° |
| | β = 89.448(2)° |
| | γ = 74.877(2)° |

Example 6

Preparation of (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide (anhydrous, Compound I Form VI)

Compound I Form VI was prepared by placing Compound I Form V in the TGA and heating the sample to about 70° C. and then cooling it back to room temperature. After being heated to about 70° C., the sample converted from Form V to Form VI.

Figure 27:
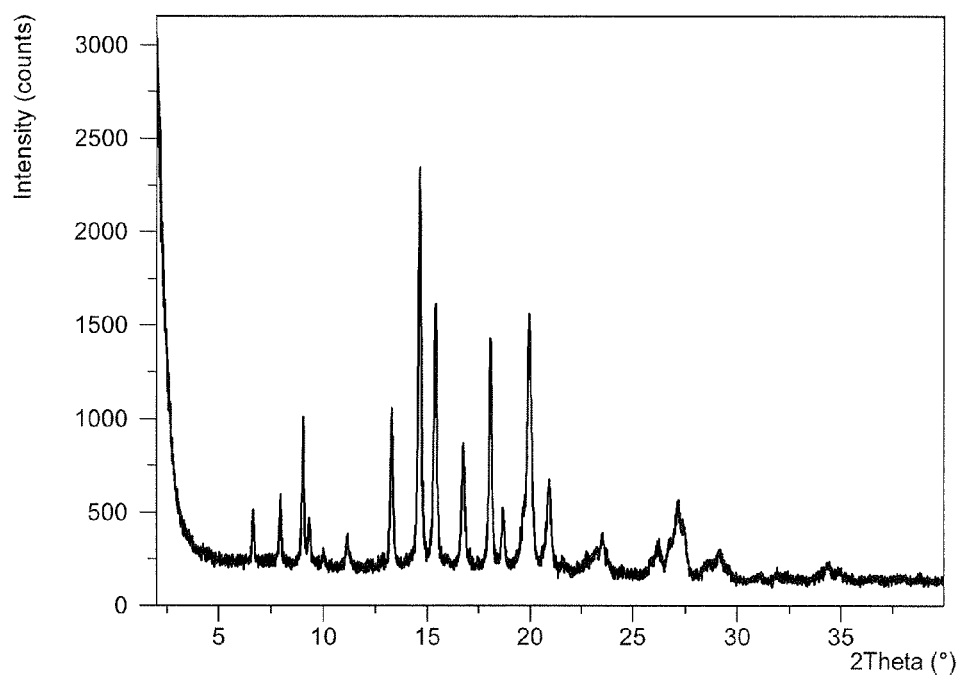
FIG. 27 is an X-ray powder diffraction pattern of Compound I Form VI.

The XRPD pattern for Form VI is as shown in FIG. 27. Major peaks and their related intensities in the XRPD pattern are shown in Table 7 below.

TABLE 7

Major Peaks in the XRPD Pattern for Compound I Form VI

| Pos. [°2Th.] | d-spacing [Å] | Rel. Int. [%] |
| --- | --- | --- |
| 14.6141 | 6.06146 | 100 |
| 15.4028 | 5.7528 | 69.18 |
| 20.0345 | 4.43207 | 64.15 |
| 18.0922 | 4.90327 | 62.51 |

The differential scanning calorimetry (DSC) curve of Form VI is shown in FIG. 28. The thermogravimetric analysis (TGA) of Form VI comprising a thermogram is shown in FIG. 29. The dynamic vapor sorption (DVS) of Form VI is shown in FIG. 30.

Example 7

Preparation of (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide (anhydrous, Compound I Form VII)

Compound I Form VII was prepared by heating Compound I Form I to about 240° C. or heating Compound I Form V to about 220° C. or heating Compound I Form IX to about 200° C.

Figure 31:
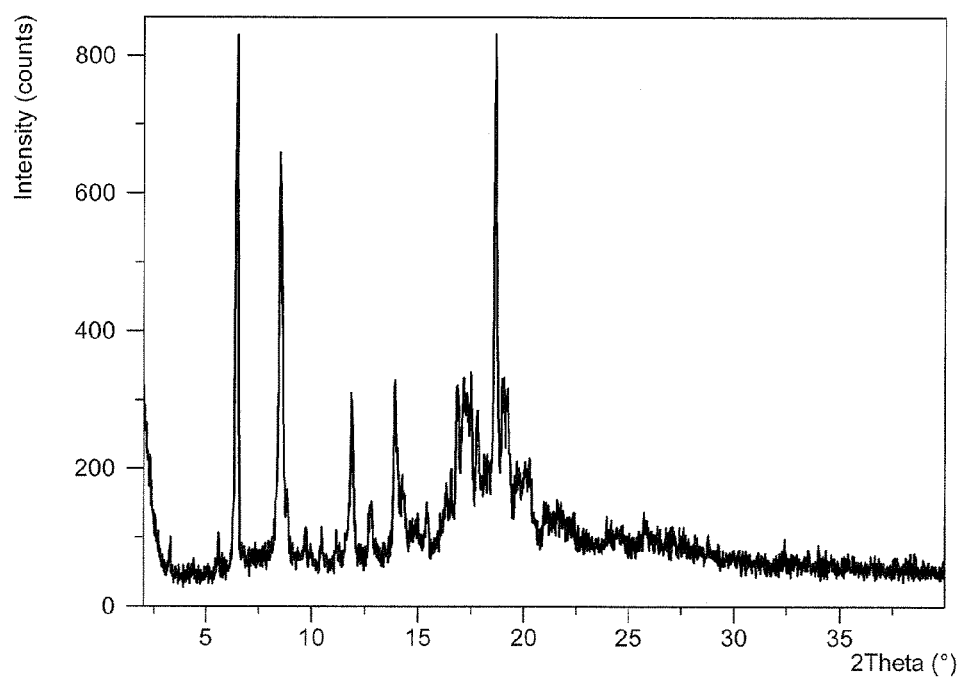
FIG. 31 is an X-ray powder diffraction pattern of Compound I Form VII.

The XRPD pattern for Form VII is as shown in FIG. 31. Major peaks and their related intensities in the XRPD pattern are shown in Table 8 below.

TABLE 8

Major Peaks in the XRPD Pattern for Compound I Form VII

| Pos. [°2Th.] | d-spacing [Å] | Rel. Int. [%] |
| --- | --- | --- |
| 18.663 | 4.75458 | 100 |
| 6.5242 | 13.54802 | 95.36 |
| 8.527 | 10.36991 | 78.68 |
| 17.5074 | 5.06571 | 35.36 |

The differential scanning calorimetry (DSC) curve of Form VII is shown in FIG. 32. The nuclear magnetic resonance spectrum ($^1$H NMR) of Form VII is shown in FIG. 33. The thermogravimetric analysis (TGA) of Form VII comprising a thermogram is shown in FIG. 34. The dynamic vapor sorption (DVS) of Form VII is shown in FIG. 35.

Example 8

Preparation of (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide (anhydrous, Compound I Form VIII)

Compound I Form VIII was prepared by charging 0.1 g of Compound I Form VI into a 25 mL round bottom flask with a magnetic stir bar. 5 mL of water was charged into the flask, which was then heated to about 85° C. Next, 1 g of Compound I Form V was charged into the flask. 5 mL of acetone water (1:4 vol./vol.) was used to wash the solids on the inner side of the flask. The contents of the flask were held at about 85° C. overnight. The next day, the contents of the flask were then cooled to room temperature and held at room temperature for another night. The solids were filtered out and analyzed to indicate that both Forms V and VI converted to a new form, Form VIII.

Figure 36:
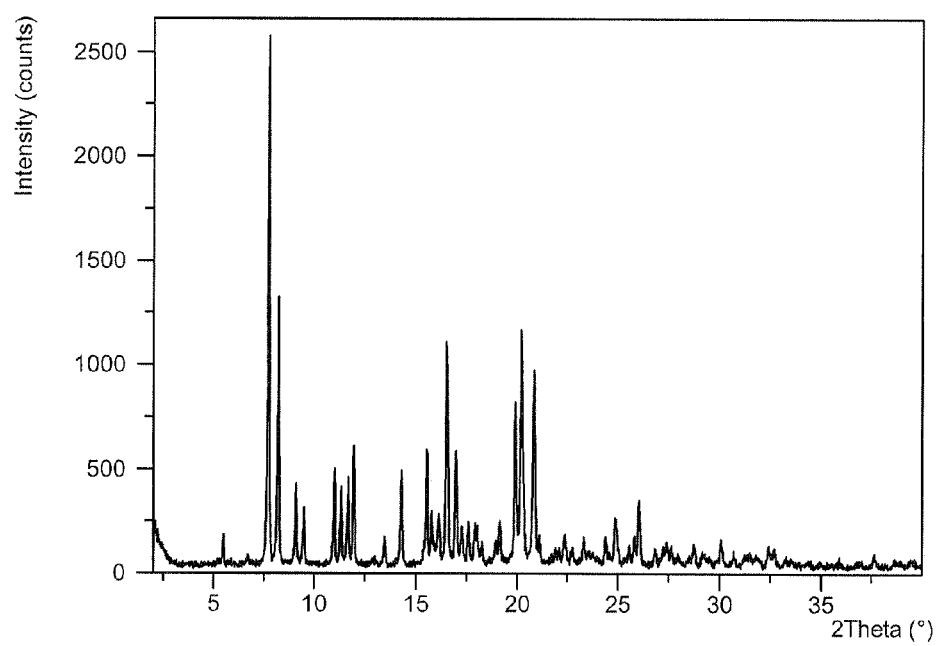
FIG. 36 is an X-ray powder diffraction pattern of Compound I Form VIII.

The XRPD pattern for Form VIII is as shown in FIG. 36. Major peaks and their related intensities in the XRPD pattern are shown in Table 9 below.

TABLE 9

Major Peaks in the XRPD Pattern for Compound I Form VIII

| Pos. [°2Th.] | d-spacing [Å] | Rel. Int. [%] |
| --- | --- | --- |
| 7.7598 | 11.39333 | 100 |
| 8.2313 | 10.74173 | 50.21 |
| 20.1662 | 4.40343 | 43.56 |
| 16.4818 | 5.37855 | 41.17 |

The differential scanning calorimetry (DSC) curve of Form VIII is shown in FIG. 37. The thermogravimetric analysis (TGA) of Form VIII comprising a thermogram is shown in FIG. 38. The dynamic vapor sorption (DVS) of Form VIII is shown in FIG. 39.

Example 9

Preparation of (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide (anhydrous, Compound I Form IX)

Compound I Form IX was prepared by charging Compound I Form VI into container, to which 10 volumes of 1:1 heptane/toluene was added and the mixture heated and slurried at 60° C. overnight. The mixture was then filtered directly without cooling and the product was dried at about 50° C. under vacuum.

Figure 40:
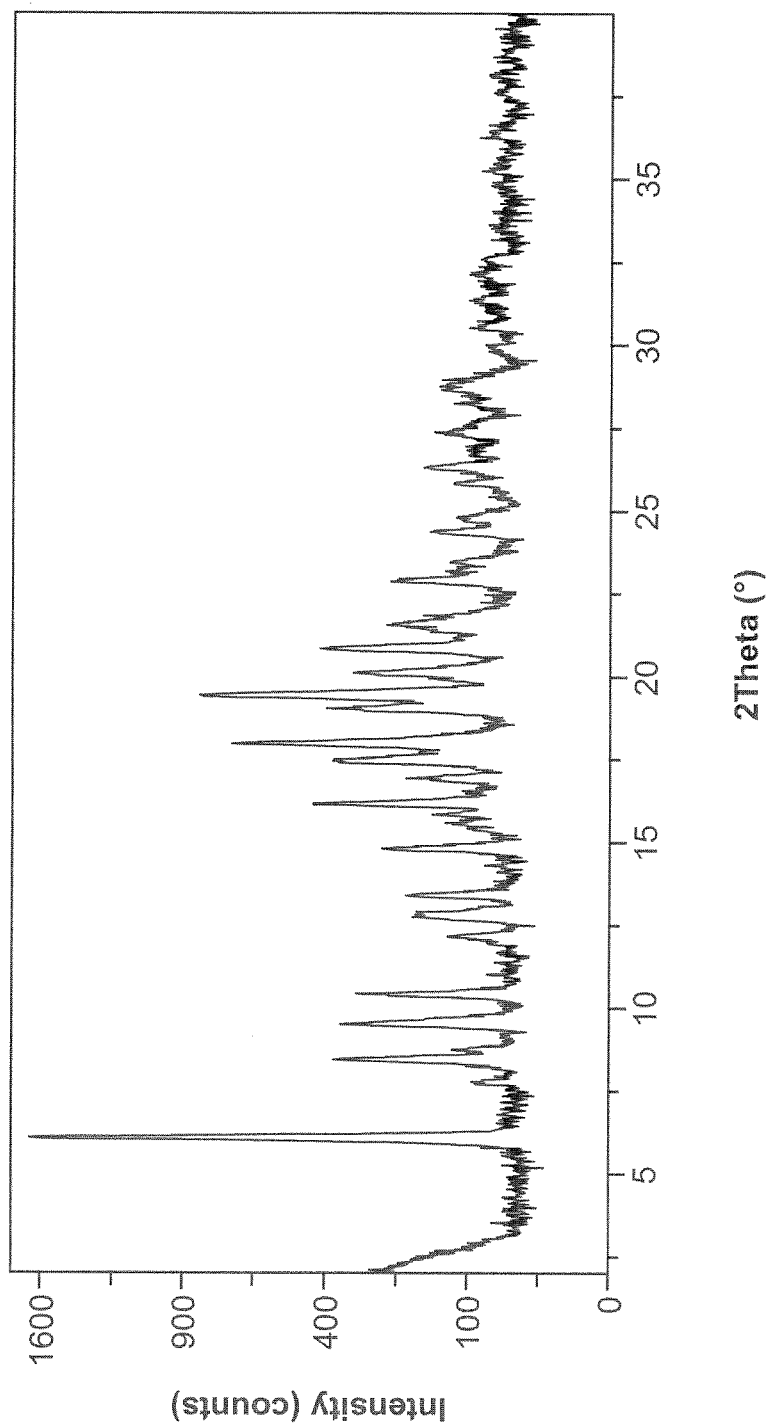
FIG. 40 is an X-ray powder diffraction pattern of Compound I Form IX.

The XRPD pattern for Form IX is as shown in FIG. 40. The differential scanning calorimetry (DSC) curve of Form IX is shown in FIG. 41. The thermogravimetric analysis (TGA) of Form IX comprising a thermogram is shown in FIG. 42. The dynamic vapor sorption (DVS) of Form IX is shown in FIG. 43.

Example 10

Preparation of (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide hemihydrate (Compound I Form X)

Compound I Form X was prepared by slurring Compound I Form VIII in water at about 80° C.

Figure 44:
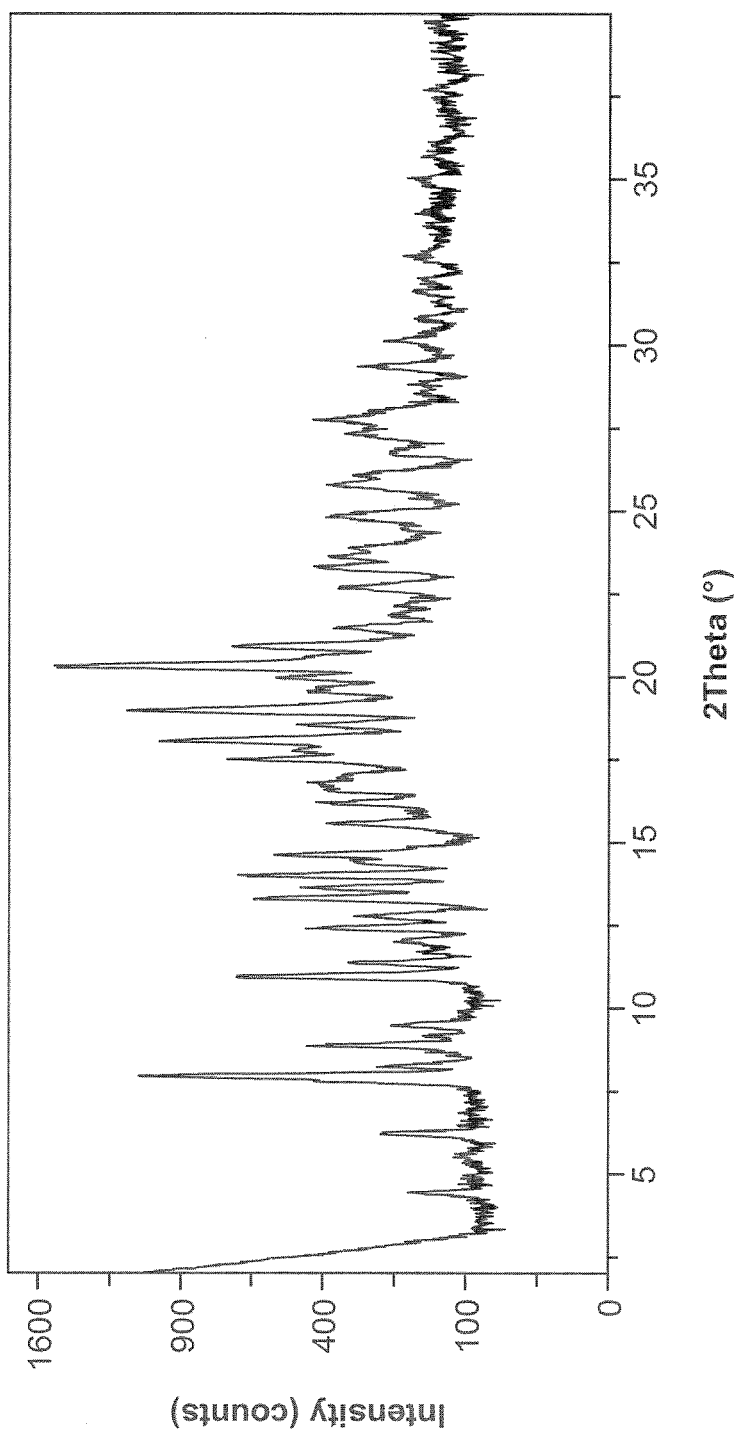
FIG. 44 is an X-ray powder diffraction pattern of Compound I Form X.

The XRPD pattern for Form X is as shown in FIG. 44. The differential scanning calorimetry (DSC) curve of Form X is shown in FIG. 45. The thermogravimetric analysis (TGA) of Form X comprising a thermogram is shown in FIG. 46. The dynamic vapor sorption (DVS) of Form X is shown in FIG. 47.

Example 11

Preparation of (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide dihydrate (Compound I Form XI)

Compound I Form XI was prepared by slurring a mixture of Compound I Form IV and Compound I Form X in 7:3 (v/v) ethanol:water.

Figure 48:
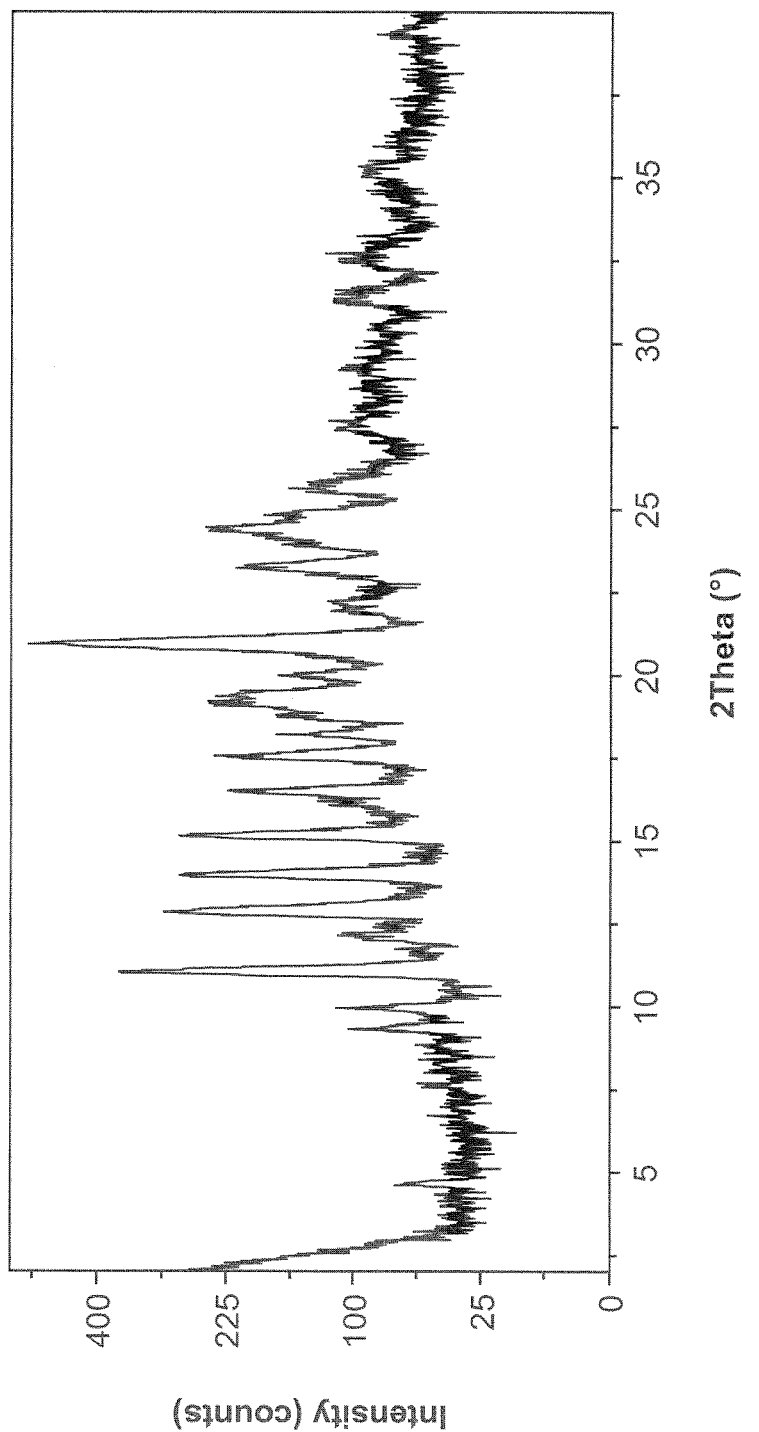
FIG. 48 is an X-ray powder diffraction pattern of Compound I Form XI.

The XRPD pattern for Form XI is as shown in FIG. 48. The differential scanning calorimetry (DSC) curve of Form XI is shown in FIG. 49. The thermogravimetric analysis (TGA) of Form XI comprising a thermogram is shown in FIG. 50. The dynamic vapor sorption (DVS) of Form XI is shown in FIG. 51.

Example 12

Preparation of (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide tetrahydrate (Compound I Form XII)

Compound I Form XII was prepared by dissolving Compound I amorphous material in 1:1 acetone:water and then sonicating the solution for about 1 hour.

Figure 52:
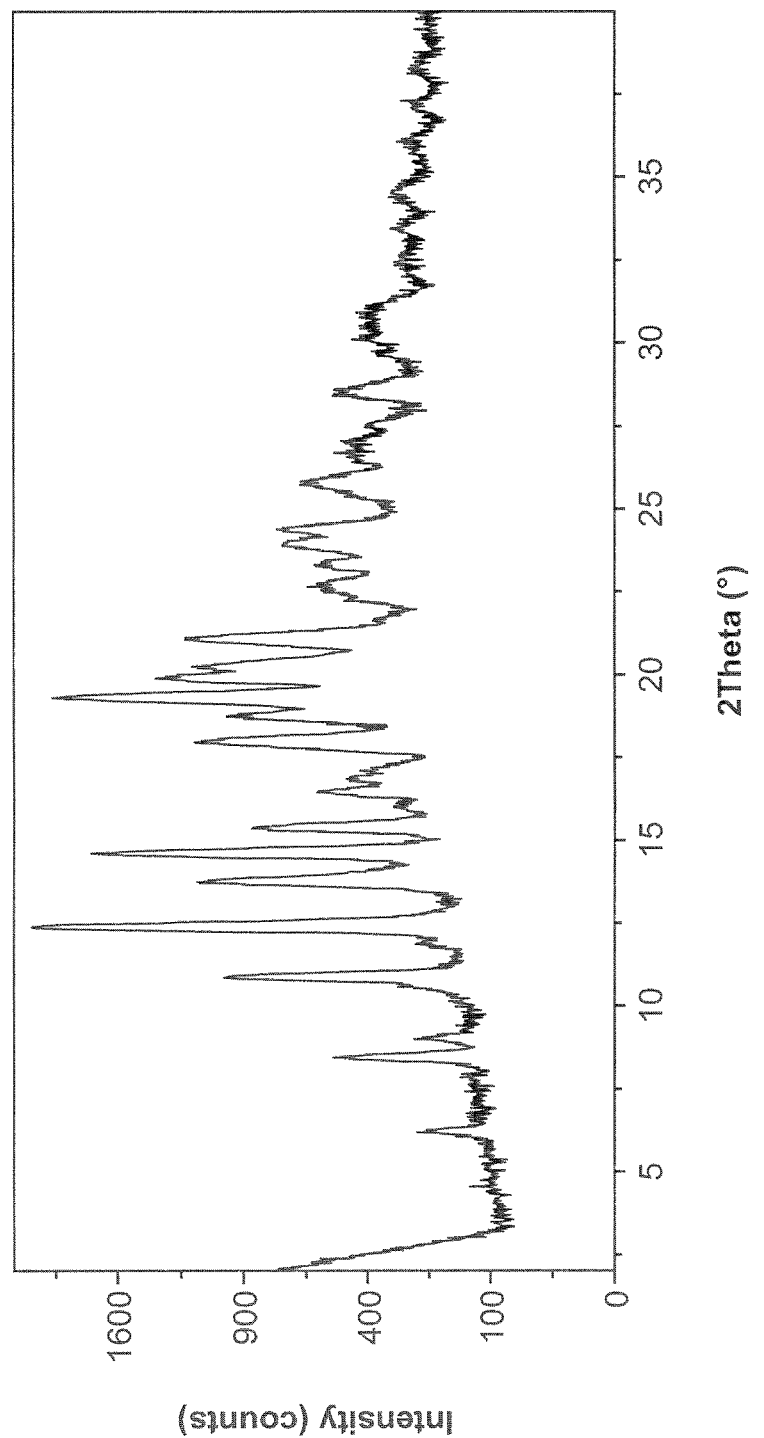
FIG. 52 is an X-ray powder diffraction pattern of Compound I Form XII.

The XRPD pattern for Form XII is as shown in FIG. 52. The differential scanning calorimetry (DSC) curve of Form XII is shown in FIG. 53. The thermogravimetric analysis (TGA) of Form XII comprising a thermogram is shown in FIG. 54. The dynamic vapor sorption (DVS) of Form XII is shown in FIG. 55.

Example 13

Preparation of (1aR,5S,8S,9S,10R,22aR)-5-tert-butyl-N-[(1R,2R)-2-(difluoromethyl)-1-{[(1-methyl-cyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide solvate (Compound I Form XIII)

Compound I Form XIII was prepared by slurring Compound I amorphous material in isopropyl acetate at room temperature.

Figure 56:
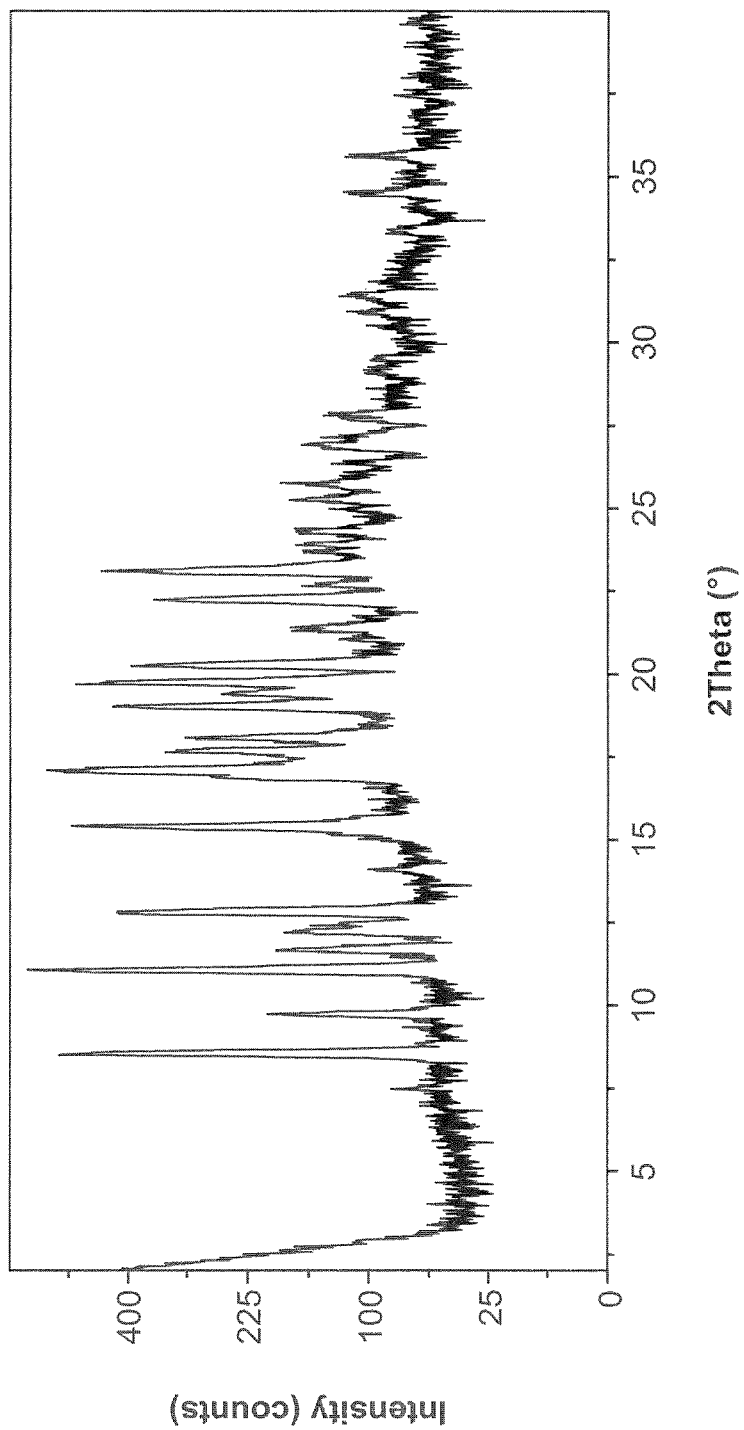
FIG. 56 is an X-ray powder diffraction pattern of Compound I Form XIII.

The XRPD pattern for Form XIII is as shown in FIG. 56. The differential scanning calorimetry (DSC) curve of Form XIII is shown in FIG. 57. The thermogravimetric analysis (TGA) of Form XIII comprising a thermogram is shown in FIG. 58. The dynamic vapor sorption (DVS) of Form XIII is shown in FIG. 59.

Example 14

Preparation of (1aR,5S,8S,9S,10R,22aR)-5-tert-butyl-N-[(1R,2R)-2-(difluoromethyl)-1-{[(1-methyl-cyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide solvate (Compound I Form XIV)

Compound I Form XIV was prepared by slurring Compound I amorphous material in 3:7 (v/v) THF:water at room temperature.

Figure 60:
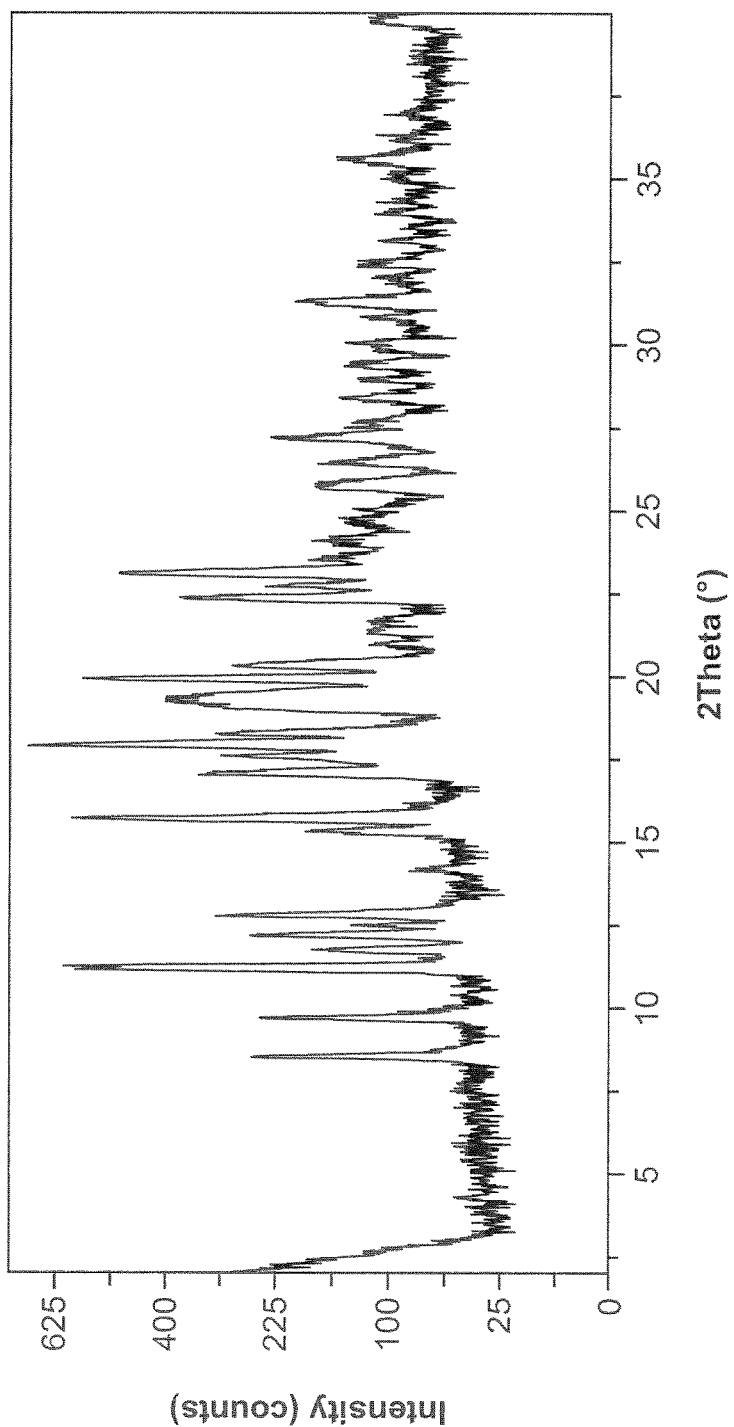
FIG. 60 is an X-ray powder diffraction pattern of Compound I Form XIV.

The XRPD pattern for Form XIV is as shown in FIG. 60. The differential scanning calorimetry (DSC) curve of Form XIV is shown in FIG. 61. The thermogravimetric analysis (TGA) of Form XIV comprising a thermogram is shown in FIG. 62. The dynamic vapor sorption (DVS) of Form XIV is shown in FIG. 63.

Example 15

Preparation of (1aR,5S,8S,9S,10R,22aR)-5-tert-butyl-N-[(1R,2R)-2-(difluoromethyl)-1-{[(1-methyl-cyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide solvate (Compound I Form XV)

Compound I Form XV was prepared by slurring Compound I amorphous material in 2-Me-THF at room temperature.

Figure 64:
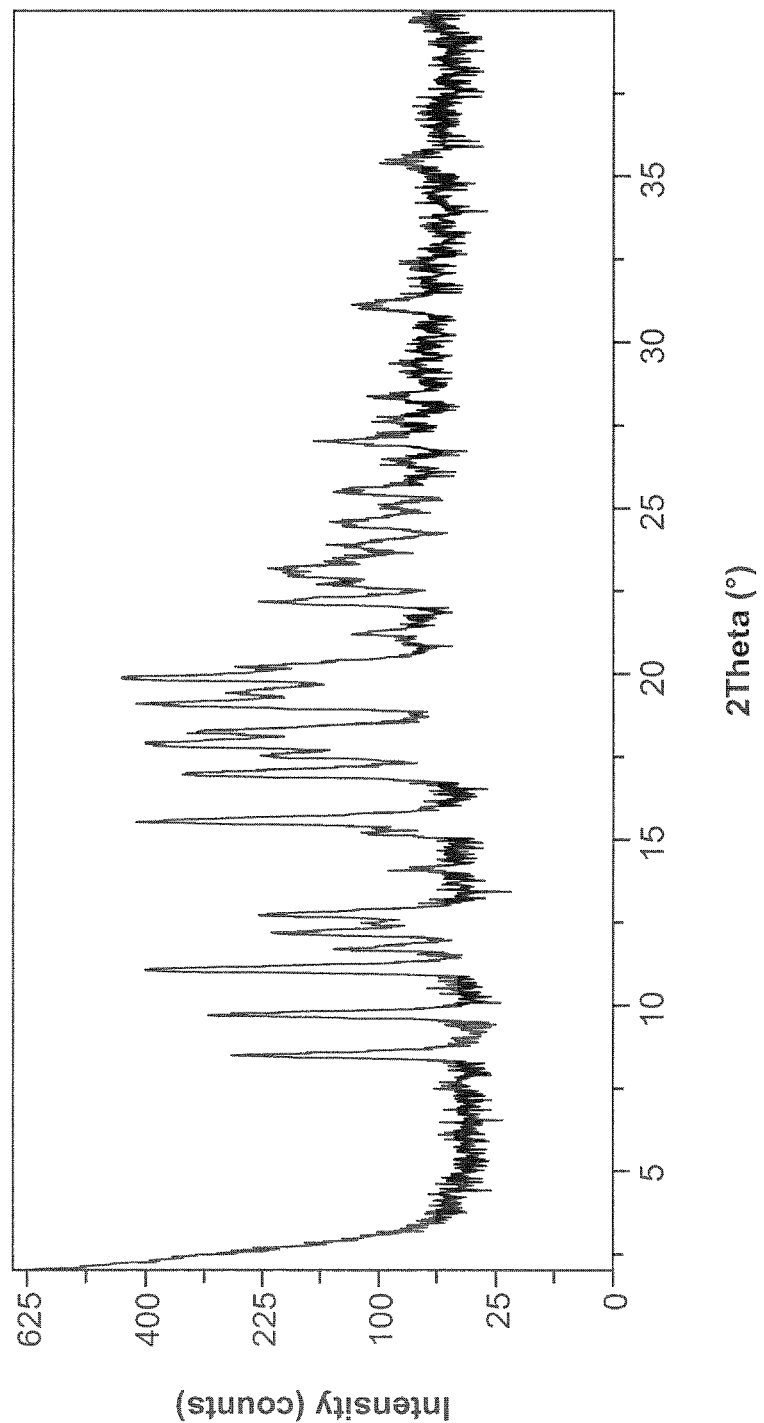
FIG. 64 is an X-ray powder diffraction pattern of Compound I Form XV.

The XRPD pattern for Form XV is as shown in FIG. 64. The differential scanning calorimetry (DSC) curve of Form XV is shown in FIG. 65. The thermogravimetric analysis (TGA) of Form XV comprising a thermogram is shown in FIG. 66. The dynamic vapor sorption (DVS) of Form XV is shown in FIG. 67.

Example 16

Preparation of (1aR,5S,8S,9S,10R,22aR)-5-tert-butyl-N-[(1R,2R)-2-(difluoromethyl)-1-{[(1-methyl-cyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide solvate (Compound I Form XVI)

Compound I Form XVI was prepared by slurring Compound I Form VIII in 4:1 (v/v) toluene:heptane.

Figure 68:
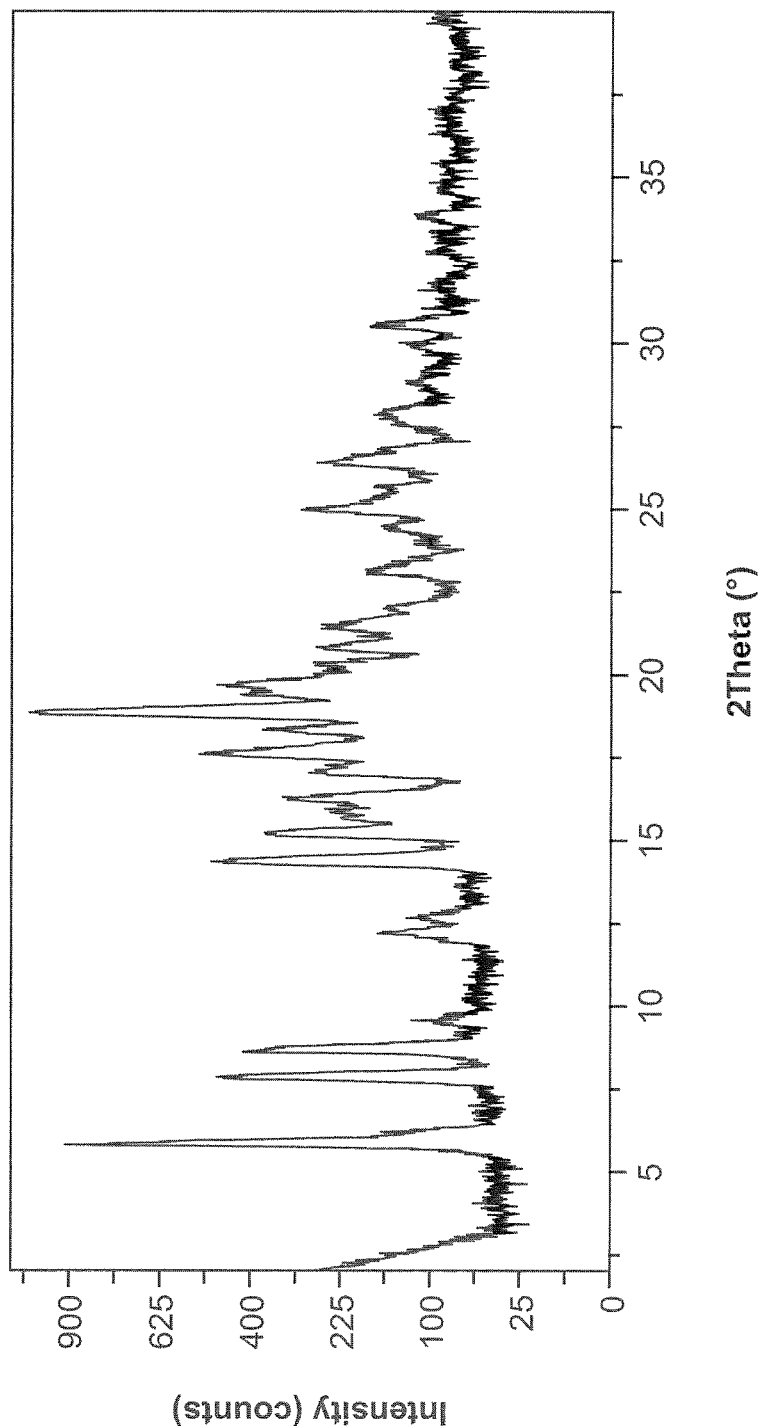
FIG. 68 is an X-ray powder diffraction pattern of Compound I Form XVI.

The XRPD pattern for Form XVI is as shown in FIG. 68. The differential scanning calorimetry (DSC) curve of Form XVI is shown in FIG. 69. The thermogravimetric analysis (TGA) of Form XVI comprising a thermogram is shown in FIG. 70.

Example 17

Preparation of (1aR,5S,8S,9S,10R,22aR)-5-tert-butyl-N-[(1R,2R)-2-(difluoromethyl)-1-{[(1-methyl-cyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide solvate (Compound I Form XVII)

Compound I Form XVII was prepared by slurring Compound I amorphous material in toluene at room temperature.

Figure 71:
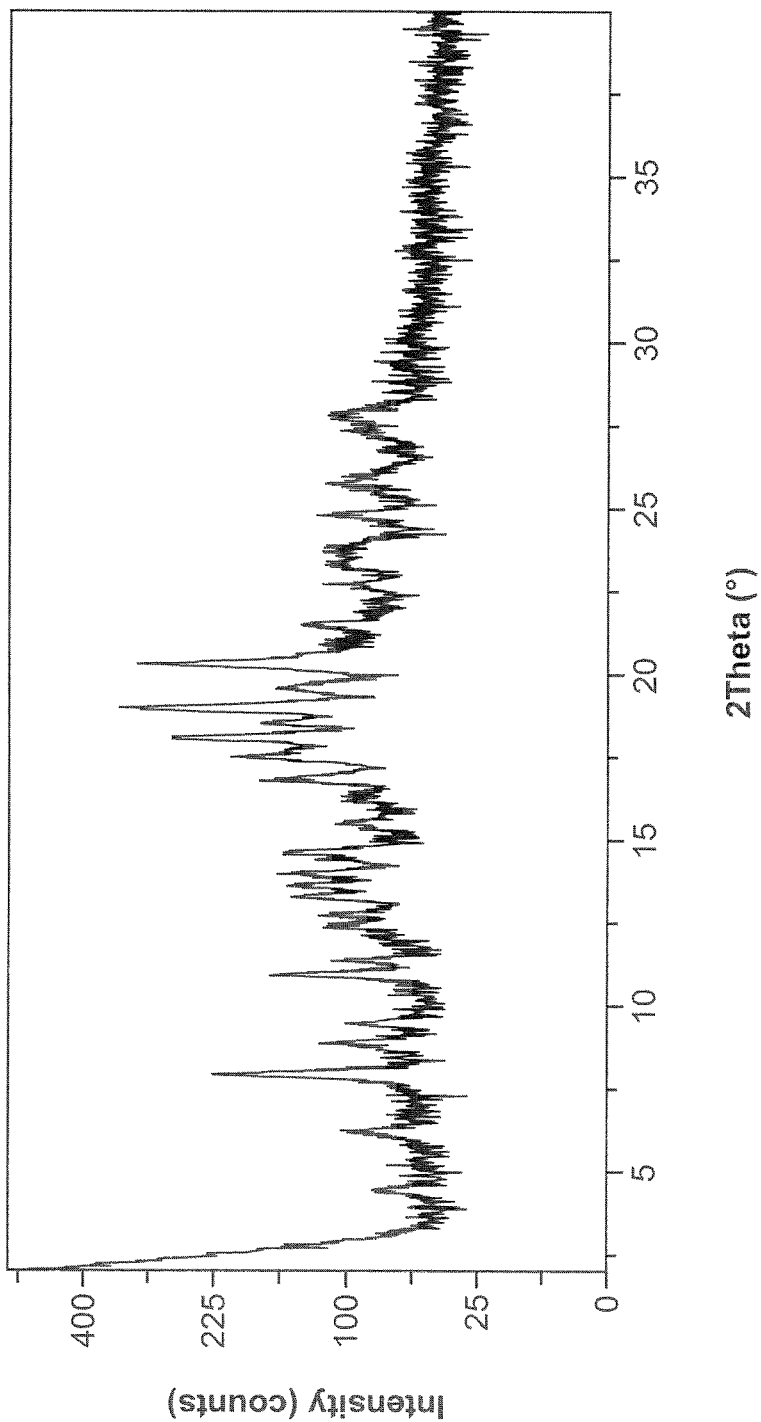
FIG. 71 is an X-ray powder diffraction pattern of Compound I Form XVII.

The XRPD pattern for Form XVII is as shown in FIG. 71. The differential scanning calorimetry (DSC) curve of Form XVII is shown in FIG. 72. The thermogravimetric analysis (TGA) of Form XVII comprising a thermogram is shown in FIG. 73.

Example 18

Preparation of (1aR,5S,8S,9S,10R,22aR)-5-tert-butyl-N-[(1R,2R)-2-(difluoromethyl)-1-{[(1-methyl-cyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide solvate (Compound I Form XVIII)

Compound I Form XVIII was prepared by slurring Compound I amorphous material in MTBE at room temperature.

Figure 74:
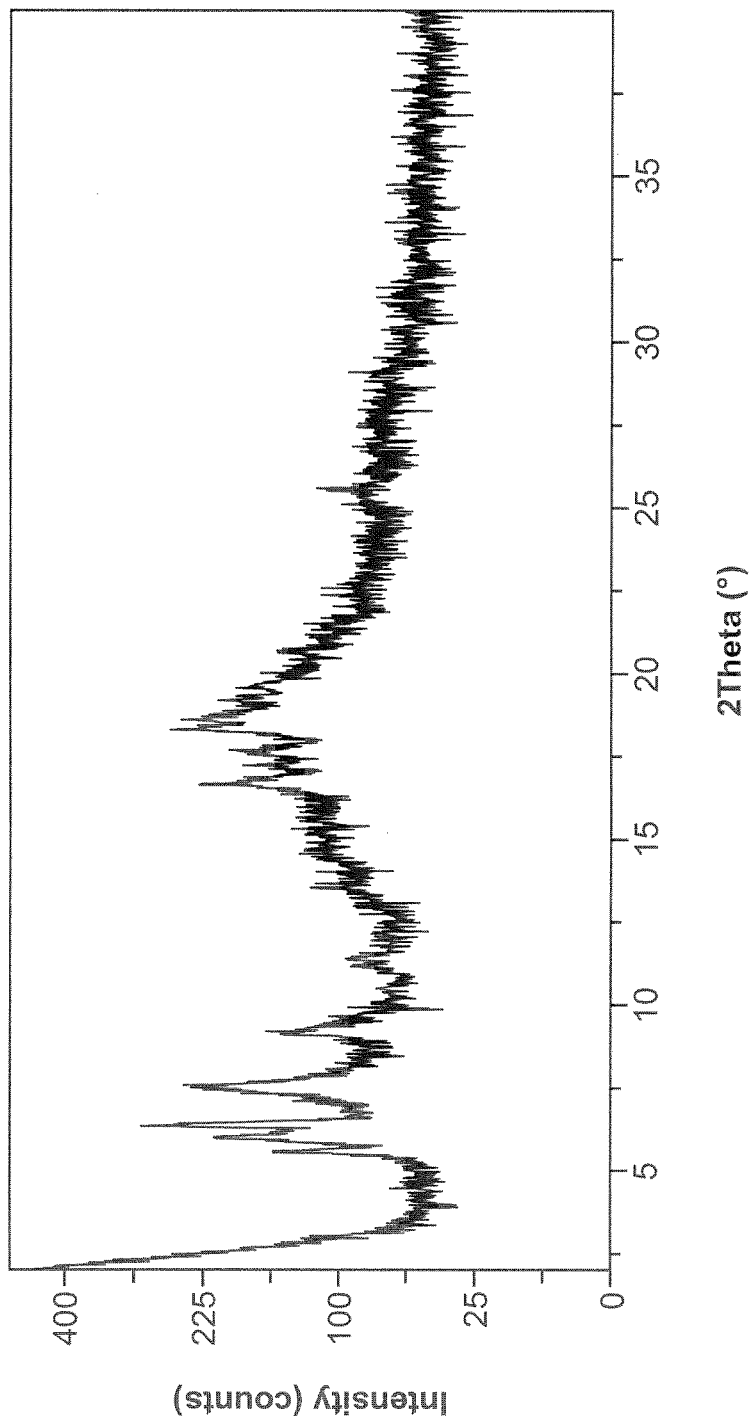
FIG. 74 is an X-ray powder diffraction pattern of Compound I Form XVIII.

The XRPD pattern for Form XVIII is as shown in FIG. 74. The differential scanning calorimetry (DSC) curve of Form XVIII is shown in FIG. 75. The thermogravimetric analysis (TGA) of Form XVIII comprising a thermogram is shown in FIG. 76. The dynamic vapor sorption (DVS) of Form XVIII is shown in FIG. 77.

Example 19

Preparation of (1aR,5S,8S,9S,10R,22aR)-5-tert-butyl-N-[(1R,2R)-2-(difluoromethyl)-1-{[(1-methyl-cyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide solvate (Compound I Form XIX)

Compound I Form XIX was prepared by crystallizing Compound I from 1:4 (v/v) MTBE:n-heptane.

The XRPD pattern for Form XIX is as shown in FIG. 78. The differential scanning calorimetry (DSC) curve of Form XIX is shown in FIG. 79. The thermogravimetric analysis (TGA) of Form XIX comprising a thermogram is shown in FIG. 80.

Example 20

Preparation of (1aR,5S,8S,9S,10R,22aR)-5-tert-butyl-N-[(1R,2R)-2-(difluoromethyl)-1-{[(1-methyl-cyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide solvate (Compound I Form XX)

Compound I Form XX was prepared by dissolving Compound I Form VIII in DMAc and allowing the sample to evaporate to dryness.

The XRPD pattern for Form XX is as shown in FIG. 81. The differential scanning calorimetry (DSC) curve of Form XX is shown in FIG. 82. The thermogravimetric analysis (TGA) of Form XX comprising a thermogram is shown in FIG. 83. The dynamic vapor sorption (DVS) of Form XX is shown in FIG. 84.

Example 21

Preparation of (1aR,5S,8S,9S,10R,22aR)-5-tert-butyl-N-[(1R,2R)-2-(difluoromethyl)-1-{[(1-methyl-cyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide solvate (Compound I Form XXI)

Compound I Form XXI was prepared by dissolving Compound I Form VIII in DMF and allowing the sample to evaporate to dryness.

The XRPD pattern for Form XXI is as shown in FIG. 85. The differential scanning calorimetry (DSC) curve of Form XXI is shown in FIG. 86. The thermogravimetric analysis (TGA) of Form XXI comprising a thermogram is shown in FIG. 87. The dynamic vapor sorption (DVS) of Form XXI is shown in FIG. 88.

Example 22

Preparation of (1aR,5S,8S,9S,10R,22aR)-5-tert-butyl-N-[(1R,2R)-2-(difluoromethyl)-1-{[(1-methyl-cyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide sodium (Compound I sodium Form I)

Compound I sodium Form I was prepared by slurring a mixture of Compound I sodium Form I and Compound I sodium Form II in ethanol.

The XRPD pattern for Compound I sodium Form I is as shown in FIG. 89. The differential scanning calorimetry (DSC) curve of Compound I sodium Form I is shown in FIG. 90. The thermogravimetric analysis (TGA) of Compound I sodium Form I comprising a thermogram is shown in FIG. 91. The dynamic vapor sorption (DVS) of Compound I sodium Form I is shown in FIG. 92.

Example 23

Preparation of (1aR,5S,8S,9S,10R,22aR)-5-tert-butyl-N-[(1R,2R)-2-(difluoromethyl)-1-{[(1-methyl-cyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide sodium (Compound I sodium Form II)

Compound I sodium Form II was prepared by exposing Compound I sodium Form I to relative humidity conditions less that 40% RH.

Figure 93:
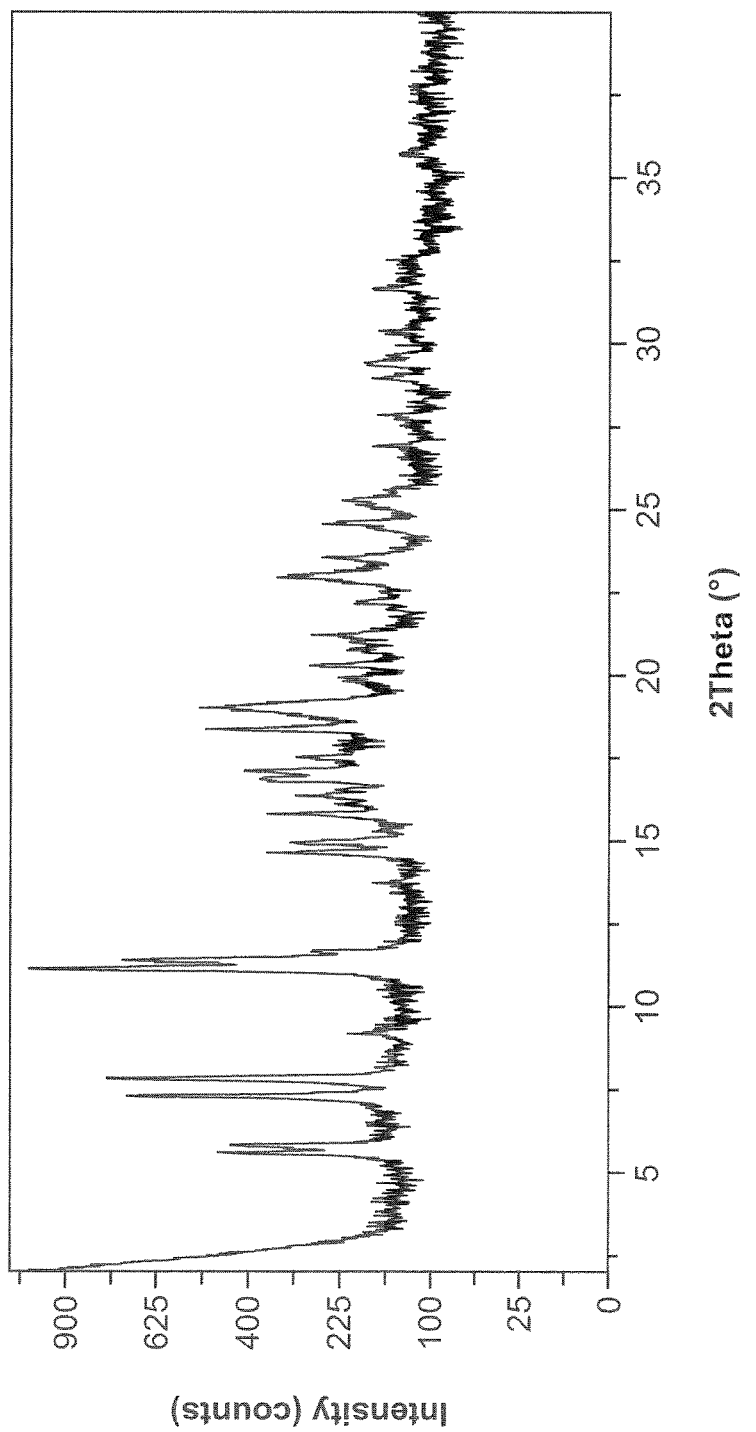
FIG. 93 is an X-ray powder diffraction pattern of Compound I sodium Form II.

The XRPD pattern for Compound I sodium Form II is as shown in FIG. 93. The differential scanning calorimetry (DSC) curve of Compound I sodium Form II is shown in FIG. 94. The thermogravimetric analysis (TGA) of Compound I sodium Form II comprising a thermogram is shown in FIG. 95. The dynamic vapor sorption (DVS) of Compound I sodium Form II is shown in FIG. 96.

Example 24

Preparation of (1aR,5S,8S,9S,10R,22aR)-5-tert-butyl-N-[(1R,2R)-2-(difluoromethyl)-1-{[(1-methyl-cyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide sodium (Compound I sodium Form III)

Compound I sodium Form III was prepared by slurring a mixture of Compound I sodium Form I and Compound I sodium Form II in either IPA, EtOAc, acetone, THF, or MEK.

Figure 97:
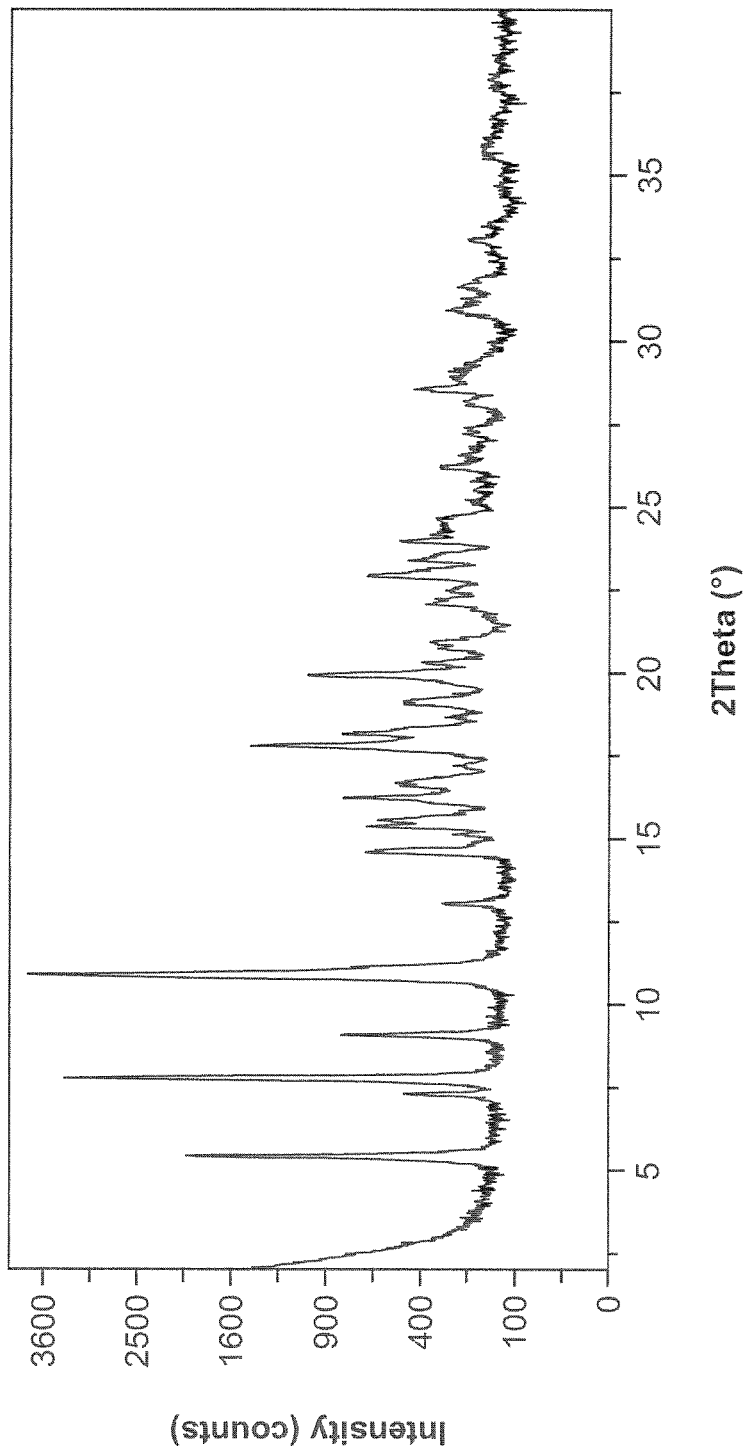
FIG. 97 is an X-ray powder diffraction pattern of Compound I sodium Form III.

The XRPD pattern for Compound I sodium Form III is as shown in FIG. 97. The differential scanning calorimetry (DSC) curve of Compound I sodium Form III is shown in FIG. 98. The thermogravimetric analysis (TGA) of Compound I sodium Form III comprising a thermogram is shown in FIG. 99. The dynamic vapor sorption (DVS) of Compound I sodium Form III is shown in FIG. 100.

Example 25

Preparation of (1aR,5S,8S,9S,10R,22aR)-5-tert-butyl-N-[(1R,2R)-2-(difluoromethyl)-1-{[(1-methyl-cyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide sodium (Compound I sodium Form IV)

Compound I sodium Form IV was prepared by slurring a mixture of Compound I sodium Form I and Compound I sodium Form II in either IPAc or MIBK.

Figure 101:
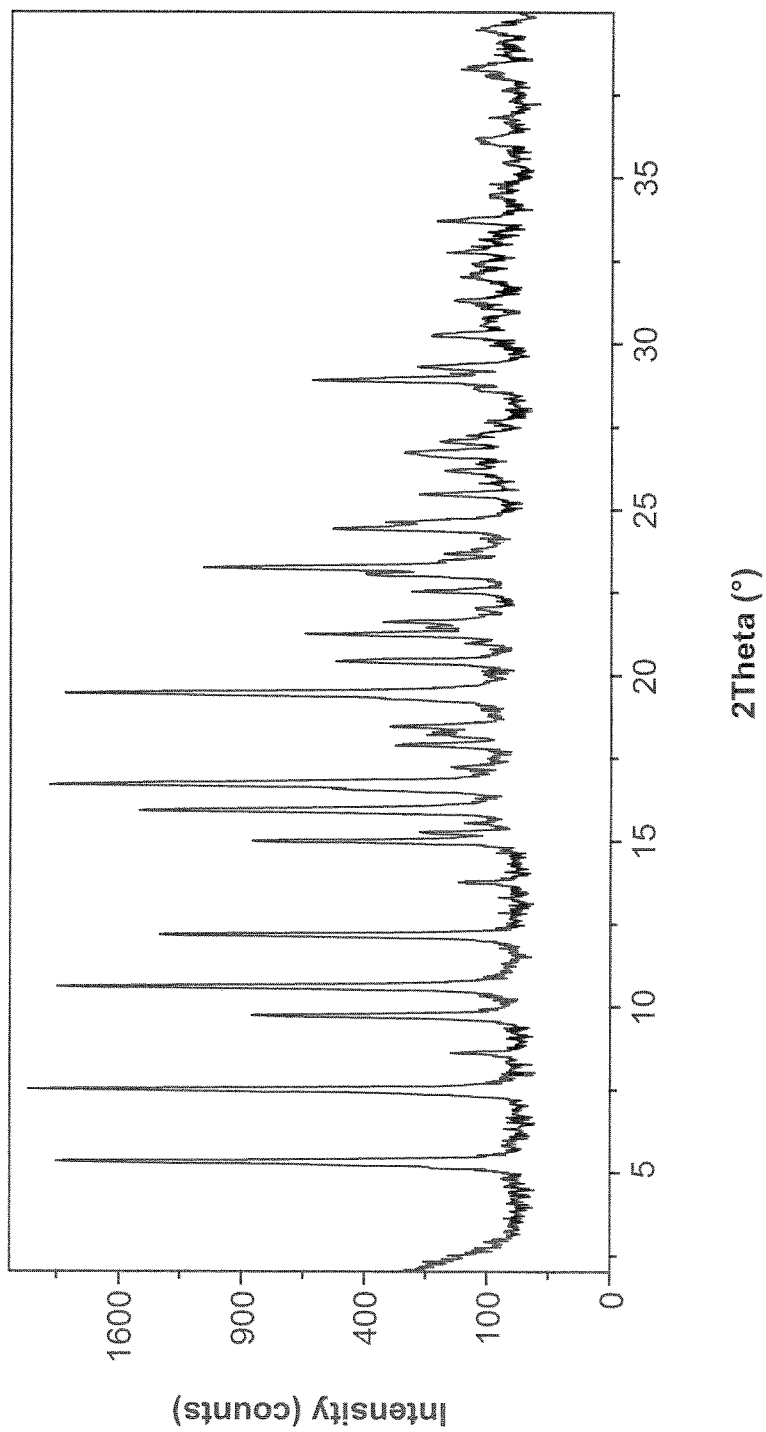
FIG. 101 is an X-ray powder diffraction pattern of Compound I sodium Form IV.

The XRPD pattern for Compound I sodium Form IV is as shown in FIG. 101. The differential scanning calorimetry (DSC) curve of Compound I sodium Form IV is shown in FIG. 102. The thermogravimetric analysis (TGA) of Compound I sodium Form IV comprising a thermogram is shown in FIG. 103. The dynamic vapor sorption (DVS) of Compound I sodium Form IV is shown in FIG. 104.

Example 26

Preparation of (1aR,5S,8S,9S,10R,22aR)-5-tert-butyl-N-[(1R,2R)-2-(difluoromethyl)-1-{[(1-methyl-cyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide meglumine (Compound I meglumine Form I)

Compound I meglumine Form I was prepared by cooling a solution of Compound I with meglumine in 1:1 (v/v) toluene:heptane from elevated temperature followed by vacuum drying at elevated temperature.

Figure 105:
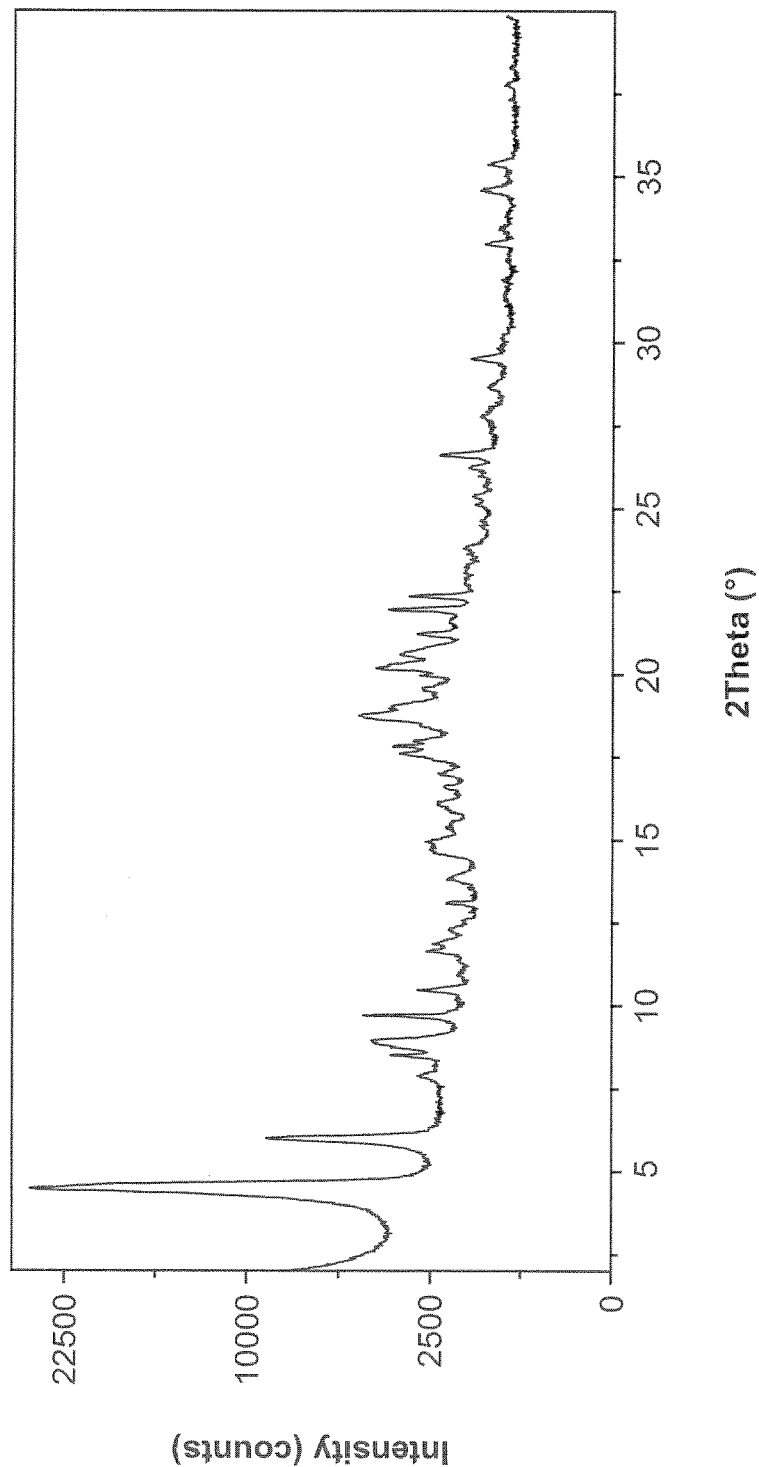
FIG. 105 is an X-ray powder diffraction pattern of Compound I meglumine Form I.

The XRPD pattern for Compound I meglumine Form I is as shown in FIG. 105. The differential scanning calorimetry (DSC) curve of Compound I meglumine Form I is shown in FIG. 106. The thermogravimetric analysis (TGA) of Compound I meglumine Form I comprising a thermogram is shown in FIG. 107.

Example 27

Preparation of (1aR,5S,8S,9S,10R,22aR)-5-tert-butyl-N-[(1R,2R)-2-(difluoromethyl)-1-{[(1-methyl-cyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide piperazine (Compound I piperazine Form I)

Compound I piperazine Form I was prepared by cooling a solution of Compound I with piperazine in 1:1 (v/v) ethanol:water from elevated temperature.

Figure 108:
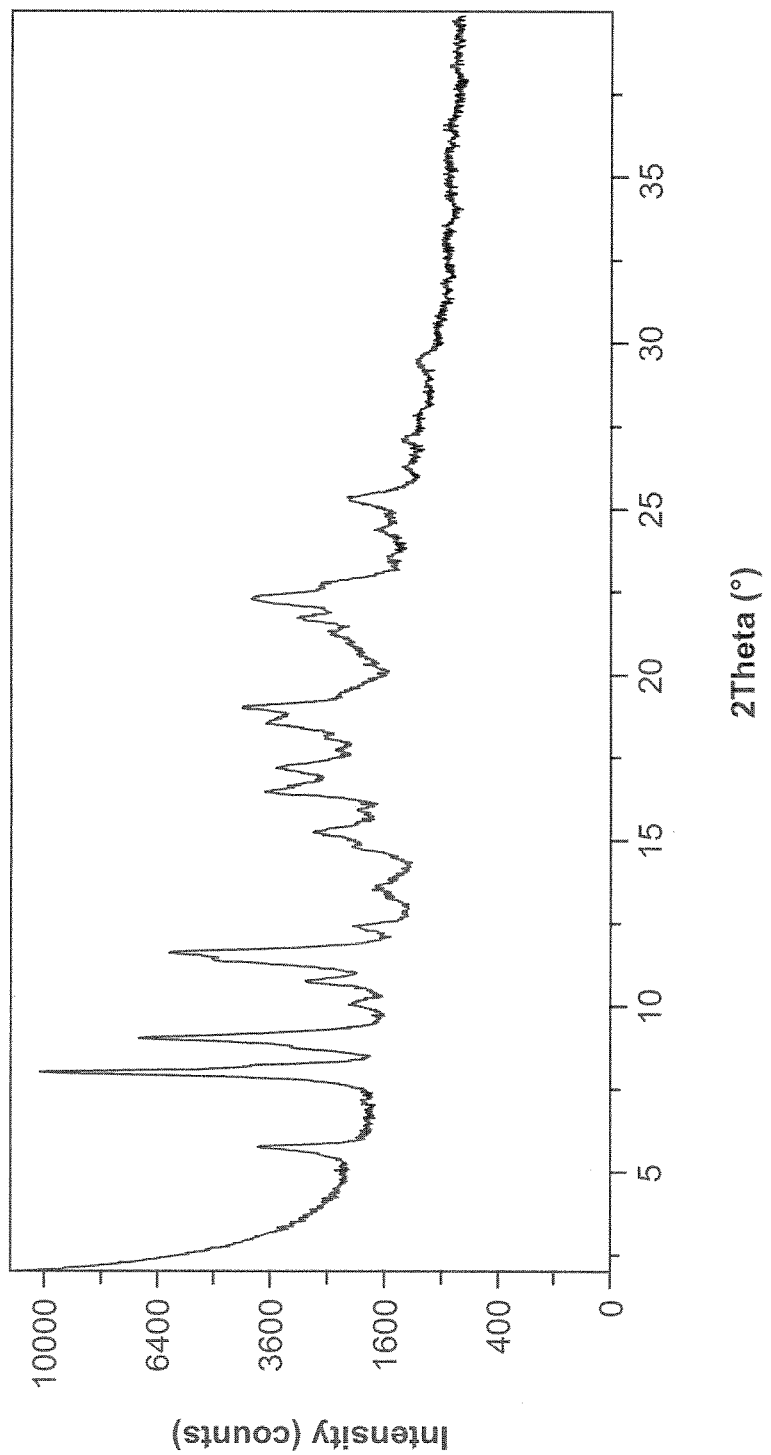
FIG. 108 is an X-ray powder diffraction pattern of Compound I piperazine Form I.

The XRPD pattern for Compound I piperazine Form I is as shown in FIG. 108. The differential scanning calorimetry (DSC) curve of Compound I piperazine Form I is shown in FIG. 109. The thermogravimetric analysis (TGA) of Compound I piperazine Form I comprising a thermogram is shown in FIG. 110.

Example 28

Preparation of (1aR,5S,8S,9S,10R,22aR)-5-tert-butyl-N-[(1R,2R)-2-(difluoromethyl)-1-{[(1-methyl-cyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide choline (Compound I choline Form I)

Compound I choline Form I was prepared by cooling a solution of Compound I with choline in 1:1 (v/v) toluene:heptane from elevated temperature followed by vacuum drying at elevated temperature.

Figure 111:
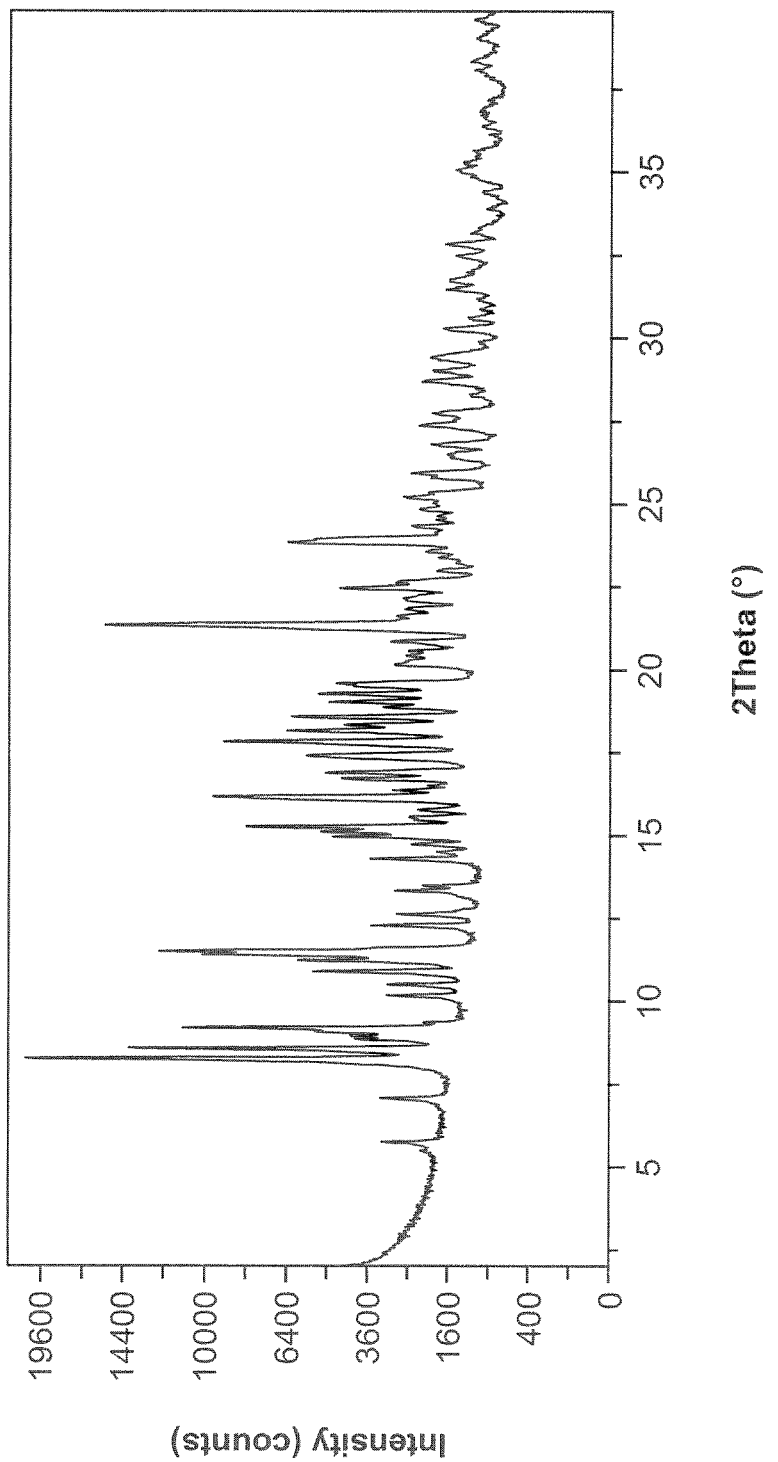
FIG. 111 is an X-ray powder diffraction pattern of Compound I choline Form I.

The XRPD pattern for Compound I choline Form I is as shown in FIG. 111. The differential scanning calorimetry (DSC) curve of Compound I choline Form I is shown in FIG. 112. The thermogravimetric analysis (TGA) of Compound I choline Form I comprising a thermogram is shown in FIG. 113.

Example 29

Preparation of (1aR,5S,8S,9S,10R,22aR)-5-tert-butyl-N-[(1R,2R)-2-(difluoromethyl)-1-{[(1-methyl-cyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide deanol (Compound I deanol Form I)

Compound I deanol Form I was prepared by slurring Compound I with deanol in 1:1 (v/v) toluene:heptane at elevated temperature.

Figure 114:
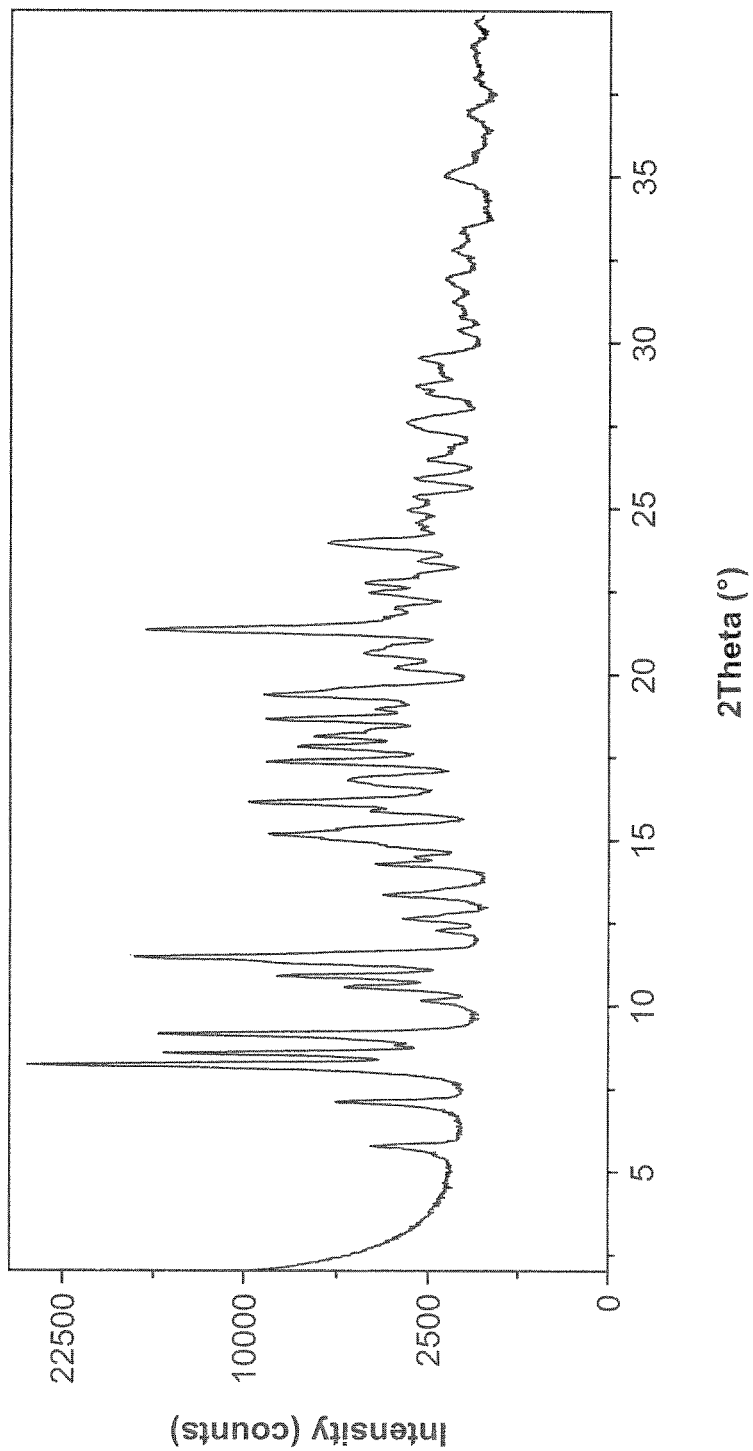
FIG. 114 is an X-ray powder diffraction pattern of Compound I deanol Form I.

The XRPD pattern for Compound I deanol Form I is as shown in FIG. 114.

Example 30

Preparation of (1aR,5S,8S,9S,10R,22aR)-5-tert-butyl-N-[(1R,2R)-2-(difluoromethyl)-1-{[(1-methyl-cyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide 1-(2-hydroxyetthyl)-pyrrolidine (Compound I 1-(2-hydroxyetthyl)-pyrrolidine Form I)

Compound I 1-(2-hydroxyetthyl)-pyrrolidine Form I was prepared by cooling a solution of Compound I with pyrrolidine in 18:83 (v/v) ethyl acetate:methanol from elevated temperature with volume reduction.

Figure 115:
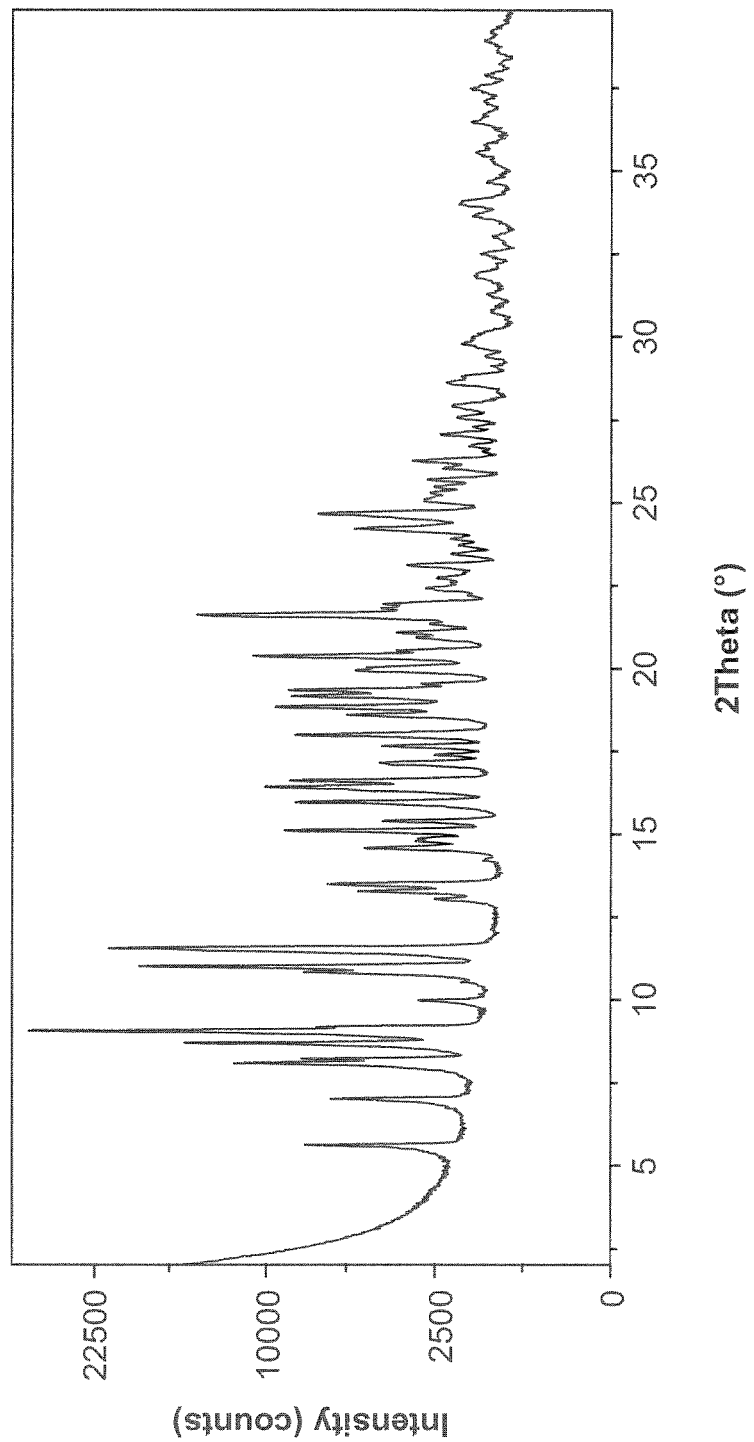
FIG. 115 is an X-ray powder diffraction pattern of Compound I 1-(2-hydroxyethyl)-pyrrolidine (HEP) Form I.

The XRPD pattern for Compound I 1-(2-hydroxyetthyl)-pyrrolidine Form I is as shown in FIG. 115. The differential scanning calorimetry (DSC) curve of Compound I 1-(2-hydroxyetthyl)-pyrrolidine Form I is shown in FIG. 116. The thermogravimetric analysis (TGA) of Compound I 1-(2-hydroxyetthyl)-pyrrolidine Form I comprising a thermogram is shown in FIG. 117.

Example 31

Preparation of (1aR,5S,8S,9S,10R,22aR)-5-tert-butyl-N-[(1R,2R)-2-(difluoromethyl)-1-{[(1-methyl-cyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide 1-(2-hydroxyetthyl)-pyrrolidine (Compound I 1-(2-hydroxyetthyl)-pyrrolidine Form II)

Compound I 1-(2-hydroxyetthyl)-pyrrolidine Form II was prepared by vacuum drying Compound I 1-(2-hydroxyetthyl)-pyrrolidine Form I at about 80° C.

Figure 118:
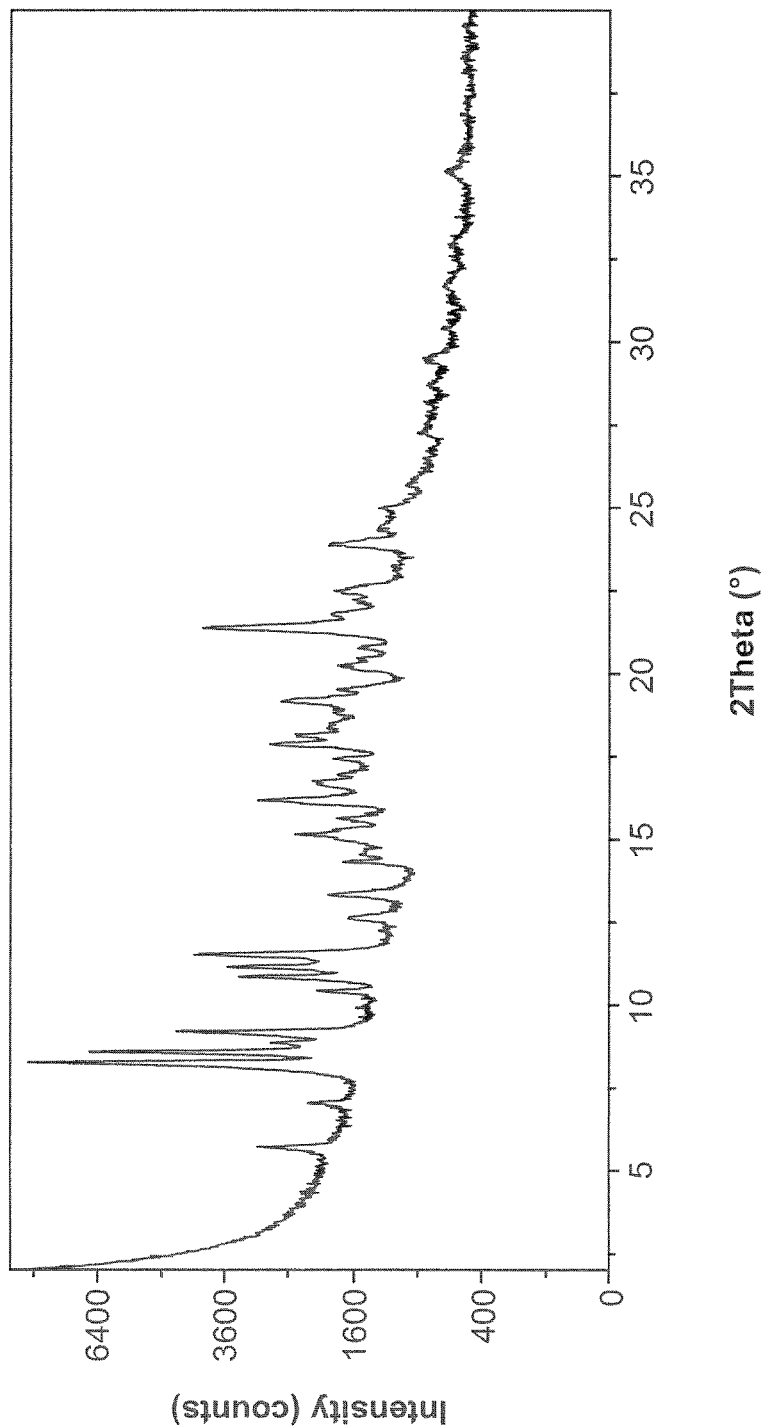
FIG. 118 is an X-ray powder diffraction pattern of Compound I 1-(2-hydroxyethyl)-pyrrolidine (HEP) Form II.

The XRPD pattern for Compound I 1-(2-hydroxyetthyl)-pyrrolidine Form II is as shown in FIG. 118.

Example 32

Preparation of (1aR,5S,8S,9S,10R,22aR)-5-tert-butyl-N-[(1R,2R)-2-(difluoromethyl)-1-{[(1-methyl-cyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide 1-(2-hydroxyetthyl)-pyrrolidine (Compound I 1-(2-hydroxyetthyl)-pyrrolidine Form III)

Figure 119:
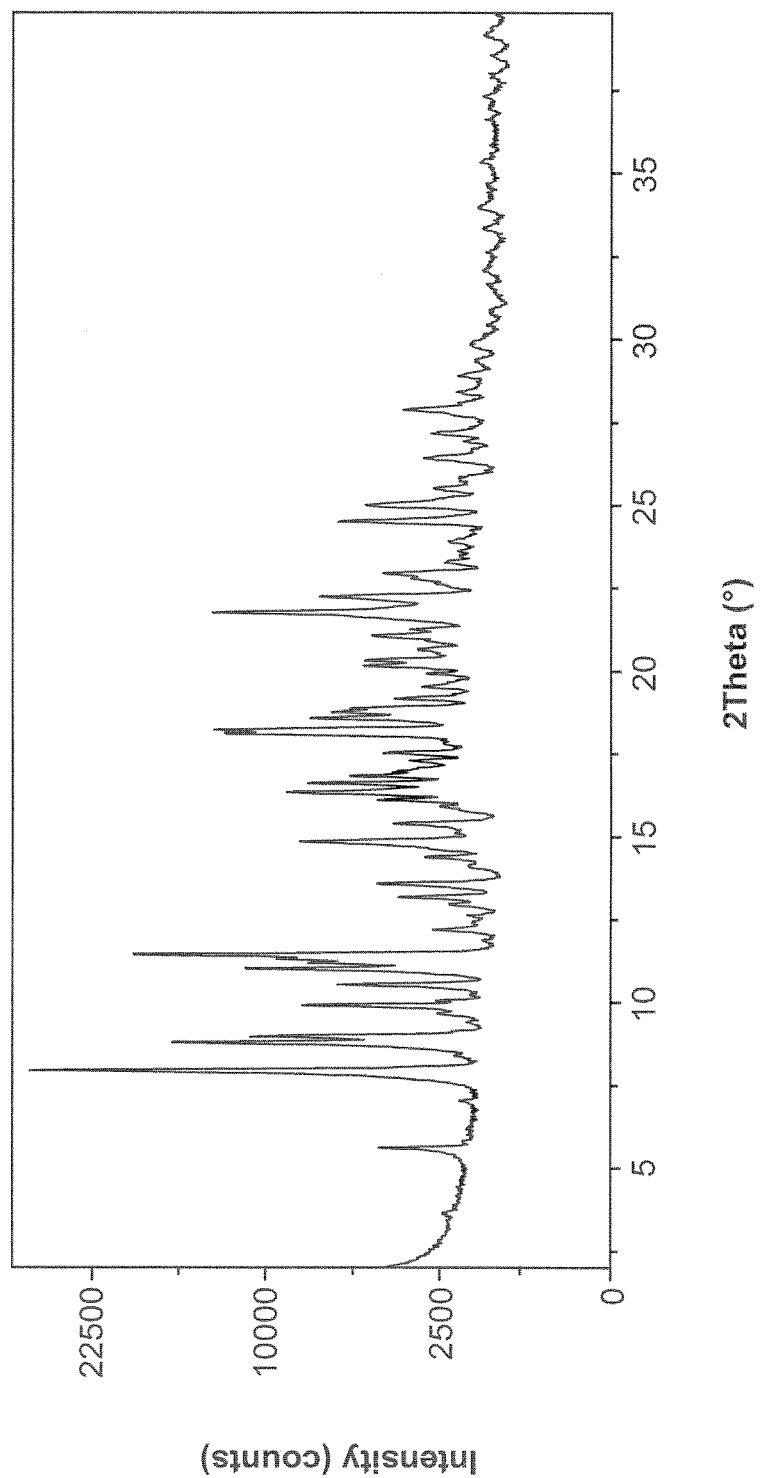
FIG. 119 is an X-ray powder diffraction pattern of Compound I 1-(2-hydroxyethyl)-pyrrolidine (HEP) Form III.

Compound I 1-(2-hydroxyetthyl)-pyrrolidine Form III was prepared by evaporation of a solution of Compound I with pyrrolidine from 1:1 (v/v) methyl-tert-butyl ether: toluene.
The XRPD pattern for Compound I 1-(2-hydroxyetthyl)-pyrrolidine Form III is as shown in FIG. 119.

Example 33

Preparation of (1aR,5S,8S,9S,10R,22aR)-5-tert-butyl-N-[(1R,2R)-2-(difluoromethyl)-1-{[(1-methyl-cyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide lysine (Compound I lysine Form I)

Figure 120:
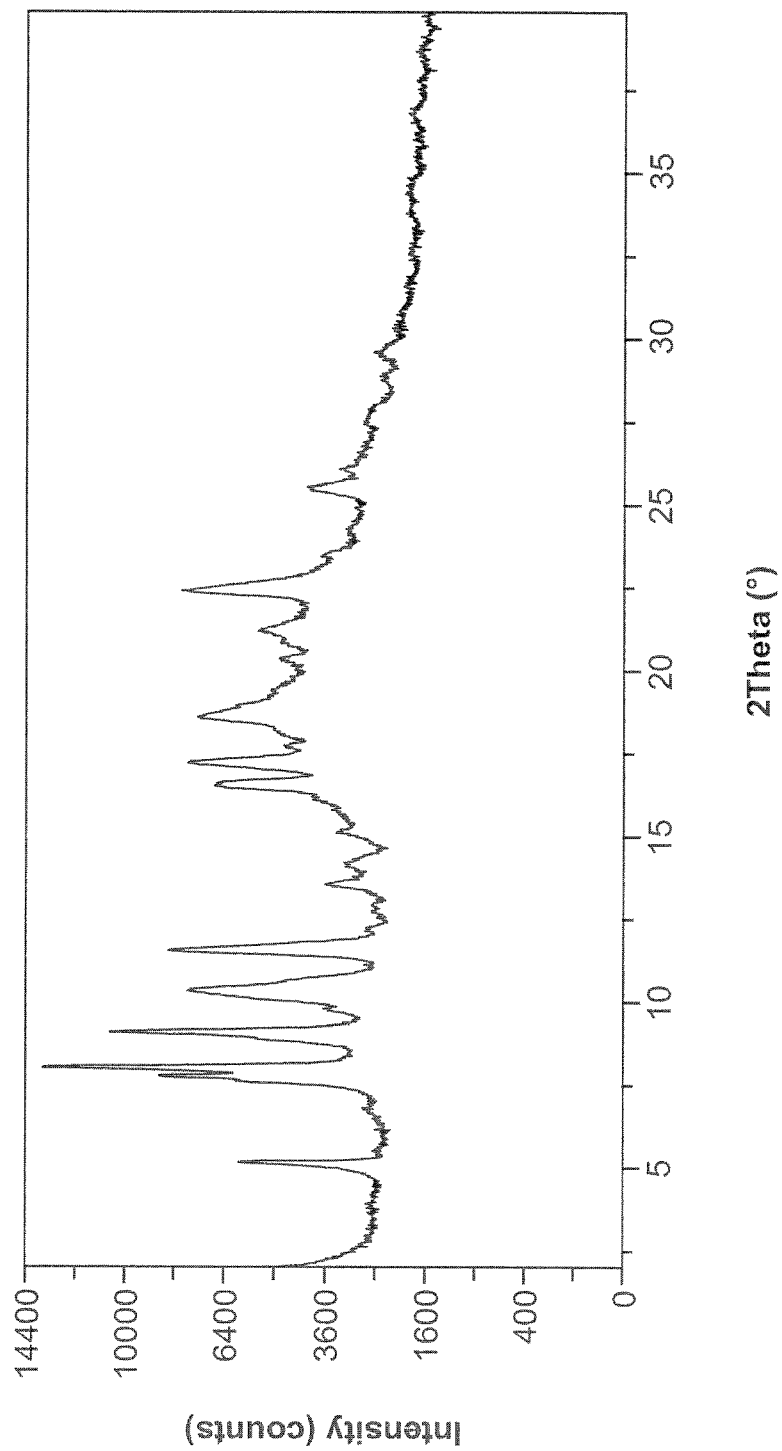

Compound I lysine Form I was prepared by cooling of a solution of Compound I with lysine from 4:1 (v/v) ethanol: water from elevated temperature.
The XRPD pattern for Compound I lysine Form I is as shown in FIG. 120.

Example 34

Preparation of (1aR,5S,8S,9S,10R,22aR)-5-tert-butyl-N-[(1R,2R)-2-(difluoromethyl)-1-{[(1-methyl-cyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide arginine (Compound I arginine Form I)

Compound I arginine Form I was prepared by evaporation of a solution of Compound I with arginine from 4:1 (v/v) isopropanol:water.

Figure 121:
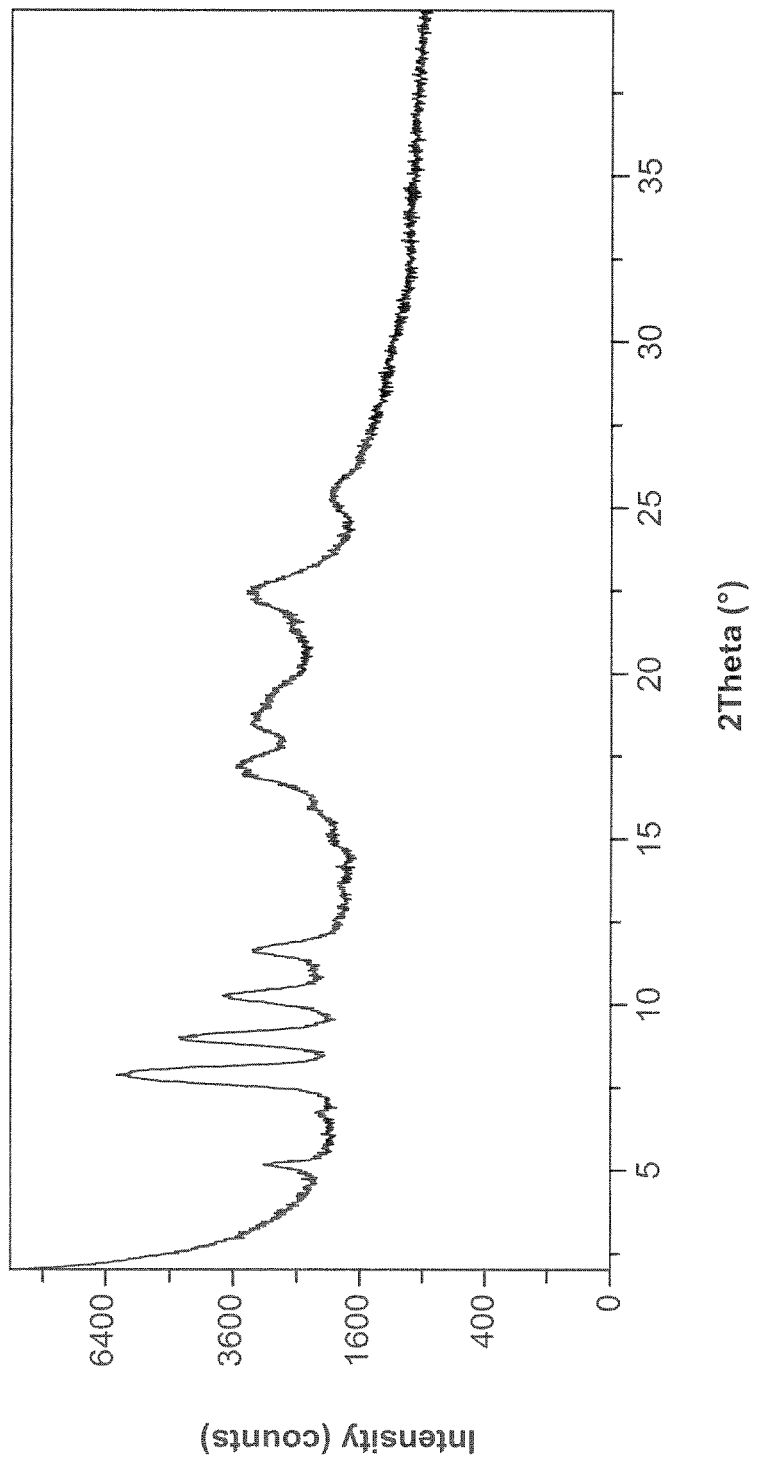

The XRPD pattern for Compound I arginine Form I is as shown in FIG. 121.

Example 35

Preparation of (1aR,5S,8S,9S,10R,22aR)-5-tert-butyl-N-[(1R,2R)-2-(difluoromethyl)-1-{[(1-methyl-cyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide potassium (Compound I potassium Form I)

Compound I potassium Form I was prepared by dissolving Compound I Form II in ~10 mL/g of IPA, followed by remove ~10% of IPA through distillation and recharged ~10% IPA. The solution was then heated to about 60° C., and 1.5 eq of KOH (aq) was charged and mixture cooled to about 10° C.

Figure 122:
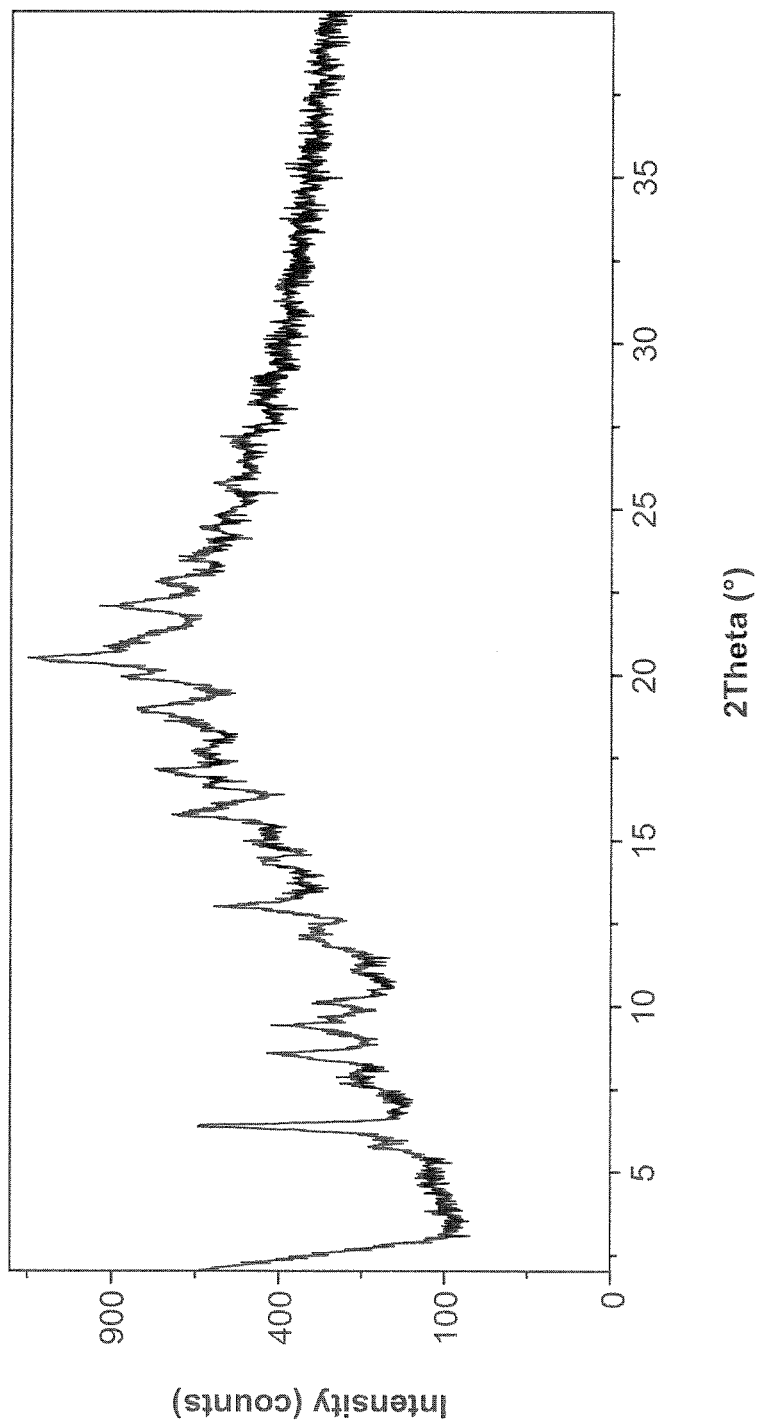

The XRPD pattern for Compound I potassium Form I is as shown in FIG. 122. The differential scanning calorimetry (DSC) curve of Compound I potassium Form I is shown in FIG. 123. The thermogravimetric analysis (TGA) of Compound I potassium Form I comprising a thermogram is shown in FIG. 124. The dynamic vapor sorption (DVS) of Compound I potassium Form I is shown in FIG. 125.

Example 36

Synthesis of (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide (I) by route I Compound of formula I was synthesized via route I as shown below:

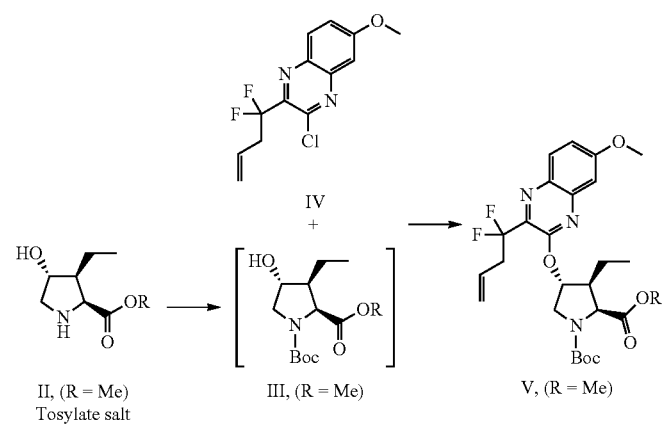
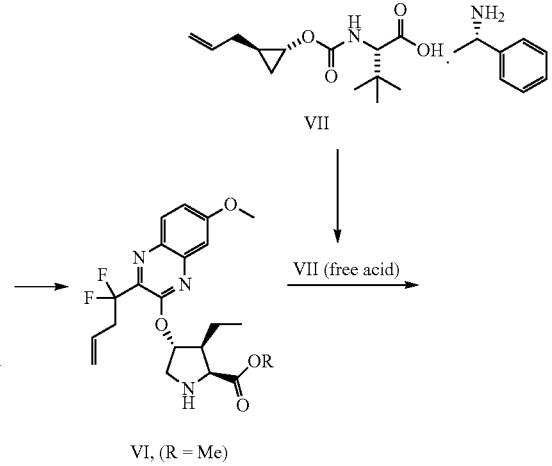

-continued
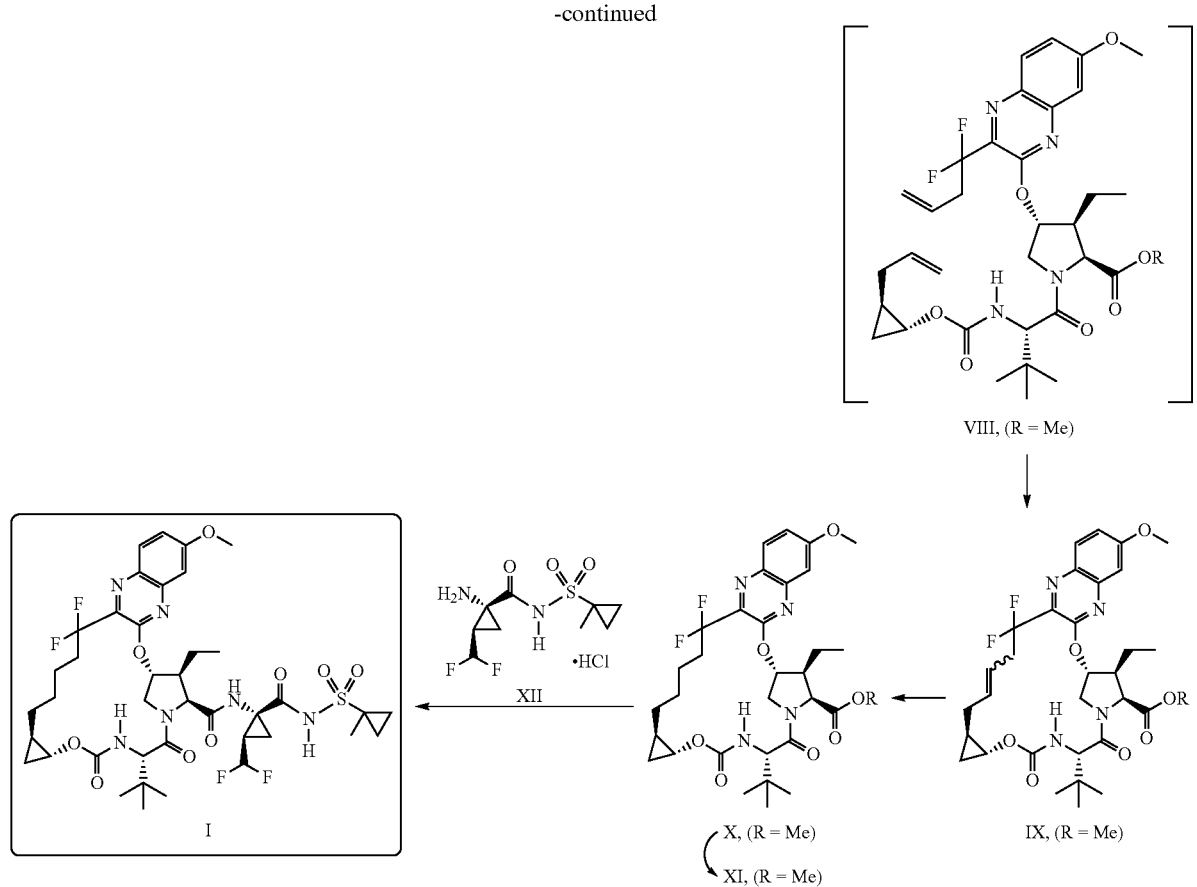
Synthesis of Intermediates for Compound of Formula I
A. Synthesis of Methyl (2S,3S,4R)-3-ethyl-4-hydroxypyrrolidine-2-carboxylate Tosylate Salt (II)
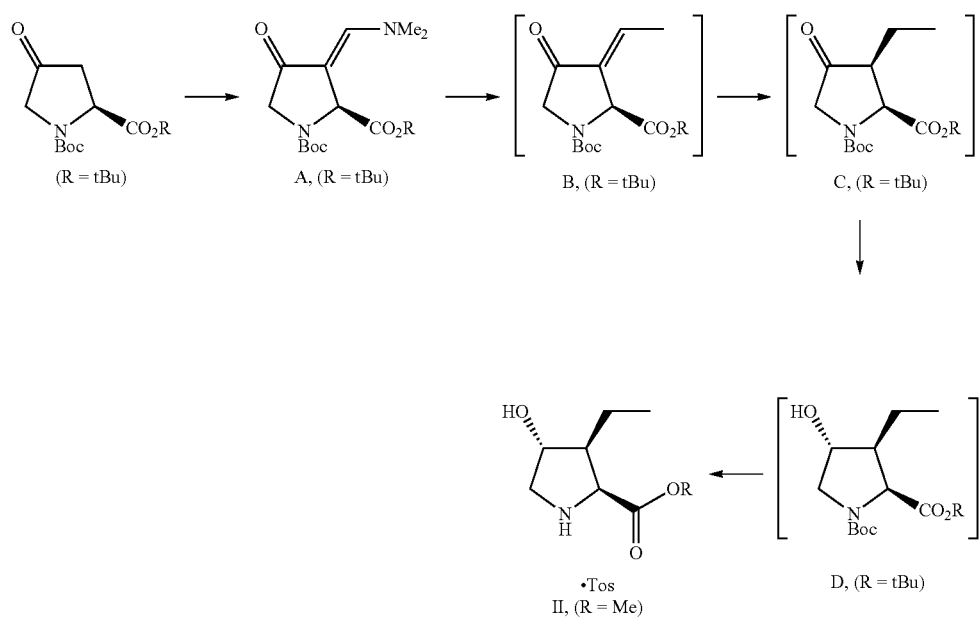

The order of reduction of the double bond and ketone was reversed so new intermediates were formed, B (R=tBu) and C (R=tBu). The t-butyl ester was used to make D in U.S. Publication No. 2014-0017198; however, it was converted directly to the methyl ester tosylate salt without chromatography and crystallized to remove diastereomeric impurities. A single crystal X-Ray of the tosylate salt II was obtained.

Step 1: Synthesis of A

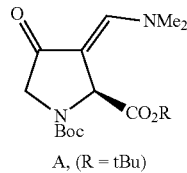

A, (R = tBu)

I. Enamine Formation to A

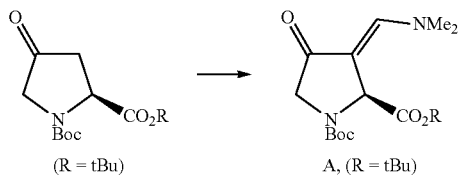

(R = tBu)    A, (R = tBu)

DMF-DMA (125.3 g, 2.0 eq.) and DCM (300 mL) were charged to a reactor under $N_2$ and heated to 45° C. In a separate container the commercially available starting material (150 g) was dissolved in DCM (300 mL) under $N_2$. This solution was charged to the reactor containing the DMF-DMA solution over 3 hours. Upon reaction completion, the solution was cooled to room temperature. 5% LiCl (750 mL) was added to the reactor and the mixture was stirred. The layers were separated and the aqueous layer was removed. Water (750 mL) was added to the reactor and the mixture was stirred. The layers were separated and the aqueous layer was removed. The organic layer was dried with $Na_2SO_4$ and the mixture was polish filtered.

The filtrate was concentrated to ~200 mL and heptane (600 mL) was charged to obtain a murky solution. The mixture was further concentrated to remove residual DCM. Additional heptane (600 mL) was added and the mixture was heated to about 50-60° C. and aged for about 1 h to obtain a slurry. The slurry was cooled to about 15° C. over about 4 hours before aging at about 15° C. overnight (~18 h). Intermediate A (R=tBu) was isolated via vacuum filtration and rinsed with 2 volumes heptane. The resulting solid was dried in a vacuum oven at about 45° C. to constant weight to obtain 141.8 g of A (R=tBu). $^1$H NMR (400 MHz, $CDCl_3$) (mixture of E/Z isomer): δ 7.4 (s, 1H), 5.2-5.3 (s, 1H), 3.8 (d, 2H) 3.2 (broad s, 6H), 1.5 (s, 9H), 1.4 (s, 9H). UPLC/MS M+1=341 amu.

Step 2: Synthesis of B (R=tBu)

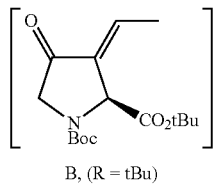

B, (R = tBu)

I. Methylation of A (R=tBu) to B (R=tBu:

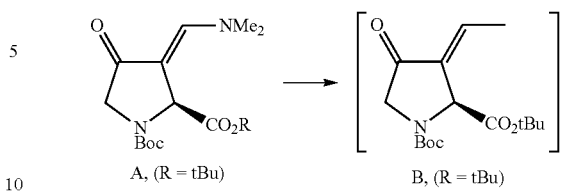

A, (R = tBu)    B, (R = tBu)

To a reaction vessel was added A (151 g, 0.44 mol, 1.0 equiv). The vessel was evacuated, purged with nitrogen, and the substrate was dissolved in MeTHF (450 mL, 3 vol). The reaction mixture was cooled to an internal temperature of about −12° C. and treated dropwise with methylmagnesium bromide (155 mL of a 3.0 M solution in diethyl ether, 0.55 mol, 1.25 equiv) over about 1 h. Upon reaction completion (about 2 h), a reverse quench was performed by adding the reaction to cold saturated aqueous ammonium chloride (400 mL). If an emulsion was observed, more aqueous ammonium chloride or 2 M HCl was added. The aqueous layer was extracted with toluene (1×200 mL). The organic layers were combined, washed with 1 M HCl (150 mL), then brine (150 mL), and concentrated in vacuo to provide B. $^1$H NMR (400 MHz, $CDCl_3$): δ 6.90-6.92 (1H, m), 5.08-5.16 (1H, m), 3.94-4.00 (2H, m), 2.02-2.04 (3H, m), 1.44-1.49 (18H, m).

Step 3: Synthesis of C (R=tBu)

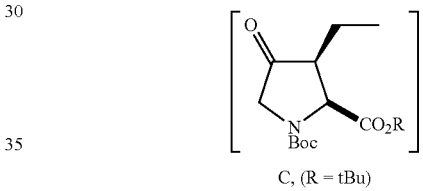

C, (R = tBu)

I. Hydrogenation of B (R=tBu) to C (R=tBu):

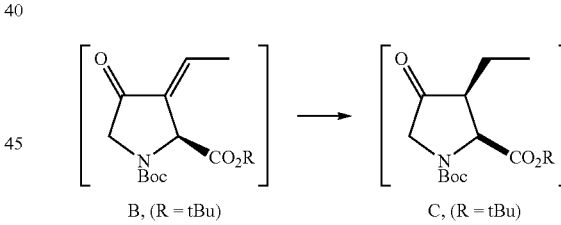

B, (R = tBu)    C, (R = tBu)

Enone B (R=tBu) (32.0 g, 0.10 mol) was dissolved in toluene (3 vol) under an atmosphere of $N_2$. Pd/C was subsequently added (1.1 g, 0.5 mol %) and the reaction was flushed with $N_2$, followed by $H_2$, and stirred vigorously at room temperature under 1 atm of $H_2$. After completion of the reaction, diatomaceous earth (0.1 S, 13.2 g) was added and the mixture was stirred for 5 minutes. The heterogeneous mixture was filtered through diatomaceous earth and rinsed with additional toluene (0.5-1 vol) and concentrated to dryness to provide C as a pale yellow solid. $^1$H NMR (400 MHz, $CD_3OD$): δ 4.68 (dd, J=36.9, 9.3 Hz, 1H), 3.99-3.75 (m, 2H), 2.63 (tdd, J=13.7, 9.2, 4.6 Hz, 1H), 1.89 (dt, J=13.8, 6.7 Hz, 1H), 1.46 (s, 9H), 1.43 (s, 9H), 1.30-1.16 (m, 1H), 1.07 (t, J=7.4 Hz, 3H). Epi-C has a characteristic peak at 4.23 ppm in MeOD (d, J=3.5 Hz, 1H) which can be used to calculate the diastereoselectivity of the hydrogenation. The diastereoselectivity was determined by NMR to be typically >50:1.

Step 4: Synthesis of D (R=tBu)

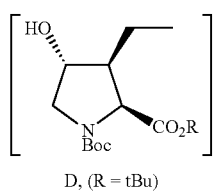

D, (R = tBu)

I. Reduction of C (R=tBu) to Provide D (R=tBu)

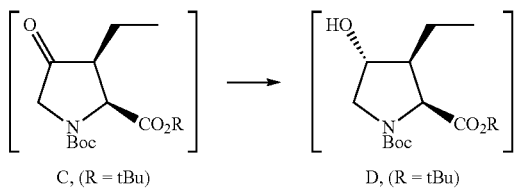

C, (R = tBu)    D, (R = tBu)

ZnCl$_2$ (27.3 g, 200 mmol, 2 equiv) and CPME (7 vol relative to C, 220 mL) were combined and the heterogeneous mixture was warmed to an internal temperature of about 95° C. and stirred for about 1.5 hours at that temperature. The resulting slurry was cooled to about 25° C. NaBH$_4$ (7.56 g, 200 mmol, 2 equiv) was added and the mixture was stirred overnight (~18 hrs).

The slurry was cooled to about 0° C., and the solution of C (R=tBu) (~100 mmol) in toluene (3 total vol) was added slowly while maintaining the temperature to about below +3° C. After addition, the mixture was stirred at about 0° C. until complete consumption of the starting material. The reaction was quenched by reverse addition into a solution of citric acid (2.5 equiv, 48 g) in ice water (200 mL). The layers were separated and the organic layer was washed with brine (60 mL, 2 vol), dried over MgSO$_4$ (0.05 S, 1.5 g), and polish filtered. The crude organic solution was concentrated to a thick oil, diluted with 2 volumes of hexanes and filtered through 2S silica gel, eluting with 1:1 acetone:hexanes. Concentration in vacuo provided compound of formula D (R=tBu).

$^1$H NMR (400 MHz, CDCl$_3$): δ 4.30 (dd, J=26.4, 8.4 Hz, 1H), 4.24-4.14 (m, 1H), 3.89 (ddd, J=14.6, 10.6, 7.5 Hz, 1H), 3.15 (ddd, J=17.7, 10.6, 7.1 Hz, 1H), 2.20-2.05 (m, 2H), 1.70-1.59 (m, 1H), 1.48 (s, 9H), 1.44 (s, 9H), 1.35-1.23 (m, 1H), 1.07 (t, J=7.4 Hz, 3H).

Synthesis of Compound of Formula II (R=CH$_3$)

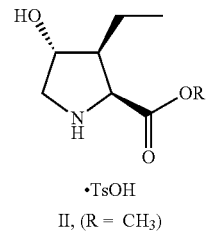

·TsOH

II, (R = CH$_3$)

Deprotection and Transesterification of D (R=tBu) to II (R=CH$_3$):

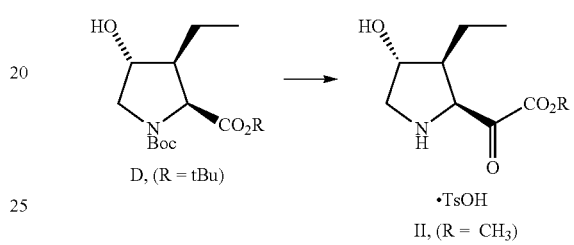

D, (R = tBu)

·TsOH

II, (R = CH$_3$)

D (R=tBu) (5.55 g, 17.6 mmol) was charged to a reactor and dissolved in methanol (55.5 mL). p-Toluenesulfonic acid (10.7 g, 3.2 eq.) was charged to the solution and the mixture is stirred for about 1 hour at room temperature. The mixture was then heated to about 60° C. The reaction was stirred until reaction completion. The reaction mixture was concentrated to about 4 volumes and cooled to about 45° C. MTBE (4 volumes) were added slowly to achieve a cloudy solution. II seed (0.05%) was charged to the solution to and the mixture was aged for about 30 minutes to obtain a thin slurry. Additional MTBE (5 volumes) were charged over about 90 minutes and the resulting slurry was stirred overnight.

The slurry was filtered and rinsed with 2 volumes of MTBE. The resulting wet cake was dried under vacuum at about 40° C. to obtain compound II (R=CH$_3$) as a tosylate salt. $^1$H NMR (400 MHz, MeOD) δ 7.7 (d, 2H), 7.2 (d, 2H), 4.7 (d, 1H), 4.3 (m, 1H), 3.8 (s, 3H), 3.6 (m, 1H), 3.2 (m, 1H), 2.4 (m, 1H), 2.3 (s, 3H), 1.3 (m, 2H), 1.0 (t, 3H). LC/MS M+1=174.1

B. Synthesis of 3-Chloro-2-(1,1-difluorobut-3-en-1-yl)-6-methoxyquinoxaline (IV)

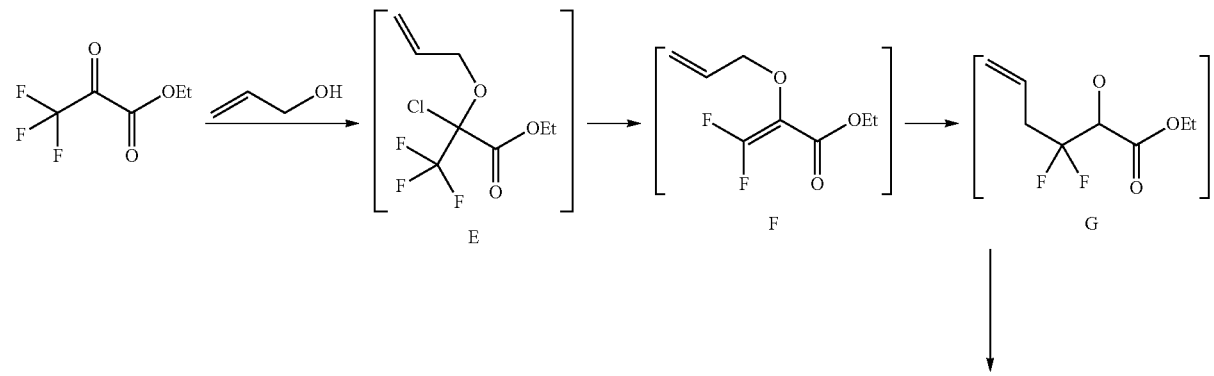

-continued

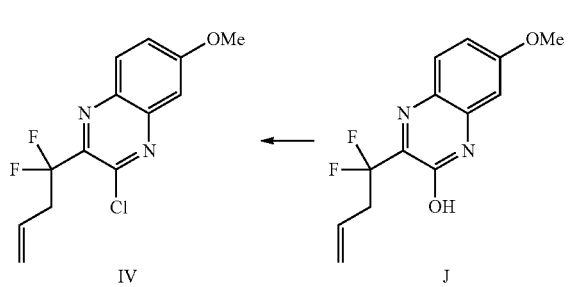

IV ← J ← 4:1 K

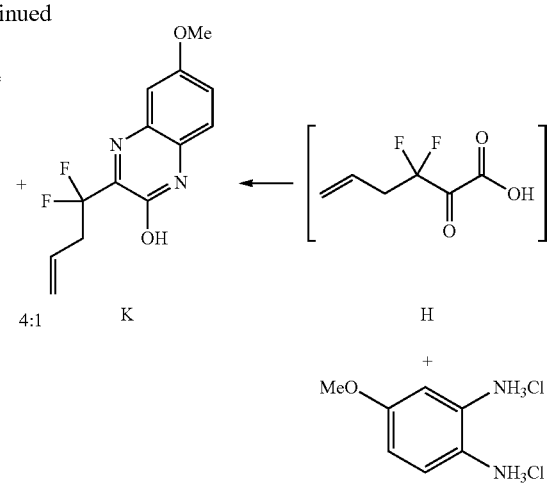

H

+

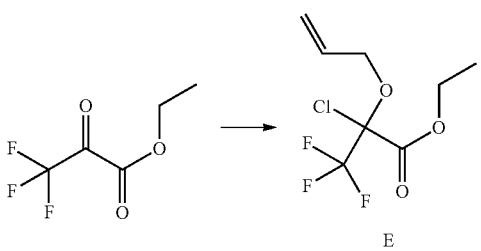

Compound IV contains one more methylene group than the analog used in U.S. Publication No. 2014-0017198 and so requires a different starting material. Ethyl trifluoropyruvate was converted to intermediate G in three steps. Intermediate G was telescoped through to a 4:1 regioisomeric mixture of J and K. In the U.S. Publication No. 2014-0017198, a nitro, amino-anisole was used for the ring formation in a two-step process of reacting the amine first and then reducing the nitro group to allow cyclization. Two regioisomers were formed. In this route, the starting material was instead the diamino analog and similar mixture was obtained. The mixture was chlorinated and the desired isomer IV was purified by conventional methods.

Step 1: Synthesis of G

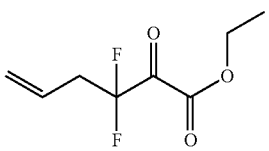

G

I. Synthesis of Intermediate of Formula G from Ethyl Trifluoropyruvate:

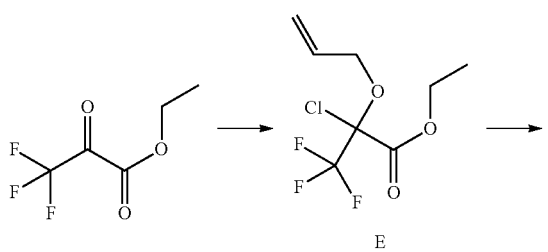

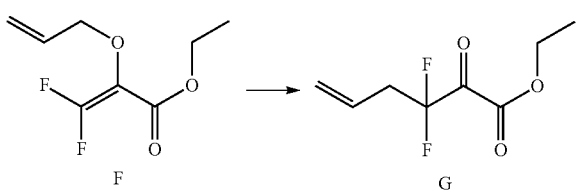

a. Allylation of Ethyl Trifluoropyruvate to Provide E:

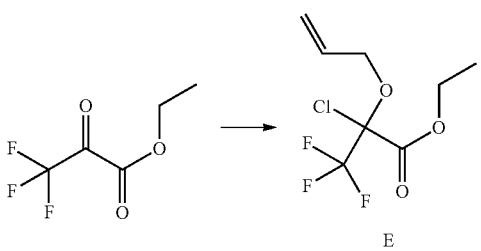

E

To a reaction vessel was charged ethyl trifluoropyruvate (86 g, 0.5056 mol, 1.0 equivalent) and dichloromethane (260 mL). Allyl alcohol (31 g, 0.5337 mol, 1.1 equivalent) was charged dropwise over about 30 minutes while maintaining the reaction temperature less than about 27° C. The reaction was cooled to about 5° C. and pyridine (123 mL, 1.52 mol, 3.0 equivalents) was charged over about 50 minutes, maintaining a reaction temperature below about 8° C., followed by charging thionyl chloride (90 g, 0.76 mol, 1.5 equivalents) over about 90 minutes while maintaining the reaction temperature below about 12° C. The reaction was stirred for about 30 minutes at about 5 to 10° C., warmed to about 22° C. over about 30 minutes and held at about 22° C. until the reaction was deemed complete. The reaction mixture was poured into 860 mL of chilled (about 8° C.) water and the phases separated. The aqueous phase was back-extracted with 200 mL dichloromethane. The combined dichloromethane phases were washed successively with water (860 mL), 5 wt % NaHCO$_3$ solution (2×250 mL), and a final water wash (250 mL) and dried over Na$_2$SO$_4$. After the removal of the solvents, the crude product E was isolated and used directly for the next step. $^1$H NMR (300 MHz, CDCl$_3$): δ 5.92 (m, 1H), 5.38 (dq, J=14.1, 1.4 Hz, 1H), 5.27 (dq, J=10.3, 1.2 Hz, 1H), 4.40 (d, J=7.1 Hz, 2H), 4.34 (m, 2H), 1.30 (t, J=7.1 Hz, 3H).

II. Zn-Mediated Elimination of ClF from E to Provide F Followed by Claisen to Provide G:

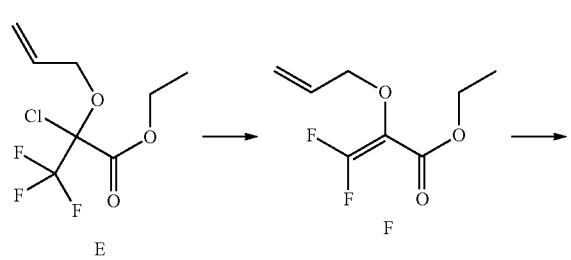

I. Synthesis of H from G

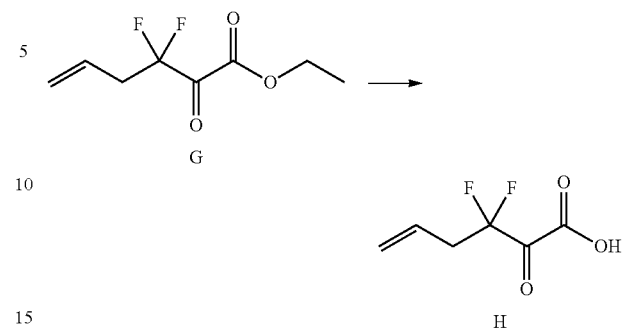

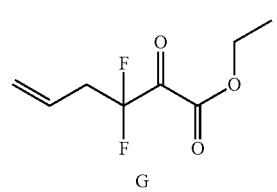

To a reaction vessel was charged zinc powder (324 g, 4.95 mol, 2.0 equivalents), CuI (6 g, 0.032 mmol, 0.013 equivalents) and N,N-dimethylformamide (DMF) (3.0 L). The mixture was stirred vigorously as Me$_3$SiCl (309 mL, 2.43 mmol, 1.0 equivalents) was charged dropwise via addition funnel over about 10 minutes, maintaining the reaction temperature at about <25° C. The reaction was stirred for about 30 minutes at about 25° C. The reaction was then cooled to about 0 to 5° C. over about 20 minutes and a solution of compound E (600 g, 2.43 mol, 1.0 equivalents) in DMF (3.0 L) was added slowly over about 60 minutes, maintaining the reaction temperature about <10° C. The reaction was stirred for about 30 minutes at 5 to 10° C., warmed to about 22° C. over about 30 minutes and then held at about 22° C. until the reaction was deemed complete by $^{19}$F NMR (typically 1-2 hours).

III. Claisen Rearrangement of F to Provide G

The above reaction mixture was filtered and washed with ethyl acetate (2×3 L). Water (1.5 L) was added to the organic phase and the layers were separated. The organic layer was washed two additional portions of water (2×1.5 L). The organic solution was concentrated to obtain crude F. This was dissolved in 3.0 L (5 volumes) of toluene and heated to about 80° C. until the reaction was deemed complete (typically 1-3 h). The reaction was cooled to about 22° C. and the solvent removed via rotary evaporation to obtain the crude product G (~70 wt %)). $^1$H NMR (300 MHz, CDCl$_3$): δ 5.90 (m, 1H), 5.28 (m, 2H), 4.40 (q, J=7.1 Hz, 2H), 2.83 (dt, J=18.5, 7.0 Hz, 2H), 1.32 (t, J=7.0 Hz, 3H); $^{19}$F NMR (CDCl$_3$) δ −112.8 (t).

Step 2: Synthesis of H

To a reaction flask e was charged G (26.2 g, 136.6 mmol, 1.0 equivalent) and THF (236 mL, 9 vol.). Water (52 mL, 2 vol.) was charged followed by LiOH.H$_2$O (14.9 g, 354.5 mmol, 2.6 equiv.) maintaining a reaction temperature below about 33° C. The reaction was held at about 22° C. for about 3 hours followed by quenching with 250 mL of 1M HCl. The pH was then adjusted to 3 by addition of 20 mL of concentrated HCl. The phases were separated and the aqueous phase was back-extracted with 260 mL of methyl-t-butyl ether. The layers were split and 52 grams of NaCl was added to the aqueous phase which was extracted with 2×130 mL of MTBE followed by 50 mL of EtOAc. All the organic phases were combined and dried over Na$_2$SO$_4$, filtered, concentrated and dried under vacuum to obtain H). $^1$H-NMR (400 MHz, DMSO-d$_6$) δ 13.2 (br s, 1H), 6.92 (br s, 2H), 5.83-5.70 (m, 1H), 5.20-5.13 (m, 2H), 2.83-2.65 (m, 2H). $^{19}$F-NMR (DMSO-d$_6$) δ −88.20 (t, J=20.8 Hz). TLC (Silica gel, 4:1 EtOAc:heptane, visualization with KMnO$_4$ stain) Rf=0.50.

Step 3: Synthesis of J

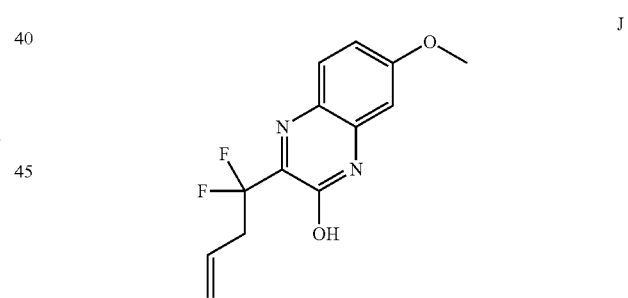

I. Condensation Followed by Cyclization to Provide J from H:

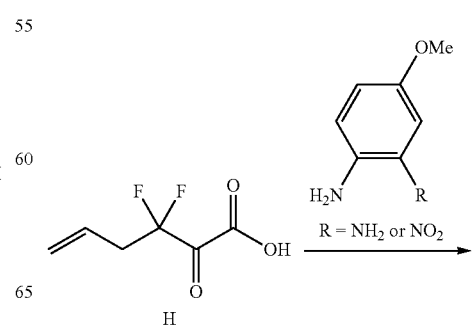

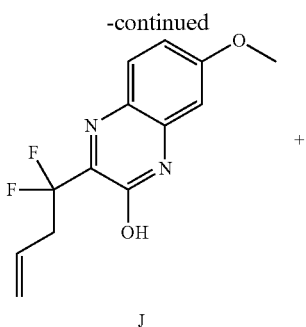

J

To a reaction vessel was charged diamine (6.06 g, 28.7 mmol, 1.0 equivalent) and ethanol (130 mL). Triethylamine (8.8 mL, 63.1 mol, 2.2 equivalents) was charged over about 5 minutes maintaining the reaction temperature about <25° C. The reaction was agitated for about 10 minutes until complete dissolution of the slurry to a homogenous solution. Acetic acid (16.4 mL, 287 mmol, 10 equiv.) followed by a solution of H (5.75 g, 31.6 mmol, 1.1 equiv.) in ethanol (40 mL) was charged and the reaction was held at about 22° C. until the reaction was complete. The reaction mixture was solvent exchanged into 80 mL of dichloromethane and washed successively with 0.1 N HCl (60 mL), saturated NaHCO₃ solution (60 mL) and a final brine wash (60 mL) and dried over Na₂SO₄. After the removal of the solvents, crude mixture of J/K was obtained. This crude mixture was dissolved in dichloromethane, washed twice with 0.1N HCl, once with water and once with brine followed by drying over sodium sulfate, filtered and concentrated to obtain J/K). $^1$H NMR (300 MHz, CDCl₃): δ 7.82 (d, J=9.0 Hz, 1H), 7.38 (m, 1H), 6.97 (dd, J=9.0, 3.0 Hz, 1H), 6.82 (d, J=3.0 Hz, 1H), 5.88 (m, 1H), 5.22 (m, 2H), 3.91 (s, 3H), 3.28 (td, J=12.0, 3.0 Hz, 2H). $^{19}$F NMR (282.2 MHz, CDCl₃): δ −100.3 ppm (J) and −100.8 ppm (K). LCMS: m/z=266.93.

Step 4: Synthesis of IV

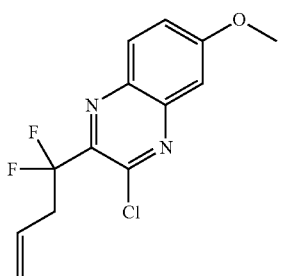

IV

I. Chlorination of J to Provide Compound of Formula IV:

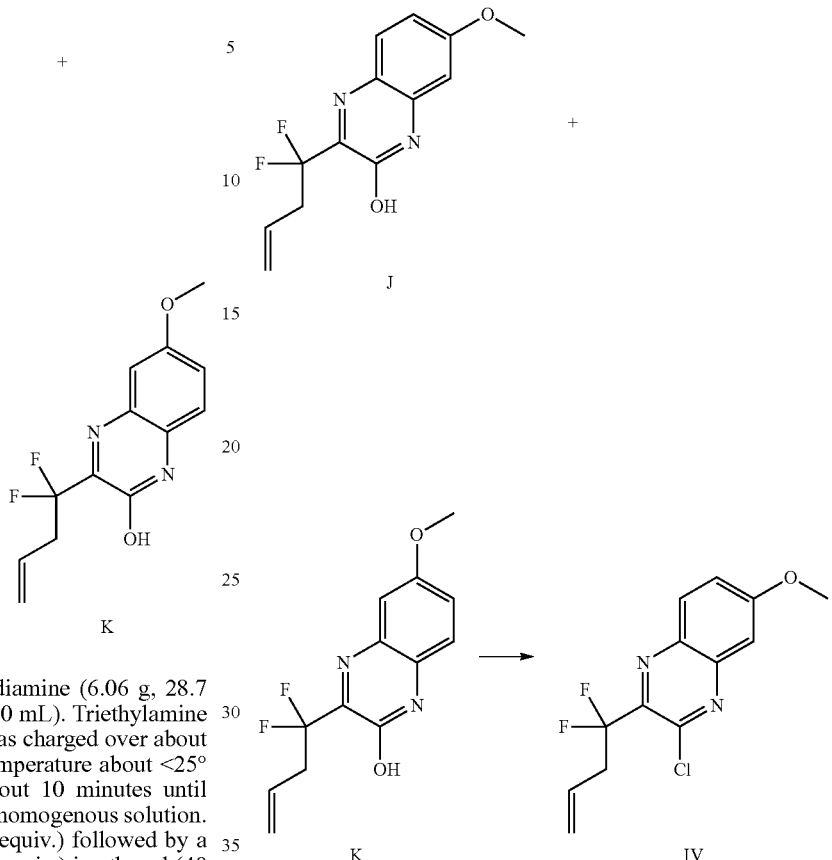

To a reaction vessel was charged J (7.4 g, 27.79 mmol, 1.0 equivalent) and N,N-dimethylformamide (148 mL). Phosphorus oxychloride (POCl₃) (4.2 mL, 44.47 m mol, 1.6 equivalent) was charged over about 3 minutes maintaining the reaction temperature was kept below about 30° C. The reaction was heated to about 75° C. until reaction completion. The reaction mixture was slowly poured into 150 mL of water while maintaining the temperature below about 25° C. Methyl-t-butyl ether (MTBE) (75 mL) was charged and the phases separated. The aqueous phase was back-extracted with 4×75 mL of MTBE. The combined MTBE phases were washed successively with saturated NaHCO₃ solution (200 mL) and saturated NaCl solution (150 mL) and dried over Na₂SO₄. After the removal of the solvents, the crude product IV was isolated. The crude material was suspended in hexanes (4.3 volumes), heated to dissolution and slowly cooled to about 20° C. resulting in slurry formation of the desired regioisomer IV which was then isolated by filtration and dried. $^1$H NMR (300 MHz, CDCl₃): δ 8.02 (d, J=9.0 Hz, 1H), 7.48 (dd, J=9.0, 3.0 Hz, 1H), 7.34 (d, J=3.0 Hz, 1H), 5.97 (m, 1H), 5.31 (m, 2H), 4.0 (s, 3H), 3.35 (td, J=12.0, 3.0 Hz, 2H). $^{19}$F NMR (282.2 MHz, CDCl₃): δ −96.3 ppm (IV) and −97.1 ppm (regioisomer). LCMS: m/z=285.27.

C. Synthesis of (S)-2-((((1R,2R)-2-allylcyclopropoxy)carbonyl)amino)-3,3-dimethylbutanoic acid (S)-1-Phenylethan-1-amine Salt (VII)

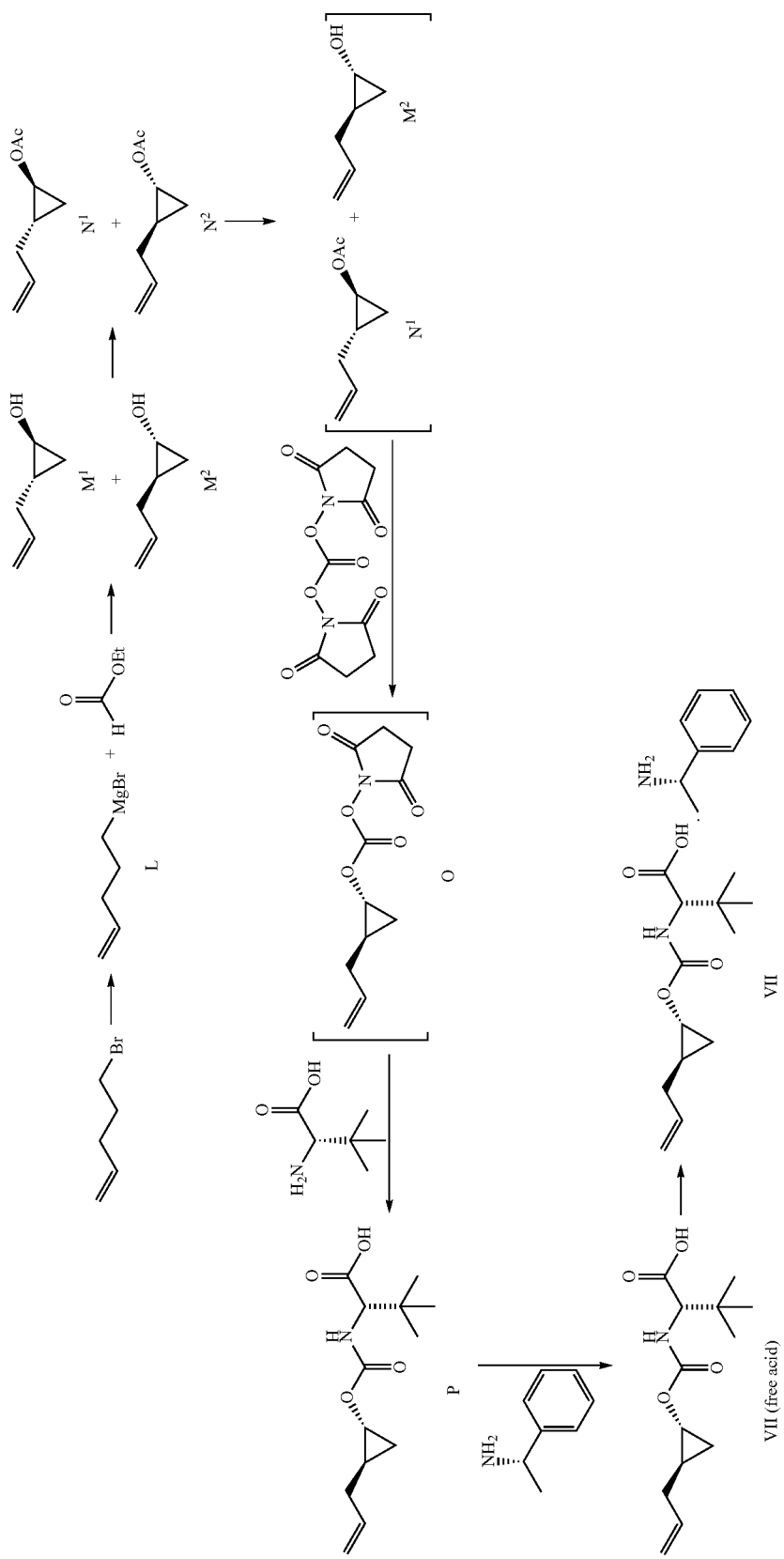

Compound of formula VII contains one less methylene than the material used in the medicinal chemistry route in order to shift the ring-closing metathesis reaction away from the difluorinated methylene on the quinoxaline fragment. A similar Kulinkovich cyclopropanation, acylation and enzymatic resolution was used with this homolog. The cyclopropanol and then cyclopropyl acetate were distilled but it was not necessary to do so. Acid-base extractions were used to remove still acetylated material. The final product was isolated as a S-1-phenylethanamine salt which improved the diastereomeric and overall purity of the product. Recrystallization may be used to further improve the purity of the product. Other salts may be possible.

Step 1: Synthesis of
(1R,2R)-2-allylcyclopropan-1-ol (M1)

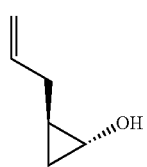

M1

Kulinkovich Reaction, Acetylation and Enzymatic Resolution:

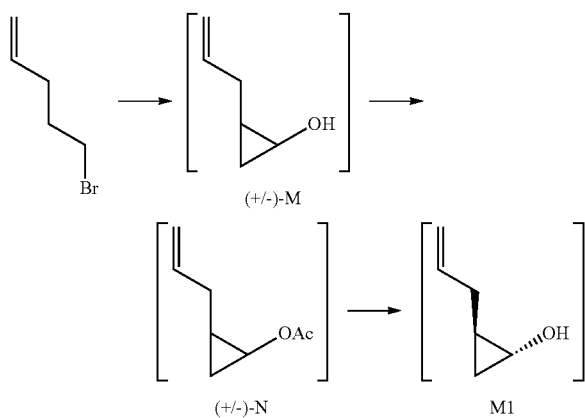

I. Kulinkovich Reaction with Ethyl Formate and 5-Bromo-1-Pentene

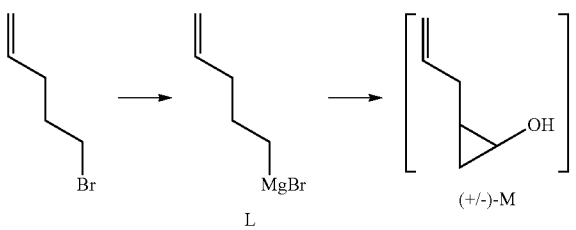

To a reaction vessel was added magnesium turnings (2.45 equivalents) and MeTHF (8 volumes). The flask was then sparged with nitrogen and 5-bromo-1-pentene (2.4 equivalents) was added to the addition funnel. The mixture was heated to about 60° C. and 0.05 volumes of 5-bromo-1-pentene were dripped into the mixture to initiate the reaction. Once the reaction initiated, the remaining portion of 5-bromo-1-pentene was slowly added into the flask over about 3 hours. After the addition, the reaction was allowed to stir at about 60° C. for about 1 hour after which Grignard L was cooled to room temperature. In a separate flask was added ethyl formate (1.0 equivalent) and titanium isopropoxide (0.5 equivalents) in MeTHF (2 volumes) under nitrogen. The mixture was cooled to about 0° C. and slowly the Grignard L was added into the flask over 3 hours. Upon complete addition, the reaction mixture was allowed to warm to room temperature and the reaction was stirred for about 12 hours. The mixture was then cooled to about 0° C. and 4M sulfuric acid (10 volumes) was added slowly. The slurry was stirred for 30 minutes after which the salts were dissolved. The mixture was then polish filtered. The biphasic mixture was separated and the organic layer was then washed twice with 10 wt. % sodium bicarbonate (10 volumes) and once with water (10 volumes). The organic layer is concentrated under reduced pressure at about 0° C. to obtain crude 2-allylcyclopentanol M. $^1$H NMR (400 MHz, CDCl$_3$): δ 5.53-5.43 (m, 1H), 4.76-4.70 (m, 1H), 4.65-4.59 (m, 1H), 2.90-2.86 (m, 1H), 1.75 (br s, 1H), 1.65-1.51 (m, 2H), 0.69-0.59 (m, 1H), 0.40-0.35 (m, 1H), 0.05-0.01 (m, 1H).

II. Acetylation of 2-allylcyclopentanol (+/−)-M:

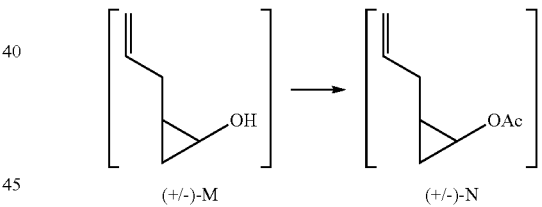

Into a reaction vessel was added 2-allylcyclopentanol M (1 equivalent) in MeTHF (10 volumes). The vessel was purged with nitrogen and the solution was then cooled to 0° C. Triethylamine (3.0 equivalents) was then slowly added to the solution over about 30 minutes. The mixture was allowed to stir for about 30 minutes after which acetyl chloride (2.5 equivalents) was added maintaining the internal temperature about below 20° C. The reaction was then allowed to stir for at least 12 hours at about 21° C. After the allotted time, water (6 volumes) was slowly charged to the reactor and the phases were separated. The organic layer was then washed with 2M hydrochloric acid (6 volumes), 10 wt. % sodium bicarbonate (6 volumes) and then brine (6 volumes). The organic layer is concentrated under reduced pressure at about 0° C. to obtain crude racemic 2-allylcyclopropyl acetate N. $^1$H NMR (400 MHz, CDCl$_3$): δ 5.85-5.73 (m, 1H), 5.10-5.04 (m, 1H), 5.00-4.97 (m, 1H), 3.85-3.82 (m, 1H), 2.13-2.07 (m, 1H), 1.99 (s, 3H), 2.01-1.89 (m, 1H), 1.14-1.03 (m, 1H), 0.87-0.76 (m, 1H), 0.64-0.57 (m, 1H).

III. Enzymatic Resolution of 2-Allylcyclopentanol

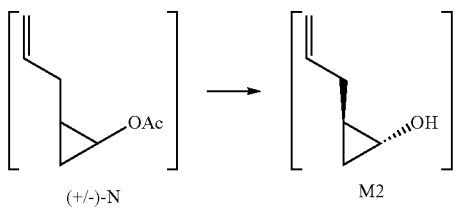

To a reaction vessel was charged 2-allylcyclopropyl acetate N in MeTHF (2 volumes) and MTBE phosphate buffer solution (10 volumes). The MTBE phosphate buffer solution was prepared by first dissolving potassium phosphate dibasic (283 g) and potassium phosphate monobasic (104.8 g) in water (1.6 L). MTBE (800 mL) was added to the solution and the biphasic mixture was stirred at about 21° C. for about 1 hour. The organic layer was then separated and used as the MTBE phosphate buffer solution. The reaction mixture was then cooled to about 0° C. and solid supported Novozyme 435 (1.7 wt. %) was charged. The reaction was allowed to stir at about 0° C. for about 6 hours after which the mixture was filtered. The filtrate was then concentrated under reduced pressure at about 0° C. to obtain the majority as (1R,2R)-2-allylcyclopropan-1-ol M1 and the racemic (1S,2S)-2-allylcyclopropan-1-ol in a 10:1 to 15:1 mixture as a mixture of the corresponding remaining acylated starting materials. The crude mixture was carried forward as is.

Step 3: Synthesis of VII

I. Coupling to VII

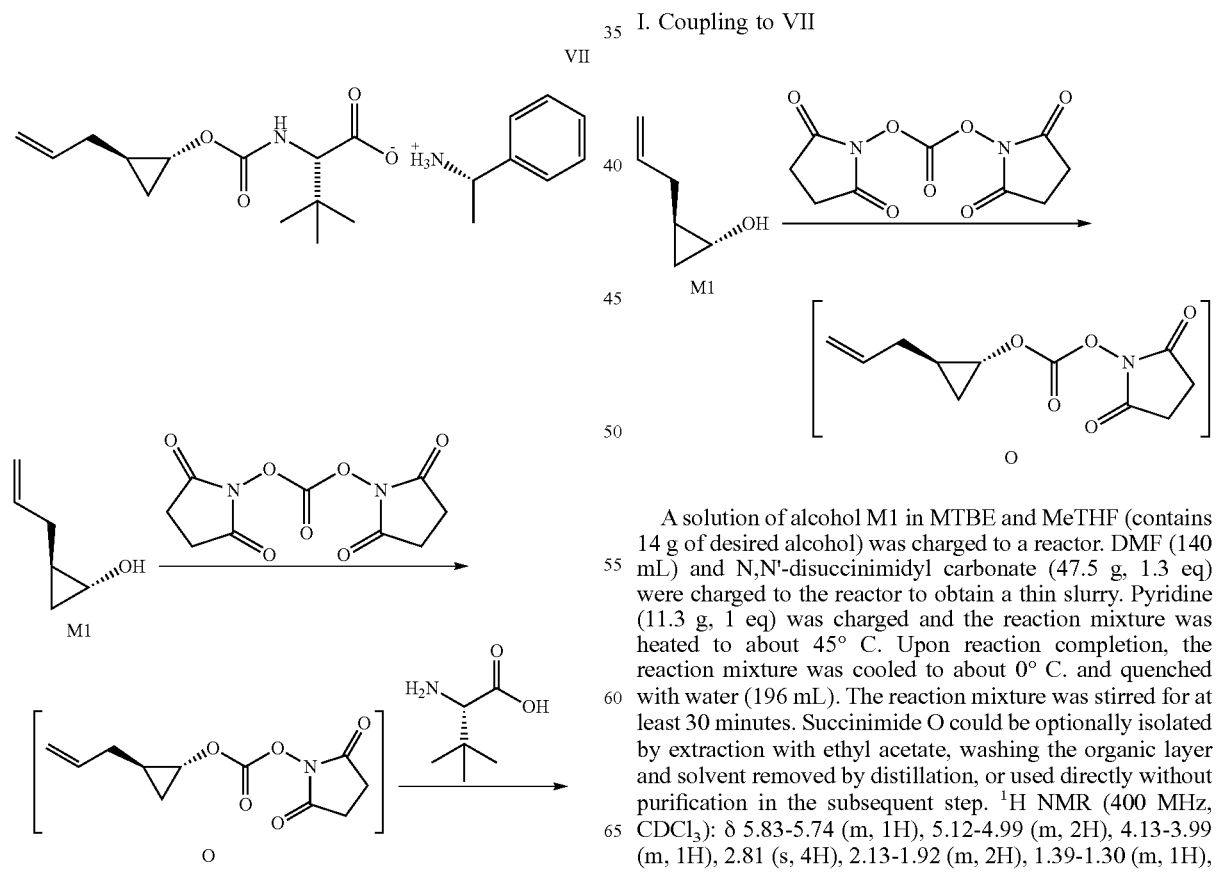

A solution of alcohol M1 in MTBE and MeTHF (contains 14 g of desired alcohol) was charged to a reactor. DMF (140 mL) and N,N'-disuccinimidyl carbonate (47.5 g, 1.3 eq) were charged to the reactor to obtain a thin slurry. Pyridine (11.3 g, 1 eq) was charged and the reaction mixture was heated to about 45° C. Upon reaction completion, the reaction mixture was cooled to about 0° C. and quenched with water (196 mL). The reaction mixture was stirred for at least 30 minutes. Succinimide O could be optionally isolated by extraction with ethyl acetate, washing the organic layer and solvent removed by distillation, or used directly without purification in the subsequent step. $^1$H NMR (400 MHz, CDCl$_3$): δ 5.83-5.74 (m, 1H), 5.12-4.99 (m, 2H), 4.13-3.99 (m, 1H), 2.81 (s, 4H), 2.13-1.92 (m, 2H), 1.39-1.30 (m, 1H), 1.11-1.04 (m, 1H), 0.73-0.68 (m, 1H).

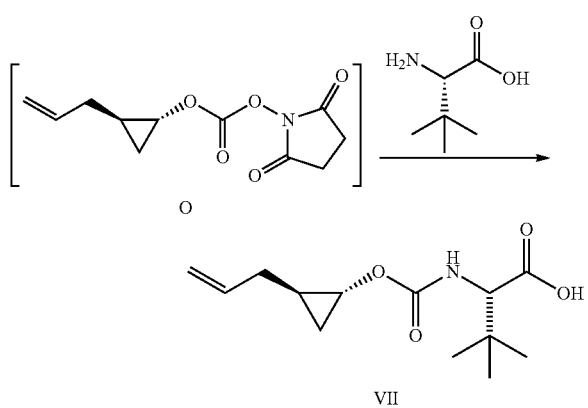

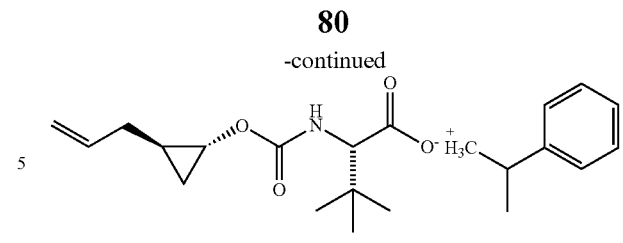

Continuing through with crude succcinate intermediate O, tert-leucine (23.4 g, 1.25 eq) and K₃PO₄ (84.8 g, 2.8 eq.) were charged to the reactor. The resulting mixture was warmed to room temperature and the resulting solution was stirred for about 18 h. Upon reaction completion, the mixture was diluted by MTBE (210 mL) and pH adjusted to pH 3 with 6M HCl (~180 mL). The layers were separated and the organic layer was pH adjusted to pH>10 with 2.5M NaOH (~70 mL). The aqueous layer was removed and the organic layer was washed with 0.5 M NaOH (100 mL). The combined basic aqueous layers was readjusted to pH<3 with 6M HCl (~50 mL) and washed twice with MTBE (100 mL×2).

The combined organic layers were solvent swapped to MTBE (107 mL). In a separate container, S(–) 1-phenylethylamine (10.9 g, 1 eq.) was dissolved in MTBE (32.7 mL). The solution of the amine was charged slowly to the solution containing the succinimide intermediate. A small amount of VII (S)-1-phenylethan-1-amine salt (0.055 g, 0.5%) was charged followed by the rest of the amine solution. The slurry was aged overnight to obtain a thick slurry. The resulting slurry was filtered and rinsed with MTBE (50 mL). The solids were dried in the vacuum oven until constant weight was reached to obtain VII as the (S)-1-phenylethan-1-amine salt. NMRs of the free acid: $^1$H NMR (400 MHz, CDCl₃) δ 7.4 (m, 5H), 6.3 (broad s, 3H), 5.8 (m, 1H), 5.3 (d, 1H), 5.1 (d, 1H), 4.2 (q, 1H), 3.8 (d, 1H), 3.7 (m, 1H), 2.1 (m, 1H), 1.9 (m, 1H), 1.5 (d, 3H), 1.1 (m, 1H), 0.9 (d, 9H), 0.8 (m, 1H), 0.5 (q, 1H). $^{13}$C-NMR (CDCl₃) δ 173.1, 157.0, 115.7, 63.3, 53.9, 36.2, 34.9, 33.7, 27.1, 17.3, 11.7.

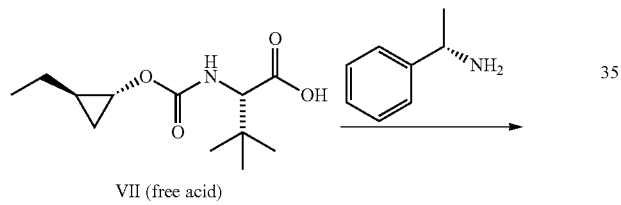

D. Synthesis of (1R,2R)-1-Amino-2-(difluoromethyl)-N-((1-methylcyclopropyl)sulfonyl)cyclopropane-1-carboxamide Hydrochloride Salt (XII)

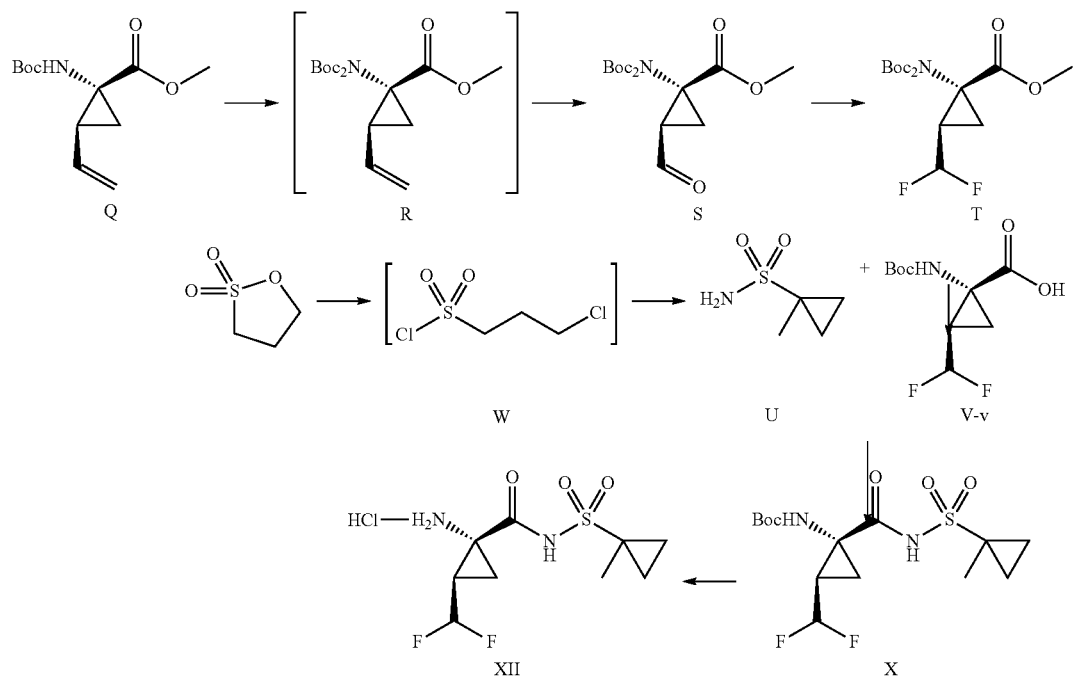

The existing process route shown above was disclosed is in the U.S. Publication No. 2014-0017198. The route shown below proceeds through a common known intermediate V-v. Racemic A-b was selectively hydrolyzed to racemic A-c with an approximate 10:1 ratio of cis/trans diastereomers. This mono acid is subjected to a classical resolution with a chiral amine to form chiral A-c as a salt. A recrystallization can be performed to enhance enantiomeric excess. The carboxylic acid was next converted to the amide A-d and isolated. In telescoping steps, the amide was subjected to a Hoffman rearrangement, hydrolysis to the amine, protection of the amine with Boc and hydrolysis of the methyl ester to form the desired amino acid, V-v. V-v was then converted to XII as shown in the above scheme.

Assembly Steps of Route I to Compound of Formula I

A. Synthesis of Compound of Formula III (R=CH$_3$)

I. Free-Basing and Boc-Protection of II (R=CH$_3$) to Provide III (R=CH$_3$):

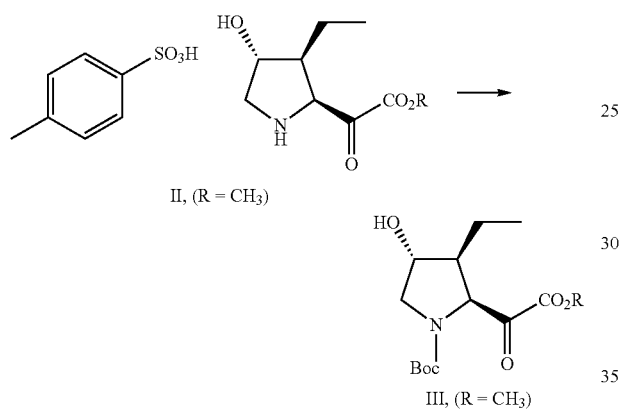

II (10.1 g, 29.3 mmol, 1.00 equivalents) was combined with dichloromethane (40 mL) and the mixture stirred at about 20 to 25° C. Triethylamine (8.36 g, 82.6 mmol, 3.00 equivalents) was added dropwise via syringe, maintaining a reaction temperature of about 20 to 25° C. To the resultant solution was charged 4-dimethylaminopyridine (360 mg, 2.95 mmol, 0.1 equivalent) followed by a solution of di-tert-butyl dicarbonate (6.52 g, 29.9 mmol, 1.02 equivalent) in dichloromethane (40 mL), while maintaining a reaction temperature of about 20 to 25° C. The mixture was stirred for about 2-4 hours and monitored for completion. Upon reaction completion, 100 mL of 1.0 N HCl was charged dropwise, while maintaining a reaction temperature below about 30° C. The biphasic mixture was vigorously stirred for about 15 minutes followed by allowing the layers to separate. The bottom organic layer was partitioned and washed successively with 5% wt/wt aqueous sodium bicarbonate (100 mL) and water (100 mL). The organic phase was concentrated under reduced pressure and dried under vacuum to afford III (R=CH$_3$). $^1$H NMR (300 MHz, CD$_3$OD): δ 4.41 (d, J=6.0 Hz, 1H), 4.01-4.07 (m, 1H), 3.65-3.79 (m, 4H), 3.05-3.15 (m, 1H), 2.10-2.20 (m, 1H), 1.50-1.60 (m, 1H), 1.39-1.45 (app d, 9H), 1.10-1.20 (m, 2H), 0.99-1.08 (m, 3H). $^{13}$C NMR (75 MHz, CDCl$_3$): δ 12.3, 21.3, 28.2, 50.5, 50.6, 51.4, 52.2, 61.8, 71.9, 80.2, 154.2, 171.9.

B. Synthesis of Compound of Formula V (R=CH$_3$)

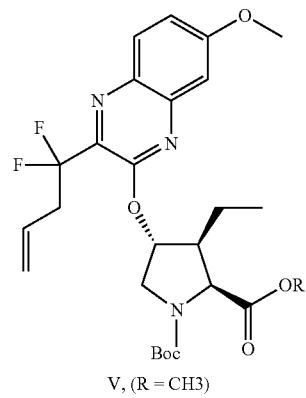

V, (R = CH3)

II. S$_N$Ar Reaction of IV with III (R=CH$_3$) to form V (R=CH$_3$)

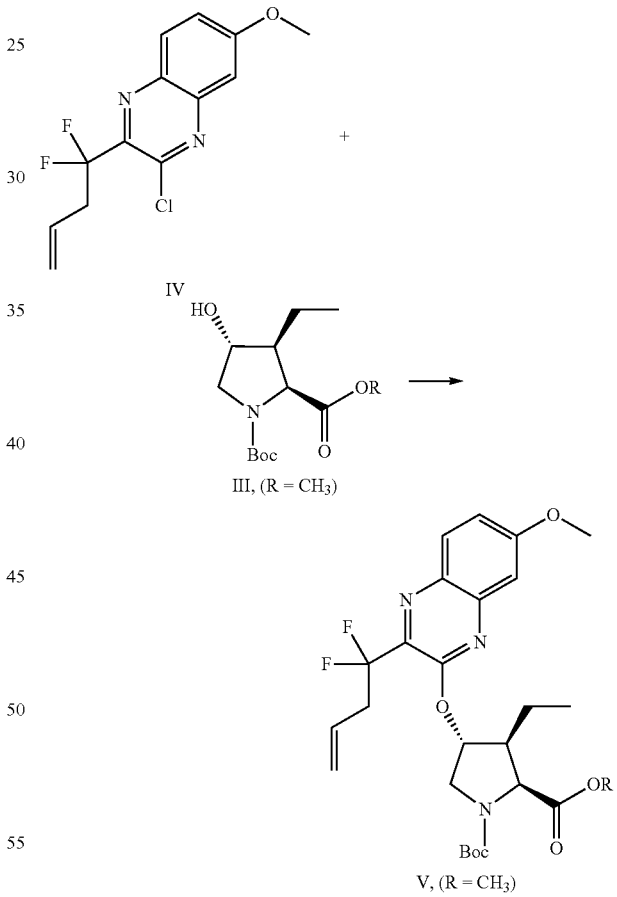

Into a reactor containing III (R=CH$_3$) (1.00 equivalent) in N,N-dimethylacetamide (6 volumes) was charged IV (1.00 equivalent) and cesium carbonate (1.20 equivalents) under nitrogen atmosphere. The heterogeneous reaction was heated to about 100 to 110° C. with stirring. Upon reaction completion, the reaction mixture was then cooled down to about 20° C. and methyl tert-butyl ether (10 volumes) was charged. The resulting mixture was washed twice with water (6 volumes) and the methyl tert-butyl ether solvent was swapped with isopropanol (6 volumes) via vacuum distillation. The solution was then heated to about 60° C. and water (3 volumes) slowly added over about 1.5 hours. Once the addition was complete, the mixture was held at about 60° C. for about 30 minutes. A small amount of V (R=CH₃) (1-2 wt/wt %) were then charged after which the temperature was slowly cooled to room temperature over about 3 hours. The contents were then aged for at least about 12 hours after which the slurry was filtered over the appropriate filter. The wet cake was washed with 2:1 isopropanol/water (3.5 volumes), followed by two water washes (3.5 volumes) and oven dried under vacuum at about 40 to 45° C. ¹H NMR (400 MHz, CDCl₃): δ 7.93-7.90 (m, 1H), 7.25-7.22 (m, 1H), 7.20-7.16 (m, 1H), 5.95-5.85 (m, 1H), 5.44-5.38 (m, 1H), 5.25-5.21 (m, 2H), 4.54-4.52 (m, 1H), 4.47-4.40 (m, 1H), 3.97 (s, 3H), 3.77 (s, 3H), 3.43-3.39 (m, 1H), 3.27-3.17 (m, 2H), 2.79-2.68 (m, 1H), 1.64-1.55 (m, 1H), 1.44-1.43 (m, 9H), 1.44-1.32 (m, 1H), 1.10-1.06 (m, 3H). LCMS (M+1): 521.97.

C. Synthesis of Compound of Formula VI (R=CH₃) Tosylate Salt

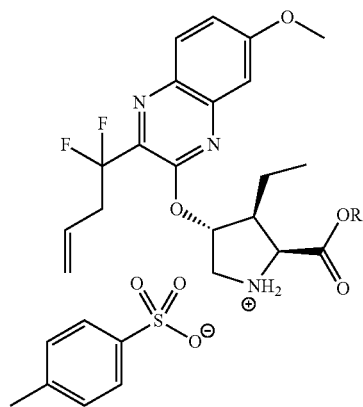

I. Boc Deprotection of V (R=CH₃) to Provide VI (R=CH₃)

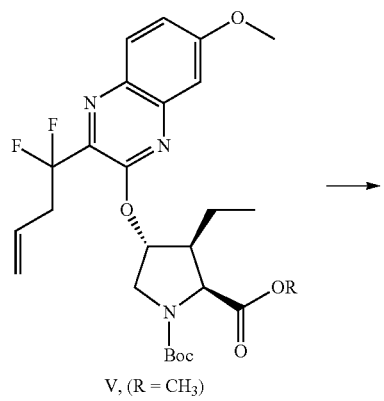

V, (R = CH₃)

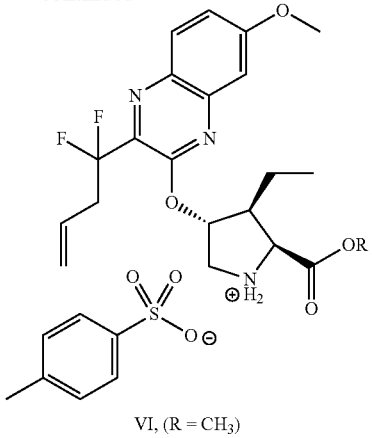

VI, (R = CH₃)

V (R=CH₃) (50.0 g, 95.9 mmol, 1.00 equivalents) is combined with methyl tetrahydrofuran (150 mL, 3 volumes) and the mixture was agitated at about 15 to 25° C., preferably about 20° C. Para-toluenesulfonic acid (45.6 g, 240 mmol, 2.50 equivalents) in methyl tetrahydrofuran (100 mL, 2 volumes) was charged to the reaction mixture. Once the acid addition was complete, the contents were heated to about 50 to 60° C. the reaction contents were agitated for about 3 to 5 hours. Upon reaction completion, methyl tert-butyl ether (100 mL, 2 volumes) was added slowly to the slurry. The contents were then cooled to about 15 to 25° C., and the slurry was filtered and washed with a mixture of methyl tetrahydrofuran (105 mL, 2.1×) and methyl tert-butyl ether (45 mL, 0.9 volumes). The solids were placed in a vacuum oven to dry at about 35 to 45° C. ¹H NMR (400 MHz, CDCl₃) δ 10.33 (s, 1H), 9.58 (s, 1H), 7.92 (d, J=9.2 Hz, 1H), 7.72 (d, J=8.1 Hz, 2H), 7.31-7.21 (m, 1H), 7.11 (t, J=5.7 Hz, 3H), 5.97-5.77 (m, 1H), 5.49 (t, J=7.1 Hz, 1H), 5.19 (dd, J=27.6, 13.7 Hz, 2H), 4.73 (dd, J=12.1, 5.7 Hz, 1H), 4.49 (dd, J=11.8, 6.4 Hz, 1H), 3.93 (d, J=9.1 Hz, 3H), 3.77 (s, 3H), 3.60 (dd, J=13.2, 3.5 Hz, 1H), 3.17 (td, J=16.8, 7.0 Hz, 2H), 2.84 (dd, J=14.1, 6.9 Hz, 1H), 2.30 (s, 3H), 1.67-1.34 (m, 2H), 1.05 (t, J=7.4 Hz, 3H). LC/MS: M/Z=422.2.

D. Synthesis of Compound of Formula VIII (R=CH₃)

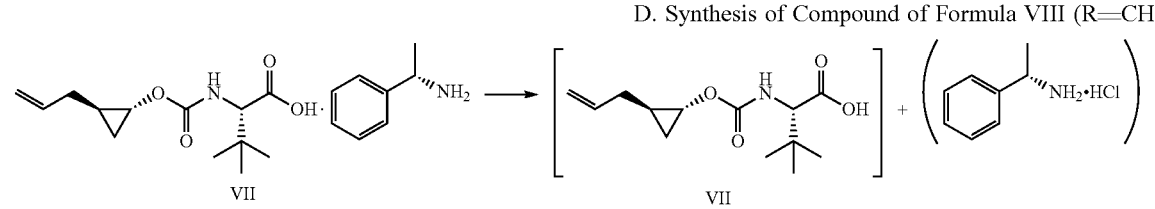

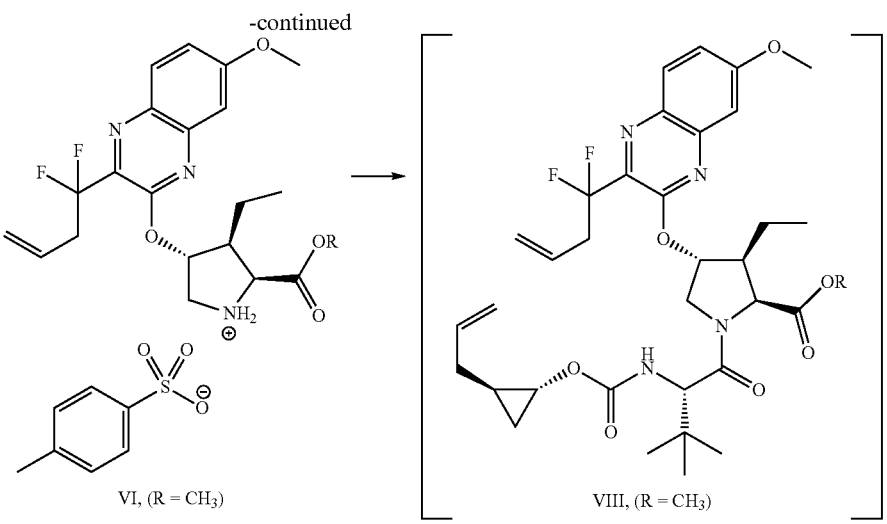

VI, (R = CH₃)

VIII, (R = CH₃)

I. Salt Break of VII to Provide VII Free-Acid

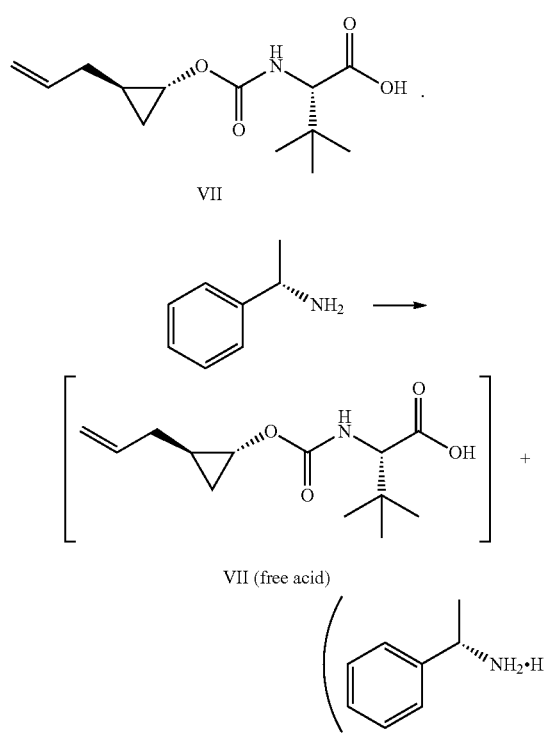

VII (33.0 g, 87.6 mmol, 1.0 equivalents) was combined with methyl tert-butyl ether (198 mL, 6 volumes) and the resulting suspension was agitated. A solution of concentrated hydrochloric acid (33 mL, 1.0 volume) and water (165 mL, 5 volumes) was charged to the suspension at a rate that maintained a reaction temperature of about 15 to 25° C. As the acid was added, the suspension became a biphasic solution. The resulting reaction mixture was agitated for about 1 hour at about 15 to 25° C. Agitation was stopped and the layers separated for about 15 minutes before the aqueous layer was removed. Water (330 mL, 10 volumes) was added to the organic and was agitated for about 15 min at about 15 to 25° C. Agitation was stopped and the layers separated for about 15 minutes before the aqueous layer was removed. Water (330 mL, 10 volumes) was added to the organic and was agitated for about 15 min at about 15 to 25° C. Agitation was stopped and the layers separated for about 15 minutes before the aqueous layer was removed. A solution of 10 wt. % sodium chloride in water (300 mL, 9 volumes) was added to the organic and the mixture was agitated for about 15 min at about 15 to 25° C. Agitation was stopped and the layers were separated for about 15 minutes before the aqueous layer was removed. The resulting organic layer was then concentrated to the minimum volume and was diluted with dimethylformamide (297 mL, 9 volumes). The final solution was removed and polish filtered.

II. Amide Coupling of VI (R=CH₃) and VII to Provide VIII (R=CH₃)

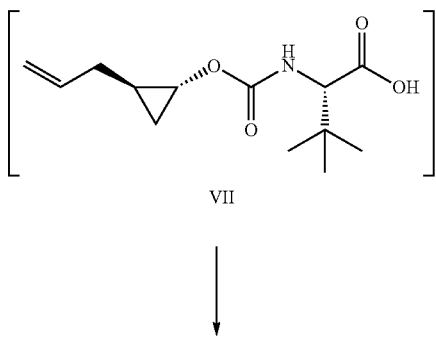

VII

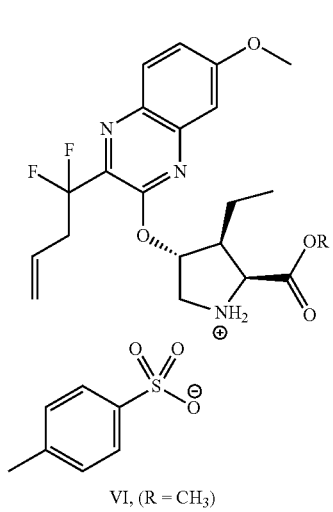

VI, (R = CH₃)

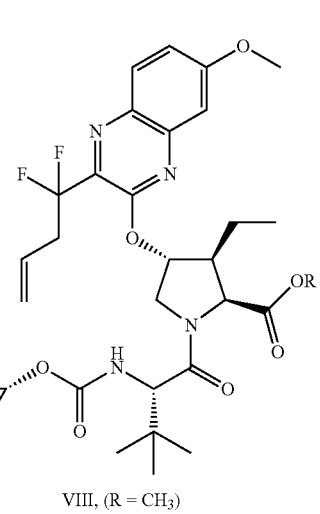

VIII, (R = CH₃)

VII (R=CH₃) (40.0 g; 67.4 mmol; 0.77 eq.), EDC.HCl (16.8 g, 87.6 mmol, 1.0 eq.), and HOBt monohydrate (13.4 g, 87.6 mmol, 1.0 eq) were combined in a reaction vessel. The previously prepared VII in DMF solution was charged to the solids, rinsed forward with DMF (39.6 mL, 1.2 vol) and agitated to form a solution. The reaction mixture was cooled to about 0 to 10° C. before NMM was charged (19.3 mL, 175 mmol, 2.0 eq.). The contents are agitated at about 0 to 10° C. for no less than about 1 hour. The reaction mixture was then adjusted to about 15 to 25° C. and agitated until reaction was complete by LC analysis. Upon reaction completion, toluene (429 mL, 13 volumes) was charged to the reactor and the temperature adjusted to about −5 to 5° C. Water (198 mL, 6 volumes) was slowly charged to maintain a reaction temperature between about 0 and 25° C. After water addition was complete, the contents were adjusted to about 15 to 25° C. Agitation was stopped and the contents settled for no less than 15 minutes before the aqueous layer was removed. A solution of potassium carbonate (20.6 g, 149 mmol, 1.7 equivalents) in water (181 mL, 5.5 volumes) was charged to the organic phase and the resulting solution permitted to and agitate for about 15 minutes before the agitation was stopped and the contents were allowed to settle for about 15 minutes. The aqueous basic layer was removed. Water (181 mL, 5.5 volumes) was charged to the organic phase and agitated for about 15 minutes before the agitation was stopped and the contents allowed to settle for about 15 minutes. The aqueous basic layer was removed. The organic phase was again partitioned between water (181 mL, 5.5 volumes) and agitated for about 15 minutes before agitation was stopped and the contents allowed to settle for about 15 minutes. The aqueous basic layer was removed. A solution of sodium chloride (20.5 g; 350 mmol 4.00 equivalents) in water (181 mL; 5.5 volumes) was charged to the organic and agitated for about 15 minutes before agitation was stopped and the contents settled for about 15 minutes. The aqueous acidic layer was removed. The organic was concentrated to minimum stirring volume and was removed and polish filtered.

¹H NMR (400 MHz, CDCl3) δ 8.01 (d, J=9.1 Hz, 1H), 7.19-7.34 (m, 3H), 6.09-5.78 (m, 2H), 5.55-5.21 (m, 3H), 5.06 (dd, J=32.9, 13.4 Hz, 2H), 4.92 (d, J=8.5 Hz, 1H), 4.59 (dd, J=10.7, 6.3 Hz, 1H), 4.35 (d, J=9.7 Hz, 1H), 4.11-3.92 (s, 3H), 3.95-3.87 (m, 1H), 3.85 (d, J=28.1 Hz, 3H), 3.78-3.70 (m, 1H), 3.37-3.17 (m, 2H), 2.81-2.69 (m, 1H), 2.18-2.06 (m, 1H), 1.95 (d, J=7.4 Hz, 1H), 1.63 (dd, J=14.4, 7.3 Hz, 1H), 1.48 (dd, J=14.4, 7.2 Hz, 1H), 1.17 (t, J=7.4 Hz, 3H), 1.12 (s, 9H), 0.84 (s, 1H), 0.54 (d, J=6.4 Hz, 1H). LC/MS: m/z=659.

E. Synthesis of Compound of Formula IX (R=CH₃)

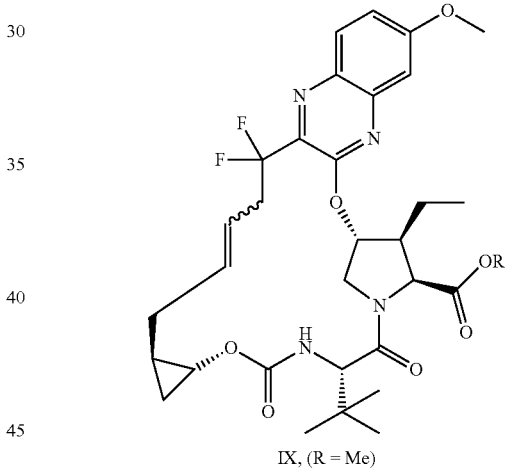

IX, (R = Me)

Ring Closing Metathesis of VIII (R=CH₃) to Provide IX (R=CH₃):

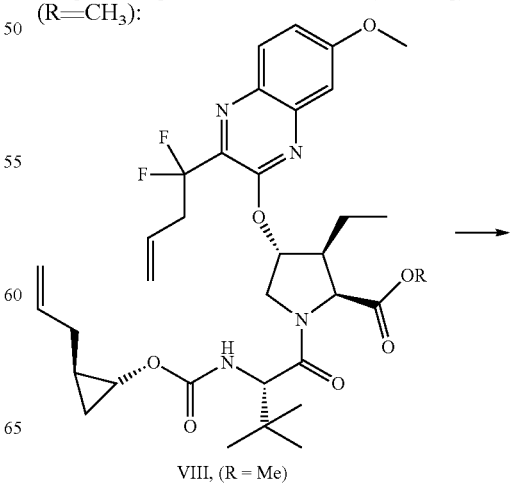

VIII, (R = Me)

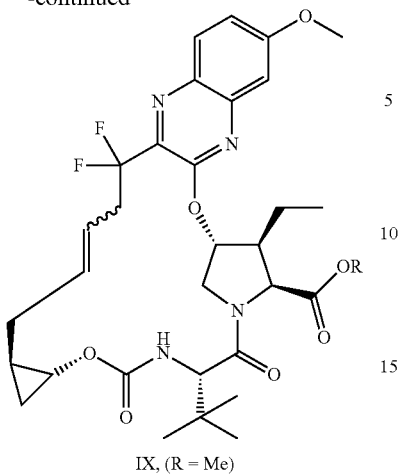

IX, (R = Me)

VIII (R=CH₃) (33 g of a 14.3 wt. % solution in toluene, 7.1 mmol, 1.00 equivalents) and toluene (27 mL) were combined and the mixture was agitated and heated to reflux (110° C.) and held at reflux temperature for about 3 to 5 hours. Separately, toluene (20 mL) was charged to a reaction vessel. and degassed vigorously. Zhan 1B catalyst (173 mg, 0.24 mmol, 0.033 equivalents) was charged and the mixture is agitated at about 20 to 25° C. for about 60 minutes to obtain a homogenous solution. The toluene solution of Zhan catalyst was added to the refluxing toluene solution of VIII (R=CH₃) over about 2 hours, maintaining a reaction temperature of about 111° C. Upon reaction completion, the reaction was cooled to about 20° C. and 9.4 grams (2S) of silica gel was charged. The slurry was vigorously agitated for about 4 hours and then filtered. The reactor and filter were washed with isopropyl acetate (2×32 mL) and the filtrate was concentrated to 50% volume (approximately 11×). To this solution was charged 2.4 grams of activated charcoal. The slurry was vigorously agitated for about 4 hours and then filtered. The reactor and filter were washed with isopropyl acetate (2×16 mL) and the filtrate was solvent exchanged to 5 volumes of isopropyl acetate and used directly next step. $^1$H NMR (300 MHz, CDCl₃): δ 7.95 (d, J=6.0 Hz, 1H), 7.26 (m, 1H), 7.12 (m, 1H), 5.89 (m, 1H), 5.69 (m, 2H), 5.22 (d, J=9.0 Hz, 1H), 4.77 (d, J=6.0 Hz, 1H), 4.40 (d, J=9.0 Hz, 1H), 4.29 (d, J=6.0 Hz, 1H), 4.02-3.95 (m, 1H), 3.96 (s, 3H), 3.85 (m, 1H), 3.73 (s, 3H), 3.21 (s, 2H), 2.90-2.70 (m, 1H), 2.49 (d, J=12.0 Hz, 1H), 1.41 (m, 2H), 1.25-1.18 (m, 4H), 1.06 (s, 9H), 1.00-0.93 (m, 2H), 0.50 (m, 1H). LCMS: m/z=631.02.

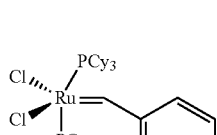

Grubbs 1

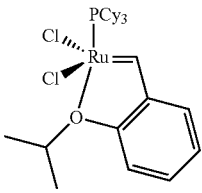

Hoveyda-Grubbs 1

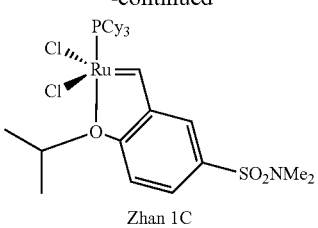

Zhan 1C

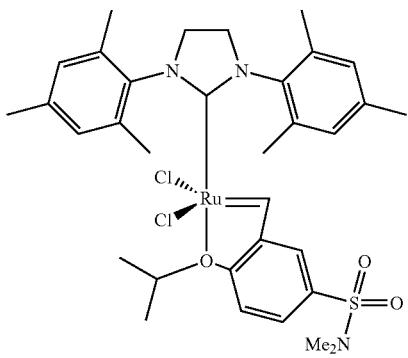

Zhan 1B

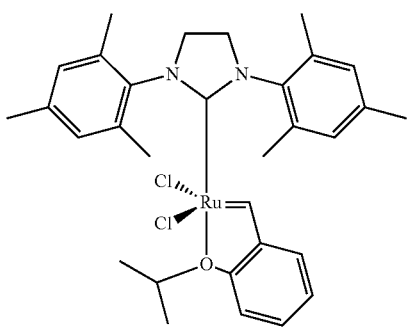

Hoveyda-Grubbs 2

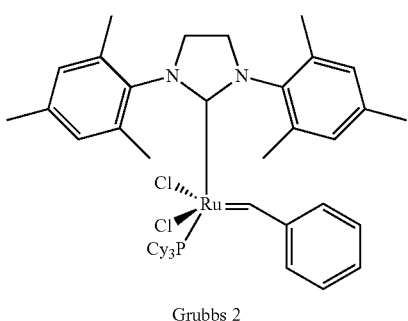

Grubbs 2

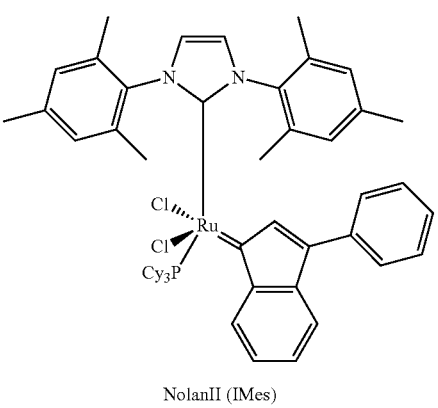

NolanII (IMes)

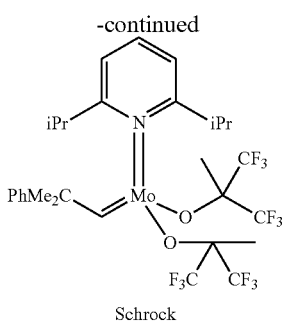

Schrock

In addition, other promoters (e.g., acetic acid, benzoquinones, CuI, CsCl, or Ti(O-i-Pr)$_4$), ethylene, or promoting conditions (e.g., microwave irradiation) may be employed. Further, temperatures ranging from about 40° C. to 110° C. may be used. Other solvents, such as halogenated (e.g., dichloromethane, 1,2-dichloroethane, chlorobenzene, or hexafluorobenzene), organic (e.g., benzene, THF, methyl-tert-butyl ether, cyclopentyl methyl ether, ethyl acetate, n-heptane, dimethyl carbonate, dimethyl formamide, acetonitrile), or alcohols (e.g., methanol, isopropanol) may be used.

F. Synthesis of Compound of Formula X (R=CHA)

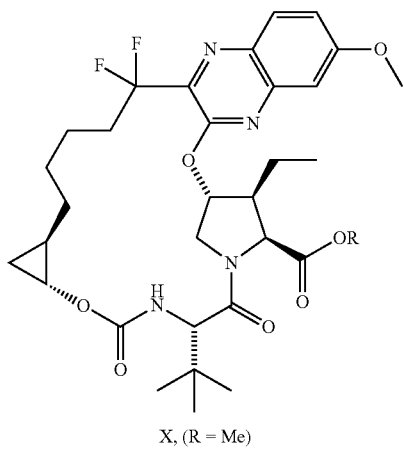

X, (R = Me)

Hydrogenation of IX (R=CH$_3$) to Provide X (R=CH$_3$):

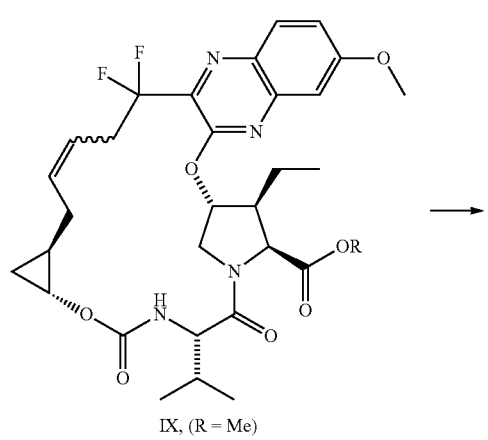

IX, (R = Me)

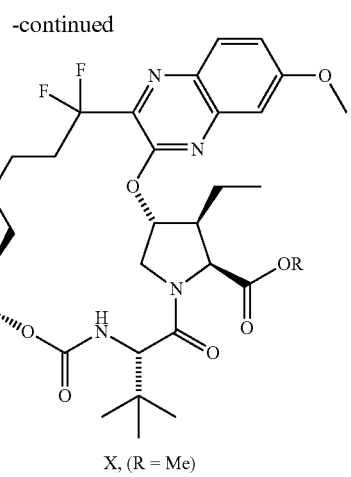

X, (R = Me)

IX (R=CH$_3$) in 5 volumes of iso-propyl acetate (IPAc) and Pt/C (5 wt % relative to IX (R=CH$_3$)) were charged to a reaction vessel. The reactor was inerted with N$_2$, then evacuated and filled with H$_2$ to 5 psig. The mixture was stirred vigorously for about 12 to 24 hours under 5 psig H$_2$ at room temperature. After completion of the reaction, diatomaceous earth (5 wt %) was charged, and mixture was filtered to remove the solids, rinsing forward with additional IPAc. The IPAc solution was treated with 6 volumes of 5% aqueous N-acetyl cysteine solution at about 50° C. for overnight under N$_2$ with vigorous agitation. After cooling to room temperature, the aqueous layer was removed and the organic layer was rinse with 6 volumes of 5-10% aqueous NaHCO$_3$ and 6 volumes of 10% aqueous NaCl. Diatomaceous earth (0.5 S) was added, the mixture was stirred for about 5 minutes, and the solids were subsequently removed by filtration. The solution of X (R=CH$_3$) was carried on without further purification.

$^1$H NMR (400 MHz, CDCl$_3$) δ 7.97 (d, J=9.2 Hz, 1H), 7.26 (dd, J=9.2, 2.7 Hz, 1H), 7.09 (d, J=2.7 Hz, 1H), 5.88 (d, J=3.9 Hz, 1H), 5.29 (d, J=9.9 Hz, 1H), 4.74 (d, J=7.2 Hz, 1H), 4.38-4.25 (m, 2H), 4.13-4.07 (m, 1H), 3.94 (s, 3H), 3.78-3.76 (m, 1H), 3.71 (s, 3H) 2.63 (app dd, J=15.0, 7.5 Hz, 1H), 2.54-2.32 (m, 1H), 2.02-1.98 (m, 1H), 1.84-1.63 (m, 4H), 1.53-1.33 (m, 3H), 1.30-1.10 (m, 4H), 1.07 (s, 9H), 0.95-0.80 (m, 2H), 0.77-0.64 (m, 1H), 0.46 (dd, J=12.9, 6.3 Hz, 1H). 19F NMR (376 MHz, CDCl3) δ −102.43 (ddd, J=250.4, 25.4, 8.6 Hz), −103.47 (ddd, J=250.4, 28.7, 11.3 Hz).

F. Synthesis of Compound of Formula XI (R=H) from X (R=CH$_3$)

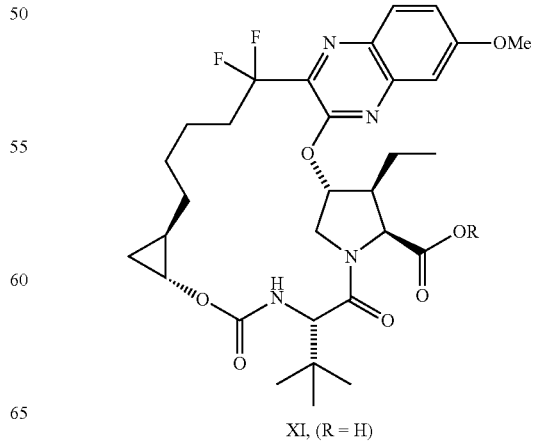

XI, (R = H)

II. Hydrolysis of X to Provide XI:

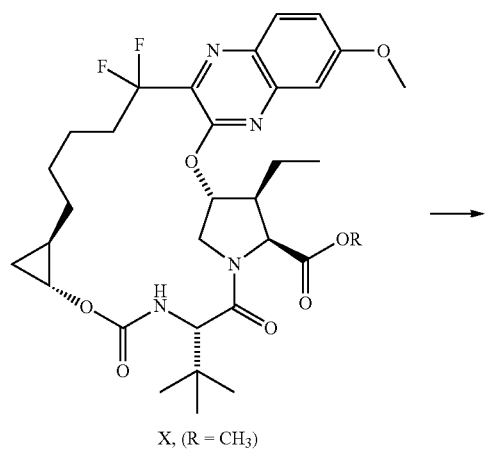

X, (R = CH₃)

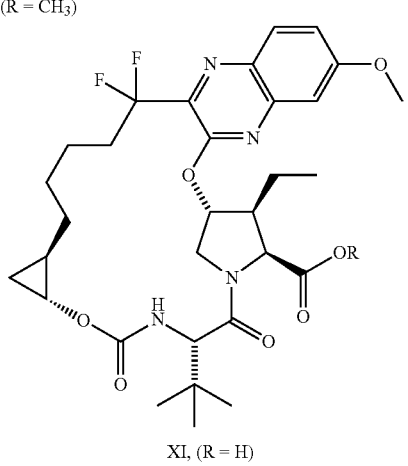

XI, (R = H)

To solution of X (R=CH₃) in IPA (7 volumes) at about 30° C. under $N_2$ was added a solution of aqueous LiOH over about 5 to 10 minutes (1M, 2.3 eq). The reaction mixture was warmed to an internal temperature of about 40° C., and stirred. After cooling to room temperature MTBE (8 volumes) was added. The resulting mixture was acidified to pH 3 with 1M HCl. The aqueous layer is removed and the organic layer is rinsed twice with 10% aqueous NaCl. Diatomaceous earth is added (0.1 S), and the resulting slurry is filtered, rinsing forward with additional MTBE. The MTBE is removed via vacuum distillation, and the resulting solids are dissolved in 5 volumes of ethanol and 5 volumes of heptane at about 60 to 65° C. The solution is then cooled to about 45 to 50° C. and seeded with a slurry of XI in ethanol/heptane (0.005 S). After stirring for about 6 hours at about 45° C., the slurry is cooled to about 15° C. over about 10 hours. An additional volumes of heptane are added over about 1 hour. XI was isolated via vacuum filtration and rinsed with 5 volumes of 1:9 EtOH:heptane. The resulting solids are dried in a vacuum oven at about 40° C. to constant weight. $^1$H NMR (400 MHz, CDCl₃) δ 7.95 (d, J=9.2 Hz, 1H), 7.24 (dd, J=9.2, 2.6 Hz, 1H), 7.07 (d, J=2.6 Hz, 1H), 5.87 (d, J=3.5 Hz, 1H), 5.47 (d, J=9.9 Hz, 1H), 4.72 (d, J=7.2 Hz, 1H), 4.33 (d, J=12.2 Hz, 1H), 4.32 (d, J=9.9 Hz, 1H), 4.04 (dd, J=11.9, 4.0 Hz, 1H), 3.93 (s, 3H), 3.7 (m, 1H), 2.64 (m, 1H), 2.43 (m, 1H), 1.99 (m, 1H), 1.8-1.3 (m, 6H), 1.25-1.15 (m, 3H), 1.0 (m, 1H). $^{13}$C NMR (75 MHz, CDCl₃): δ 172.63, 171.64, 162.06, 157.49, 153.37, 142.42, 139.12 (dd, $J_{CF}$=30.6, 25.8 Hz), 133.06, 130.44, 120.1 (t, $J_{CF}$=245 Hz), 119.93, 105.31, 77.45, 61.66, 59.49, 55.74, 54.98, 51.92, 46.52, 36.42 (t, $J_{CF}$=25.0), 34.91, 30.35, 27.74, 26.19, 21.53, 19.99, 18.34, 12.06, 11.33.

G. Synthesis of Compound of Formula I from X (R=CH₃)

Synthesis of compound of formula I from X was similar to that described in U.S. Publication No. 2014-0017198. X (R=CH₃) was hydrolyzed to form XI (R=H) which was coupled with XII to form I.

What is claimed is:

1. A crystalline form of compound I:

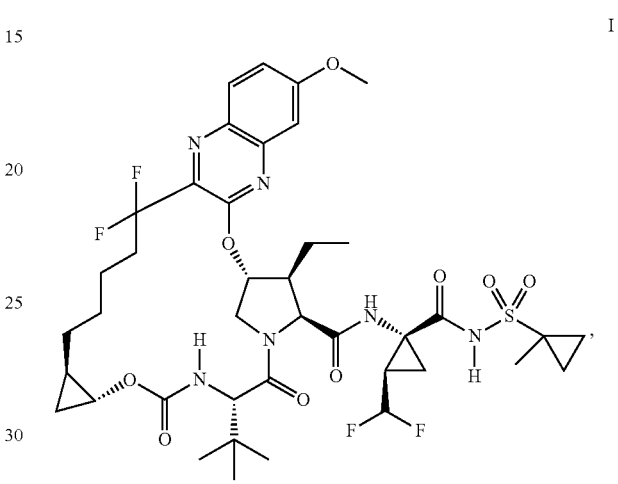

I wherein, the crystalline form is
an ethanol solvate (Compound I Form I), characterized by an X-ray powder diffractogram comprising peaks (±0.2°) at 8.6, 11.1, and 15.5 °2θ as determined on a diffractometer using Cu-Kα radiation.

2. Compound I Form I according to claim 1, wherein the diffractogram further comprises
a peak at 12.9 °2θ±0.2°.

3. A pharmaceutical composition comprising a Compound I Form I according to claim 1, and a pharmaceutically acceptable excipient.

4. A method for treating a subject suffering from hepatitis C virus (HCV), comprising administering to the subject a therapeutically effective amount of a Compound I Form I according to claim 1 and a pharmaceutically acceptable excipient.

5. The method according to claim 4, comprising further administering to the subject at least one anti-HCV agent.

6. Compound I Form I according to claim 1, wherein the diffractogram is substantially as shown in FIG. 1.

7. Compound I Form I according to claim 1, characterized by a differential scanning calorimetry (DSC) curve substantially as shown in FIG. 2.

8. Compound I Form I according to claim 1, characterized by a differential scanning calorimetry (DSC) curve that comprises an endotherm at about 149° C., an exotherm at about 212° C., and an endotherm at about 275° C.

9. Compound I Form I according to claim 1, characterized by a thermogravimetric analysis (TGA) comprising a thermogram substantially as shown in FIG. 3.

10. Compound I Form I according to claim 1, characterized by a thermogravimetric analysis (TGA) with a weight loss of about 8.4% in a temperature range of about 30° C. to about 350° C.

11. Compound I Form I according to claim 1, characterized by a dynamic vapor sorption (DVS) curve substantially as shown in FIG. 4.

12. New Compound I Form I according to claim 1, characterized by a nuclear magnetic resonance spectrum ($^1$H NMR) substantially as shown in FIG. 5.

13. Compound I Form I according to claim 1, further comprising about 1.7 mole equivalents of ethanol.

* * * * *

UNITED STATES PATENT AND TRADEMARK OFFICE
CERTIFICATE OF CORRECTION

PATENT NO. : 9,562,058 B2
APPLICATION NO. : 14/575966
DATED : February 7, 2017
INVENTOR(S) : Dustin Bringley et al.

It is certified that error appears in the above-identified patent and that said Letters Patent is hereby corrected as shown below:

In the Claims

In Claim 10, Column 94, Lines 64-67, please replace "Compound I Form I according to claim 1, characterized by a thermogravimetric analysis (TGA) with a weight loss of about 8.4% in a temperature range of about 30° C. to about 350° C." with --Compound I Form I according to claim 1, characterized by a thermogravimetric analysis (TGA) with a weight loss of about 8.4%.--.

In Claim 12, Column 95, Lines 4-6, please replace "New Compound I Form I according to claim 1, characterized by a nuclear magnetic resonance spectrum ($^1$H NMR) substantially as shown in FIG. 5." with --Compound I Form I according to claim 1, characterized by a nuclear magnetic resonance spectrum ($^1$H NMR) substantially as shown in FIG. 5.--.

Signed and Sealed this
Eighteenth Day of June, 2019

Andrei Iancu
*Director of the United States Patent and Trademark Office*